US012728160B2

(12) United States Patent
Moser et al.

(10) Patent No.: US 12,728,160 B2
(45) Date of Patent: Sep. 8, 2026

(54) VACCINE USING M2/BM2-DEFICIENT INFLUENZA VECTORS

(71) Applicant: FluGen, Inc., Madison, WI (US)

(72) Inventors: Michael J. Moser, Madison, WI (US); David J. Marshall, Madison, WI (US); Liam I. Marshall, Madison, WI (US); Yasuko Hatta, Madison, WI (US); Pamuk Bilsel, Madison, WI (US)

(73) Assignee: FluGen, Inc., Madison, WI (US)

( * ) Notice: Subject to any disclaimer, the term of this patent is extended or adjusted under 35 U.S.C. 154(b) by 731 days.

(21) Appl. No.: 18/017,371

(22) PCT Filed: Jul. 21, 2021

(86) PCT No.: PCT/US2021/042561
§ 371 (c)(1),
(2) Date: Jan. 20, 2023

(87) PCT Pub. No.: WO2022/020460
PCT Pub. Date: Jan. 27, 2022

(65) Prior Publication Data
US 2023/0256086 A1 Aug. 17, 2023

Related U.S. Application Data

(60) Provisional application No. 63/054,700, filed on Jul. 21, 2020.

(51) Int. Cl.

| | |
|---|---|
| ***A61K 39/215*** | (2006.01) |
| ***A61K 39/00*** | (2006.01) |
| ***C07K 14/11*** | (2006.01) |

(52) U.S. Cl.
CPC ............ *A61K 39/215* (2013.01); *C07K 14/11* (2013.01); *A61K 2039/543* (2013.01); *A61K 2039/70* (2013.01); *C12N 2770/20022* (2013.01)

(58) Field of Classification Search
CPC .................. A61K 39/215; A61K 39/12; A61K 2039/543; A61K 2039/70; A61K 2039/5254; A61K 2039/575; C07K 14/11; C07K 14/005; C12N 2770/20022; C12N 2770/20034; C12N 2760/16134; C12N 2760/16143; C12N 2760/16234; C12N 2760/16243; C12N 15/86
See application file for complete search history.

(56) References Cited

U.S. PATENT DOCUMENTS

| | | | |
|---|---|---|---|
| 6,270,958 | B1 | 8/2001 | Olivo et al. |
| 6,544,785 | B1 | 4/2003 | Palese et al. |
| 6,872,395 | B2 | 3/2005 | Kawaoka |
| 7,176,021 | B2 | 2/2007 | Kawaoka |
| 7,226,774 | B2 | 6/2007 | Kawaoka |
| 7,276,356 | B1 | 10/2007 | Palese et al. |
| 7,312,064 | B2 | 12/2007 | Hoffmann |
| 7,384,774 | B2 | 6/2008 | Palese et al. |
| 7,459,162 | B2 | 12/2008 | Yang et al. |
| 7,510,719 | B2 | 3/2009 | Dang et al. |
| 7,566,458 | B2 | 7/2009 | Yang et al. |
| 7,585,657 | B2 | 9/2009 | Kawaoka |
| 7,588,769 | B2 | 9/2009 | Kawaoka |
| 7,723,094 | B2 | 5/2010 | Kawaoka et al. |
| 7,790,434 | B2 | 9/2010 | Duke et al. |
| 7,959,930 | B2 | 6/2011 | De Wit et al. |
| 7,968,101 | B2 | 6/2011 | Kawaoka et al. |
| 7,972,843 | B2 | 7/2011 | Hoffmann |
| 7,993,924 | B2 | 8/2011 | Billeter et al. |
| 8,012,736 | B2 | 9/2011 | Hoffman et al. |
| 8,012,737 | B2 | 9/2011 | Dang et al. |
| 8,043,856 | B2 | 10/2011 | Kawaoka et al. |
| 8,048,430 | B2 | 11/2011 | Yang et al. |
| 8,057,806 | B2 | 11/2011 | Kawaoka |
| 8,163,523 | B2 | 4/2012 | Bilsel et al. |
| 8,202,726 | B2 | 6/2012 | Liu et al. |
| 8,288,145 | B2 | 10/2012 | Röthl et al. |
| 8,298,805 | B2 | 10/2012 | Kawaoka |
| 8,333,975 | B2 | 12/2012 | Yang et al. |
| 8,404,248 | B2 | 3/2013 | Yang et al. |

(Continued)

FOREIGN PATENT DOCUMENTS

| | | | |
|---|---|---|---|
| CN | 102864127 | A | 1/2013 |
| CN | 102864128 | A | 1/2013 |

(Continued)

OTHER PUBLICATIONS

Furusawa et al., "Influenza Virus Polymerase Mutation Stabilizes a Foreign Gene Inserted into the Virus Genome by Enhancing the Transcription/Replication Efficiency of the Modified Segment," mBio 10(5): e01794-19 (2019).
Heaton et al., "In Vivo Bioluminescent Imaging of Influenza A Virus Infection and Characterization of Novel Cross-Protective Monoclonal Antibodies," Journal of Virology, 87(15): 8272-8281 (2013).
Hoffmann et al., "Universal primer set for the full-length amplification of all influenza A viruses," Arch. Virol., 146: 2275-2289 (2001).
Jin et al., "Multiple amino acid residues confer temperature sensitivity to human influenza virus vaccine strains (FluMist) derived from cold-adapted A/Ann Arbor/6/60," Virology, 306: 18-24 (2003).

(Continued)

*Primary Examiner* — Thomas J. Visone
*Assistant Examiner* — Cassandra Senn Grizer
(74) *Attorney, Agent, or Firm* — LEYDIG, VOIT & MAYER, LTD.

(57) ABSTRACT

The invention provides a recombinant virus comprising an influenza viral backbone, wherein the influenza viral backbone comprises PB1, PB2, PA, NP, M, NS, HA, and NA gene segments, wherein at least one of the PB1, PB2, PA, NP, M, NS, HA, and NA gene segments comprises at least one nucleotide sequence that encodes one or more antigens. The invention provides a recombinant virus wherein the antigen is an immunogenic fragment of SARS-CoV-2 spike glycoprotein. The invention also provides a pharmaceutical formulation and a method of eliciting an immune response.

24 Claims, 22 Drawing Sheets

Specification includes a Sequence Listing.

(56) References Cited

U.S. PATENT DOCUMENTS

| | | | |
|---|---|---|---|
| 8,465,960 | B2 | 6/2013 | Kawaoka et al. |
| 8,475,806 | B2 | 7/2013 | Kawaoka et al. |
| 8,507,247 | B2 | 8/2013 | Kawaoka et al. |
| 8,574,593 | B2 | 11/2013 | Yang et al. |
| 8,592,196 | B2 | 11/2013 | Kittel et al. |
| 8,597,661 | B2 | 12/2013 | Kawaoka et al. |
| 8,673,613 | B2 | 3/2014 | Jin et al. |
| 8,679,819 | B2 | 3/2014 | Kawaoka |
| 8,685,410 | B2 | 4/2014 | Yang et al. |
| 8,691,239 | B2 | 4/2014 | Yang et al. |
| 8,715,940 | B2 | 5/2014 | Kawaoka et al. |
| 8,859,208 | B2 | 10/2014 | Kawaoka et al. |
| 8,877,209 | B2 | 11/2014 | Kawaoka et al. |
| 8,877,210 | B2 | 11/2014 | Yang et al. |
| 8,877,448 | B2 | 11/2014 | Kawaoka et al. |
| 8,883,479 | B2 | 11/2014 | Krenn et al. |
| 9,023,603 | B2 | 5/2015 | Kawaoka et al. |
| 9,068,986 | B2 | 6/2015 | Jin et al. |
| 9,085,753 | B2 | 7/2015 | Liu et al. |
| 9,101,653 | B2 | 8/2015 | Kawaoka et al. |
| 9,109,013 | B2 | 8/2015 | Kawaoka et al. |
| 9,119,810 | B2 | 9/2015 | Montelione et al. |
| 9,157,096 | B2 | 10/2015 | Kawaoka et al. |
| 9,254,318 | B2 | 2/2016 | Kawaoka et al. |
| 9,284,533 | B2 | 3/2016 | Bilsel et al. |
| 9,474,798 | B2 | 10/2016 | Watanabe et al. |
| 9,580,693 | B2 | 2/2017 | Kawaoka et al. |
| 9,732,313 | B2 | 8/2017 | Hirschel et al. |
| 9,757,446 | B2 | 9/2017 | LeFebvre et al. |
| 9,890,363 | B2 | 2/2018 | Kawaoka et al. |
| 9,919,042 | B2 | 3/2018 | Bilsel et al. |
| 9,919,043 | B2 | 3/2018 | Bilsel et al. |
| 9,926,535 | B2 | 3/2018 | Kawaoka et al. |
| 9,950,057 | B2 | 4/2018 | Kawaoka et al. |
| 10,022,434 | B2 | 7/2018 | Weiner et al. |
| 10,053,671 | B2 | 8/2018 | Kawaoka et al. |
| 10,059,925 | B2 | 8/2018 | Kawaoka et al. |
| 10,119,124 | B2 | 11/2018 | Watanabe et al. |
| 10,130,697 | B2 | 11/2018 | Watanabe et al. |
| 10,172,934 | B2 | 1/2019 | Kawaoka et al. |
| 10,246,686 | B2 | 4/2019 | Kawaoka et al. |
| 10,358,630 | B2 | 7/2019 | Kawaoka et al. |
| 10,494,613 | B2 | 12/2019 | Kawaoka et al. |
| 10,500,267 | B2 | 12/2019 | LeFebvre et al. |
| 10,513,692 | B2 | 12/2019 | Kawaoka et al. |
| 10,570,376 | B2 | 2/2020 | Peterka et al. |
| 10,633,422 | B2 | 4/2020 | Kawaoka et al. |
| 10,808,229 | B2 | 10/2020 | Kawaoka et al. |
| 11,007,262 | B2 | 5/2021 | Watanabe et al. |
| 11,046,934 | B2 | 6/2021 | Kawaoka et al. |
| 11,180,737 | B2 | 11/2021 | Kawaoka et al. |
| 11,197,925 | B2 | 12/2021 | Kawaoka et al. |
| 2003/0035814 | A1 | 2/2003 | Kawaoka et al. |
| 2004/0180058 | A1 | 9/2004 | Shneider et al. |
| 2009/0246830 | A1 | 10/2009 | Kawaoka et al. |
| 2011/0300604 | A1 | 12/2011 | Kawaoka et al. |
| 2013/0115242 | A1 | 5/2013 | Moules et al. |
| 2013/0243804 | A1 | 9/2013 | Stoloff et al. |
| 2015/0017205 | A1 | 1/2015 | Kawaoka et al. |
| 2015/0166967 | A1 | 6/2015 | Kawaoka et al. |
| 2015/0368621 | A1 | 12/2015 | Kawaoka et al. |
| 2016/0002606 | A1 | 1/2016 | Peterka et al. |
| 2016/0284020 | A1 | 9/2016 | Williams |
| 2017/0198264 | A1 | 7/2017 | Kawaoka et al. |
| 2017/0216425 | A1 | 8/2017 | Ahmed et al. |
| 2017/0258888 | A1 | 9/2017 | Kawaoka et al. |
| 2017/0354730 | A1 | 12/2017 | Kawaoka et al. |
| 2018/0340152 | A1 | 11/2018 | Kawaoka et al. |
| 2019/0048324 | A1 | 2/2019 | Kawaoka et al. |
| 2019/0060441 | A1 | 2/2019 | Bilsel et al. |
| 2019/0167781 | A1 | 6/2019 | Kawaoka et al. |
| 2019/0184007 | A1 | 6/2019 | Ahmed et al. |
| 2020/0061182 | A1 | 2/2020 | Bilsel et al. |
| 2020/0188506 | A1 | 6/2020 | Kawaoka et al. |
| 2020/0263143 | A1 | 8/2020 | Kawaoka et al. |
| 2022/0241397 | A1 | 8/2022 | Hatta et al. |
| 2023/0295582 | A1 | 9/2023 | Moser et al. |

FOREIGN PATENT DOCUMENTS

| | | | |
|---|---|---|---|
| CN | 102864129 | A | 1/2013 |
| WO | 2005115448 | A2 | 12/2005 |
| WO | 2006083286 | A2 | 8/2006 |
| WO | WO 2010/117786 | A1 | 10/2010 |
| WO | 2011014504 | A1 | 2/2011 |
| WO | 2015063085 | A1 | 5/2015 |
| WO | 2015142671 | A2 | 9/2015 |
| WO | WO 2017/007839 | A1 | 1/2017 |
| WO | 2017184626 | A1 | 10/2017 |
| WO | WO 2018/157028 | A1 | 8/2018 |
| WO | WO 2018/157047 | A1 | 8/2018 |
| WO | WO 2022/020460 | A1 | 1/2022 |
| WO | WO 2022/020469 | A1 | 1/2022 |

OTHER PUBLICATIONS

Manicassamy et al., "Analysis of in vivo dynamics of influenza virus infection in mice using a GFP reporter virus," PNAS, 107(25): 11531-11536 (2010).

Nogales et al., "A Novel Fluorescent and Bioluminescent Bireporter Influenza A Virus to Evaluate Viral Infections," Journal of Virology, 93(10): e00032-19 (2019).

Pan et al., "Development and application of bioluminescence imaging for the influenza A virus," J. Thorac. Dis., 10 (Suppl. 19): S2230-S2237 (2018).

Wang et al., "Generation of a Reassortant Influenza A Subtype H3N2 Virus Expressing Gaussia Luciferase," Viruses, 11(7): 665 (2019).

European Patent Office, Extended European Search Report in European Patent Application No. 21845261.3 (Sep. 30, 2024).

European Patent Office, Extended European Search Report in European Patent Application No. 21845413.0 (Oct. 14, 2024).

Japan Patent Office, Notice of Reasons for Refusal in Japanese Patent Application No. 504319-2023 (Jul. 29, 2025).

Globaldata Healthcare, "Influenza vaccine: FluGen has successful Phase II trial for M2SR," Feb. 22. 2019, XP093027811, Retrieved from the Internet Mar. 1, 2023 https://www.pharmaceutical-technology.com/comment/flugen-successbrings-the-reality-of-universal-influenza-vaccines-closer/.

Hatta et al., "M2SR, a novel live influenza vaccine, protects mice and ferrets against highly pathogenic avian influenza," *Vaccine 35*(33): 4177-4183 (2017).

Hu et al., "A Vero-cell-adapted vaccine donor strain of influenza A virus generated by serial passages," *Vaccine 33*(2): 374-381 (2014).

European Patent Office, Extended European Search Report in European Patent Application No. 20 818 294.9 (Mar. 13, 2023).

Clark, et al.,"Functional Evolution of Influenza Virus NS1 Protein in Currently Circulating Human 2009 Pandemic H1N1 Viruses," *Journal of Virology*, 91(17): 1-22 (Aug. 10, 2017).

Davis et al., "Identification of influenza A nucleoprotein body domain residues essential for viral RNA expression expose antiviral target," *Virology Journal*, 14(22): 1-13 (Feb. 7, 2017).

Liedmann et al., "Viral suppressors of the RIG-I-mediated interferon responses are pre-packaged in influenza virions," *Nature Communications*, 5(5645): 1-8 (Dec. 9, 2014).

Ping et al., "Development of high-yield influenza A virus vaccine viruses," *Nature Communications*, 6(8148): 1-15 (Sep. 2, 2015).

U.S. Patent and Trademark Office, International Search Report for International Patent Application PCT/US2020/036455 (Sep. 30, 2020).

U.S. Patent and Trademark Office, International Search Report in International Patent Application No. PCT/US2021/042561 (Dec. 21, 2021).

U.S. Patent and Trademark Office, Written Opinion in International Patent Application No. PCT/US2021/042561 (Dec. 21, 2021).

(56) References Cited

OTHER PUBLICATIONS

U.S. Patent and Trademark Office, International Search Report in International Patent Application No. PCT/US2021/042572 (Nov. 10, 2021).

U.S. Patent and Trademark Office, Written Opinion in International Patent Application No. PCT/US2021/042572 (Nov. 10, 2021).

Uniprot, Identification No. A0A0M3Z509_9INFA, NP.5 (Jun. 5, 2019) [retrieved from the internet URL https://www.uniprot.org/uniprot/A0A0M3Z509.txt?version=21> on Sep. 2, 2020].

Uniprot, Identification No. A0A0M5HQ96_9INFA, PB1.5 (Jun. 5, 2019) [retrieved from the internet URL https://www.uniprot.org/uniprot/A0A0M5HQ96.txt?version=20> on Sep. 2, 2020].

Watanabe et al., "Influenza A Virus Lacking M2 Protein as a Live Attenuated Vaccine," *Journal of Virology*, 83(11): 5947-5950 (2009).

Yamaji et al., "Mammalian Adaptive Mutations of the PA Protein of Highly Pathogenic Avian H5N1 Influenza Virus," *Joumal of Virology*, 89(8): 4117-4133 (Jan. 28, 2015).

UTR
Gene of Interest
MD
TM
2A
HA
UTR
3' Packaging Signal
Duplication
3' Packaging Signal
5' Packaging Signal

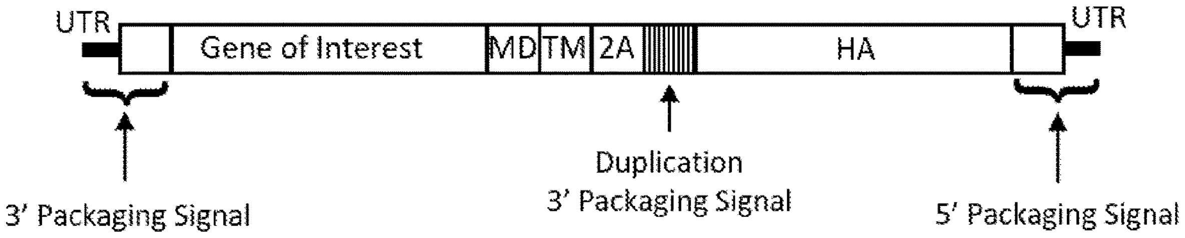

FIG. 15

UTR
Gene of Interest
TM
2A
HA
UTR
3' Packaging Signal
Duplication
3' Packaging Signal
5' Packaging Signal

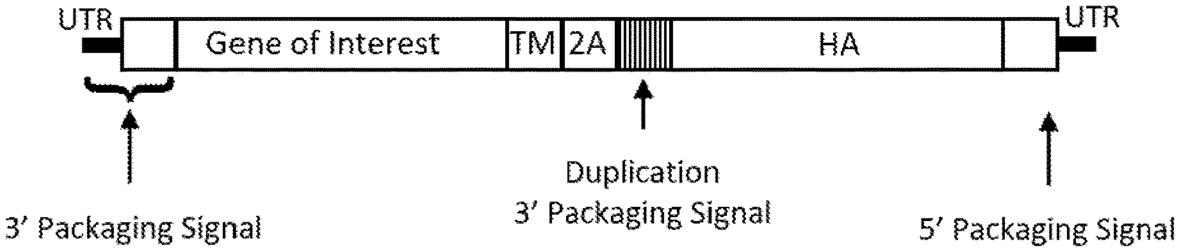

FIG. 16

UTR
NS1
2A
Gene of Interest
MD
TM
2A
NEP
UTR
3' Packaging Signal
Duplication
3' Packaging Signal
5' Packaging Signal

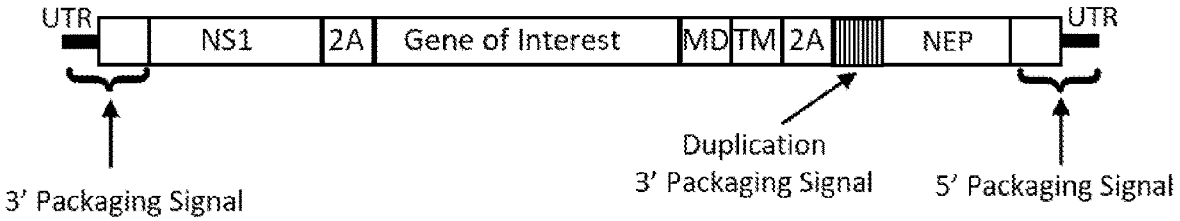

FIG. 17

UTR
NS1
2A
Gene of Interest
TM
2A
NEP
UTR
3' Packaging signal
Duplicated
3' packaging signal
5' Packaging signal

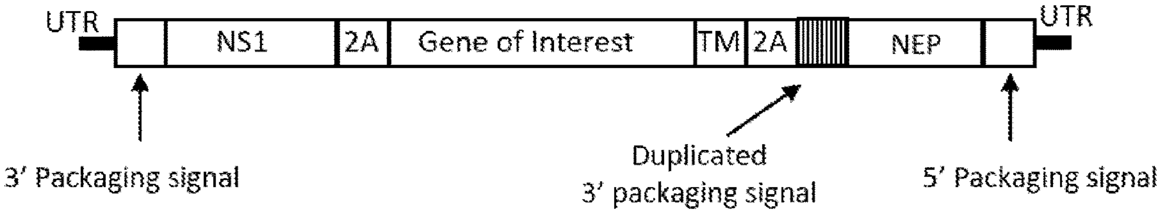

FIG. 18

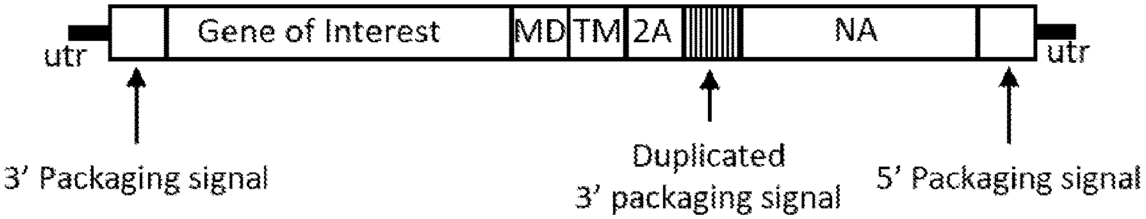

FIG. 19

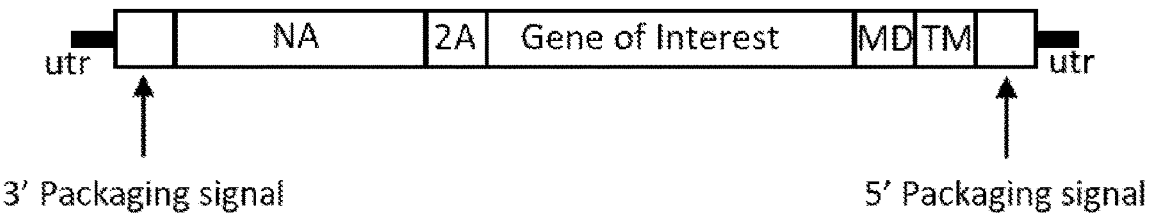

FIG. 20

```
                  ....|....| ....|....| ....|....| ..
                          10         20         30
NS1 ORF           ATGGATCCAA ACACTGTGTC AAGCTTTCAa (SEQ ID NO: 118)
NEP Exon 1              CCtA AtACaGTGTC tAGCTTcCAG (SEQ ID NO: 119)
```

FIG. 21

```
             ....|....| ....|....| ....|....| ....|....| ....|....|
                     10         20         30         40         50
NS1 ORF      GACATACTGC TGAGGtTGTC AAgAATGCtG TTGGAGTgCT aATCGGAGGA
NEP Exon 2   GACATACTGC TGAGGATGTC AAAAATGCAG TTGGAGTCCT CATCGGAGGA

             ....|....| ....|....| ....|....| ....|....| ....|....|
                     60         70         80         90        100
NS1 ORF      CTTGAATGGA AcGAcAACAC tGTgCGAGTC agcGAAACTt tgCAGAGATT
NEP Exon 2   CTTGAATGGA ATGATAACAC AGTTCGAGTC TCTGAAACTC TACAGAGATT

             ....|....| ....|....| ....|....| ....|....| ....|....|
                    110        120        130        140        150
NS1 ORF      tGCTTGGAGA AGCtctAATG AGAAcGGGAG ACCTCCACTg ACTCCAAAgC
NEP Exon 2   CGCTTGGAGA AGCAGTAATG AGAATGGGAG ACCTCCACTC ACTCCAAAAC

             ....|....| ....|....| ....|....| ....|...
                    160        170        180
NS1 ORF      AGAAACGAGA cATGGCtGGA ACAATTAGaa gcGAAGTT (SEQ ID NO: 120)
NEP Exon 2   AGAAACGAGA AATGGCGGGA ACAATTAGGT CAGAAGTT (SEQ ID NO: 121)
```

FIG. 22

Mini-Spike: S1 RBD:Foldon:RSV TM Virus Infected M2VeroA cells
Cell Surface Staining Anti SARS-CoV-2 Spike S1 bnAb CR3022

RBD:HA Direct Fusion
Cell Surface Staining

Virus Infected M2VeroA cells
Anti SARS-CoV-2 Spike S1 bnAb CR3022

RSV G:HA Direct Fusion
Cell Surface Staining

Transfected 293T cells
Anti RSV G mAb 131-2G

VACCINE USING M2/BM2-DEFICIENT INFLUENZA VECTORS

This patent application is the U.S. national phase of International Patent Application No. PCT/US2021/042561, filed Jul. 21, 2021, which claims the benefit of U.S. Provisional Patent Application No. 63/054,700, filed Jul. 21, 2020, each of which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 271,106 Byte ASCII (Text) file named "755022ReplacementSequenceListing.txt," created on Oct. 6, 2021.

BACKGROUND OF THE INVENTION

Vaccines are important tools for preventing illness from infectious disease. Infectious diseases can infect millions of people worldwide. Thus, it is important to develop vaccines against many different types of diseases and to do so quickly and efficiently. For example, the novel coronavirus disease 2019 (COVID-19) is a global pandemic caused by the newly emerged virus severe acute respiratory syndrome coronavirus 2 (SARS-CoV-2). Over 10 million people worldwide have been diagnosed with the disease and hundreds of thousands have died from it. In its severe form, the disease is characterized by acute respiratory distress syndrome (ARDS) and there are currently no targeted intervention strategies to treat or prevent it. The immune response to the virus is thought to both contribute to the pathogenesis of the disease and provide protection during its resolution. Thus, there is an unprecedented need to develop a safe and effective vaccine to immunize an extraordinarily large number of individuals.

BRIEF SUMMARY OF THE INVENTION

The invention provides a recombinant virus comprising an influenza viral backbone, wherein the influenza viral backbone comprises PB1, PB2, PA, NP, M, NS, HA, and NA gene segments, wherein at least one of the PB1, PB2, PA, NP, M, NS, HA, and NA gene segments comprises at least one nucleotide sequence that encodes at least one antigen. In a preferred embodiment, the antigen is an immunogenic fragment of Severe Acute Respiratory Syndrome Coronavirus 2 (SARS-CoV-2) spike glycoprotein.

BRIEF DESCRIPTION OF THE SEVERAL VIEWS OF THE DRAWING(S)

FIG. 1 is a schematic of an influenza A NS segment engineered to express NS1 to SARS-CoV-2 Spike receptor binding domain fusion protein. The construct includes a full length influenza A PR/8/1934 NS1 protein, a first linker (GSG1), amino acids 331-530 of SARS-COV-2 Wuhan-Hu-1 spike S1 protein encoding RBD (receptor binding domain), a second linker (GSG2), a cleavage site (P2A), and cDNA of essential PR8 nuclear export protein (NEP or NS2) with both Exon 1 and 2.

FIG. 2 is a schematic of an influenza A NS segment engineered to express SARS-CoV-2 Spike receptor binding domain as separate polypeptide. The construct includes a full length influenza A PR/8/1934 NS1 protein, a first linker (GSG1), a first cleavage site (T2A), amino acids 331-530 of SARS-COV-2 Wuhan-Hu-1 spike S1 protein encoding RBD, a second linker (GSG2), a second cleavage site (P2A), and cDNA of essential PR8 nuclear export protein (NEP or NS2) with both Exon 1 and 2.

FIG. 3 depicts an image of an immunoblot of cell lysates from Vero cells infected with CoV2 NS M2SR, M2SR control, and MOCK medium only. Proteins were separated by sodium dodecyl sulfate-polyacrylamide gel electrophoresis (SDS-PAGE) and subjected to immunoblot analysis. The primary antibody was anti-SARS-CoV-2 RBD (Sino Biological Inc., Beijing, China) and the secondary antibody was an anti-rabbit IgG-horseradish peroxidase (HRP) with 3,3',5,5'-tetramethylbenzidine (TMB) detection.

FIG. 4 is a set of images showing that both CoV2 NS1 M2SR and the standard M2SR infected cells express detectable levels of the influenza A NP protein. Meanwhile the FITC labeling of the RBD could only be detected in CoV2 NS1 M2SR infected cells providing significant detectable fluorescence.

FIG. 5 is a schematic of an influenza B M segment 7 engineered to express BM2 SARS-CoV-2 Spike RBD fusion to amino and carboxy termini of BM2 protein (SEQ ID NOs: 84, 96). The construct includes a full length influenza B/Florida/4/2006 M1 protein, 5-mer translation stop/start site, amino acids 1-8 BM2 open reading frame (ORF), amino acids 330-524 of SARS-COV-2 Wuhan-Hu-1 spike S1 protein encoding RBD, and BM2 RBD fusion protein.

FIG. 6 is a schematic of an influenza B M segment 7 engineered to express BM2 SARS-CoV-2 Spike RBD fusion to amino terminus of BM2 protein (SEQ ID NOs: 83, 95). The construct includes a full length influenza B/Florida/4/2006 M1 protein, 5-mer translation stop/start site, BM2 RBD fusion protein comprising amino acids 1-3 BM2 ORF, and 330-524 of SARS-COV-2 Wuhan-Hu-1 spike S1 protein encoding RBD.

FIG. 7 depicts an image of an immunoblot of cell lysates from Vero cells. Total cell lysates from cells infected with 2 SARS-CoV-2 BM2SR strains (SEQ ID Nos: 83, 84, 95, 96) BM2SR, and MOCK medium only negative controls. Proteins were separated by SDS-PAGE and then subjected to immunoblot analysis. The primary antibody was anti-SARS-CoV-2 RBD (Sino Biological Inc.) and the secondary antibody anti-rabbit IgG-HRP with TMB detection. Location of the RBD fusion protein is indicated in the image by pound signs.

Figure 10A:
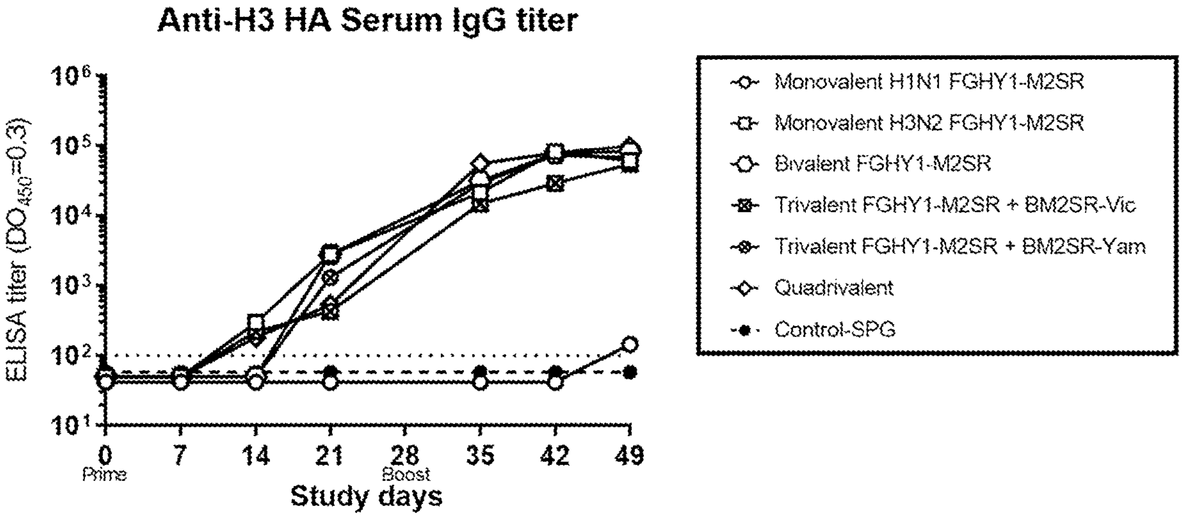
Figure 10B:
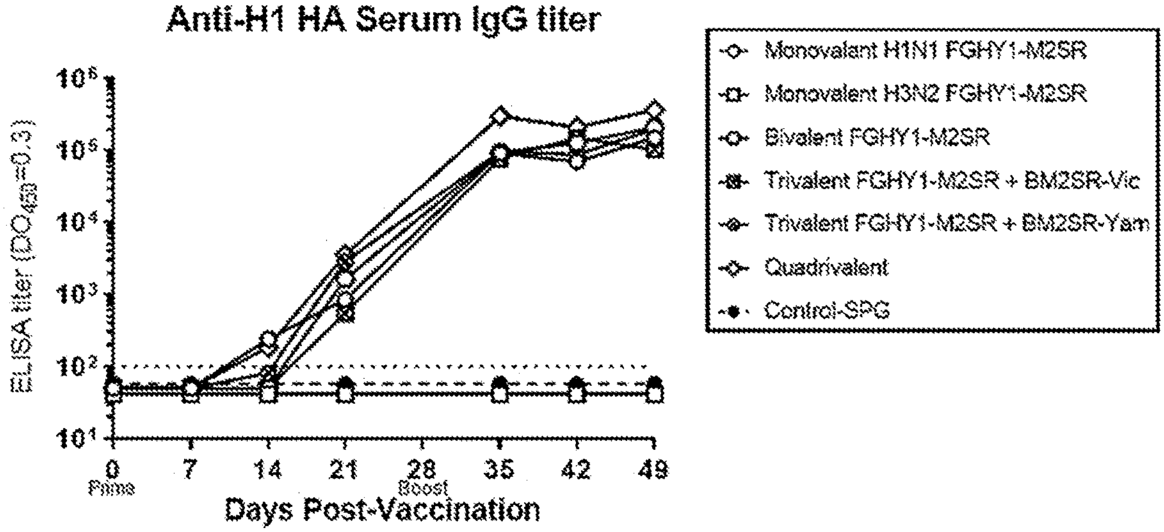
Figure 10C:
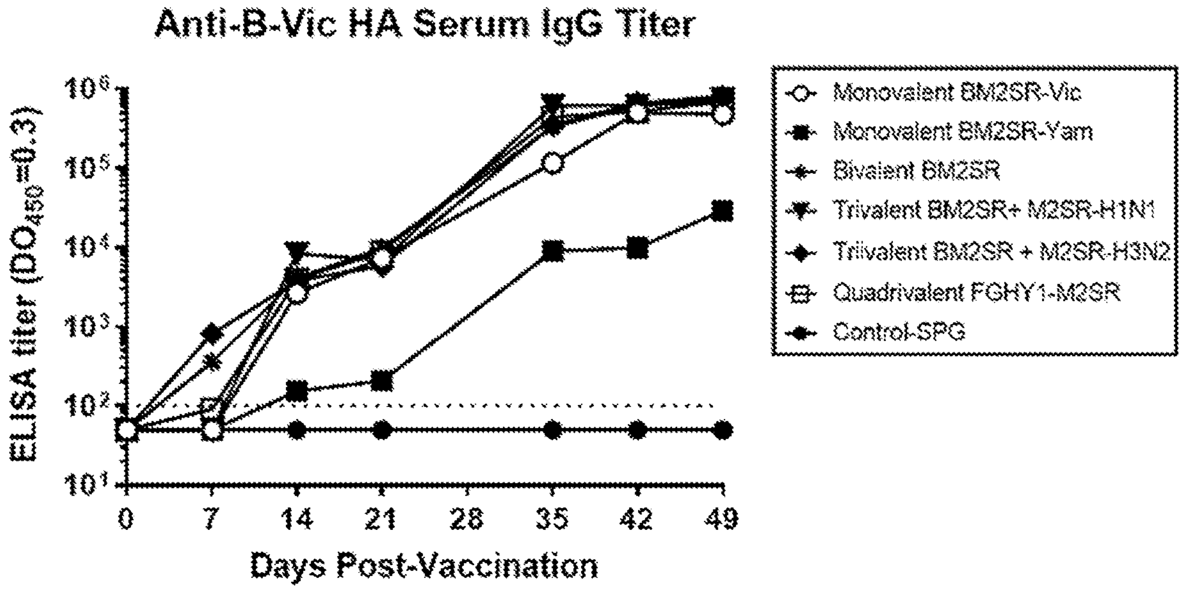
Figure 10D:
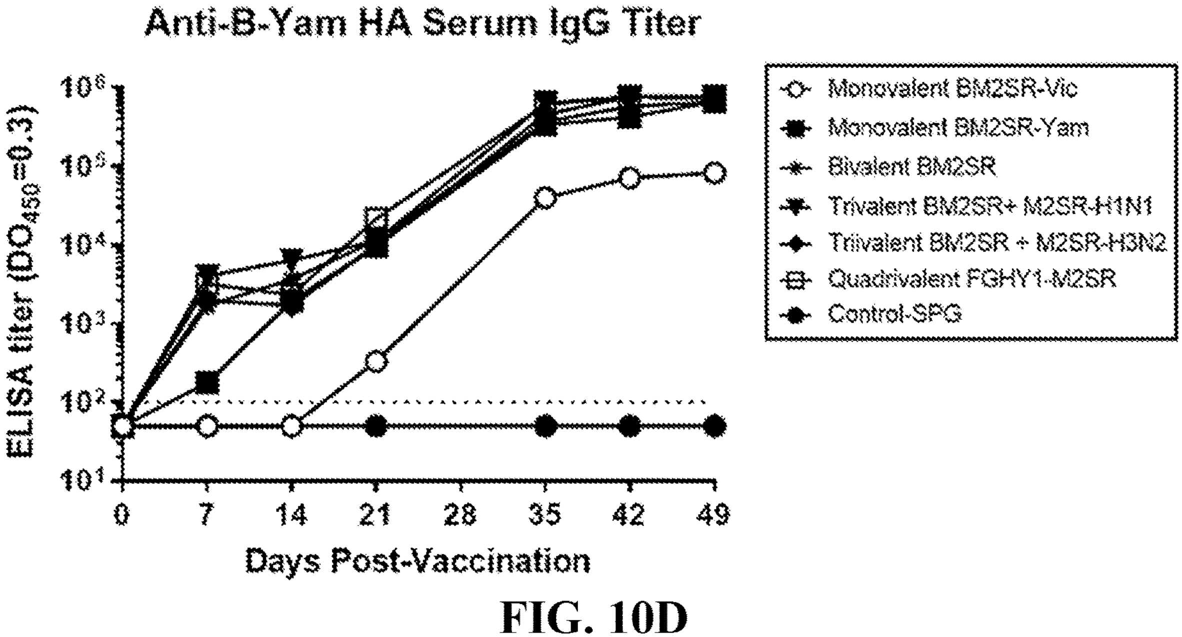

FIGS. 10A-10D are a set of graphs depicting the results of a study wherein mice (N=8) were immunized intranasally with monovalent H1N1 FGHY1-M2SR, monovalent H3N2 FGHY1-M2SR, bivalent H1N1 and H3N2 FGHY1-M2MR, monovalent BM2SR-Vic, monovalent BM2SR-Yam, bivalent BM2SR, trivalent H1N1 and H3N2 FGHY1-M2SR and BM2SR Victoria or Yamagata, or quadrivalent H1N1 and H3N2 FGHY1-M2SR and BM2SR Victoria and Yamagata vaccines or control (SPG). FIG. 10A depicts anti-H1 HA serum IgG ELISA titer data, FIG. 10B depicts anti-H3 HA data, FIG. 10C depicts anti-influenza B-Vic HA data, and FIG. 10D depicts data anti-influenza B-Yam HA.

Figure 11:
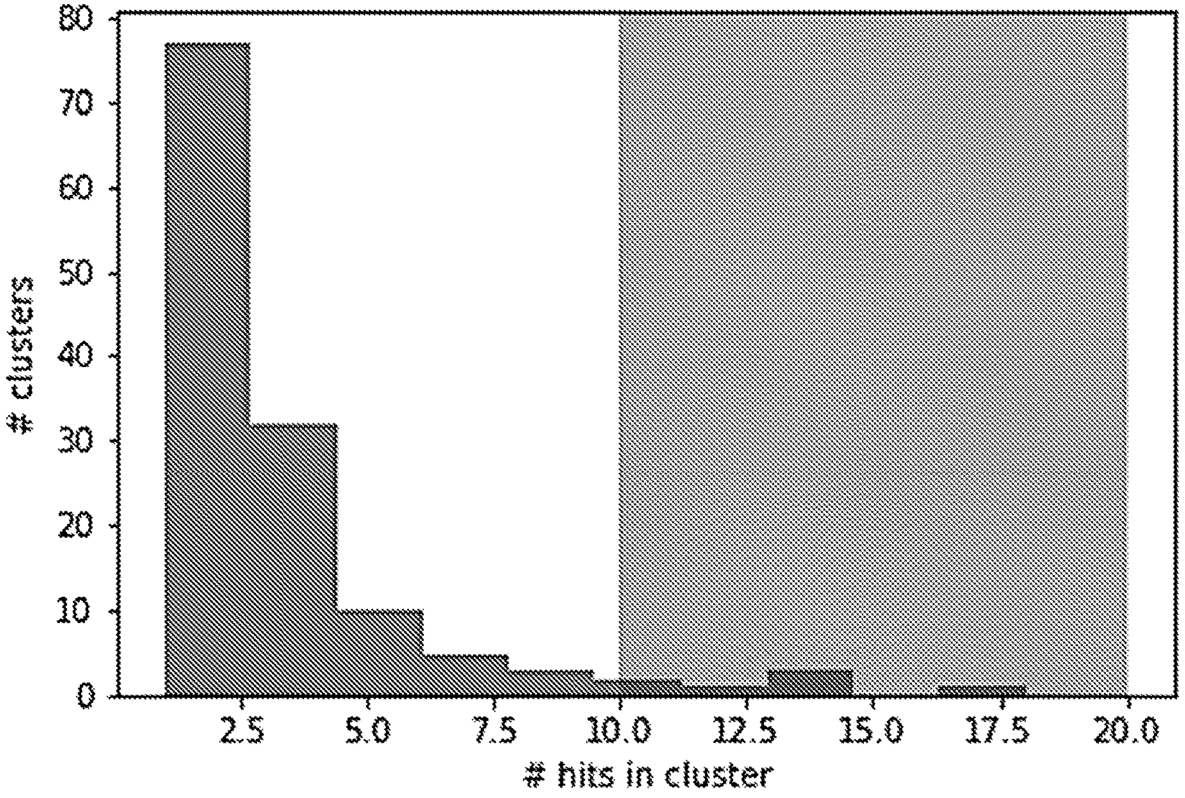

FIG. 11 depicts a histogram of total cluster count versus number of hits in the cluster. Very few clusters had more than 10 hits as indicated by the grey shading between 10.0 and 20.0 hits.

Figure 12:
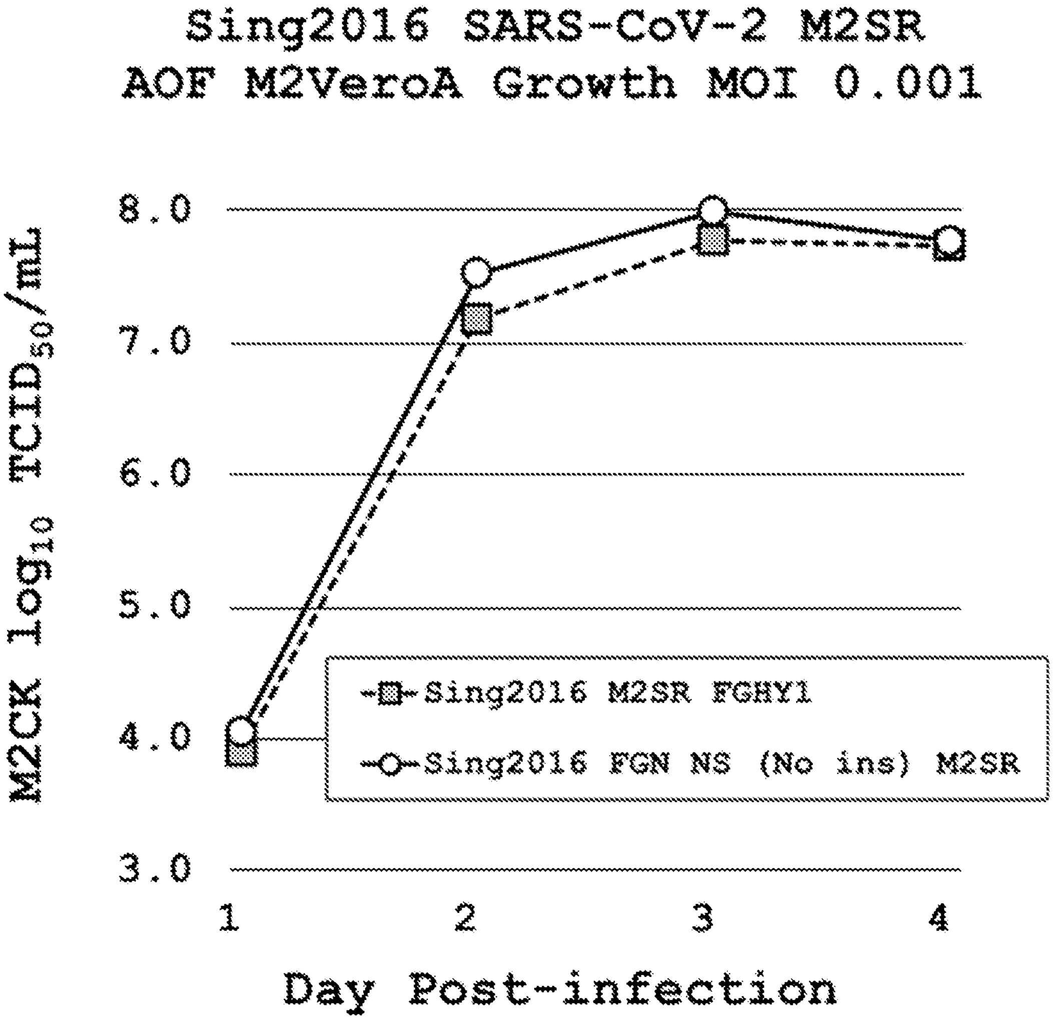

FIG. 12 depicts a graph showing virus titer $TCID_{50}$ curves for two strains indicating that virus growth is not impaired by the synthetic segment expressing NS1 and NEP as a single self-cleaving peptide.

Figure 13:
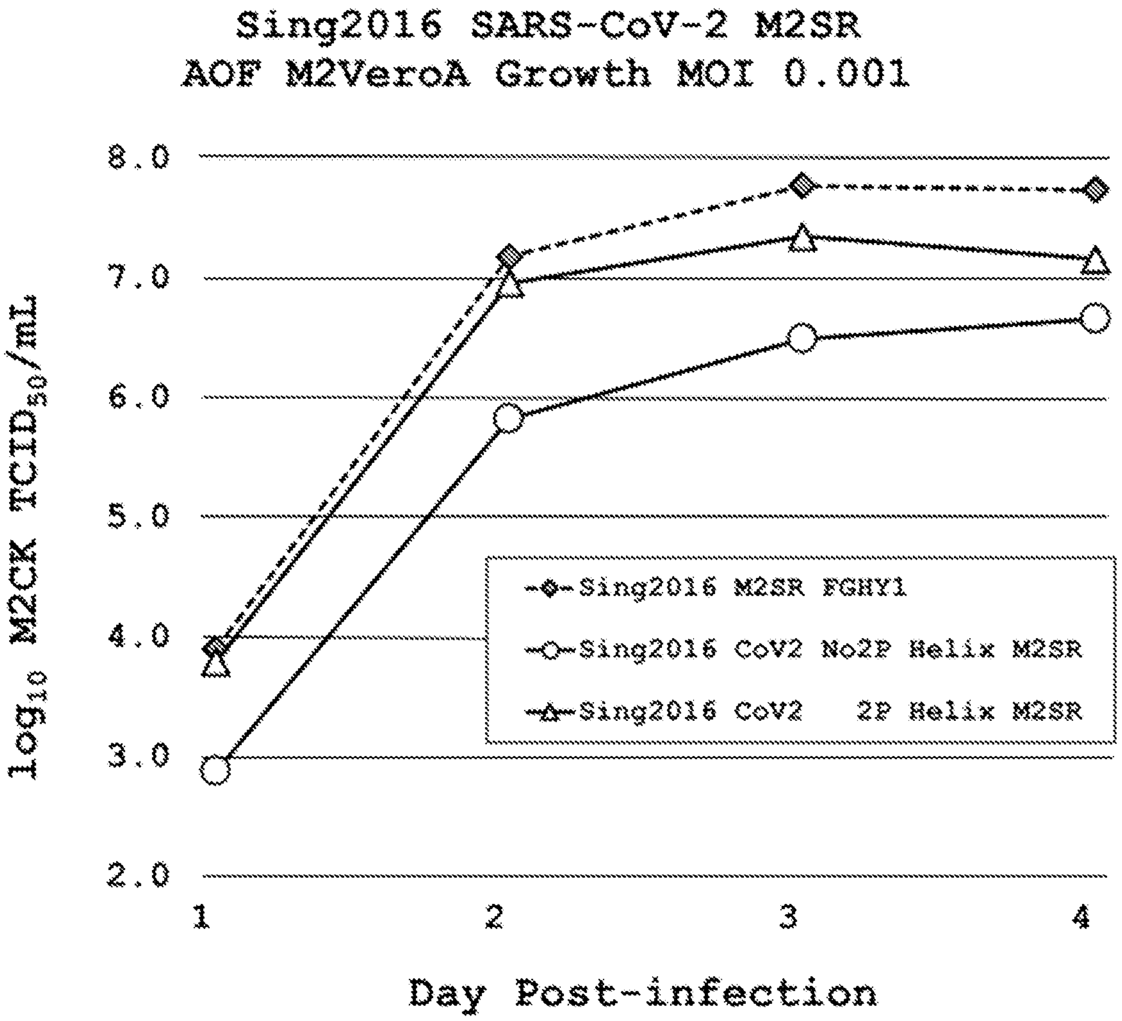

FIG. 13 depicts a graph showing a growth curve indicating that segment 8 with NS1 fusion to unmodified SARS-CoV-2 helix antigen impairs the virus growth as compared to wild-type.

Figure 14:
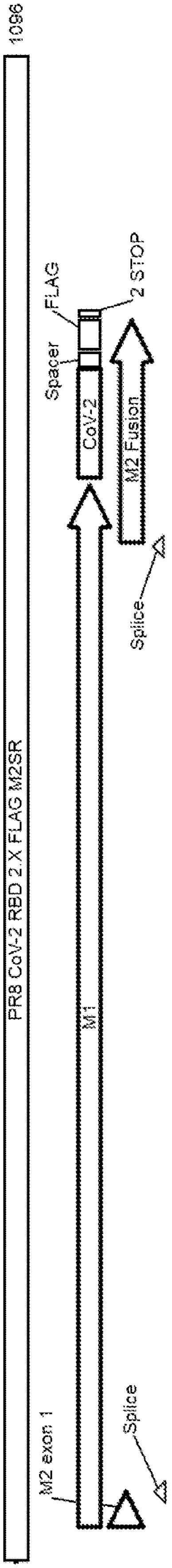

FIG. 14 is a schematic of an influenza A M segment 7 engineered to express SARS-CoV-2 Spike receptor binding domain fusion to amino terminus of M2 protein. The construct includes a full-length influenza A/PR/8/34 M1 protein, splice site, M2 RBD FLAG fusion protein comprising amino acids 1-25 M2 ORF, SARS-CoV-2 MHC I compatible RBD antigen and FLAG tag, and stop codons.

FIG. 15 is a schematic of an influenza HA gene segment design for the creation of M2SR influenza virus capable of driving expression of antigen anchored to the extracellular membrane of infected cells. For FIGS. 15-20, "UTR" refers to "Untranslated Region," "2A" refers to "2A self-cleaving peptide," "MD" refers to "Multimerization Domain," "TM" refers to "Transmembrane Domain," and "ncr" refers to "Noncoding Region."

FIG. 16 is a schematic of an influenza HA gene segment design for the creation of M2SR influenza virus capable of driving expression of antigen anchored to the extracellular membrane of infected cells.

FIG. 17 is a schematic of an influenza NS gene segment design for the creation of M2SR influenza virus capable of driving expression of antigen anchored to the extracellular membrane of infected cells.

FIG. 18 is a schematic of an influenza gene NS segment design for the creation of M2SR influenza virus capable of driving expression of antigen anchored to the extracellular membrane of infected cells.

FIG. 19 is a schematic of an influenza gene NA segment design for the creation of M2SR influenza virus capable of driving expression of antigen anchored to the extracellular membrane of infected cells.

FIG. 20 is a schematic of an influenza gene NA segment design for the creation of M2SR influenza virus capable of driving expression of antigen anchored to the extracellular membrane of infected cells.

FIG. 21 depicts the sequences of duplicated region encoding NS1 ORF and NEP Exon 1. Lower case letters indicate a mutation from A/PR/8/34. Bases 1-6 are deleted in the second copy of the NEP Exon 1 for NEP delta 2N mutant (SEQ ID NO: 110). The second copy of the duplicated region of NS segment encoding NEP Exon 1 is 63% identical to the first copy which is wild-type A/PR/8/34 NS segment cDNA sequence with a single nucleotide mutation that abolishes the splice donor site. (SEQ ID NO: 109).

FIG. 22 depicts the sequences of NS1 ORF and NEP Exon 2. Lower case letters indicate mutations from A/PR/8/34. The first copy of the duplicated region of the NS segment from NEP Exon 2 is 88% identical (SEQ ID NO: 111) to the second copy which is wild-type A/PR/8/34 NS segment cDNA sequence (SEQ ID NO: 112).

Figure 23:
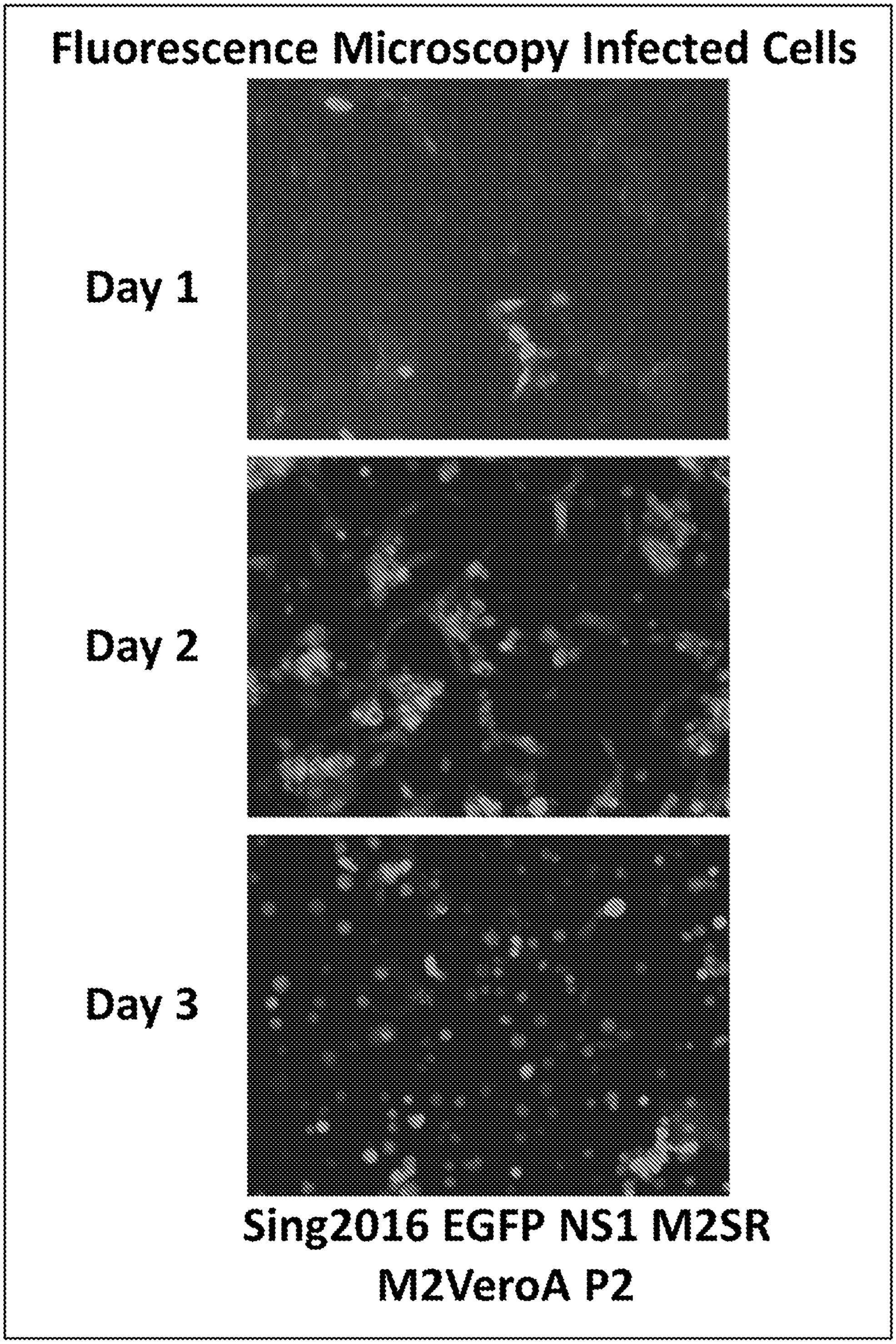

FIG. 23 depicts fluorescence micrograph images from 3 consecutive days post-inoculation of M2VeroA cells at MOI=10 by M2SR virus with engineered NS segment (SEQ ID NOs: 111, 112, and 114) expressing a tripartite polyprotein of NS1, EGFP and NEP peptides separated by T2A and P2A sites respectively (SEQ ID NO: 113).

Figure 24:
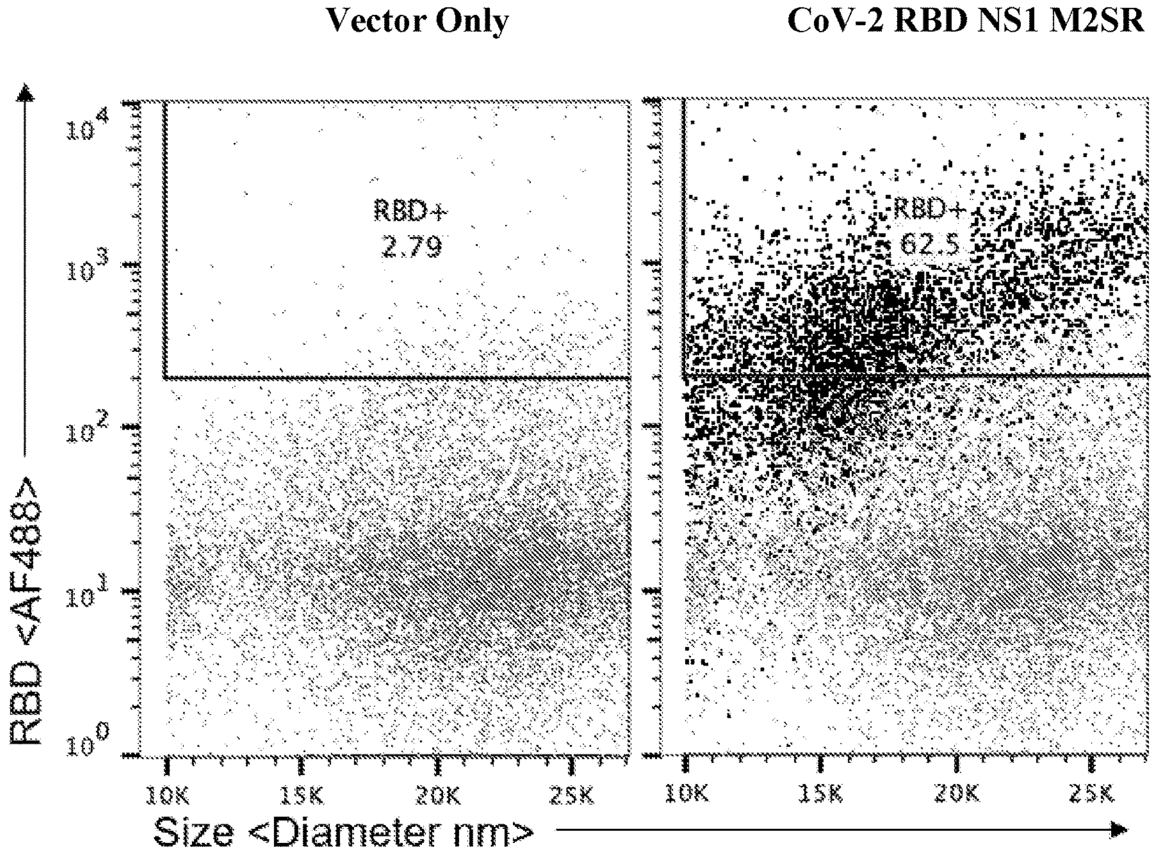

FIG. 24 depicts flow cytometric analysis of immune stained live M2VeroA cells infected by M2SR vector virus only, or by M2SR virus with NS1 segment designed to direct expression of SARS-CoV-2 S1 RBD mini-spike protein trimer at cell surface using SARS-CoV-2 Spike signal sequence of only 12 amino acids, T4 Foldon and TM from RSV (SEQ ID NO: 115).

Figure 25:
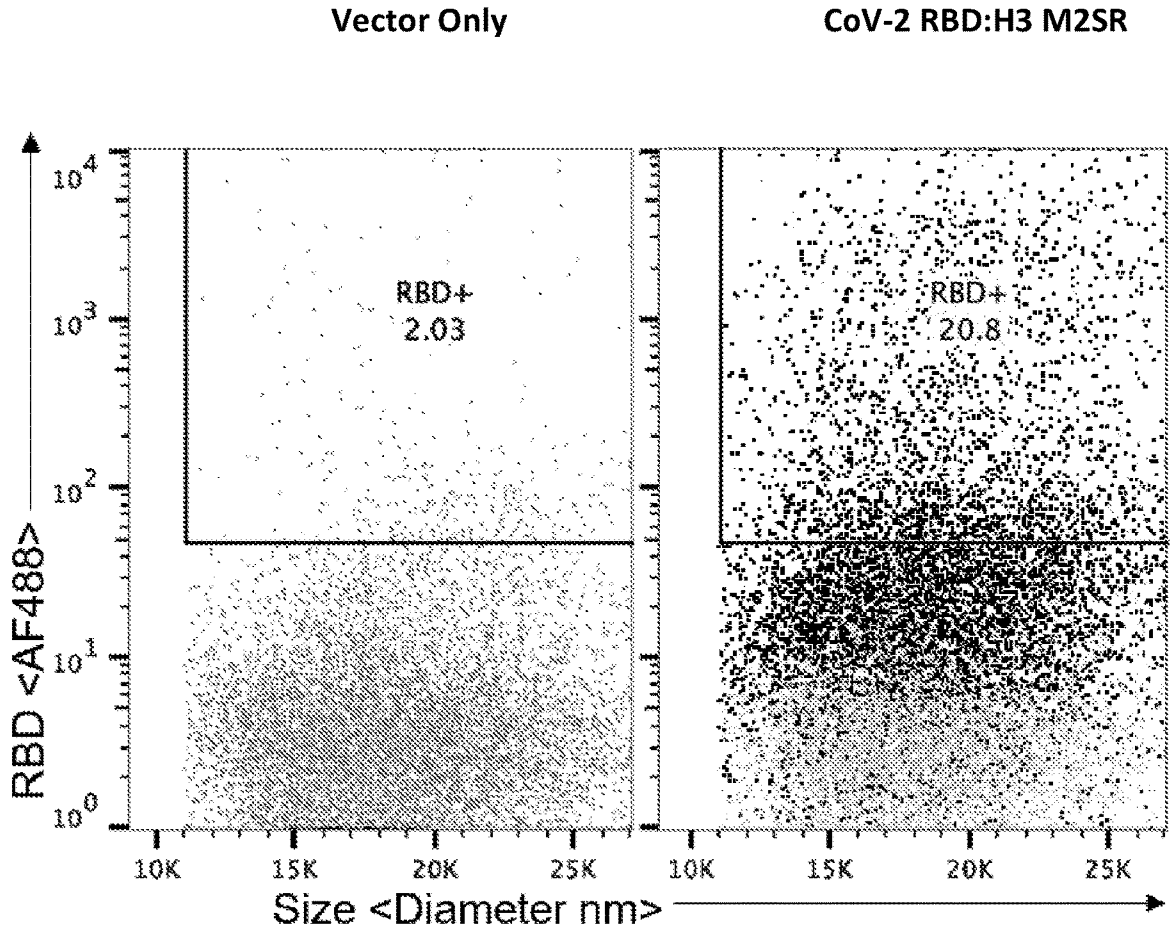

FIG. 25 depicts flow cytometric analysis of immune stained live M2VeroA cells infected by M2SR vector virus only, or by M2SR virus with HA segment with direct fusion of SARS-CoV-2 S1 RBD to amino terminus of hemagglutinin from A/Singapore/2016 H3N2 influenza virus (SEQ ID NO: 116).

Figure 26:
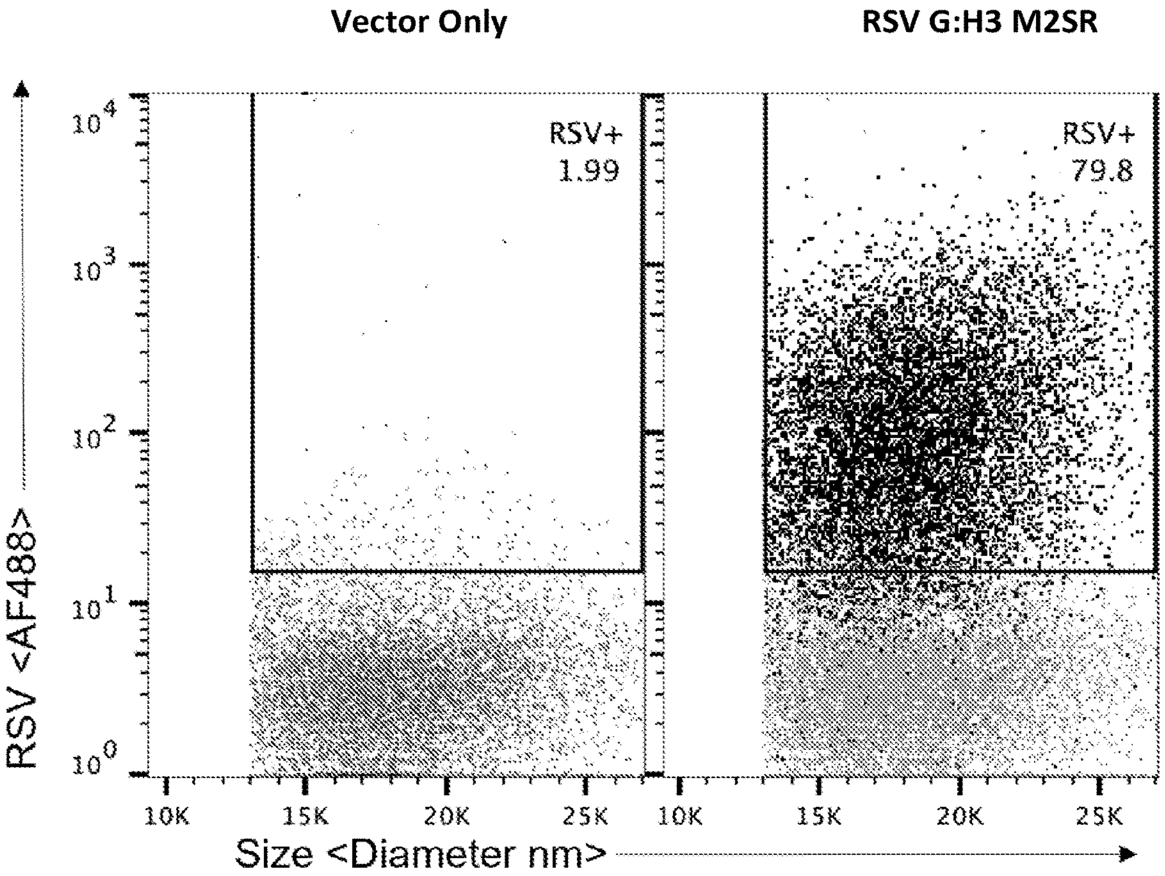

FIG. 26 depicts flow cytometric analysis of human 293T cells transfected with replicon DNA plasmid system with HA segment encoding direct fusion of respiratory syncytial virus surface glycoprotein G (RSV G) antigen to amino terminus of hemagglutinin from A/Singapore/2016 H3N2 influenza virus (SEQ ID NO: 117).

Figure 27:
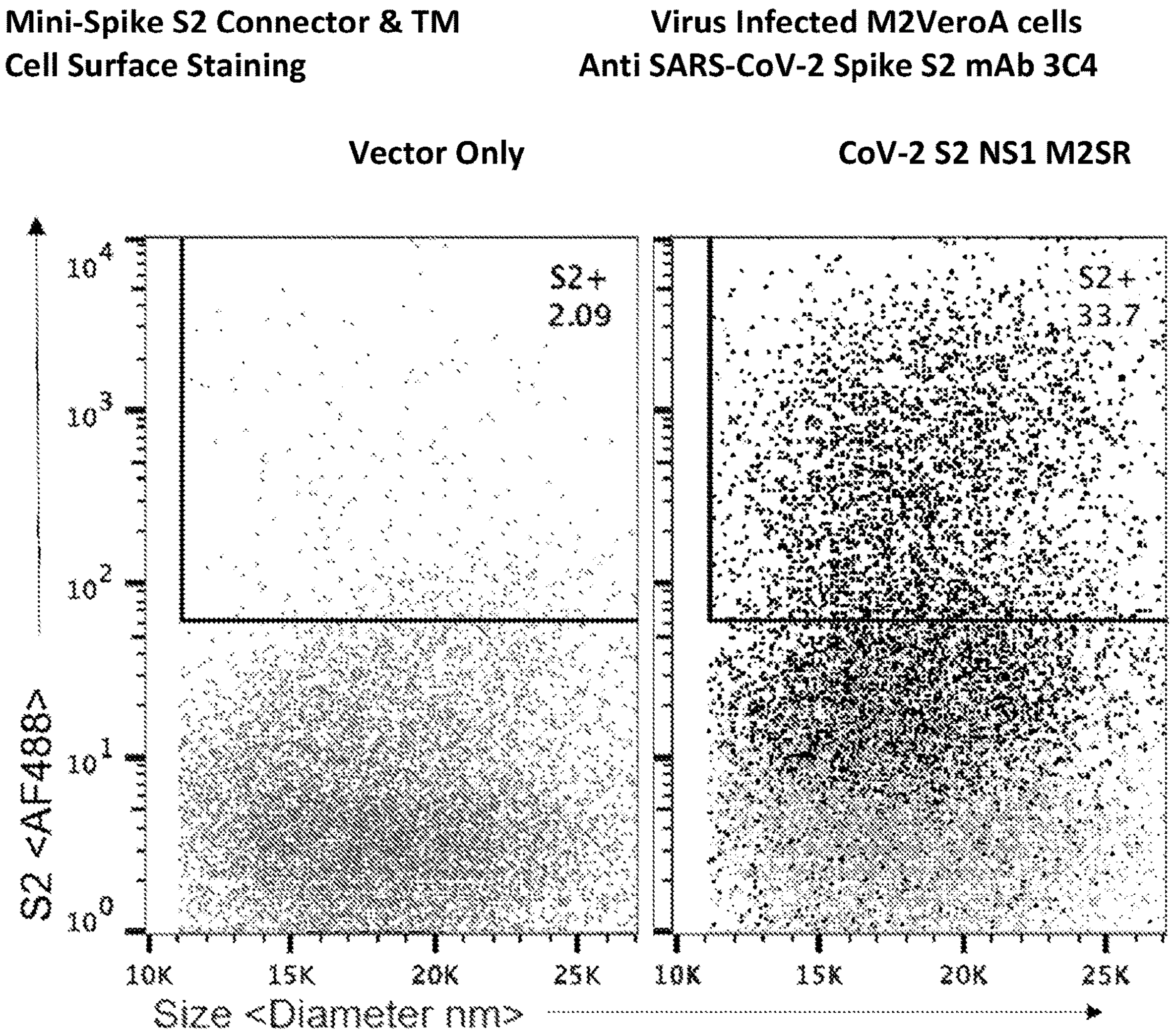

FIG. 27 depicts flow cytometric analysis of live M2VeroA cells infected by M2SR vector virus only, or by M2SR virus with NS1 segment designed to direct expression of SARS-CoV-2 mini-spike protein at cell surface using SARS-CoV-2 S protein signal sequence, and S2 helical connector domain with SARS-CoV-2 S protein TM (SEQ ID NO: 119).

Figure 28:
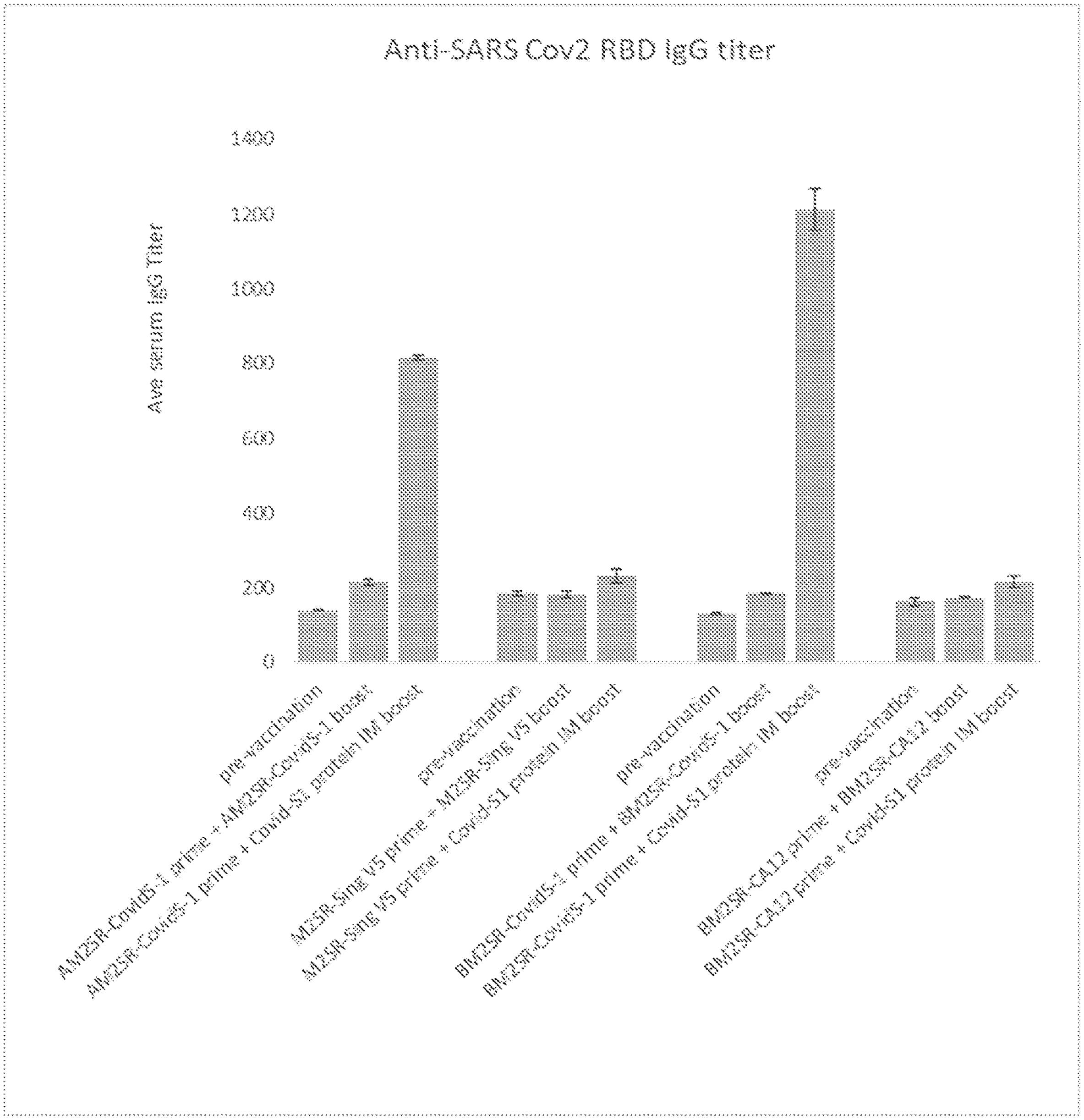

FIG. 28 is a graph of average serum anti-SARS-CoV2 RBD IgG titer of four dosing regimens pre-vaccination and post-prime and boost administration as described in Example 6.

DETAILED DESCRIPTION OF THE INVENTION

The recombinant virus of the invention may be any type of virus. As used herein, a recombinant virus (e.g., a reassortant or different virus) is a virus comprising genetic material (e.g., gene segments) derived from a genetically distinct virus (e.g., heterologous gene segments).

As used herein, the term "gene segment" refers to the nucleotide sequence that encodes a viral protein. The gene segment may be represented by the cDNA (complementary DNA) sequence encoding the viral RNA (vRNA), i.e., SEQ ID NOs: 43-47, 53, 56, 58, 60, 63-67, and 73, that encodes the viral protein.

As used herein, the term "backbone" refers to the influenza gene segments encoding the PB1, PB2, PA, NP, NS1 and/or NS2, and M proteins. The gene segments of the invention encode proteins having selected amino acids. The viral backbone is an influenza viral backbone. There are four types of influenza viruses (i.e., A, B, C, and D) categorized based on their core proteins, although seasonal epidemics are most often caused by circulating influenza A and B viruses. In one embodiment, the influenza viral backbone is an influenza A backbone. In another embodiment, the influenza viral backbone is an influenza B backbone.

As used herein, the term "selected amino acid" refers to a specific amino acid in a particular position of an amino acid sequence. In some embodiments, the selected amino acid is the result of a genetic mutation to a parent amino acid sequence. The parent amino acid sequence may be identical to the amino acid sequence comprising the selected amino acid, except for the position corresponding to the selected amino acid.

The Recombinant Virus (A) Influenza A Backbone Proteins

The PB1 (polymerase basic protein 1) gene segment of the invention may encode a protein, i.e., a PB1 protein, comprising at least one selected amino acid. In a preferred embodiment, the selected amino acids comprise a leucine at position 40 and a tryptophan at position 180. The selected amino acids of the PB1 protein further comprise at least one of an asparagine at position 464 or a serine at position 607. The PB1 gene segment may optionally comprise a cytosine to uracil promoter mutation at nucleotide position 4.

The selected amino acids may be acquired by genetic mutation to a parent PB1 sequence, e.g., a sequence identical to the PB1 amino acid sequence of the invention, except for the positions corresponding to the selected amino acids. The amino acid position 464 of the PB1 protein is located in the palm region of the influenza PB1 protein and connects RNA-dependent RNA polymerase activity domains. Generally, the aspartic acid at position 464 is highly conserved among influenza viruses isolated in eggs and in MDCK cells. Although the role of this amino acid has not been identified, the observed amino acid change to asparagine (N) at this position may affect PB1 protein conformation and may affect interaction with a host cell factor and, therefore, influenza polymerase activity in Vero cells. Moreover, influenza RNA polymerase is a heterotrimer composed of PA, PB1, and PB2 subunits. The histidine at position 465 of the PB1 protein interacts with glutamic acid at position 243 of the PA protein, and the amino acid change at position 464 of PB1 may alter interactions between PB1 and PA. The function of the amino acid at position 607 of the PB1 protein is also unknown; however, this amino acid is located between the RNA-dependent RNA polymerase region and the PB2 binding region, suggesting that it may alter interactions between PB1 and PB2, thereby affecting polymerase activity in Vero cells.

The PB2 (polymerase basic protein 2) gene segment of the invention may also encode a protein, i.e., a PB2 protein, comprising at least one selected amino acid. In a preferred embodiment, the selected amino acids comprise a valine at position 504 and optionally an isoleucine at position 467 and a valine at position 529. The PB2 gene segment may optionally comprise a cytosine to uracil promoter mutation at nucleotide position 4. The amino acids at position 467 and 529 of the PB2 protein are in the PB2-C portion. Specifically, the amino acid at portion 467 is located in the cap-binding region of the PB2 protein, and the amino acid at position 529 is located in the cap-627 linker domain. In some influenza viruses, the PB2 protein binds the cap structure of host capped RNA and utilizes the cap from the host RNA in order to make influenza mRNAs. This process is known as "cap-snatching." Moreover, the amino acid at position 627 of PB2 is known to be a key determinant in host range and viral pathogenicity. Therefore, amino acid changes proximate to a cap-binding region may affect the efficiency of viral mRNA synthesis.

The PA (polymerase acidic protein) gene segment of the invention may also encode a protein, i.e., a PA protein, comprising at least one selected amino acid. In a preferred embodiment, the selected amino acids comprise a lysine at position 401. The PA gene segment may optionally comprise a cytosine to uracil promoter mutation at nucleotide position 4.

The NP (nucleoprotein) gene segment of the invention may also encode a protein, i.e., an NP protein, comprising at least one selected amino acid. In a preferred embodiment, the selected amino acids comprise a leucine at position 116 and at least one of a lysine at position 294 or an arginine at position 311. The amino acid positions 294 and 311 of the NP protein are located in the body of the NP protein, such that they neither serve as nuclear localization signals nor nuclear export signals.

The NS (non-structural) gene segment of the invention may also encode a protein, i.e., an NS1 and/or NS2 protein, comprising at least one selected amino acid. In a preferred embodiment, the selected amino acids comprise a proline at position 30 (NS1 protein) and a lysine at position 118 (NS1 protein).

In one embodiment of the invention, the influenza viral backbone comprises a PB1 gene segment encoding a protein, i.e., a PB1 protein, having selected amino acids at positions 40, 180, and 464, i.e., a leucine at position 40, a tryptophan at position 180, and an asparagine at position 464. The PB1 gene segment may have a nucleotide sequence represented by SEQ ID NO: 44. The PB1 gene segment may encode a protein, i.e., a PB1 protein, having an amino acid sequence of SEQ ID NO: 49. In another aspect of the embodiment, the influenza viral backbone may comprise a PB2 gene segment encoding a protein, i.e., a PB2 protein, having a selected amino acid at position 504, i.e., a valine at position 504. The PB2 gene segment may have a nucleotide sequence represented by SEQ ID NO: 56. The PB2 gene segment may encode a protein, i.e., a PB2 protein, having an amino acid sequence of SEQ ID NO: 57. The NP gene segment of the embodiment may encode a protein, i.e., an NP protein, having selected amino acids at positions 116 and 294, i.e., a leucine at position 116 and a lysine at position 294. The NP gene segment may have a nucleotide sequence represented by SEQ ID NO: 43. The NP gene segment may encode a protein, i.e., an NP protein, having an amino acid sequence of SEQ ID NO: 48. The PA and NS gene segments of the embodiment may also encode proteins, i.e., a PA protein and NS1 and/or NS2 protein, comprising selected amino acids at position 401 (PA protein), position 30 (NS1 protein), and position 118 (NS1 protein), i.e., a lysine at position 401 (PA protein), a proline at position 30 (NS1 protein), and a lysine at position 118 (NS1 protein). The PA gene segment may have a nucleotide sequence represented by SEQ ID NO: 58. The PA gene segment may encode a protein, i.e., a PA protein, having an amino acid sequence of SEQ ID NO: 59. The NS gene segment may have a nucleotide sequence represented by SEQ ID NO: 60. The NS gene segment may encode a protein, i.e., an NS1 protein, having an amino acid sequence of SEQ ID NO: 61. The NS gene segment may encode a protein, i.e., an NS2 protein, having an amino acid sequence of SEQ ID NO: 62. The PB1, PB2, and PA gene segments of the embodiment may also comprise a cytosine to uracil promoter mutation at nucleotide position 4.

In another embodiment of the invention, the influenza viral backbone comprises a PB1 gene segment encoding a protein, i.e., a PB1 protein, having selected amino acids at positions 40, 180, and 607, i.e., a leucine at position 40, a tryptophan at position 180, and a serine at position 607. The PB1 gene segment may have a nucleotide sequence represented by SEQ ID NO: 46. The PB1 gene segment may encode a protein, i.e., a PB1 protein, having an amino acid sequence of SEQ ID NO: 51. In another aspect of the embodiment, the influenza viral backbone may comprise a PB2 gene segment encoding a protein, i.e., PB2 protein, having selected amino acids at positions 504, 467, and 529, i.e., a valine at position 504, an isoleucine at position 467, and a valine at position 529. The PB2 gene segment may have a nucleotide sequence represented by SEQ ID NO: 47.

The PB2 gene segment may encode a protein, i.e., a PB2 protein, having an amino acid sequence of SEQ ID NO: 52. The NP gene segment of the embodiment may encode a protein, i.e., an NP protein, having selected amino acids at positions 116 and 311, i.e., a leucine at position 116 and an arginine at position 311. The NP gene segment may have a nucleotide sequence represented by SEQ ID NO: 45. The NP gene segment may encode a protein, i.e., an NP protein, having an amino acid sequence of SEQ ID NO: 50. The PA and NS gene segments may also encode proteins, i.e., a PA protein and NS1 and/or NS2 protein, comprising selected amino acids at position 401 (PA protein), position 30 (NS1 protein), and position 118 (NS1 protein), i.e., a lysine at position 401 (PA protein), a proline at position 30 (NS1 protein), and a lysine at position 118 (NS1 protein). The PA gene segment may have a nucleotide sequence represented by SEQ ID NO: 58. The PA gene segment may encode a protein, i.e., a PA protein, having an amino acid sequence of SEQ ID NO: 59. The NS gene segment may have a nucleotide sequence represented by SEQ ID NO: 60. The NS gene segment may encode a protein, i.e., an NS1 protein, having an amino acid sequence of SEQ ID NO: 61. The NS gene segment may encode a protein, i.e., an NS2 protein, having an amino acid sequence of SEQ ID NO: 62. The PB1, PB2, and PA gene segments of the embodiment may also comprise a cytosine to uracil promoter mutation at nucleotide position 4.

The selected amino acids of the embodiments, particularly in most proteins of the backbone, confer enhanced growth properties onto the influenza viral backbone, as compared to an influenza viral backbone that is the same except without the selected amino acids, under the same conditions. For example, the influenza viral backbone of the invention exhibits enhanced growth in Vero cells.

The influenza viral backbone of the invention may also comprise an M (matrix protein) gene segment. In one embodiment of the invention, the M gene segment may be a mutant gene segment from influenza A, such that the virus lacks expression of functional M2 protein. Such a virus is herein referred to as an "M2SR" virus. As used herein, "M2SR" and "AM2SR" are interchangeable. The M2SR virus is a single replication influenza virus. The M gene segment of the M2SR virus may be represented by SEQ ID NO: 53. The M gene segment may encode a protein, e.g., a truncated M2 protein, having the amino acid sequence of SEQ ID NO: 54. The M2SR virus may be propagated in Vero cells that stably express the wild-type M2 protein (i.e., M2VeroA cells) to allow for multicycle replication. High yield in Vero cells is not dependent on mutation in the M gene segment. Therefore, the influenza viral backbone of the invention may comprise an M gene segment that encodes a functional M2 protein (SEQ ID NO: 1).

(B) Influenza B Backbone Proteins

In one embodiment of the invention, the recombinant virus comprises an influenza viral backbone comprising PA, NP, and NS gene segments, wherein (a) the PA gene segment comprises a thymine at nucleotide position 2272; (b) the NP gene segment encodes a NP protein having an amino acid sequence comprising selected amino acids, wherein the selected amino acids comprise a serine at position 40, an asparagine or glycine at position 161, a threonine at position 204, and optionally a valine at position 93; and (c) the NS gene segment comprises a guanine at nucleotide position 39, and the NS gene segment encodes an NS protein having an amino acid sequence comprising selected amino acids, wherein the selected amino acids comprise a glutamine at position 176.

The PB1 (polymerase basic protein 1) gene segment of the invention may encode a protein, i.e., a PB1 protein, comprising at least one selected amino acid. The selected amino acids may be acquired by genetic mutation to a parent PB1 sequence, e.g., a sequence identical to the PB1 amino acid sequence of the invention, except for the positions corresponding to the selected amino acids. The PB2 (polymerase basic protein 2) gene segment of the invention may also encode a protein, i.e., a PB2 protein, comprising at least one selected amino acid.

The PA (polymerase acidic protein) gene segment of the invention may also encode a protein, i.e., a PA protein, comprising at least one selected amino acid. In a preferred embodiment, the gene segment comprises a thymine at nucleotide position 2272.

The NP (nucleoprotein) gene segment of the invention may also encode a protein, i.e., an NP protein, comprising at least one selected amino acid. In a preferred embodiment, the NP segment comprises a thymine at position 177, an adenine at position 540 and a thymine at position 670 and the NP gene segment encodes a protein having selected amino acids comprise a serine at position 40, an asparagine or glycine at position 161, a threonine at position 204, and optionally a valine at position 93.

The NS (non-structural) gene segment of the invention may also encode a protein, i.e., an NS1 and/or NS2 protein, comprising at least one selected amino acid. In a preferred embodiment, the NS segment comprises a guanine at nucleotide position 39 and a cytosine at position 570 and the NS gene segment encodes an NS protein having selected amino acids comprising a glutamine at position 176 (NS1 protein).

In one embodiment of the invention, the influenza virus comprises a PB1 gene segment encoding a protein, i.e., a PB1 protein, having selected amino acids. The PB1 gene segment may have a nucleotide sequence represented by SEQ ID NO: 63. The PB1 gene segment may encode a protein, i.e., a PB1 protein, having an amino acid sequence of SEQ ID NO: 68. In another aspect of the embodiment, the influenza virus may comprise a PB2 gene segment encoding a protein, i.e., a PB2 protein, having selected amino acids. The PB2 gene segment may have a nucleotide sequence represented by SEQ ID NO: 64. The PB2 gene segment may encode a protein, i.e., a PB2 protein, having an amino acid sequence of SEQ ID NO: 69. In another aspect of the embodiment, the influenza virus may comprise a NP gene segment encoding a protein, i.e., a NP protein, having selected amino acids at positions 40, 161, and 204, i.e., a serine at position 40, an asparagine or glycine at position 161, a threonine at position 204, and optionally a valine at position 93. The NP gene segment may have a nucleotide sequence represented by SEQ ID NO: 66. The NP gene segment may encode a protein, i.e., an NP protein, having an amino acid sequence of SEQ ID NO: 71. In another aspect of the embodiment, the influenza virus may comprise a NS gene segment encoding a protein, i.e., a NS1 and/or NS2 protein, having selected amino acids at position 176, i.e., a glutamine at position 176. The NS gene segment may comprise a guanine at nucleotide position 39 and cytosine at position 570. The NS gene segment may have a nucleotide sequence represented by SEQ ID NO: 67. The NS gene segment may encode a protein, i.e., an NS1 and/or NS2 protein, having an amino acid sequence of SEQ ID NO: 72. In another aspect of the embodiment, the influenza virus may comprise a PA gene segment encoding a protein, i.e., a PA protein. The PA gene segment may have a nucleotide sequence represented by SEQ ID NO: 65. The PA gene segment may encode a protein, i.e., a PA protein, having an amino acid sequence of SEQ ID NO: 70.

The selected amino acids of the embodiments, particularly in most proteins of the backbone, confer enhanced growth properties onto the influenza virus, as compared to an influenza virus that is the same except without the selected amino acids, under the same conditions. For example, the influenza virus of the invention exhibits enhanced growth in Vero cells.

The influenza virus of the invention may also comprise an M (matrix protein) gene segment. In one embodiment of the invention, the M gene segment may be a mutant gene segment from influenza B, such that the virus lacks expression of functional BM2 protein. Such a virus is herein referred to as a "BM2SR" virus. The BM2SR virus is a single replication influenza virus. The M gene segment of the BM2SR virus may be represented by SEQ ID NO: 73. The M gene segment may encode a protein, e.g., a truncated BM2 protein, having the amino acid sequence of SEQ ID NO: 78. The BM2SR virus may be propagated in Vero cells that stably express the BM2 protein (i.e., BM2VeroA cells) to allow for multicycle replication. High yield in Vero cells is not dependent on mutation in the M gene segment. Therefore, the influenza virus of the invention may comprise an M gene segment that encodes a functional BM2 protein (SEQ ID NO: 2).

(C) Influenza A Surface Proteins

In a further embodiment of the invention, the influenza viral backbone comprises an NA (neuraminidase) and HA (hemagglutinin) gene segment. In one embodiment of the invention, the HA gene segment may encode an HA protein having an amino acid sequence comprising at least one selected amino acid (e.g., an amino acid mutation) in the HA1 subunit of the protein and/or at least one selected amino acid (e.g., amino acid mutation) in the HA2 subunit of the protein. For example, the at least one amino acid mutation in the HA2 subunit may be an asparagine at position 107. Such mutations may also contribute to enhanced growth of the virus during production.

In one embodiment of the invention, the PB1, PB2, PA, NP, and NS gene segments are derived from a single influenza strain. The HA gene segment may be derived from an influenza strain different from the single influenza strain from which the PB1, PB2, PA, NP, and NS gene segments are derived. Likewise, the NA gene segment may be derived from an influenza strain different from the single influenza strain from which the PB1, PB2, PA, NP, and NS gene segments are derived. Accordingly, the recombinant virus of the invention may be a pandemic virus (e.g., H5N1 and H7N9) or a seasonal virus (e.g., H1N1, H3N2, and influenza B).

(D) Influenza B Surface Proteins

In a further embodiment of the invention, the recombinant virus comprises an influenza viral backbone further comprising an NA (neuraminidase) and HA (hemagglutinin) gene segment. In one embodiment of the invention, the HA gene segment may encode a HA protein having an amino acid sequence comprising at least one selected amino acid (e.g., an amino acid mutation) in the HA1 subunit of the protein and/or at least one selected amino acid (e.g., amino acid mutation) in the HA2 subunit of the protein. For example, the at least one amino acid mutation in the HA2 subunit may be a glutamic acid at position 61. In another embodiment, the at least one amino acid mutation in the HA2 subunit may be glutamic acid at position 112. The amino acid mutations may be present in any of the subtypes or lineages of influenza B virus (i.e., Victoria or Yamagata).

In a preferred embodiment, the amino acid mutation in the HA2 subunit may be glutamic acid at position 61 in the Victoria lineage of influenza B virus. In another preferred embodiment, the amino acid mutation in the HA2 subunit may be glutamic acid at position 112 in the Yamagata lineage of the influenza B virus. Such mutations may also contribute to enhanced growth of the virus during production.

In one embodiment of the invention, the PB1, PB2, PA, NP, and NS gene segments are derived from a single influenza strain. The HA gene segment may be derived from an influenza strain different from the single influenza strain from which the PB1, PB2, PA, NP, and NS gene segments are derived. Likewise, the NA gene segment may be derived from an influenza strain different from the single influenza strain from which the PB1, PB2, PA, NP, and NS gene segments are derived. Accordingly, the influenza virus of the invention may be a seasonal influenza virus (e.g., influenza B).

(E) Antigens

In one embodiment, the recombinant virus comprises an influenza viral backbone comprising PB1, PB2, PA, NP, M, NS, HA, and NA gene segments, at least one of the PB2, PB2, PA, NP, M, NS, HA, and NA gene segments comprises a nucleotide sequence that encodes one or more antigens. As used herein, the term "antigen" refers to an antigen heterologous with respect to the HA gene segment. The antigen can be viral (including influenza), bacterial, fungal, or protozoal. For example, a viral antigen or epitope sequence that is inserted into a gene segment (e.g., PB1, PB2, PA, NP, M, NS, HA, or NA gene segments) would be an antigen as to the virus. In one embodiment, the antigen is an immunogenic fragment of SARS-CoV-2 spike glycoprotein (e.g., S1 protein). In another embodiment, the antigen is an influenza gene segment or fragment thereof (i.e., PB1, PB2, PA, NP, M, NS, HA, or NA gene segments or fragments thereof) that is heterologous to the HA gene segment in the influenza viral backbone. In another embodiment the antigen is respiratory syncytial virus (RSV) or a fragment thereof. In another embodiment, the antigen is parainfluenza virus (PIV) or a fragment thereof. In some embodiments, the one or more antigens are expressed from within a viral gene segment.

In one embodiment of the invention, at least one gene segment that comprises a nucleotide sequence that encodes one or more antigens further comprises a nucleotide sequence that encodes at least one flexible linker protein, at least one cleavable cleavage sequence, and/or at least one FLAG protein. Such a gene segment may encode at least two flexible linker proteins, at least two cleavable cleavage sequences, and/or at least two FLAG proteins.

In an embodiment of the invention, the cleavable cleavage sequence comprises a "self cleaving" sequence. In an embodiment, the "self cleaving" sequence is a "self cleaving" 2A peptide. In an embodiment, the "self cleaving" sequence is a "self cleaving" 2A peptide. "Self cleaving" 2A peptides are described, for example, in Liu et al., *Sci. Rep.,* 7(1): 2193 (2017), and Szymczak et al., *Nature Biotechnol.,* 22(5): 589-594 (2004). The 2A peptides are viral oligopeptides that mediate cleavage of polypeptides during translation in eukaryotic cells. The designation "2A" refers to a specific region of the viral genome. Without being bound to a particular theory or mechanism, it is believed that the mechanism of 2A-mediated "self cleavage" is ribosome skipping of the formation of a glycyl-prolyl peptide bond at the C-terminus of the 2A peptide. Different 2A peptides may comprise, at the C-terminus, the consensus amino acid sequence of GDVEXNPGP (SEQ ID NO: 19), wherein X of SEQ ID NO: 19 is any naturally occurring amino acid residue. In an embodiment of the invention, the cleavable ribosomal skip sequence is a porcine teschovirus-1 2A (P2A) amino acid sequence, equine rhinitis A virus (E2A) amino acid sequence, thosea asigna virus 2A (T2A) amino acid sequence, or foot-and-mouth disease virus (F2A) amino acid sequence. In an embodiment of the invention, the ribosomal skip sequence is a 2A peptide amino acid sequence comprising, consisting, or consisting essentially of, the amino acid sequence of P2A.

In an embodiment of the invention, the flexible linker protein is 1 to 20 amino acid residues selected, independently, from the group consisting of glycine and serine. In some embodiments, the flexible linker protein is defined as $(Xaa1)_r$, wherein each Xaa1 is selected independently from glycine and serine and r is an integer from 1 to 20. An example of such linker includes, but is not limited to GSG (SEQ ID NO: 75), GGGGSGGGGSGGGGS (SEQ ID NO: 76), and $(G4S)_3$. In one embodiment of the invention the at least one gene segment that comprises an amino acid sequence that encodes an antigen further comprises at least one flexible linker proteins. In another embodiment, such a gene segment further comprises at least two flexible linker proteins.

In a preferred embodiment, the antigen is an immunogenic fragment of SARS-CoV-2 spike glycoprotein (e.g., S1 protein). In one embodiment, the M gene segment encodes a nucleotide sequence encoding at least one immunogenic fragment of SARS-CoV-2 spike glycoprotein. The M gene segment may encode a mutated M2 or BM2 protein. The M gene segment may further encode at least one flexible linker protein and at least one FLAG protein. In one embodiment, the M gene segment encodes a fusion protein comprising a mutated M2 protein, a flexible linker protein and a FLAG epitope tag protein. For example, the M gene segment may have a nucleotide sequence represented by any one of SEQ ID NOs: 79 and 81-84. The M gene segment may encode a protein comprising any one of SEQ ID NOs: 1-14 and 92-96.

In another embodiment, the NS gene segment encodes a nucleotide sequence encoding at least one immunogenic fragment of SARS-CoV-2 spike glycoprotein. The NS gene segment may encode a NS1 protein and NS2 (i.e., NEP) protein or fragment thereof. The NS gene segment may also encode at least one flexible linker protein or fragment thereof. The NS gene segment may also encode at least one cleavable cleavage sequence. The NS gene segment may have a nucleotide sequence represented by any one of SEQ ID NOs: 80 and 85-91. The NS gene segment may encode a protein comprising SEQ ID NOs: 97-104.

In one embodiment of the invention, the cleavable cleavage sequence is a P2A peptide sequence. In such an embodiment, the P2A peptide sequence is bound to the C-terminus of the NS1 protein on one end and the antigen on the other. In such an embodiment, the antigen can be bound to the NEP Open Reading Frame (ORF). In another embodiment of the invention, the P2A peptide sequence is bound to the C-terminus of the NS1 protein on one end and a first flexible linker protein on the other end. In such an embodiment, a first flexible linker protein can be bound to the antigen, which is attached to the NEP ORF. In another embodiment, a second cleavable cleavage sequence is present. In one embodiment, the second cleavable cleavage sequence is a P2A or T2A peptide sequence. The optional second cleavable cleavage sequence may be bound to the antigen on one end and the NEP ORF on the other end. In another embodiment, the second cleavable cleavage sequence may be bound to a flexible linker protein, which is then bound to either the antigen or the NEP ORF.

In one embodiment at least one (i.e., PB2, PB2, PA, NP, M, NS, HA, or NA) gene segment will encode a nucleotide sequence that encodes one or more antigens. In some embodiments, at least two (i.e., PB1 and PB2, PB1 and PA, PB1 and NP, PB1 and M, PB1 and NS, PB1 and HA, and PB1 and NA, PB2 and PA, PB2 and NP, PB2 and M, PB2 and NS, PB2 and HA, PB2 and NA, PA and NP, PA and M, PA and NS, PA and HA, PA and NA, NP and M, NP and NS, NP and HA, NP and NA, M and NS, M and HA, M and NA, NS and HA, NS and NA, or HA and NA gene segments) of the eight influenza viral backbone segments will encode a nucleotide sequence that encodes one or more antigens, such as an immunogenic fragment of SARS-CoV-2 spike glycoprotein (e.g., S1 protein)).

In some embodiments, the gene segment that comprises at least one nucleotide sequence that encodes one or more antigens further comprises a downstream duplication, wherein the downstream duplication comprises at least one silent nucleotide mutation. In one embodiment, the gene segment that comprises at least one nucleotide sequence that encodes one or more antigens further comprises a downstream direct tandem duplication, wherein the downstream duplication comprises at least one silent nucleotide mutation. A downstream duplication refers to a nucleotide sequence in which a portion of the nucleotide sequence is repeated one or more times in the same orientation. The repeat nucleotide sequences can be lined up one directly after another, or they can contain optional nucleotide sequences between each of the repeat nucleotide sequences. In addition, the number of duplicated bases is not limited.

In some embodiments, a downstream duplication of a nucleotide sequence of the gene segment occurs during insertion of the nucleotide sequence encoding an antigen. In some embodiments, the downstream duplication can reduce the stability of the nucleotide sequence and the encoded amino acid sequences and proteins. To improve stability, at least one silent mutation (i.e., a mutation that does not affect the amino acid sequence encoded by the nucleotide sequence) is introduced to reduce the homology between a first nucleotide sequence and the second downstream duplicated nucleotide sequence. For example, in a preferred embodiment, the NS gene segment comprises a nucleotide sequence encoding an antigen. During the insertion of the nucleotide sequence encoding an antigen, a portion of the nucleotide sequence is duplicated, creating a downstream duplication. The first copy of the nucleotide sequence is part of the packaging sequence, and the second copy can interfere with packaging. To prevent interference, silent mutations are added to the downstream duplication to reduce homology with the first copy. In one embodiment, the downstream duplication has at least one (i.e., at least one, at least two at least three, at least four, at least five, at least six, at least seven, at least eight, at least nine, or at least ten) silent mutation(s).

The recombinant virus may have one or more (i.e., at least two, at least three, at least four, at least five, at least six, at least seven, or at least eight) gene segments that comprise at least one nucleotide sequence that encodes one or more antigens and further comprise a downstream duplication, wherein the downstream duplication comprises at least one silent nucleotide mutation. For example, in one embodiment, such one or more gene segments can be the PB1, PB2, PA, NP, NS, M, HA, or NA gene segments. In another embodiment, such one or more gene segments can be the PB1 and PB2, PB2 and PA, PB1 and NP, PB1 and NS, PB1 and M, PB1 and HA, PB1 and NA, PB2 and PA, PB2 and NP, PB2 and NS, PB2 and M, PB2 and HA, PB2 and NA, PA and NP, PA and NS, PA and M, PA and HA, PA and NA, NP and NS, NP and M, NP and HA, NP and NA, NS and M, NS and HA, NS and NA, M and HA, M and NA, or HA and NA gene segments.

(F) Properties of the Influenza Viral Backbone

The backbone of the inventive recombinant virus confers high growth properties onto influenza viruses, particularly in Vero cells, regardless of the type of influenza virus (e.g., influenza A or B, seasonal or pandemic influenza viruses). The inventive influenza virus exhibits high yields even in manufacturing processes using low multiplicity of infection (MOI) (e.g., 0.001). MOI refers to the average number of agent (e.g., virus) per infection target (e.g., cell). A lower MOI is used when multiple cycles of infection are required (e.g., virus vaccine production). Current Good Manufacturing Practice regulations are enforced by the US FDA and generally necessitate use of the lowest MOI that still produces high yields of the virus. This is because master seed stocks are costly, and toxicity resulting from noninfectious particles and excess cellular proteins can decrease virus production.

In a further embodiment of the invention, the influenza virus is genetically stable, such that the selected amino acids of the backbone proteins, particularly the PB1, PB2, PA, NP, and NS1 proteins, are highly conserved, even when propagated at low MOI. For example, in one embodiment of the invention, the selected amino acids are conserved in at least one of the PB1, PB2, and NP proteins after at least one, at least two, at least three, at least four, at least five, at least six, at least seven, at least eight, at least nine, at least ten, or more than ten serial passages in a Vero cell line. In one embodiment, the Vero cell line may comprise Vero cells that stably express the M2 ion channel protein of influenza A virus (i.e., M2VeroA cells). In another embodiment of the invention, the Vero cell line may comprise Vero cells that stably express the BM2 ion channel protein of influenza B virus (SEQ ID NO: 74) (i.e., BM2Vero cells). BM2 is known to be a functional counterpart to influenza A virus M2. Influenza B virus M2 protein can functionally replace its influenza A virus counterpart in promoting virus replication (Wanitchang et al., *Virology* 498: 99-108 (2016)). In such an embodiment, the selected amino acids may be conserved even when the influenza virus is an influenza A virus.

Genetically modified Vero cells (i.e., those that express influenza M2 or BM2 proteins) behave like normal Vero cells and support growth of influenza A or B viruses comparable to normal Vero cells. Virus titers for M2SR viruses in M2VeroA cells are comparable to replicating influenza viruses that express functional M2 in unmodified Vero cell lines. Further, virus titers for BM2SR viruses (i.e., influenza viruses that comprise a mutant M gene segment from influenza B and consequently do not express a functional BM2 protein) in BM2Vero cells are comparable to replicating influenza viruses that express functional BM2 in unmodified Vero cell lines. Accordingly, M2SR and BM2SR viruses behave like replicating influenza viruses in the M2VeroA and BM2Vero cell lines.

In one embodiment of the invention, the influenza virus is capable of replication in human cells.

Pharmaceutical Formulation

The invention provides a pharmaceutical formulation (e.g., a vaccine or other immunogenic composition) comprising the inventive recombinant virus as described herein.

The pharmaceutical formulation can further comprise at least one pharmaceutically acceptable carrier or excipient. As used herein, the term "pharmaceutically acceptable carrier or excipient" refers to any component of the pharmaceutical formulation other than the inventive influenza virus. The pharmaceutically acceptable carrier or excipient can enhance efficacy of the inventive recombinant virus or maintain stability of the pharmaceutical formulation, desirably without significantly inactivating the inventive recombinant virus.

The at least one pharmaceutically acceptable carrier or excipient may be any suitable pharmaceutically acceptable carrier or excipient, many of which are known in the art. Exemplary pharmaceutically acceptable carriers or excipients include components that maintain a pH of the pharmaceutical formulation (e.g., buffers), adjust tonicity (e.g., tonicity modifying agents such as an inorganic salt), improve protein (e.g., virus) stability and/or immunogenicity, improve mucoadhesion, prevent protein aggregation, and/or preserve the pharmaceutical formulation (e.g., preservatives). For example, the pharmaceutically acceptable carrier or excipient may comprise at least one of an inorganic salt, surfactant, amino acid, polymer or polymeric compound (e.g., protein, polysaccharide, or hydrogel), chelating agent, sugar, polyol, and/or adjuvant (e.g., any substance that augments a specific immune response), many of which are known in the art. A particular carrier or excipient may serve more than one purpose in the pharmaceutical formulation, and, thus, the following embodiments are not limited to the descriptions recited herein.

Any suitable buffer can be present in the pharmaceutical formulation. In one embodiment, the buffer comprises at least one of an imidazole buffer, a potassium phosphate buffer, phosphate-buffered saline (PBS), Dulbecco's phosphate-buffered saline (DPBS) (e.g., 1×DPBS), a histidine buffer, a sodium citrate buffer, and sucrose phosphate glutamate buffer (SPG). PBS and/or DPBS preparations may comprise, for example, sodium chloride, potassium chloride, potassium phosphate monobasic, and sodium phosphate dibasic, and may optionally further comprise calcium chloride and/or magnesium chloride. In some embodiments, the PBS and/or DPBS preparations comprise about 136.9 mM sodium chloride, about 2.67 mM potassium chloride, about 1.47 mM potassium phosphate monobasic, and about 8.1 mM sodium phosphate dibasic, although any suitable PBS and/or DPBS preparation, many of which are known in the art, may be used as a buffer in the pharmaceutical formulation.

The buffer can be present in the pharmaceutical formulation in any suitable concentration. The buffer can be present in the pharmaceutical formulation at a concentration of about 0.1 mM or more, about 1 mM or more, about 10 mM or more, about 20 mM or more, about 30 mM or more, about 40 mM or more, about 50 mM or more, about 60 mM or more, about 70 mM or more, about 80 mM or more, about 90 mM or more, about 100 mM or more, about 120 mM or more, about 140 mM or more, about 160 mM or more, about 180 mM or more, about 200 mM or more, about 250 mM or more, about 300 mM or more, about 350 mM or more, about 400 mM or more, about 450 mM or more, or about 500 mM or more. Alternatively, or in addition, the buffer can be present in the pharmaceutical formulation at a concentration of about 1,000 mM or less, about 500 mM or less, about 450 mM or less, about 400 mM or less, about 350 mM or less, about 300 mM or less, about 250 mM or less, about 200 mM or less, about 180 mM or less, about 160 mM or less, about 140 mM or less, about 120 mM or less, about 100 mM or less, about 90 mM or less, about 80 mM or less, about 70 mM or less, about 60 mM or less, about 50 mM or less, about 40 mM or less, about 30 mM or less, about 20 mM or less, about 10 mM or less, or about 1 mM or less. The buffer can be present in the pharmaceutical formulation at any concentration within a range bounded by any of the aforementioned endpoints. For example, the buffer can be present in the pharmaceutical formulation at a concentration of about 0.1 mM to about 1000 mM, about 0.1 mM to about 500 mM, about 0.1 mM to about 100 mM, about 1 mM to about 1000 mM, about 1 mM to about 500 mM, about 1 mM to about 100 mM, about 100 mM to about 1000 mM, about 100 mM to about 500 mM, and the like.

In further embodiments, the buffer is present in the pharmaceutical formulation at a percentage concentration (e.g., volume/volume percentage (% v/v); weight/volume percentage (% w/v); or weight/weight percentage (% w/w)). The buffer can be present in the pharmaceutical formulation at a percentage concentration of about 0.1% or more, about 1% or more, about 5% or more, about 10% or more, about 15% or more, about 20% or more, about 30% or more, about 40% or more, or about 50% or more. Alternatively, or in addition, the buffer can be present in the pharmaceutical formulation at a percentage concentration of about 60% or less, about 50% or less, about 40% or less, about 30% or less, about 20% or less, about 15% or less, about 10% or less, about 5% or less, or about 1% or less. The buffer can be present in the pharmaceutical formulation at any percentage concentration within a range bounded by any of the foregoing endpoints. For example, the buffer can be present in the pharmaceutical formulation at a percentage concentration of about 0.1% to about 60%, about 1% to about 60%, about 10% to about 60%, about 0.1% to about 50%, about 1% to about 50%, about 10% to about 50%, about 20% to about 60%, about 20% to about 50%, about 20% to about 40%, about 20% to about 30%, about 30% to about 40%, about 40% to about 50%, and the like.

The buffer can maintain the pH of the pharmaceutical formulation at any suitable pH. The buffer can maintain the pH of the pharmaceutical formulation at a pH of, for example, about 4 or higher, about 4.5 or higher, about 5 or higher, about 5.5 or higher, about 6 or higher, about 6.5 or higher, about 7 or higher, or about 7.5 or higher. Alternatively, or in addition, the buffer can maintain the pH of the pharmaceutical formulation at a pH of, for example, about 8 or lower, about 7.5 or lower, about 7 or lower, about 6.5 or lower, about 6 or lower, about 5.5 or lower, about 5 or lower, or about 4.5 or lower. The buffer can maintain the pH of the pharmaceutical formulation at a pH within a range bounded by any of the foregoing endpoints. For example, the buffer can maintain the pH of the pharmaceutical formulation at a pH of about 4 to about 8, about 4.5 to about 8, about 5 to about 8, about 5.5 to about 8, about 6 to about 8, about 6.5 to about 8, about 7 to about 8, about 7.5 to about 8, about 4 to about 7.5, about 5 to about 7.5, about 6 to about 7.5, about 7 to about 7.5, about 4 to about 7, about 5 to about 7, about 6 to about 7, and the like.

Any suitable tonicity modifying agent can be present in the pharmaceutical formulation. In certain embodiments, one or more inorganic salts are present in the pharmaceutical formulation as tonicity modifying agents. The inorganic salt(s) may be at least one of sodium chloride (NaCl), magnesium sulfate ($MgSO_4$), and magnesium chloride ($MgCl_2$). The tonicity modifying agent, e.g., inorganic salt(s), can be present in the pharmaceutical formulation in any suitable amount. The tonicity modifying agent, e.g., inorganic salt(s), can be present in the pharmaceutical formulation at a concentration of about 0.1 mM or more, about 0.2 mM or more, about 0.4 mM or more, about 0.6 mM or more, about 0.8 mM or more, about 1 mM or more, about 1.2 mM or more, about 1.4 mM or more about 1.6 mM or more, about 1.8 mM or more, about 2 mM or more, about 3 mM or more, about 4 mM or more, about 5 mM or more, about 6 mM or more, about 7 mM or more, about 8 mM or more, about 9 mM or more, about 10 mM or more, about 20 mM or more, about 30 mM or more, about 40 mM or more, about 50 mM or more, about 100 mM or more, about 200 mM or more, about 300 mM or more, about 400 mM or more, about 500 mM or more, about 600 mM or more, about 700 mM or more, about 800 mM or more, about 900 mM or more, about 1000 mM or more, or about 1500 mM or more. Alternatively, or in addition, the tonicity modifying agent, e.g., inorganic salt(s), can be present in the pharmaceutical formulation at a concentration of about 2000 mM or less, about 1500 mM or less, about 1000 mM or less, about 900 mM or less, about 800 mM or less, about 700 mM or less, about 600 mM or less, about 500 mM or less, about 450 mM or less, about 400 mM or less, about 350 mM or less, about 300 mM or less, about 250 mM or less, about 200 mM or less, about 150 mM or less, about 100 mM or less, about 50 mM or less, about 45 mM or less, about 40 mM or less, about 35 mM or less, about 30 mM or less, about 25 mM or less, about 20 mM or less, about 10 mM or less, about 9 mM or less, about 8 mM or less, about 7 mM or less, about 6 mM or less, about 5 mM or less, about 4 mM or less, about 3 mM or less, about 2 mM or less, about 1.8 mM or less, about 1.6 mM or less, about 1.4 mM or less, about 1.2 mM or less, about 1 mM or less, about 0.8 mM or less, about 0.6 mM or less, about 0.4 mM or less, or about 0.2 mM or less. The tonicity modifying agent, e.g., inorganic salt(s), can be present in the pharmaceutical formulation at any concentration within a range bounded by any of the aforementioned endpoints. For example, the tonicity modifying agent, e.g., inorganic salt(s), can be present in the pharmaceutical formulation at a concentration of about 0.1 mM to about 2000 mM, about 0.1 mM to about 1500 mM, about 0.1 mM to about 1000 mM, about 0.1 mM to about 500 mM, about 0.1 mM to about 250 mM, about 0.1 mM to about 100 mM, about 0.1 to about 50 mM, about 0.1 mM to about 10 mM, about 1 mM to about 2000 mM, about 1 mM to about 1500 mM, about 1 mM to about 1000 mM, about 1 mM to about 500 mM, about 1 mM to about 250 mM, about 1 mM to about 100 mM, about 1 mM to about 50 mM, about 1 mM to about 10 mM, about 10 mM to about 2000 mM, about 10 mM to about 1500 mM, about 10 mM to about 1000 mM, about 10 mM to about 500 mM, about 10 mM to about 250 mM, about 10 mM to about 100 mM, about 10 mM to about 50 mM, about 100 mM to about 2000 mM, about 100 mM to about 1500 mM, about 100 mM to about 1000 mM, about 100 mM to about 500 mM, about 100 mM to about 250 mM, about 500 mM to about 2000 mM, about 500 mM to about 1500 mM, about 500 mM to about 1000 mM, and the like.

In further embodiments, the inorganic salt is present in the pharmaceutical formulation at a percentage concentration (e.g., volume/volume percentage (% v/v); weight/volume percentage (% w/v); or weight/weight percentage (% w/w)). The tonicity modifying agent, e.g., inorganic salt(s), be present in the pharmaceutical formulation at a percentage concentration of about 0.1% or more, about 1% or more, about 2% or more, about 3% or more, about 4% or more, about 5% or more, about 6% or more, about 7% or more, about 8% or more, about 9% or more, or about 10% or more. Alternatively, or in addition, the tonicity modifying agent, e.g., inorganic salt(s), can be present in the pharmaceutical formulation at a percentage concentration of about 10% or less, about 9% or less, about 8% or less, about 7% or less, about 6% or less, about 5% or less, about 4% or less, about 3% or less, about 2% or less, or about 1% or less. The tonicity modifying agent, e.g., inorganic salt(s), can be present in the pharmaceutical formulation at any percentage concentration within a range bounded by any of the foregoing endpoints. For example, the tonicity modifying agent, e.g., inorganic salt(s), can be present in the pharmaceutical formulation at a percentage concentration of about 0.1% to about 1%, about 0.1% to about 2%, about 0.1% to about 5%, about 0.1% to about 10%, about 1% to about 2%, about 1% to about 5%, about 1% to about 10%, about 2% to about 10%, about 3% to about 10%, about 4% to about 10%, about 5% to about 10%, and the like.

Any suitable surfactant can be present in the pharmaceutical formulation. In certain embodiments, the surfactant can comprise at least one of polysorbate 20, polysorbate 80, sodium deoxycholate, and poloxamer 188. The surfactant can be present in the pharmaceutical formulation in any suitable amount. In some embodiments, the surfactant is present in the pharmaceutical formulation at a percent concentration (e.g., volume/volume percentage (% v/v); weight/volume percentage (% w/v); or weight/weight percentage (% w/w)). The surfactant can be present in the pharmaceutical formulation at a percentage concentration of about 0.01% or more, about 0.02% or more, about 0.03% or more, about 0.04% or more, about 0.05% or more, about 0.06% or more, about 0.07% or more, about 0.08% or more, about 0.09% or more, about 0.1% or more, about 0.2% or more, about 0.3% or more, about 0.4% or more, about 0.5% or more, about 0.6% or more, about 0.7% or more, about 0.8% or more, about 0.9% or more, or about 1% or more. Alternatively, or in addition, the surfactant can be present in the pharmaceutical formulation at a percentage concentration of about 1% or less, about 0.9% or less, about 0.8% or less, about 0.7% or less, about 0.6% or less, about 0.5% or less, about 0.4% or less, about 0.3% or less, about 0.2% or less, or about 0.1% or less. The surfactant can be present in the pharmaceutical formulation at any percentage concentration within a range bounded by any of the foregoing endpoints. For example, the surfactant can be present in the pharmaceutical formulation at a percentage concentration of about 0.01% to about 1%, about 0.01% to about 0.1%, about 0.05% to about 1%, about 0.05% to about 0.1%, about 0.1% to about 1%, about 0.1% to about 0.5%, about 0.2% to about 1%, about 0.5% to about 1%, and the like.

Any suitable amino acids can be present in the pharmaceutical formulation. In certain embodiments, the amino acid may be one or more of arginine, glutamic acid or glutamate, asparagine, histidine, and glycine. The amino acid(s) can be present in the pharmaceutical formulation in any suitable amount. The amino acid(s) can be present in the pharmaceutical formulation at a concentration of about 1 mM or more, about 2 mM or more, about 3 mM or more, about 5 mM or more, about 6 mM or more, about 7 mM or more, about 8 mM or more, about 9 mM or more, or about 10 mM or more. Alternatively, or in addition, the amino acid(s) can be present in the pharmaceutical formulation at a concentration of about 100 mM or less, about 90 mM or less, about 80 mM or less, about 70 mM or less, about 60 mM or less, about 50 mM or less, about 40 mM or less, about 30 mM or less, about 20 mM or less, or about 10 mM or less. The amino acid(s) can be present in the pharmaceutical formulation at any concentration within a range bounded by any of the foregoing endpoints. For example, the amino acid(s) can be present in the pharmaceutical formulation at a concentration of about 1 mM to about 10 mM, about 1 mM to about 50 mM, about 1 mM to about 100 mM, about 5 mM to about 50 mM, about 10 mM to about 50 mM, about 20 mM to about 50 mM, and the like.

In some embodiments, the amino acid(s) is present in the pharmaceutical formulation at a percentage concentration (e.g., volume/volume percentage (% v/v); weight/volume percentage (% w/v); or weight/weight percentage (% w/w)). The amino acid(s) can be present in the pharmaceutical formulation at a percentage concentration of about 0.1% or more, about 0.2% or more, about 0.3% or more, about 0.4% or more, about 0.5% or more, about 0.6% or more, about 0.7% or more, about 0.8% or more, about 0.9% or more, about 1% or more, about 2% or more, about 3% or more, about 4% or more, or about 5% or more. Alternatively, or in addition, the amino acid(s) can be present in the pharmaceutical formulation at a percentage concentration of about 10% or less, about 9% or less, about 8% or less, about 7% or less, about 6% or less, about 5% or less, about 4% or less, about 3% or less, about 2% or less, or about 1% or less. The amino acid(s) can be present in the pharmaceutical formulation at any percentage concentration within a range bounded by any of the foregoing endpoints. For example, the amino acid(s) can be present in the pharmaceutical formulation at a percentage concentration of about 0.1% to 10%, 0 about 0.2% to about 10%, about 0.5% to about 10%, about 0.1% to about 5%, about 0.1% to about 2%, about 0.2% to about 2%, about 0.5% to about 1%, and the like.

Any suitable polymers or polymeric compounds can be present in the pharmaceutical formulation. The polymer or polymeric compound can be, for example, a protein, a polysaccharide, a hydrogel, or any other suitable polymer or polymeric compound, many of which are known in the art. The polymers may preferably be polyanionic such as carboxymethylcellulose or poly(acrylic acid). For example, the polymer or polymeric compound can be recombinant human serum albumin (rHSA), serum albumin (SA), gelatin, hydroxyethyl starch (HES), chitosan, dextran (DEX70K, DEX40K), and polyvinylpyrrolidone (PVP40K).

The polymer(s) or polymeric compound(s) can be present in the pharmaceutical formulation in any suitable amount. The polymer(s) or polymeric compound(s) can be present in the pharmaceutical formulation at a percentage concentration (e.g., volume/volume percentage (% v/v); weight/volume percentage (% w/v); or weight/weight percentage (% w/w)). The polymer(s) or polymeric compound(s) can be present in the pharmaceutical formulation at a percentage concentration of about 0.1% or more, about 0.2% or more, about 0.3% or more, about 0.4% or more, about 0.5% or more, about 0.6% or more, about 0.7% or more, about 0.8% or more, about 0.9% or more, about 1% or more, about 2% or more, about 3% or more, about 4% or more, or about 5% or more. Alternatively, or in addition, the polymer(s) or polymeric compound(s) can be present in the pharmaceutical formulation at a percentage concentration of about 10% or less, about 9% or less, about 8% or less, about 7% or less, about 6% or less, about 5% or less, about 4% or less, about 3% or less, about 2% or less, or about 1% or less. The polymer(s) or polymeric compound(s) can be present in the pharmaceutical formulation at any percentage concentration within a range bounded by any of the foregoing endpoints. For example, the polymer(s) or polymeric compound(s) can be present in the pharmaceutical formulation at a percentage concentration of about 0.1% to about 10%, about 0.2% to 1 about 0%, about 0.5% to about 10%, about 0.1% to about 5%, about 0.1% to about 2%, about 0.2% to about 2%, about 0.5 to about 2%, about 0.1% to about 1%, about 0.2% to about 1%, about 0.5% to about 1%, and the like.

Any suitable chelating agent can be present in the pharmaceutical formulation. The chelating agent can be, for example, ethylenediaminetetraacetic acid (EDTA), an amidoxime compound (AOX), and/or dithiothreitol (DTT). The chelating agent can be present in the pharmaceutical formulation at any suitable concentration. The chelating agent can be present in the pharmaceutical formulation at a concentration of 10 μM or more, about 20 μM or more, about 30 μM or more, about 40 μM or more, about 50 μM or more, about 60 μM or more, about 70 μM or more, about 80 μM or more, about 90 μM or more, about 100 μM or more, about 120 μM or more, or about 150 μM or more. Alternatively, or in addition, the chelating agent can be present in the pharmaceutical formulation at a concentration of about 500 μM or less, about 400 μM or less, about 300 μM or less, about 200 μM or less, about 150 μM or less, about 140 μM or less, about 130 μM or less, about 120 μM or less, about 110 μM or less, about 100 μM or less, about 80 μM or less, about 70 μM or less, about 60 μM or less, or about 50 μM or less. The chelating agent can be present in the pharmaceutical formulation at any concentration within a range bounded by any of the foregoing endpoints. For example, the chelating agent can be present in the pharmaceutical formulation at a concentration of about 10 μM to about 500 μM, about 10 μM to about 200 μM, about 10 μM to about 150 μM, about 10 μM to about 100 μM, about 50 μM to about 500 μM, about 50 μM to about 200 μM, about 50 μM to about 150 μM, about 50 μM to about 100 μM, and the like.

Any suitable sugar can be present in the pharmaceutical formulation. The sugar can be, for example, one or more of sucrose, trehalose, mannose, and lactose. The sugar(s) can be present in the pharmaceutical formulation at any suitable concentration. The sugar(s) can be present in the pharmaceutical formulation at a concentration of about 0.1 mM or more, about 0.2 mM or more, about 0.4 mM or more, about 0.6 mM or more, about 0.8 mM or more, about 1 mM or more, about 1.2 mM or more about 1.4 mM or more about 1.6 mM or more about 1.8 mM or more, about 2 mM or more about 3 mM or more about 4 mM or more, about 5 mM or more, about 6 mM or more, about 7 mM or more, about 8 mM or more, about 9 mM or more, about 10 mM or more, about 20 mM or more, about 30 mM or more, about 40 mM or more, about 50 mM or more, about 60 mM or more, about 70 mM or more, about 80 mM or more, about 90 mM or more, or about 100 mM or more, about 200 mM or more, about 300 mM or more, about 400 mM or more, about 500 mM or more, about 600 mM or more, about 700 mM or more, about 800 mM or more, about 900 mM or more, about 1000 mM or more, or about 1500 mM or more. Alternatively, or in addition, the sugar(s) can be present in the pharmaceutical formulation at a concentration of about 2000 mM or less, about 1500 mM or less, about 1000 mM or less, about 900 mM or less, about 800 mM or less, about 700 mM or less, about 600 mM or less, about 500 mM or less, about 450 mM or less, about 400 mM or less, about 350 mM or less, about 300 mM or less, about 250 mM or less, about 200 mM or less, about 150 mM or less, about 100 mM or less, about 50 mM or less, about 45 mM or less, about 40 mM or less, about 35 mM or less, about 30 mM or less, about 25 mM or less, about 20 mM or less, about 10 mM or less, about 9 mM or less, about 8 mM or less, about 7 mM or less, about 6 mM or less, about 5 mM or less, about 4 mM or less, about 3 mM or less, about 2 mM or less, about 1.8 mM or less, about 1.6 mM or less, about 1.4 mM or less, about 1.2 mM or less, about 1 mM or less, about 0.8 mM or less, about 0.6 mM or less, about 0.4 mM or less, or about 0.2 mM or less. The sugar(s) can be present in the pharmaceutical formulation at any concentration within a range bounded by any of the foregoing endpoints. For example, the sugar(s) can be present in the pharmaceutical formulation at a concentration of about 0.1 mM to about 2000 mM, about 0.1 mM to about 1500 mM, about 0.1 mM to about 1000 mM, about 0.1 mM to about 500 mM, about 0.1 mM to about 250 mM, about 0.1 mM to about 100 mM, about 0.1 to about 50 mM, about 0.1 mM to about 10 mM, about 1 mM to about 2000 mM, about 1 mM to about 1500 mM, about 1 mM to about 1000 mM, about 1 mM to about 500 mM, about 1 mM to about 250 mM, about 1 mM to about 100 mM, about 1 mM to about 50 mM, about 1 mM to about 10 mM, about 10 mM to about 2000 mM, about 10 mM to about 1500 mM, v10 mM to about 1000 mM, about 10 mM to about 500 mM, about 10 mM to about 250 mM, about 10 mM to about 100 mM, about 10 mM to about 50 mM, about 100 mM to about 2000 mM, about 100 mM to about 1500 mM, about 100 mM to about 1000 mM, about 100 mM to about 500 mM, about 100 mM to about 250 mM, about 500 mM to about 2000 mM, about 500 mM to about 1500 mM, about 500 mM to about 1000 mM, and the like.

In other embodiments, the sugar(s) is present in the pharmaceutical formulation at a percentage concentration (e.g., volume/volume percentage (% v/v); weight/volume percentage (% w/v); or weight/weight percentage (% w/w)). The sugar(s) can be present in the pharmaceutical formulation at a percentage concentration of about 0.1% or more, about 1% or more, about 5% or more, about 10% or more, about 15% or more, about 20% or more, about 30% or more, about 40% or more. Alternatively, or in addition, the sugar(s) can be present in the pharmaceutical formulation at a percentage concentration of about 50% or less, about 40% or less, about 30% or less, about 20% or less, about 15% or less, about 10% or less, about 5% or less, or about 1% or less. The sugar(s) can be present in the pharmaceutical formulation at any percentage concentration within a range bounded by any of the foregoing endpoints. For example, the sugar(s) can be present in the pharmaceutical formulation at a percentage concentration of about 0.1% to about 50%, about 1% to about 50%, about 10% to about 50%, about 0.1% to about 20%, about 1% to about 20%, about 10% to about 20%, about 0.1% to about 10%, about 1% to about 10%, and the like.

Any suitable polyol can be present in the pharmaceutical formulation. The polyol can be, for example, sorbitol and/or mannitol. The polyol can be present in the pharmaceutical formulation at any suitable concentration. The polyol can be present in the pharmaceutical formulation at a concentration of about 0.1 mM or more, about 1 mM or more, about 10 mM or more, about 20 mM or more, about 30 mM or more, about 40 mM or more, about 50 mM or more, about 60 mM or more, about 70 mM or more, about 80 mM or more, about 90 mM or more, about 100 mM or more, about 120 mM or more, about 140 mM or more, about 160 mM or more, about 180 mM or more, about 200 mM or more, about 250 mM or more, about 300 mM or more, about 350 mM or more, about 400 mM or more, about 450 mM or more, or about 500 mM or more. Alternatively, or in addition, the polyol can be present in the pharmaceutical formulation at a concentration of about 1000 mM or less, about 500 mM or less, about 450 mM or less, about 400 mM or less, about 350 mM or less, about 300 mM or less, about 250 mM or less, about 200 mM or less, about 180 mM or less, about 160 mM or less, about 140 mM or less, about 120 mM or less, about 100 mM or less, about 90 mM or less, about 80 mM or less, about 70 mM or less, about 60 mM or less, about 50 mM or less, about 40 mM or less, about 30 mM or less, about 20 mM or less, about 10 mM or less, or about 1 mM or less. The polyol can be present in the pharmaceutical formulation at any concentration within a range bounded by any of the foregoing endpoints. For example, the polyol can be present in the pharmaceutical formulation at a concentration of about 0.1 mM to about 1000 mM, about 0.1 mM to about 500 mM, about 0.1 mM to about 100 mM, about 1 mM to about 1000 mM, about 1 mM to about 500 mM, about 1 mM to about 100 mM, about 100 mM to about 1000 mM, about 100 mM to about 500 mM, and the like.

In other embodiments, the polyol is present in the pharmaceutical formulation at a percentage concentration (e.g., volume/volume percentage (% v/v); weight/volume percentage (% w/v); or weight/weight percentage (% w/w)). The polyol can be present in the pharmaceutical formulation at a percentage concentration of about 0.1% or more, about 1% or more, about 2% or more, about 3% or more, about 4% or more, or about 5% or more, about 10% or more, about 15% or more, about 20% or more, about 25% or more, about 30% or more, about 35% or more, about 40% or more, about 45% or more. Alternatively, or in addition, the polyol can be present in the pharmaceutical formulation at a percentage concentration of about 50% or less, about 45% or less, about 40% or less, about 35% or less, about 30% or less, about 25% or less, about 20% or less, about 15% or less, about 10% or less, about 5% or less, about 4% or less, about 3% or less, about 2% or less, or about 1% or less. The polyol can be present in the pharmaceutical formulation at any percentage concentration within a range bounded by any of the foregoing endpoints. For example, the polyol can be present in the pharmaceutical formulation at a percentage concentration of about 0.1% to about 50%, about 1% to about 50%, about 5% to about 50%, about 10% to about 50%, about 15% to about 50%, about 0.1% to about 25%, about 1% to about 25%, about 5% to about 25%, about 10% to about 25%, about 15% to about 25%, about 0.1% to about 15%, about 1% to about 15%, about 5% to about 15%, about 10% to about 15%, about 0.1% to about 10%, about 1% to about 10%, about 5% to about 10%, about 0.1% to about 5%, about 1% to about 5%, and the like.

In one embodiment, the pharmaceutical formulation comprises the inventive influenza virus, about 0.5 M sucrose, about 0.1 M or about 0.5 M mannose, about 0.3 M or about 0.5 M trehalose, about 50% SPG, and about 0.05% polysorbate 20. In another embodiment, the pharmaceutical formulation comprises the inventive influenza virus, about 0.5 M sucrose, about 0.3 M trehalose, and about 0.05% polysorbate 20.

The at least one pharmaceutically acceptable carrier or excipient can be a component that serves to bind the ingredients of the pharmaceutical formulation (e.g., a binder). The binder may include, but is not limited to, proteins (e.g., gelatin), polymers (e.g., polyethylene glycol, polyvinylpyrrolidone), and/or polysaccharides or derivatives thereof (e.g., starch and cellulose). The at least one pharmaceutically acceptable carrier or excipient can be a component that increases bulk of the pharmaceutical formulation (e.g., a bulking agent, diluent, and/or filler). Such bulking agents may include, but are not limited to, polysaccharides or derivatives thereof, sugars, and/or inorganic compounds. The pharmaceutically acceptable carrier or excipient can be a component that enhances taste and/or appearance of the pharmaceutical formulation (e.g., a flavor, sweetener, and/or color). The pharmaceutically acceptable carrier or excipient can be a component that moisture-proofs the pharmaceutical formulation by absorbing or adsorbing liquids or gases (e.g., a sorbent). A sorbent includes, but is not limited to, starch, calcium phosphate, and/or colloidal silicon dioxide. The pharmaceutically acceptable carrier or excipient can be a component that promotes dissolution of the pharmaceutical formulation (e.g., a disintegrant), such as a starch, cellulose and/or any other polymer known in the art, or derivative thereof (e.g., cross-linked polyvinylpyrrolidone or sodium carboxymethylcellulose).

In some embodiments, the pharmaceutically acceptable carrier or excipient is a component that reduces interparticle adhesion and/or optimizes product flow in and during manufacture of a pharmaceutical formulation (e.g., a glidant). Examples of glidants include, but are not limited to, talc, colloidal silicon dioxide, and corn starch. The pharmaceutically acceptable carrier or excipient can be a component that provides non-sticking properties, such as reducing adhesion between the ingredients and, for example, the punch faces or lubricant in and during manufacture of a pharmaceutical formulation (e.g., an anti-adherent), particularly when the pharmaceutical formulation is formulated as an oral preparation. For example, the anti-adherent may comprise magnesium stearate. In other embodiments, the pharmaceutically acceptable carrier or excipient can be a component that reduces clumping of ingredients and/or reduce friction between, for example, the surface of a pharmaceutical formulation, i.e., formulated as an oral preparation, and the die wall during manufacture (e.g., a lubricant). Both water-soluble or water-insoluble lubricants may be used according to certain embodiments, such as magnesium stearate, stearic acid, vegetable oil, mineral oil, polyethylene glycol, and/or sodium lauryl sulfate. The pharmaceutically acceptable carrier or excipient can be a component that acts as a coating agent. Coating agents include, but are not limited to, gelatin and/or cellulose-based coating agents (e.g., hydroxypropyl methylcellulose).

Other suitable binders, flavors, sweeteners, colors, disintegrants, glidants, anti-adherents, lubricants, and coating agents are well known and readily identifiable in the art.

The pharmaceutical formulation can further comprise a therapeutic agent (e.g., a chemotherapeutic or anti-inflammatory agent). The pharmaceutical formulation can also comprise an agent that triggers an immune response separate from the influenza virus. Such additional components other than the inventive influenza virus can be present in any suitable amount(s).

The additional components can be mixed with the other components to form the pharmaceutical formulation prior to presentation to the immune system. The additional components can also be presented to the immune system separately from the pharmaceutical formulation. For example, the additional components and the pharmaceutical formulation can be presented to the immune system (e.g., administered to an organism) separately. When the additional components and the pharmaceutical formulation are administered separately, the additional components and the pharmaceutical formulation can be administered to the same site of the organism being immunized.

In one embodiment of the pharmaceutical formulation, the pharmaceutical formulation is a virus vaccine. The virus vaccine may be a live, attenuated virus vaccine or an inactivated virus vaccine (e.g., a whole virus vaccine, split virus vaccine, or subunit vaccine). The virus vaccine may be formulated with multiple influenza viral backbone subtypes (i.e., with different hemagglutinin and neuraminidase subtypes for influenza A and either Yamagata or Victoria lineages for influenza B) as a monovalent vaccine, a bivalent vaccine (e.g., H1H3, H1By H1Bv, H3Bv, or BvBy), a trivalent vaccine (e.g., H1H3By, H1H3Bv, BvByH1, or BvByH3), or a quadrivalent vaccine (e.g., H1H3ByBv). For example, the vaccine may comprise multiple embodiments of the inventive recombinant virus. In some embodiments, the vaccine may further comprise at least one recombinant virus different from the recombinant virus of the invention.

The virus vaccine can be formulated into a composition for any suitable means of administration. For example, the virus vaccine can be formulated as an oral preparation (e.g., capsule, tablet, or oral film), a spray (e.g., nasal spray), or any composition suitable for intranasal administration, or parenteral administration, e.g., intravenous, intramuscular, intradermal or subcutaneous administration, such as an aqueous or non-aqueous emulsion, solution, or suspension. Embodiments:

(1) A recombinant virus comprising an influenza viral backbone, wherein the influenza viral backbone comprises PB1, PB2, PA, NP, M, NS, HA, and NA gene segments, wherein at least one of the PB1, PB2, PA, NP, M, NS, HA, and NA gene segments comprises at least one nucleotide sequence that encodes one or more antigens, and wherein (a) the PB1 gene segment encodes a PB1 protein having an amino acid sequence comprising selected amino acids, wherein the selected amino acids comprise a leucine at position 40 and a tryptophan at position 180, and at least one of an asparagine at position 464, an isoleucine at position 563, or a serine at position 607, and wherein the PB1 gene segment optionally comprises a cytosine to uracil promoter mutation at nucleotide position 4; (b) the PB2 gene segment encodes a PB2 protein having an amino acid sequence comprising selected amino acids, wherein the selected amino acids comprise a valine at position 504, and optionally an isoleucine at position 467 and a valine at position 529, and wherein the PB2 gene segment optionally comprises a cytosine to uracil promoter mutation at nucleotide position 4; (c) the PA gene segment encodes a PA protein having an amino acid sequence comprising selected amino acids, wherein the selected amino acids comprise a lysine at position 401, and wherein the PA gene segment optionally comprises a cytosine to uracil promoter mutation at nucleotide position 4; (d) the NP gene segment encodes an NP protein having an amino acid sequence comprising selected amino acids, wherein the selected amino acids comprise a leucine at position 116, and at least one of a lysine at position 294 or an arginine at position 311; and (e) the NS gene segment encodes an NS1 protein having amino acid sequence comprising selected amino acids, wherein the selected amino acids comprise a proline at position 30, a lysine at position 55, and a lysine at position 118.

(2) The recombinant virus of embodiment 1, wherein the antigen is an immunogenic fragment of SARS-CoV-2 spike glycoprotein.

(3) The recombinant virus of embodiment 1 or 2, wherein the M gene segment comprises at least one nucleotide sequence that encodes an antigen, wherein the antigen is an immunogenic fragment of SARS-CoV-2 spike glycoprotein.

(4) The recombinant virus of any of embodiments 1-3, wherein the M gene segment encodes a mutated M2 protein.

(5) The recombinant virus of embodiment 4, wherein the M gene segment encodes a protein comprising at least one linker protein and FLAG epitope tag.

(6) The recombinant virus of any one of embodiments 1-5, wherein the M segment encodes a protein comprising any one of SEQ ID NOs: 1-14 and 92-96.

(7) A recombinant virus comprising an influenza viral backbone, wherein the influenza viral backbone comprises PB1, PB2, PA, NP, M, NS, HA, and NA gene segments comprises at least one nucleotide sequence that encodes one or more antigens, wherein (a) the PA gene segment comprises a thymine at nucleotide position 2272; (b) the NP gene segment encodes a NP protein having an amino acid sequence comprising selected amino acids, wherein the selected amino acids comprise a serine at position 40, an asparagine or glycine at position 161, a threonine at position 204, and optionally a valine at position 93; and (c) the NS gene segment comprises a guanine at nucleotide position 39, and wherein the NS gene segment encodes an NS protein having an amino acid sequence comprising selected amino acids, wherein the selected amino acids comprise a glutamine at position 176.

(8) The recombinant virus of embodiment 7, wherein the antigen is an immunogenic fragment of SARS-CoV-2 spike glycoprotein.

(9) The recombinant virus of embodiment 7 or 8, wherein the M gene segment comprises at least one nucleotide sequence that encodes an antigen, wherein the antigen is an immunogenic fragment of SARS-CoV-2 spike glycoprotein and further encodes a mutated BM2 protein.

(10) The recombinant virus of any one of embodiments 1-9, wherein the NS gene segment comprises at least one nucleotide sequence that encodes one or more antigens.

(11) The recombinant virus of any one of embodiments 1-10 wherein the antigen is an immunogenic fragment of SARS-CoV-2 spike glycoprotein.

(12) (The recombinant virus of any one of embodiments 1-11, wherein the NS gene segment encodes a (1) a NS1 protein, (2) at least one flexible linker protein, (3) an immunogenic fragment of SARS-CoV-2 spike glycoprotein, (4) at least one cleavable cleavage sequence, and (5) a NEP protein.

The recombinant virus of embodiment 12, wherein the at least one cleavable cleavage sequence is a T2A peptide sequence or a P2A peptide sequence.

(14) The recombinant virus of any one of embodiments 1-13, wherein the NS gene segment encodes a protein comprising any one of SEQ ID NOs: 97-104.

(15) The recombinant virus of embodiment 1 or 7, wherein each of the M and NS gene segments comprises at least one nucleotide sequence that encodes one or more antigens, and wherein the antigens are immunogenic fragments of SARS-CoV-2 spike glycoprotein.

(16) The recombinant virus of embodiment 1 or 7, wherein each of the NA and NS gene segments comprises at least one nucleotide sequence that encodes one or more antigens, and wherein the antigens are immunogenic fragments of SARS-CoV-2 glycoprotein.

(17) The recombinant virus of embodiment 1 or 7, wherein each of the M and NA gene segments comprises at least one nucleotide sequence that encodes one or more antigens, and wherein the antigens are immunogenic fragments of SARS-CoV-2 glycoprotein.

(18) The recombinant virus of embodiment 1 or 7, wherein each of the M and HA gene segments comprises at least one nucleotide sequence that encodes one or more antigens, and wherein the antigens are immunogenic fragments of SARS-CoV-2 glycoprotein.

(19) The recombinant virus of embodiment 1 or 7, wherein each of the NS and NA gene segments comprises at least one nucleotide sequence that encodes one or more antigens, and wherein the antigens are immunogenic fragments of SARS-CoV-2 glycoprotein.

(20) The recombinant virus of embodiment 1 or 7, wherein each of the NS and HA gene segments comprises at least one nucleotide sequence that encodes one or more antigens, and wherein the antigens are immunogenic fragments of SARS-CoV-2 spike glycoprotein.

(21) The recombinant virus of any one of embodiments 1-20, wherein the virus is capable of replication in human cells.

(22) The recombinant virus of any one of embodiments 1-21, wherein the virus has enhanced growth as compared to a recombinant virus that is the same except without the selected amino acids in Vero cells under the same conditions.

(23) The recombinant virus of any one of embodiments 1-22, wherein the gene segment that comprises at least one nucleotide sequence that encodes one or more antigens further comprises a downstream duplication and wherein the downstream duplication comprises at least one silent nucleotide mutation.

(24) A pharmaceutical formulation comprising the recombinant virus of any one of embodiments 1-23.

(25) The pharmaceutical formulation of embodiment 24, wherein the vaccine is formulated as a monovalent vaccine.

(26) The pharmaceutical formulation of embodiment 24, wherein the vaccine is formulated as a bivalent vaccine.

(27) The pharmaceutical formulation of embodiment 24, wherein the vaccine is formulated as a trivalent vaccine.

(28) The pharmaceutical formulation of embodiment 24, wherein the vaccine is formulated as a quadrivalent vaccine.

(29) A method of eliciting an immune response in a mammal, the method comprising administering the recombinant virus of any one of embodiments 1-23 or the pharmaceutical formulation of any one of embodiments 24-28 to the mammal, thereby eliciting an immune response to the antigen in the mammal.

(30) The method of embodiment 29, wherein the mammal is a human

EXAMPLES

The following examples further illustrate the invention but, of course, should not be construed as in any way limiting its scope.

Example 1

This example demonstrates the methods used to select the MHC I peptides used in the influenza vectors. The peptides were suitable for insertion into the M2, BM2, and NS genes.

Peptide antigens for vaccine were selected based on their ability to stimulate immune response from the broadest possible number of MHC genotypes, thus providing benefit to the largest possible number of potential vaccines. This approach was taken because high specificity to the interaction of MHC class I molecules on the cell surface and cognate antigen peptides bound and displayed for presentation to immune effector T-cells. Antigen peptides with higher specific MHC I affinity elicit a stronger immune response upon vaccination. Many models have been developed that were able to predict the affinity of any peptide sequence for a given MHC Class I molecule. This interaction is also allele-specific amongst the many known MHC Class I genotypes found worldwide within individuals from differing genetic backgrounds. Thus, any single peptide will have a different affinity for a MHC Class I receptor that is dependent upon the individual MHC I genotype.

The S1 or spike surface glycoprotein from the SARS-CoV-2 coronavirus was used as the target antigen protein for identification of the best peptide. The amino acid sequence of 51 protein (SEQ ID NO: 77) was predicted from the complete genome sequence of Severe acute respiratory syndrome coronavirus 2 isolate Wuhan-Hu-1 (Genbank NC_045512.2) by standard codon usage table. The primary S1 protein sequence was used to identify the best MHC Class I compatible 9-mer peptides by prediction of peptide affinities across a 27-member human MHC Class I allele panel. Peptide predictions were ranked by predicted consensus percentile rank across all predictors in an ensemble; those with percentile rank ≤1 were selected. Cluster analysis was applied to these peptides using known methods (see e.g., Dhanda et al., *Front. Immunol.,* 9: 1369 (2018)), picking epitope clusters predicted to have high affinity for many MHC Class I molecules from high genetic diversity. Top scoring peptides were ranked using a two-step process. Initially peptides were ranked by cluster connectivity to locate peptide affinity "smears" that were regions of high predicted affinity where multiple 9-mers were tiled (i.e., peptides align and overlap). In this way peptide smears that were longer than 9 residues can be identified and targeted for inclusion within the vaccine. The number of times a given peptide was scored in the top 1% was tabulated to score the cumulative hit count and median epitope rank to select the top peptide smears that were expected to bind MHC I within human subjects with high genetic diversity. This method is described in more detail below.

Predicting Epitopes with MHC-I Activity

Immune Epitope Database and Analysis Resource's (IEDB) TepiTool was used to extract MHC I-relevant epitope predictions from the amino acid sequence for SARS-CoV-2 spike protein. Epitopes were predicted for human MHC-I alleles, using a 27-allele panel; epitope sizes were allowed to range from 8-mers to 11-mers. Duplicate peptides were removed, and the IEDB recommended prediction method was used. Peptides were selected with predicted consensus percentile rank less than or equal to 1, producing 647 epitopes meeting the rank condition and 136566 overall tuples (epitope, allele, predictor, rank).

Clustering Epitopes to Smears

IEDB's Epitope Cluster Analysis tool was used to cluster the previously selected epitopes into a cluster of relevant epitopes, herein referred to as an "epitope smear." A minimum sequence identity threshold of 70% was chosen, with no size filters placed upon the epitope list. Predicted epitopes were clustered into smears as those with consensus percentile rank less than or equal to 1. The cluster-breaking clustering algorithm was used, and clusters with their epitope alignments were output into a comma separated values (CSV) file format. In this use case, the clusters were effectively ordered by decreasing connectedness. Using this method, clusters were ranked in lexicographic cluster-subcluster sorted order.

Analyzing Smears

Using a Python script, clusters were ingested, normalized, and then aligned to the spike S1 protein open reading frame obtained from GenBank RefSeq genome NC 045512.2. Various qualitative statistical analyses were performed on the distributions of hits, sequence length, etc., to inform smear selection. Hit count (number of epitopes per cluster) and median rank (median of consensus percentile ranks for each epitope in the cluster) were added as columns. The total number of hits was a useful metric to select top candidate smears sequences. Only a small subset of peptide smears were found to contain greater than 10 hits per cluster (FIG. 11). By setting an arbitrary cut-off of 9 hits per cluster only 8 total smears were identified within the SARS-CoV-2 S1 protein of 1273 amino acids in length.

The results from statistical analyses were compiled and re-output to CSV format for visualization. Top candidate smears were compared to each other and curated manually. In three cases candidate smears were overlapping or nearly adjacent which that allowed combination into super consensus smear sequences that span two candidate sequences. The selected 8 candidate smears are shown in Table 1.

TABLE 1

Top 8 Candidate MHC I Compatible Peptide Smears SARS-COV-2 S1 Protein

| Smear Cluster Sub-Cluster | Peptide Type | Peptide Sequence | Description | Start | End | Length | #Hits |
|---|---|---|---|---|---|---|---|
| 1.1 | Consensus | QELGKYEQYIKWPWYIWLGFIAGLI (SEQ ID NO: 21) | Spike HR2 + Transmembrane | 1201 | 1225 | 25 | 18 |
| 2.1 | Consensus | NLDSKVGGNYNYLYRLFRK (SEQ ID NO: 22) | | 440 | 458 | 19 | 12 |
| 2.2 | Consensus | YRLFRKSNLKPFER (SEQ ID NO: 23) | Spike RBD | 453 | 466 | 14 | 6 |
| 2.X | Super Consensus | NLDSKVGGNYNYLYRLFRKSNLKPFER (SEQ ID NO: 24) | | 440 | 466 | 27 | 18 |
| 3.1 | Consensus | AALQIPFAMQMAYRENGIGV (SEQ ID NO: 25) | Spike Other | 892 | 911 | 20 | 14 |
| 4.1 | Consensus | EVFNATRFASVYAWNRKRI (SEQ ID NO: 26) | | 340 | 358 | | 13 |
| 4.2 | Singleton | GEVFNATRF (SEQ ID NO: 27) | Spike RBD | 339 | 347 | 9 | 1 |
| 4.X | Super Consensus | **G**EVFNATRFASVYAWNRKRI (SEQ ID NO: 28) | | 339 | 358 | 20 | 14 |
| 5.1 | Consensus | YSVLYNSASFSTFKCYGV (SEQ ID NO: 29) | Spike RBD | 365 | 382 | 18 | 13 |
| 6.1 | Consensus | SPRRA**RS**VASQSIIAY (SEQ ID NO: 30) | Spike Cleavage Site | 680 | 695 | 16 | 11 |
| 7.1 | Consensus | MSLGAENSVAYSNNSIAI (SEQ ID NO: 31) | Spike Other | 697 | 714 | 18 | 10 |
| 6 + 7 | Super Consensus | SPRRA**RS**VASQSIIAYTMSLGAENSVAYSNNSIAI (SEQ ID NO: 32) | Spike Cleavage Site | 680 | 714 | 35 | 21 |
| 8.1 | Consensus | LPPLLTDEMIAQYTSAL (SEQ ID NO: 33) | Spike Other | 861 | 877 | 17 | 7 |
| 8.2 | Consensus | MIAQYTSALL (SEQ ID NO: 34) | | 869 | 878 | 10 | 2 |
| 8.X | Super Consensus | LPPLLTDEMIAQYTSALL (SEQ ID NO: 35) | | 861 | 878 | 18 | 9 |

Optimal Spacer Design

Epitopes were assembled into concatemers by extension from a published algorithm (Schubert et al., *Genome Medicine,* 8 (1): 9 (2016)) previously implemented in Fred2 (Schubert et al., *Bioinformatics,* 32(13): 1367-4803, 2044 (2016)). Spacers and epitope ordering should both be optimized to minimize neoepitope formation and to maximize MHC processing cut probability in the spacer regions. In theory, manipulating carefully chosen entries in the cost matrix to plus or minus infinity could provide optimized spacers, but the ILP solver in use (CBC) fails to solve the problem with infinite coefficients in the objective. In the new method the k-mer spacers were optimized for kmax={3, 6}. To properly optimize cutting and neoepitope formation at the termini of epitope chain inserts that were bounded at the C or N terminus by existing amino acid strings, a four-part modification was designed to improve upon the previous methods:

1. C/N-terminal bounding strings were added to the peptide set in the Traveling Salesman model (formulated as an ILP in Miller-Tucker-Zemlin form),
2. Spacer optimization was modified to generate spacers to the bounding sequences, on the correct terminus for all epitope peptides,
3. Constraints were added to the model to enforce correct ordering of epitopes and bounding sequences,
4. The objective was modified to ignore the missing entries in a TSP cost matrix introduced by the bounding sequences.

TABLE 2

| M2 and BM2 Protein SARS-COV2 Protein Amino Acid Sequences: Influenza A/PR/8 M2, Influenza B/Lee/40 BM2 and Chimeric Fusion Proteins Thereof |
|---|
| A/PR/8 M2 (SEQ ID NO: 1) 97 amino acid wild-type influenza A/Puerto Rico/1934 (H1N1) M2 protein.<br>MSLLTEVETPIRNEWGCRCNGSSDPLTIAANIIGILHLTLWILDRLFFKCIYRRFKYGLK<br>GGPSTEGVPKSMREEYRKEQQSAVDADDGHFVSIELE<br>UPPER CASE = M2 Protein<br>UNDER LINE = Transmembrane Domain<br>ITALIC = Canonical Proton Channel Residues |
| B/Lee/40 BM2 (SEQ ID NO: 2) 109 amino acid wild-type influenza B/Lee/1940 BM2 protein.<br>**MLEPLQILSICSFILSALHFMAWTIGHLNQIRRGVNLKIQIRNPNKEAINREVSILR**<br>**HNYQKEIQAKETMKKILSDNMEVLGDHIVVEGLSTDEIIKMGETVLEVEELQ**<br>BOLD UPPER CASE = BM2 Protein<br>BOLD UNDER LINE = BM2 Transmembrane Domain<br>ITALIC = Canonical Proton Channel Residues |
| A/PR/8 M2 (SEQ ID NO: 3) 25 amino acid influenza A/Puerto Rico/1934 (H1N1) M2 truncation protein.<br>MSLLTEVETPIRNEWGCRCNGSSDP<br>UPPER CASE = M2 Protein |
| /PR/8 M2 (SEQ ID NO: 4) 33 amino acid influenza A/Puerto Rico/1934 (H1N1) M2 truncation FLAG epitope tag fusion protein.<br>MSLLTEVETPIRNEWGCRCNGSSDP*AGAG***DYKDDDDK**<br>UNDERLINE UPPER CASE = M2 Protein amino acids 1 to 25<br>ITALIC UPPER CASE = Linker between antigen and epitope tag<br>BOLD UPPER CASE = FLAG epitope tag |
| A/PR/8 M2SR M2e + P delTM TM1.1 (SEQ ID NO: 5) 56 amino acid influenza A/Puerto Rico/1934 (H1N1) M2 truncation, SARS-COV-2 S1 antigen fusion protein.<br>MSLLTEVETPIRNEWGCRCNGSSDPIDLQELGKYEQYIKWPWYIWLGFIAGLIAIV<br>UNDERLINE UPPER CASE = M2 Protein amino acids 1 to 25<br>UPPER CASE = 31 amino acid selected MHC epitope smear, TM1.1, SARS-COV-2 S1 protein amino acids 1198 to 1228 |
| A/PR/8 M2SR M2e + P delTM TM1.1 FLAG (SEQ ID NO: 6) 68 amino acid influenza A/Puerto Rico/1934 (H1N1) M2 truncation, SARS-COV-2 S1 antigen, FLAG epitope tag fusion protein.<br>MSLLTEVETPIRNEWGCRCNGSSDPIDLQELGKYEQYIKWPWYIWLGFIAGLIAIV*AGA*<br>*G***DYKDDDDK**<br>UNDERLINE UPPER CASE = M2 Protein amino acids 1 to 25<br>UPPER CASE = 31 amino acid selected MHC epitope smear, TM1.1, SARS-COV-2 S1 protein amino acids 1198 to 1228<br>ITALIC UPPER CASE = Linker between antigen and epitope tag<br>BOLD UPPER CASE = FLAG epitope tag |
| A/PR/8 M2SR M2e + P delTM RBD 2.X (SEQ ID NO: 7) 52 amino acid influenza A/Puerto Rico/1934 (H1N1) M2 truncation, SARS-COV-2 S1 antigen fusion protein.<br>MSLLTEVETPIRNEWGCRCNGSSDPNLDSKVGGNYNYLYRLFRKSNLKPFER<br>UNDERLINE UPPER CASE = M2 Protein amino acids 1 to 25<br>UPPER CASE = 27 amino acid selected MHC epitope, RBD2.X, SARS-COV-2 S1 protein amino acids 440 to 466 |
| A/PR/8 M2SR M2e + P delTM RBD 2.X FLAG (SEQ ID NO: 8) 64 amino acid influenza A/Puerto Rico/1934 (H1N1) M2 truncation, SARS-COV-2 S1 antigen, FLAG epitope tag fusion protein.<br>MSLLTEVETPIRNEWGCRCNGSSDPNLDSKVGGNYNYLYRLFRKSNLKPFERAGAGD<br>**YKDDDDK**<br>UNDERLINE UPPER CASE = M2 Protein amino acids 1 to 25<br>UPPER CASE = 27 amino acid selected MHC epitope smear, RBD 2.X, SARS-COV-2 S1 protein amino acids 440 to 466<br>ITALIC UPPER CASE = Linker between antigen and epitope tag<br>BOLD UPPER CASE = FLAG epitope tag |
| A/PR/8 M2SR M2e + P delTM RBD 5.1 (SEQ ID NO: 9) 43 amino acid influenza A/Puerto Rico/1934 (H1N1) M2 truncation, SARS-COV-2 S1 antigen fusion protein.<br>MSLLTEVETPIRNEWGCRCNGSSDPYSVLYNSASFSTFKCYGV<br>UNDERLINE UPPER CASE = M2 Protein amino acids 1 to 25<br>UPPER CASE = 18 amino acid selected MHC epitope smear, RBD2.X, SARS-COV-2 S1 protein amino acids 365 to 382 |
| A/PR/8 M2SR M2e + P delTM RBD 5.1 FLAG (SEQ ID NO: 10) 55 amino acid influenza A/Puerto Rico/1934 (H1N1) M2 truncation, SARS-COV-2 S1 antigen, FLAG epitope tag fusion protein.<br>MSLLTEVETPIRNEWGCRCNGSSDPYSVLYNSASFSTFKCYGV*AGAG***DYKDDDDK**<br>UNDERLINE UPPER CASE = M2 Protein amino acids 1 to 25<br>UPPER CASE = 18 amino acid selected MHC epitope smear, RBD 5.1, SARS-COV-2 S1 protein amino acids 365 to 382 |

TABLE 2-continued

M2 and BM2 Protein SARS-COV2 Protein Amino Acid Sequences: Influenza A/PR/8 M2, Influenza B/Lee/40 BM2 and Chimeric Fusion Proteins Thereof ITALIC UPPER CASE = Linker between antigen and epitope tag
BOLD UPPER CASE = FLAG epitope tag A/PR/8 M2SR M2e + P delTM Concatemer 3MAX (SEQ ID NO: 11) 205 amino acid influenza A/Puerto Rico/1934 (H1N1) M2 truncation, SARS-COV-2 S1 antigen smear concatemer fusion protein.
MSLLTEVETPIRNEWGCRCNGSSDPLPPLLTDEMIAQYTSALLMNDNLDSKVGGNYN
YLYRLFRKSNLKPFERWNWSPRRARSVASQSIIAYSNWAALQIPFAMQMAYRFNGIG
VSWYSVLYNSASFSTFKCYGVSWGEVFNATRFASVYAWNRKRIGWMSLGAENSVA
YSNNSIAIYFWQELGKYEQYIKWPWYIWLGFIAGLI
UNDERLINE UPPER CASE = M2 Protein amino acids 1 to 25
UPPER CASE = 8 selected MHC epitope smears
UNDERLINE BOLD UPPER CASE = Linker of maximum length 3 amino acids between peptide smears A/PR/8 M2SR M2e + P delTM Concatemer 3MAX FLAG (SEQ ID NO: 12) 217 amino acid influenza A/Puerto Rico/1934 (H1N1) M2 truncation, SARS-COV-2 S1 antigen smear concatemer fusion protein.
MSLLTEVETPIRNEWGCRCNGSSDPLPPLLTDEMIAQYTSALLMNDNLDSKVGGNYN
YLYRLFRKSNLKPFERWNWSPRRARSVASQSIIAYSNWAALQIPFAMQMAYRFNGIG
VSWYSVLYNSASFSTFKCYGVSWGEVFNATRFASVYAWNRKRIGWMSLGAENSVA
YSNNSIAIYFWQELGKYEQYIKWPWYIWLGFIAGLI*AGAG*DYKDDDDK
UNDERLINE UPPER CASE = M2 Protein amino acids 1 to 25
UPPER CASE = 8 selected MHC epitope smears, SARS-COV-2 S1 protein
UNDERLINE BOLD UPPER CASE = Linker of maximum length 3 amino acids between peptide smears
ITALIC UPPER CASE = Linker between antigen and epitope tag
BOLD UPPER CASE = FLAG epitope tag A/PR/8 M2SR M2e + P delTM Concatemer 6MAX (SEQ ID NO: 13) 205 amino acid influenza A/Puerto Rico/1934 (H1N1) M2 truncation, SARS-COV-2 S1 antigen smear concatemer fusion protein.
MSLLTEVETPIRNEWGCRCNGSSDPLPPLLTDEMIAQYTSALLMNDNLDSKVGGNYN
YLYRLFRKSNLKPFERWNWSPRRARSVASQSIIAYSNWAALQIPFAMQMAYRFNGIG
VSWYSVLYNSASFSTFKCYGVSWGEVFNATRFASVYAWNRKRIGWMSLGAENSVA
YSNNSIAIYFWQELGKYEQYIKWPWYIWLGFIAGLI
UNDERLINE UPPER CASE = M2 Protein amino acids 1 to 25
UPPER CASE = 8 selected MHC epitope smears
UNDERLINE BOLD UPPER CASE = Linker of maximum length 6 amino acids between peptide smears A/PR/8 M2SR M2e + P delTM Concatemer 6MAX FLAG (SEQ ID NO: 14) 217 amino acid influenza A/Puerto Rico/1934 (H1N1) M2 truncation, SARS-COV-2 S1 antigen smear concatemer fusion protein.
MSLLTEVETPIRNEWGCRCNGSSDPLPPLLTDEMIAQYTSALLMNDNLDSKVGGNYN
YLYRLFRKSNLKPFERWNWSPRRARSVASQSIIAYSNWAALQIPFAMQMAYRFNGIG
VSWYSVLYNSASFSTFKCYGVSWGEVFNATRFASVYAWNRKRIGWMSLGAENSVA
YSNNSIAIYFWQELGKYEQYIKWPWYIWLGFIAGLI*AGAG*DYKDDDDK
UNDERLINE UPPER CASE = M2 Protein amino acids 1 to 25
UPPER CASE = 8 selected MHC epitope smears, SARS-COV-2 S1 protein
UNDERLINE BOLD UPPER CASE = Linker of maximum length 6 amino acids between peptide smears
ITALIC UPPER CASE = Linker between antigen and epitope tag
BOLD UPPER CASE = FLAG epitope tag

TABLE 3 cDNA Sequences Encoding M2 and Chimeric M2 Protein Amino Acid Sequences: Influenza A/PR/8 M2, Influenza B/Lee/40 BM2, Codon-Optimized Influenza A/PR/8 M2, Codon-Optimized Influenza B/Lee/40 BM2, and Codon-Optimized Chimeric Fusion Proteins Thereof.

A/PR/8 M2 (SEQ ID NO: 15) wild-type influenza A/Puerto Rico/1934 (H1N1) M2 cDNA.
5'ATGAGTCTTCTAACCGAGGTCGAAACGCCTATCAGAAACGAATGGGGG
TGCAGATGCAACGGTTCAAGTGATCCTCTCACTATTGCCGCAAATATCAT
TGGGATCTTGCACTTGACATTGTGGATTCTTGATCGTCTTTTTTTCAAAT
GCATTTACCGTCGCTTTAAATACGGACTGAAAGGAGGGCCTTCTACGGAA
GGAGTGCCAAAGTCTATGAGGGAAGAATATCGAAAGGAACAGCAGAGTGC
TGTGGATGCTGACGATGGTCATTTTGTCAGCATAGAGCTGGAGtaa
UNDER LINE = Start Codon
Small Case = Stop Codon TABLE 3-continued cDNA Sequences Encoding M2 and Chimeric M2 Protein Amino Acid Sequences: Influenza A/PR/8 M2, Influenza B/Lee/40 BM2, Codon-Optimized Influenza A/PR/8 M2, Codon-Optimized Influenza B/Lee/40 BM2, and Codon-Optimized Chimeric Fusion Proteins Thereof.

B/Florida/06/2006 BM2 (SEQ ID NO: 16) wild-type influenza B/Florida/06/2006 BM2 cDNA.
5'**ATGCTCGAACCACTTCAGATTCTTTCAATTTGTTCTTTCATTTTATCA
GCTCTCCATTTCATGGCTTGGACAATAGGGCATTTGAATCAAATAAGAAG
AGGGGTAAACCTGAAAATACAAATAAGGAATCCAAATAAGGAGGCAATAA
ACAGAGAGGTGTCAATTCTGAGACACAATTACCAAAAGGAAATCCAAGCC
AAAGAAACAATGAAGAAAATACTCTCTGACAACATGGAAGTATTGGGTGA
CCACATAGTAGTTGAAGGGCTTTCAACTGATGAGATAATAAAAATGGGTG
AAACAGTTTTGGAGGTGGAAGAATTGCAAtaa**

TABLE 3-continued cDNA Sequences Encoding M2 and Chimeric M2 Protein Amino Acid Sequences: Influenza A/PR/8 M2, Influenza B/Lee/40 BM2, Codon-Optimized Influenza A/PR/8 M2, Codon-Optimized Influenza B/Lee/40 BM2, and Codon-Optimized Chimeric Fusion Proteins Thereof.

BOLD UNDER LINE = BM2 Start Codon
Bold Small Case = BM2 Stop Codon

A M2 OPT (SEQ ID NO: 17) codon-optimized wild-type influenza A/Puerto Rico/1934 (H1N1) M2 cDNA.
5'ATGTCCCTGCTGACCGAAGTGGAAACTCCTATTAGAAACGAGTGGGGC
TGTAGATGTAACGGCTCAAGCGACCCTCTGACCATTGCTGCCAACATCAT
TGGCATCCTGCACCTGACCCTGTGGATTCTGGACCGACTGTTCTTTAAGT
GCATCTACCGGAGATTCAAGTATGGACTGAAAGGAGGACCAAGCACAGAG
GGAGTGCCTAAATCCATGAGGGAGGAATACCGCAAAGAGCAGCAGAGCGC
CGTGGACGCAGATGATGGACATTTCGTGAGCATTGAACTGGAAtga
UNDER LINE = Start Codon
Small Case = Stop Codon BM2 OPT (SEQ ID NO: 18) codon-optimized wild-type influenza B/Lee/1940 BM2 cDNA.
5'ATGCTGGAACCACTGCAGATCCTGAGTATTTGCTCTTTTATCCTGAGC
GCACTGCACTTTATGGCCTGGACTATCGGGCACCTGAACCAGATCAGAAG
GGGCGTGAACCTGAAGATCCAGATCAGAAACCCAAACAAGGAGGCCATCA
ACCGCGAAGTGAGCATCCTGAGACACAATTACCAGAAGGAGATCCAGGCT
AAAGAAACCATGAAGAAAATCCTGTCTGACAATATGGAGGTGCTGGGCGA
TCACATCGTGGTGGAAGGACTGAGCACCGACGAAATCATCAAAATGGGCG
AGACTGTCCTGGAAGTGGAAGAACTGCAGtaa
BOLD UNDER LINE = BM2 Start Codon
Bold Small Case = BM2 Stop Codon

Example 2

This example demonstrates successful expression of a SARS-CoV-2 receptor binding domain (RBD) antigen from an influenza A M2SR vector.

Figure 1:
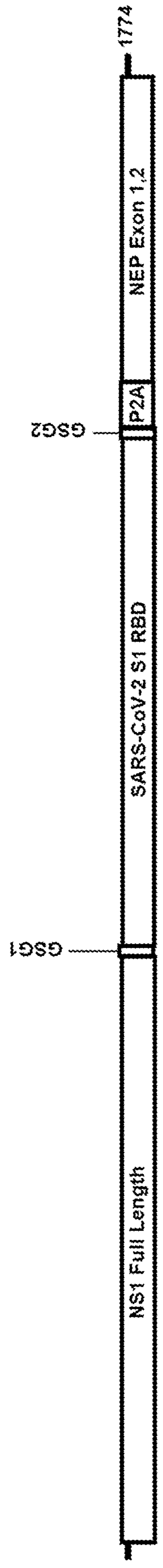

To express the SARS-CoV-2 RBD antigen from the influenza A M2SR vector an engineered NS segment 8 was constructed synthetically (FIG. 1). The designed gene was then inserted into a RNA Pol I vector for expression as negative sense vRNA. The segment 8 was designed to express a single fusion polypeptide of three major open reading frames (ORFs): first the complete influenza A PR/8/1934 NS1 protein, a flexible GSG linker, amino acids 331-530 of SARS-COV-2 Wuhan-Hu-1 spike S1 protein, another GSG linker, and the PR8 nuclear export protein (NEP or NS2) ORF. The NS1 to RBD fusion protein was separated from NEP by the P2A peptide derived from porcine teschovirus-1 2A. During translation, the P2A site allows expression of the downstream NEP protein as a separate polypeptide by an unknown mechanism, thought to involve ribosome slippage. For example, the NEP protein may be represented by SEQ ID NO: 108. Thus, the required function of NEP was maintained and NS1 functionality should be preserved because the entire NS1 ORF was also maintained. Artificial segments 8 may be unstable due to at least 2 reasons. To improve the stability of the sequence two changes were implemented. When splicing was eliminated a portion of the segment that encodes NEP exon 1 and part of exon 2 had to be duplicated (see FIGS. 21 and 22). So, a number of silent mutations were introduced throughout both the NS1 and NEP ORFS to reduce the homology between these duplications. Additionally, both the GSG and the P2A site sequences were optimized to reflect the A-T rich codon bias of influenza. The SARS-CoV-2 sequence was not changed as it was already >60% A-T.

Figure 2:
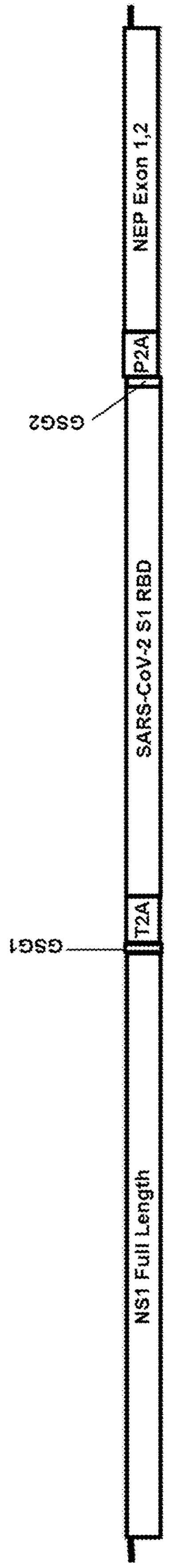

It is possible that the NS1-RBD fusion may not perform the NS1 functions or the NS1 function may be impaired. If so, the recombinant virus may be deficient in ability to alter mRNA polyadenylation and splicing as well to repress both interferon and RIG-I mediated innate responses. To address this possibility, another construct with a cleavage site from thosea asigna virus 2A (T2A) between the NS1 and the RBD was constructed (FIG. 2). This design was intended to allow expression of three separate polypeptides: NS1, RBD and NEP.

The vectors encoding new CoV2 NS segments were used in standard plasmid based influenza virus reverse genetics procedure to rescue the M2 deficient single replication (M2SR) viruses with SARS-CoV-2 RBD segment 8. Both viruses were obtained successfully using the HA and NA segments from WHO-recommended vaccine strain of A/Singapore/INFIMH-16-0019/2016 IVR-186 (H3N2). Virus were recovered using M2VeroA cells that were engineered to constitutively express the M2 protein (SEQ ID NOs: 1, 15, 17) missing from M2SR grown in animal origin free (AOF) media. This virus rescue and culture system was appropriate for preparation of virus seed for cGMP production of M2SR vaccine candidate intended for testing in human clinical trial.

Figure 3:
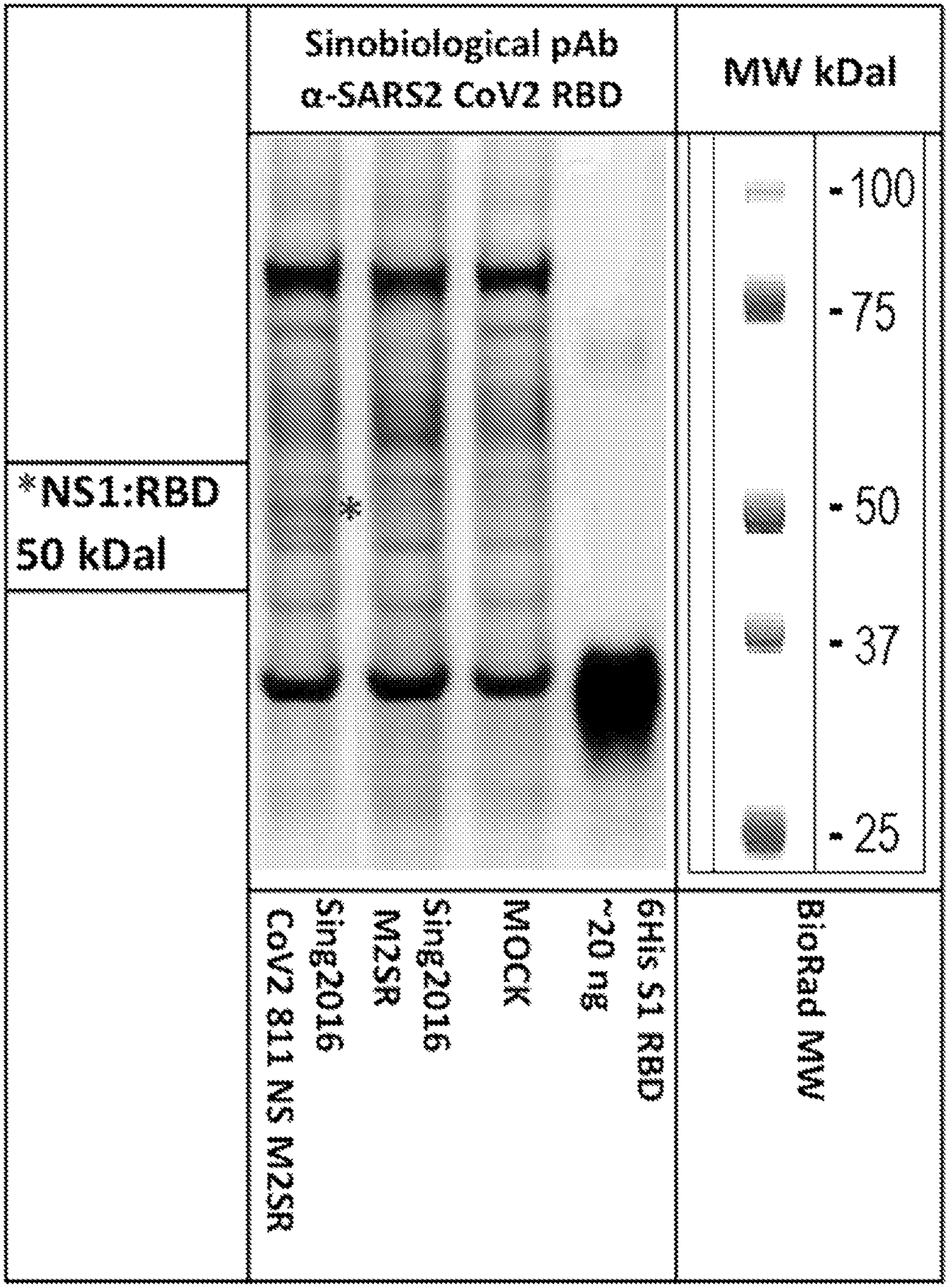

Expression of the NS1 SARS-CoV-2 fusion construct was tested by infecting Vero cells with the CoV2 NS1 M2SR virus strain at high multiplicity of infection (MOI)>1.0. Both a MOCK no virus and Singapore 2016 M2SR with no RBD insert infections were also performed. Eleven hours after inoculation cells were harvested for immunoblot analysis of total cell lysates. Results indicate that antisera to SARS RBD binds a protein of the expected size. The band was only detected in the RBD virus infected cell extract but not in the controls (FIG. 3).

Figure 4:
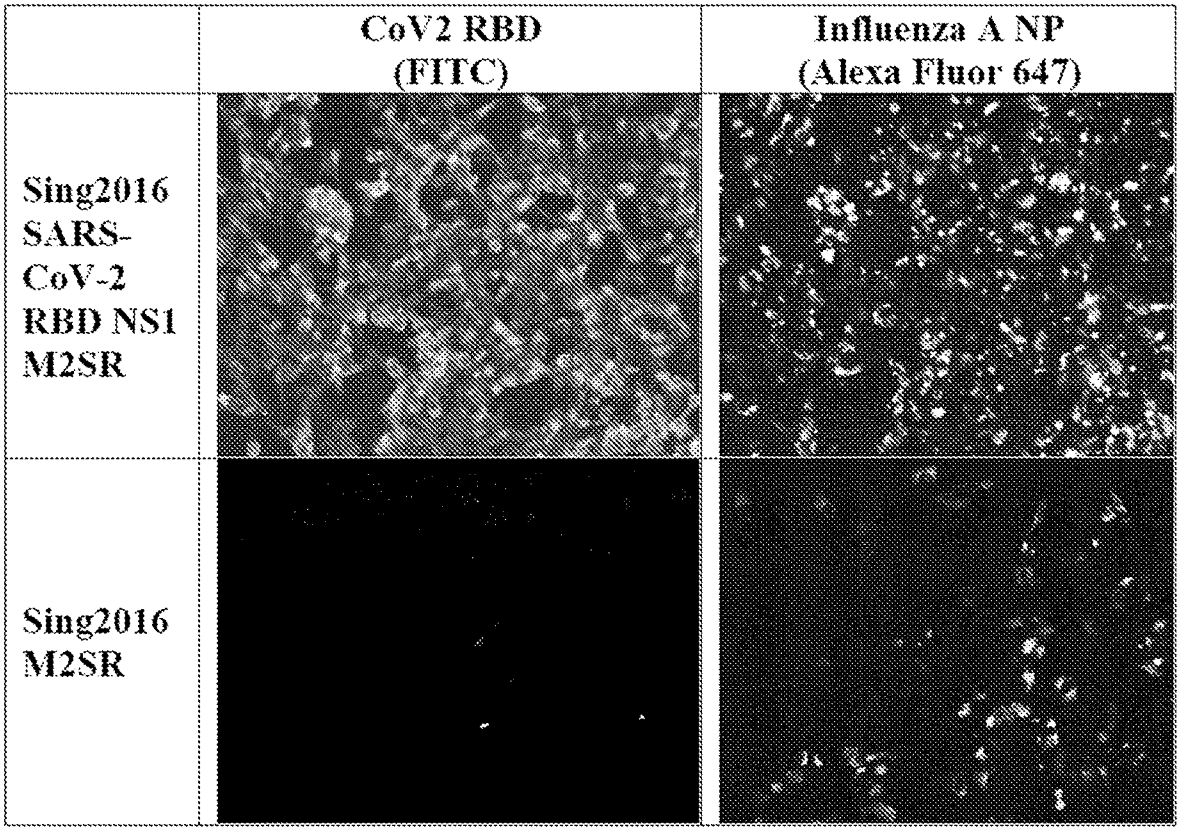

To confirm expression of the NS1 SARS-CoV-2 fusion construct the same Vero cells were infected at high MOI and cells were fixed with formalin for immune-fluorescent staining. Cells were incubated with antisera to antisera to SARS RBD. After washing cells were stained by an anti-Rabbit Fluorescein Isothiocyanate (FITC) labeled secondary and an anti-influenza A NP antibody direct labeled by ALEXA FLOUR' 647. Images shown in FIG. 4 show that both CoV-2 NS1 M2SR and the standard M2SR infected cells express detectable levels of the influenza A NP protein. Meanwhile the FITC labeling of the RBD could only be detected in CoV-2 NS1 M2SR infected cells which gave significant detectable fluorescence. The staining indicates that the NS1-RBD fusion protein is cytoplasmic.

Example 3

This example demonstrates successful expression of SARS-CoV-2 RBD from the influenza B BM2SR vector.

Figure 5:
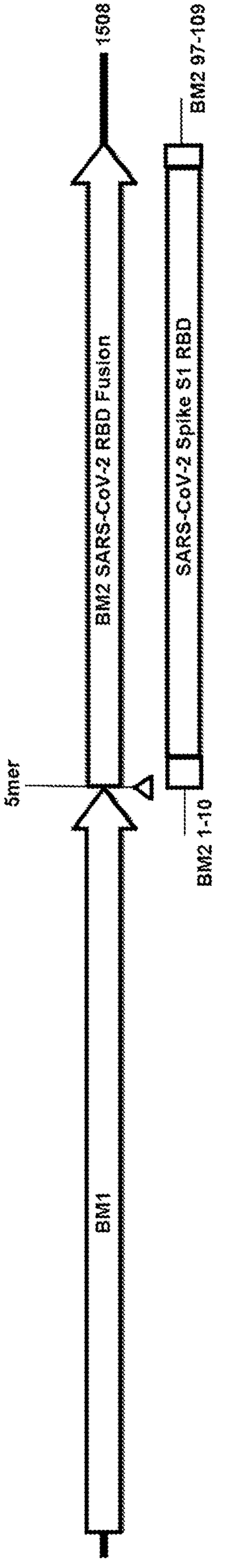
Figure 6:
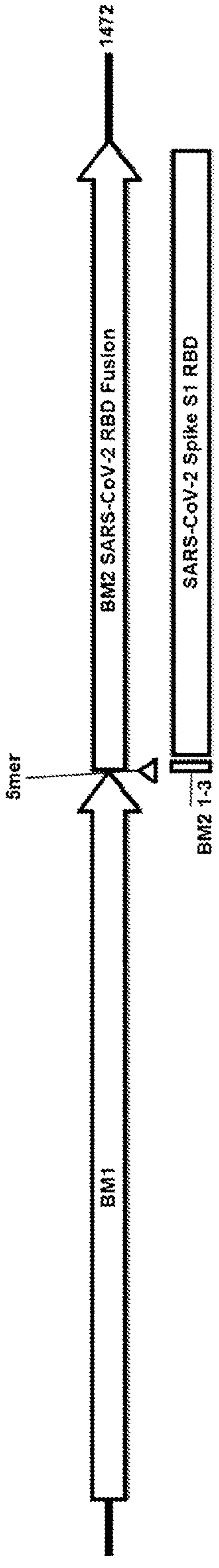

To express the SARS-CoV-2 RBD antigen from the influenza B BM2SR vector engineered influenza BM2-deficient segment 7s were constructed synthetically (FIG. 5-6, SEQ ID NOs: 83, 84). The designed gene segments were then inserted into an RNA Pol I vector for expression as negative sense vRNA. The segment 7s were designed to express 2 polypeptide ORFs from within a single viral mRNA: first the complete influenza B/Florida/4/2006 M1 protein, a 5-mer ribosomal stop-start slippage site; and second a fusion protein of BM2 to amino acids 330-524 of SARS-COV-2 Wuhan-Hu-1 spike S1 protein. A 5 base (5-mer) sequence motif found naturally between BM1 and BM2, TTATG (SEQ ID NO: 20), contains both BM1 ORF translation stop codon (bold) and the start codon for BM2

ORF (italics). Ribosome slippage and re-initiation of translation allows the viral expression of BM2 in a second reading frame without need for splicing, in contrast to the influenza A segment 7. In the synthetic SARS-CoV-2 RBD-containing influenza B segment 7 a small portion of the BM2 ORF was fused to the S1 RBD (SEQ ID NOs: 95, 96).

Artificial influenza segments may be unstable leading to poor virus growth in culture that is incompatible with manufacturing. This due to at least two reasons. First expression of an essential activity, in this case the M1 matrix protein may be impacted. To maintain the stability of the sequence the local RNA structure near the 5-mer was maintained so that M1 translation was not affected. Thus, amino terminal amino acids of BM2 ORF were fused to the SARS-CoV-2 RBD. A segment may be lost due to low packaging efficiency. The termini of all influenza genomic segments are self-complementary so they can pair via hybridization, initiating formation of a complex tertiary structure dependent on sequences both untranslated and translated located up to 100 bp from both ends of the segment. Preservation of the correct UTR of the segment was paramount. In the vaccine segment 7 coronavirus sequence was fused to the influenza B 3' UTR (mRNA sense). The UTR was longer than the UTR of influenza A at 85 bp long. Two versions were constructed. A more conservative version encodes insertion of the RBD into BM2 so that longer stretches from both ends of the BM2 ORF were preserved (FIG. 5, SEQ ID NO: 84). The longer version retains 10 and 13 terminal amino acids of BM2 respectively (FIG. 6, SEQ ID NO: 96).

A more trimmed down version only contains 9 bp, 3 residues of the N-terminus of BM2 fused to RBD (SEQ ID NO: 95) and then directly to the segment UTR (FIG. 6, SEQ ID NO: 83). The SARS-CoV-2 sequences were examined to see if they reflect the A-T rich codon bias of influenza. The SARS-CoV-2 sequence was not altered as it was already about 60% A-T.

The vectors encoding 2 SARS-CoV-2 M segments (SEQ ID NOs: 83, 84) were used in standard plasmid-based influenza virus reverse genetics procedure to rescue the BM2-deficient single-replication (BM2SR) viruses containing SARS-CoV-2 RBD BM2SR segment 7. Both viruses were obtained successfully using the HA and NA segments from WHO-recommended vaccine strain of B/CA/12/2015 (YL). Virus were recovered using BM2Vero cells that were engineered to constitutively express the BM2 protein (SEQ ID NOs: 2, 16, 18) missing from BM2SR virus grown in animal origin free (AOF) media. This virus rescue and culture system was appropriate for preparation of virus seed for cGMP production of BM2SR vaccine candidate intended for testing in human clinical trial.

Figure 7:
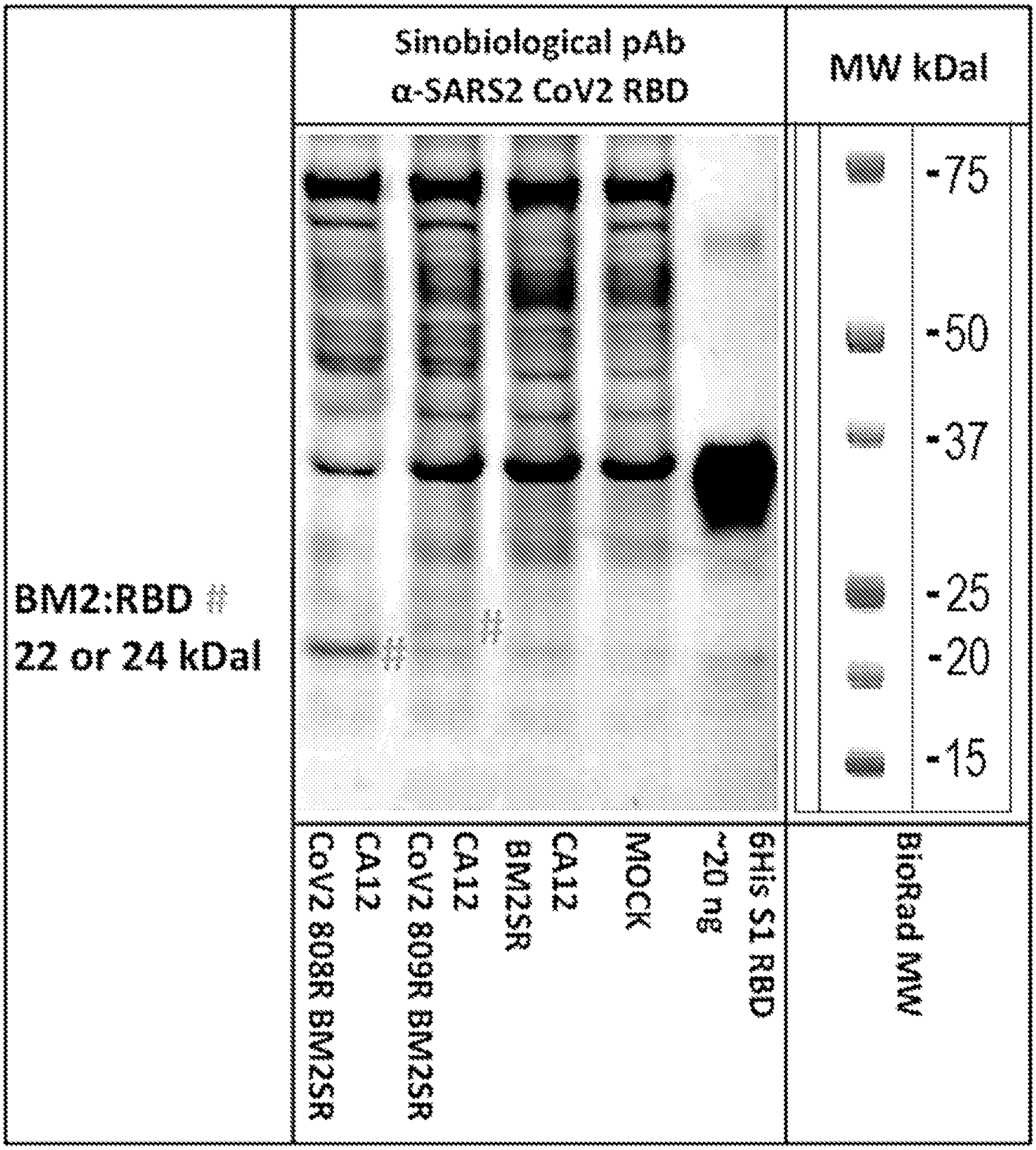

Expression of the SARS-CoV-2 BM2 fusion protein constructs (SEQ ID NOs: 95, 96) were tested by infecting Vero cells with the CoV-2 BM2SR virus strain at high multiplicity of infection (MOI)>1.0. Both a MOCK no virus and vector only CA12 BM2SR with no RBD insert infections were also performed. Eleven hours after inoculation cells were harvested for immunoblot analysis of total cell lysates. Results indicate that antisera to SARS RBD binds a protein of the expected size. The bands were only detected in the RBD virus infected cell extracts and not in the control extracts (FIG. 7). These results suggest that the minimal 22 kDa RBD construct expresses to higher levels than the longer 24 kDa version.

Example 4

This example demonstrates that M2SR and BM2SR viruses that encode sequences from SARS-CoV-2 were attenuated in vivo.

Seven-week-old BALB/c, female mice were immunized intranasally with the following viral constructs as shown in Table 4. The M2SR and BM2SR backbone sequences and sequences for the segments encoding the SARS-CoV-2 sequences are set forth in SEQ ID NOs: 43-47, 56, 58, 60, 63-67, 73, 80, 83, 95, 97 and 107. These viruses were administered at a dose of $1\times10^6$ $TCID_{50}$ per mouse. A control group of mice was given DPBS, pH 7.2 containing 10% sucrose and 5 mM sodium glutamate (SPGNa). The mice were observed for 14 days after immunization for any change in body weight and symptoms of infection.

TABLE 4

| Vaccine Groups | | | | |
|---|---|---|---|---|
| Flu A M2SR | cage | Prime antigen | Boost antigen | N |
| Mouse | 1 | AM2SR-CovidS-1 | AM2SR-CovidS-1 | 6 |
| exp. C1 | 2 | AM2SR-CovidS-1 | Covid-S1 protein IM | 6 |
| Group A | 5 | M2SR-Sing V5 (empty vector) | M2SR-Sing V5 | 6 |
| | 6 | M2SR-Sing V5 (empty vector) | Covid-S1 protein IM | 6 |
| | 9 | PBS/SPGNa | Covid-S1 protein IM | 3 |
| | 10 | PBS/SPGNa | PBS/SPGNa | 6 |
| Flu B BM2SR | cage | Prime antigen | Boost antigen | n= |
| Mouse | 3 | BM2SR-CovidS-1 | BM2SR-CovidS-1 | 6 |
| exp. C1 | 4 | BM2SR-CovidS-1 | Covid-S1 protein IM | 6 |
| Group B | 7 | BM2SR-CA12 (empty vector) | BM2SR-CA12 | 6 |
| | 8 | BM2SR-CA12 (empty vector) | Covid-S1 protein IM | 6 |
| | 9 | PBS/SPGNa | Covid-S1 protein IM | 3 |
| | 10 | PBS/SPGNa | PBS/SPGNa | 6 |

Figure 8A:
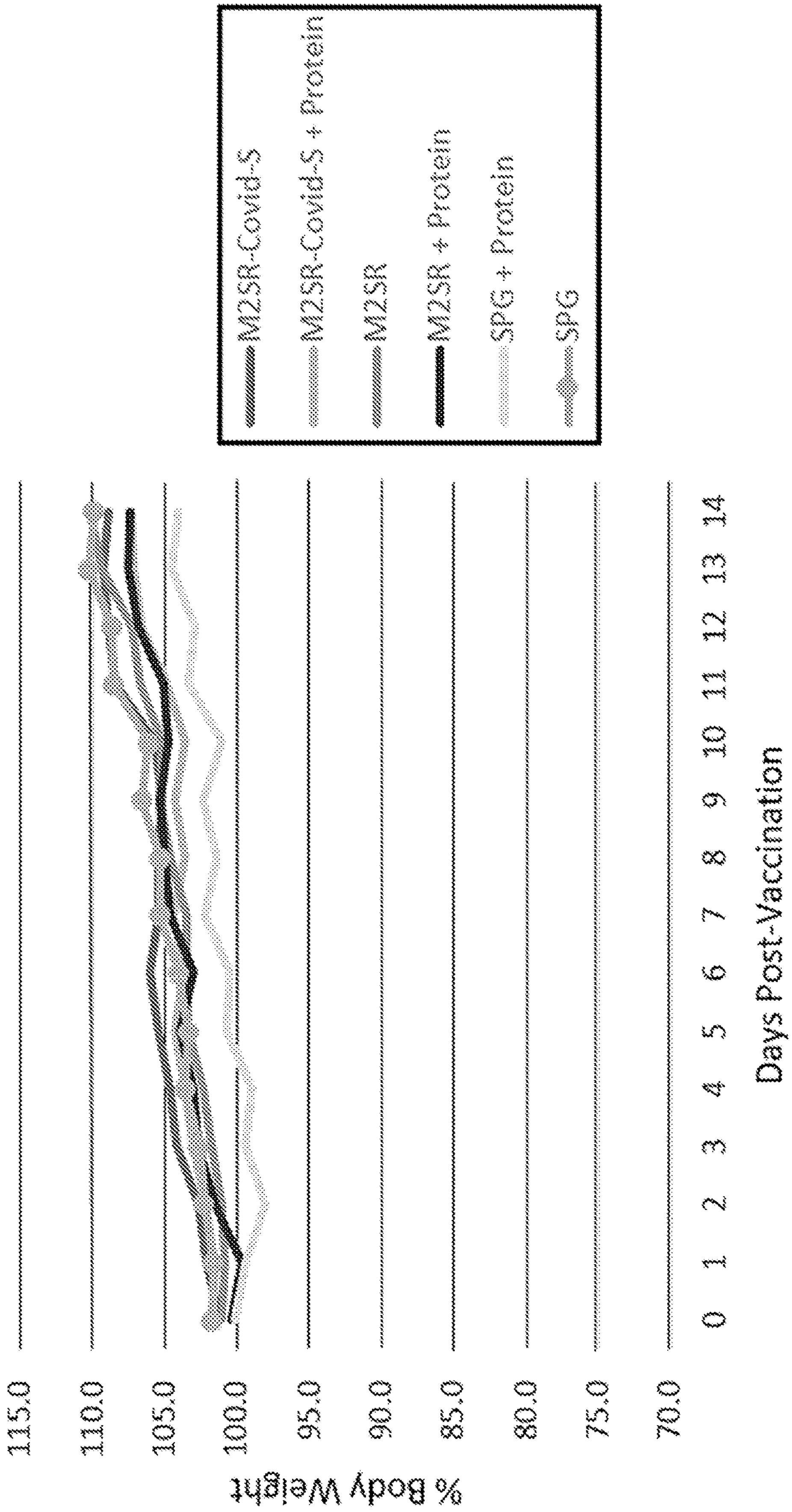
FIG. 8A is a graph depicting mouse percent body weight change after immunization with the M2SR recombinant viruses.
Figure 8B:
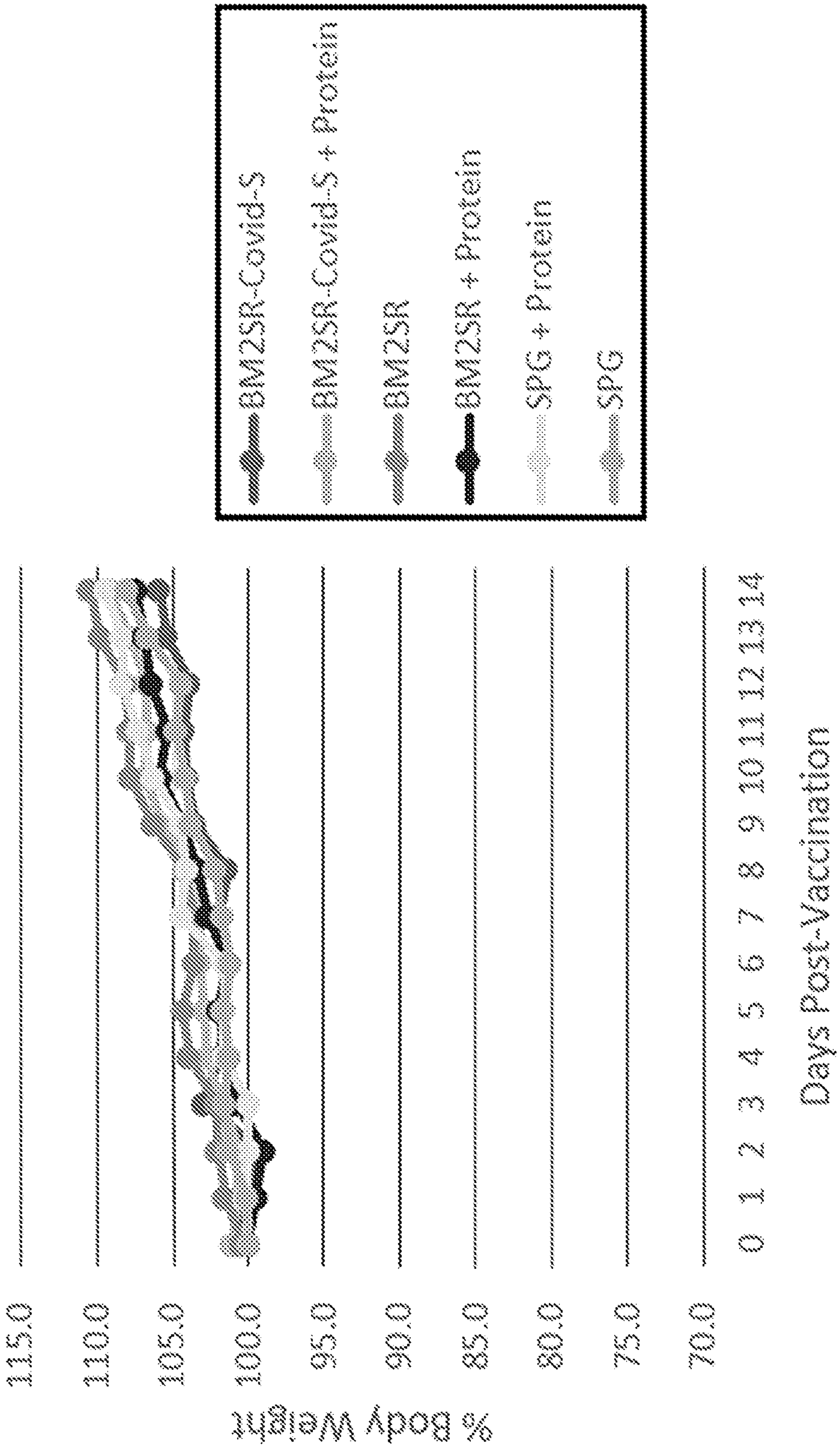
FIG. 8B is a graph depicting mouse percent body weight change after immunization with the BM2SR recombinant viruses.

No clinical symptoms of infection or body weight loss were observed in mice immunized with the M2SR or BM2SR mutants or SPG control over the 14-day period. FIG. 8A depicts the mouse percent body weight change after immunization for the M2SR recombinant viruses and FIG. 8B for the BM2SR recombinant viruses. Moreover, the change in body weight between the groups was comparable over the 14-day period. These results indicate that the M2SR and BM2SR viruses that contain SARS-CoV-2 sequences were attenuated and not pathogenic in mice.

Example 5

This example demonstrates that M2SR and BM2SR viruses from Example 4 elicit antibody responses against SARS-CoV-2.

Serum was collected from mice before prime immunization and about 3 weeks after the primary dose. Anti-spike RBD serum IgG antibody titers from the serum samples were pooled for each group were determined by enzyme-linked immunosorbent assay (ELISA).

The ELISA was performed using soluble SARS-CoV-2 recombinant RBD protein with a C-terminal HIS-tag expressed in 293T cells and purified by using COMPLETE™ His-Tag Purification resin (F. Hoffmann-La Roche AG, Basel, Switzerland). The ELISA plates were coated overnight at 4° C. with 100 μL of the RBD protein at a concentration of 2 μg/mL in phosphate-buffered saline (PBS). After blocking the plate with PBS containing 0.1% polysorbate 20 (PBS-T) and 1% gelatin from cold water fish skin, the plates were incubated in duplicate with mouse serum diluted in PBS-T with 1% gelatin from cold water fish skin. After a two-hour incubation at room temperature, the plates were washed with PBS-T six times and then incubated with anti-mouse IgG secondary antibody conjugated with horseradish peroxidase (KPL; 1:2,000 dilution in PBS-T with 1% gelatin from cold water fish skin). After a one-hour incubation with the secondary antibody, the plates were washed six times with PBS-T and then developed with 1-STEP™ Ultra TMB-ELISA Substrate Solution (Thermo Fisher Scientific, Waltham, MA). After a ten-minute incubation, the reaction was stopped with the addition of 4N sulfuric acid. The absorbance was measured at a wavelength of 450 nm ($OD_{450}$). Endpoint titers were the reciprocal of the dilution that was above the cut-off value determined by subtracting the mean value of the blanks plus 6× standard deviations.

Figure 9:
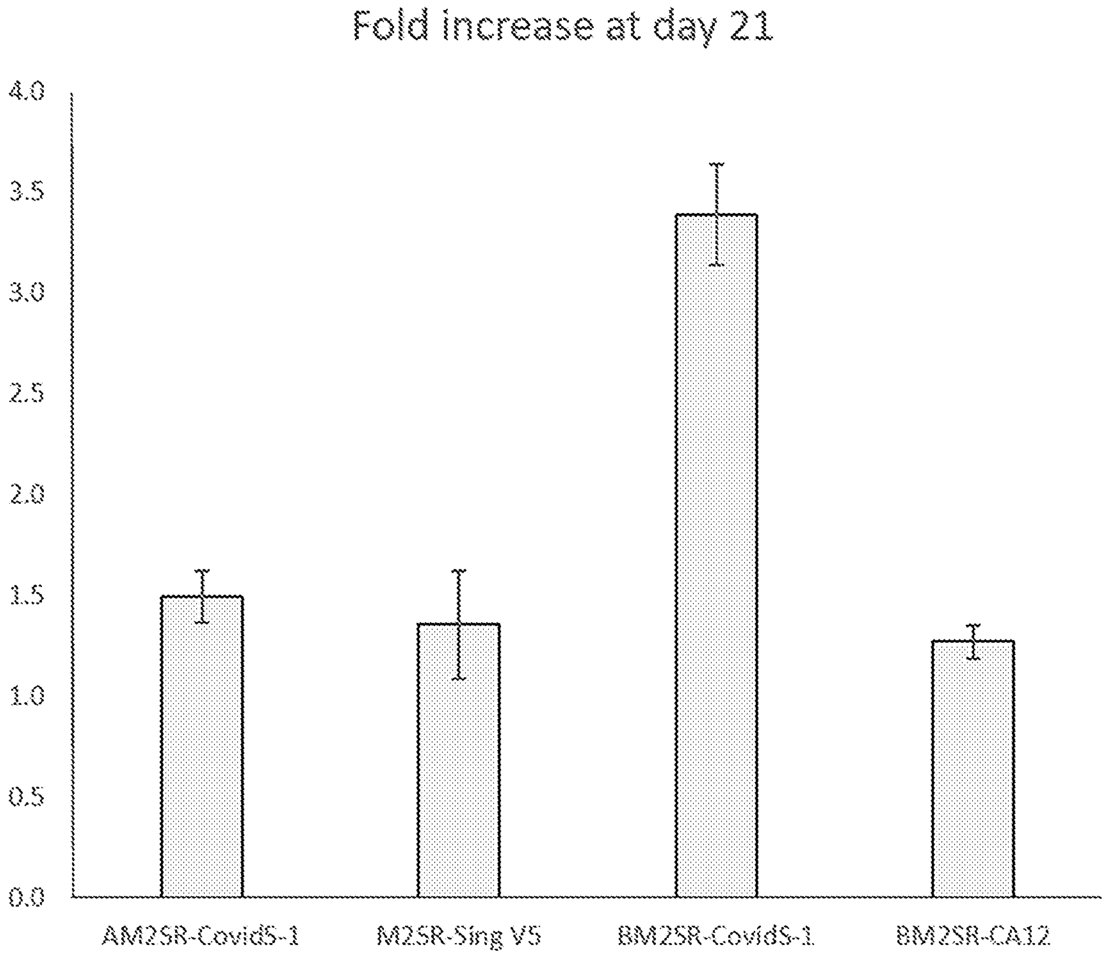
FIG. 9 is a bar graph showing the fold increase in enzyme-linked immunosorbent assay (ELISA) titer from pre-immunization baseline.

The fold increase in ELISA titer from pre-immunization baseline is shown in FIG. 9. The empty vectors that did not encode spike RBD sequences did not show an increase in ELISA titer on day 21. The M2SR and BM2SR viruses that encoded SARS-CoV-2 sequences elicited an increase in RBD spike ELISA titer.

Example 6

This example demonstrates that systemic antibodies are generated after a second dose of vaccine used for prime or spike protein.

Four dosing regimens of viruses in Example 4 were assessed: (1) mice primed with one of the M2SR-COVID-19 vaccine candidates (i.e., AM2SR-CovidS-1) or M2SR vector virus (i.e., M2SR-Sing V5) and then boosted with the same (i.e., AM2SR-CovidS-1 or M2SR-Sing V5) intranasally approximately 4 weeks post prime, (2) mice primed with one of the M2SR-COVID-19 vaccine candidates (i.e., AM2SR-CovidS-1) or M2SR vector virus (i.e., M2SR-Sing V5) intranasally and boosted about 4 weeks post prime with purified SARS-CoV-2 protein intramuscularly, (3) mice primed with one of the BM2SR-COVID-19 vaccine candidates (i.e., BM2SR-CovidS-1) or BM2SR vector viruses (i.e., BM2SR-CA12) and then boosted with the same intranasally approximately 4 weeks post prime, and (4) mice primed with one of the BM2SR-COVID-19 vaccine candidates (i.e., BM2SR-CovidS-1) or BM2SR vector viruses (i.e., BM2SR-CA12) intranasally and boosted about 4 weeks post prime with purified SARS-CoV-2 protein intramuscularly. All mice were terminally bled then euthanized about 3 weeks post-secondary immunization (boost) and serum samples were collected for analysis.

Serum samples were analyzed by ELISA as described above with respect to Example 5.

The anti-SARS-CoV-2 RBD IgG titers are shown in FIG. 28. The empty vectors that do not encode spike RBD sequences (i.e., M2SR-Sing V5 and BM2SR-CA12) administered twice (prime-boost) did not elicit an increase in RBD spike ELISA titer. The M2SR and BM2SR viruses that encoded SARS-CoV-2 sequences (i.e., AM2SR-CovidS-1 and BM2SR-CovidS-1) administered twice (prime-boost) elicited an increase in RBD spike ELISA titer. Priming with M2SR and BM2SR viruses that encoded SARS-CoV-2 sequences (i.e., AM2SR-CovidS-1 and BM2SR-CovidS-1) substantially increased the RBD spike ELISA titer when boosted with purified SARS-CoV-2 protein whereas priming with empty M2SR vector viruses did not elicit a substantial increase in RBD spike ELISA titer when boosted with purified SARS-CoV-2.

Example 7

This example demonstrates that the M2SR and BM2SR vectors can be used in multivalent formulations and retain immunogenicity to each.

Influenza A H1N1 or H3N2 FGHY1-M2SR or BM2SR-Vic or BM2SR-Yam viruses elicit antibody responses when formulated as a monovalent, bivalent, trivalent, or quadrivalent vaccine.

Seven-week-old BALB/c female mice (N=8) were immunized intranasally with monovalent H1N1 FGHY1-M2SR, monovalent H3N2 FGHY1-M2SR, bivalent H1N1 and H3N2 FGHY1-M2MR, monovalent BM2SR-Victoria, monovalent BM2SR-Yamagata, bivalent BM2SR, trivalent H1N1 and H3N2 FGHY1-M2SR and BM2SR Victoria or Yamagata, or quadrivalent H1N1 and H3N2 FGHY1-M2SR and BM2SR Victoria and Yamagata vaccines. A control group of mice were mock immunized with SPG. At 28 days after vaccination, the mice were immunized intranasally with a boost immunization consisting of the same vaccine administered for the prime immunization. Serum samples were taken on days 7, 14, and 21 following prime immunization and on days 35, 42 and 49 following the boost immunization (day 28). Anti-H1 HA, anti-H3 HA, anti-influenza B-Vic HA and anti-influenza B-Yam HA serum IgG antibody titers from the serum samples were determined by ELISA.

The resulting anti-H1 HA data is shown in FIG. 10A. The resulting anti-H3 HA data is shown in FIG. 10B. The resulting anti-influenza B-Vic HA data is shown in FIG. 10C. The resulting anti-influenza B-Yam HA data is shown in FIG. 10D. The results demonstrated that all vaccines were able to elevate anti-influenza virus antibodies above SPG control and that these increases were comparable across vaccine formulations. Further, these results demonstrate that the monovalent components maintain ability to elicit immune responses to the monovalent components when formulated into multivalent vaccines.

Example 8

This example is expected to demonstrate that the M2SR-SARS-CoV-2 vaccine elicits antibody responses in vivo that were increased upon repeat dosing with no toxicity to the host.

To demonstrate that the M2SR-SARS-CoV-2 vaccine virus elicits immune responses against the component without causing toxicity to the host, 15 male and 15 female ferrets will be immunized intranasally with the M2SR-SARS-CoV-2 vaccine at a dose level of $1\times10^8$ $TCID_{50}$ (low dose) or $1\times10^9$ $TCID_{50}$ (high dose). A third group of ferrets will be mock immunized intranasally with SPG as a placebo control. A three-dose vaccination regimen will be utilized for each treatment group. Ferrets will be administered the prime immunization (study day 1) and the 2 boost immunizations 13 and 27 days later (study days 14 and 28). Following each immunization, ferrets will be observed for 7 days for mortality, with body weights, body temperatures and clinical signs measured daily. Blood will be collected to assess clinical pathology pre-study and on study days 14, 16, 30, and 49 from all surviving ferrets. Serum samples will be collected pre-study and on study days 14, 30, and 49 to evaluate antibody levels over time by ELISA, hemagglutination inhibition (HAI) assay, and virus neutralization (VN) assay. Necropsy will be performed on 5 males and 5 females per group on study days 3, 30, and 49, including examination of the external surface of the body, all orifices, the cranial, thoracic and peritoneal cavities, and their contents.

Vaccine Virus Immunization. Ferrets will be immunized intranasally with three doses of an M2SR-SARS-CoV-2 vaccine at either a dose of $1\times10^8$ $TCID_{50}$ or a dose of $1\times10^9$ $TCID_{50}$. Vials of frozen vaccine virus stock will be thawed at room temperature for at least 10 minutes and then stored refrigerated, or on wet ice, until use. Ferrets will be anesthetized with ketamine/xylazine and the virus dose administered intranasally in a volume of 500 μL (250 per nare).

The M2SR-SARS-CoV-2 vaccine virus is a recombinant influenza A virus that does not express a functional M2 protein, encoding the HA and NA genes of influenza A/Singapore/INFIMH-16-0019/2016 (H3N2) and the RBD of the SARS-CoV-2 spike protein.

Experimental Design: Ninety (90) ferrets (Triple F Farms, Sayre, PA), 45 males and 45 females, 16 to 22 weeks old at the time of study initiation, will be utilized for the study. All animal procedures will be performed in an animal biosafety level 2 facility in accordance with the protocols approved by the animal care and use committee at IIT Research Institute. Prior to immunization, ferrets will be monitored for 4 days to establish baseline body temperatures. Temperature readings will be recorded daily through a transponder (BioMedic data systems, Seaford, DE) implanted subcutaneously in each ferret. Blood will be collected prior to study initiation, and serum tested for influenza antibodies. Pre-immunization serum samples will be treated with receptor destroying enzyme (RDE) (Denka Seiken, Tokyo, Japan) to remove nonspecific inhibitors, then serially diluted, tested against a defined amount of influenza A/Michigan/45/2015 (H1N1), A/Singapore/INFIMH-16-0019/2016 (H3N2), B/Phuket/3073/2013 (Yamagata lineage), and B/Colorado/06/2017 (Victoria lineage) viruses and mixed with 0.5% turkey red blood cells. Antibody titers will be defined by the lowest serum dilution causing inhibition of red blood cell agglutination. Only ferrets with HAI titers less than 40 will be considered seronegative and used in this study. Study animals will be randomized and divided into 3 groups (15 male and 15 female ferrets/group).

To assess the vaccine efficacy and toxicity, ferrets will be immunized intranasally with three doses of $1\times10^8$ $TCID_{50}$ or three doses of $1\times10^9$ $TCID_{50}$ of the M2SR-SARS-CoV-2 on study days 1, 14, and 28. The control group will be mock immunized intranasally with SPG on study days 1, 14, and 28. Ferret body temperatures, weights, and clinical symptoms will be monitored daily for 7 days post-immunizations. Blood will be collected to assess clinical pathology on study days −5, 14, 16, 30, and 49 from all surviving ferrets. Serum samples will be collected on study days −5, 14, 30, and 49 and kept frozen at approximately −70° C. until measurement of antibody titer by ELISA, virus neutralization assay and HAI assay. All study animals will be euthanized on their scheduled dates (day 3, 30, or 49, 5 males and 5 females per group) and necropsied. Necropsy consists of examination of the external surface of the body, all orifices, and the cranial, thoracic and peritoneal cavities and their contents. The tissues will be collected, fixed, and evaluated histopathologically by a board-certified veterinary pathologist.

Moribundity/Mortality and Clinical Observations: All ferrets are expected to survive until their scheduled date of sacrifice. All ferrets are expected to have an activity level score of "0" (alert and playful) for all time points measured during Days 1-49.

Body Weights and Body Weight Changes: No differences are expected to be observed.

Body Temperatures: No differences are expected to be observed.

Enzyme-linked immunosorbent assay (ELISA): Anti-HA IgG antibody titers from serum samples will be determined by ELISA. ELISA plates will be coated by recombinant HA protein from A/Singapore/INFIMH-16-0019/2016 (H3N2) (Immune Technology Corp., New York, NY) or spike RBD, blocked by skim milk, and samples were applied. Ferret IgG antibodies were detected by horseradish peroxidase labeled anti-ferret IgG goat antibodies (SeraCare Life Sciences, Milford, MA) and 1-STEP™ Ultra TMB-ELISA (Thermo Fisher Scientific Inc.) substrate.

Ferrets in each of the immunized groups are expected to show significant elevation of anti-H3 HA antibody in serum, while antibody levels in animals that received SPG only are not expected to change from baseline. Anti-H3 HA antibody titers will be higher in immunized groups than SPG control groups two weeks after the prime dose. Mean antibody titers per immunized group will be increased further following first and second administrations of the vaccine.

Hemagglutination Inhibition (HAI) Assay: To demonstrate the functional activity of antibodies detected by ELISA, serum samples will be analyzed by HAI assay. Serum samples will be treated with RDE to eliminate inhibitors of nonspecific hemagglutination. RDE will be reconstituted per the manufacturer's instructions. Serum will be diluted 1:3 in RDE and incubated 18-20 hours in a 37° C.±2° C. water bath. After the addition of an equal volume of 2.5% (v/v) sodium citrate, the samples will be incubated in a 56±2° C. water bath for 30±5 minutes. A solution comprised of 0.85% NaCl will be added to each sample to a final serum dilution of 1:10 after the RDE treatment. The samples will then be further diluted two-fold (1:10 to 1:1,280) in PBS and incubated with 4 hemagglutinating units of influenza A/Singapore/INFIMH-16-0019/2016 (H3N2) viruses. After incubation, 0.5% avian red blood cells will be added to each sample and incubated for 30±5 minutes. Presence or absence of hemagglutination will then be scored.

High dose ($1\times10^9$ $TCID_{50}$) groups are expected to show higher HAI titer than low dose ($1\times10^8$ $TCID_{50}$) groups, and the SPG (control) group is not expected to elicit any HAI titers. M2SR-SARS-COV-2 immunized ferrets are expected to demonstrate equal to or higher than 80 HAI titers against test virus. The CDC states that serum HAI antibody titers of 40 were associated with at least a 50% reduction in risk for influenza infection or disease in populations. Therefore, these results are expected to show that M2SR-SARS-COV-2 virus is able to elicit protective immune responses.

Virus Neutralization Assay: Pre-study and treatment phase serum samples (from study days 3, 14, 30, and 49) will be tested against A/Singapore/INFIMH-16-0019/2016 (H3N2) influenza virus in a virus neutralization assay. The serum samples will be inactivated at 56° C. for 30 minutes. The sera then will be serially diluted 2-fold and incubated with standardized virus (concentration of 80-140 PFU) at 37±2° C. in 5.0±1% $CO_2$ for 60 minutes. One hundred microliter (100 μL) of each serum and virus mixture will then be transferred into the respective wells of a 96-well plate containing a monolayer of MDCK cells. The plate (with samples) will then be incubated for 18-22 hours at 37±2° C. in 5.0±1% $CO_2$. After incubation, the cells will be fixed with paraformaldehyde and stained with an anti-influenza A nucleoprotein monoclonal antibody pool (1 part MAB8257:1 part MAB8258 (Millipore; Billerica, MA)) followed by peroxidase-conjugated goat anti-mouse IgG. The spots will be developed using TrueBlue Peroxidase Substrate (Kirkegaard and Perry Laboratories, Gaithersburg, MD). The plaques will be visualized and counted using an enzyme-linked immunospot (ELISPOT™) instrument (AID GmbH, Strassberg, Germany). The 50% plaque reduction neutralization titer ($PRNT_{50}$) will be calculated by counting plaques and reporting the titer as the reciprocal of the last serum dilution to show 50% reduction of the input control virus plaque count as based on the back-titration of control plaques.

Ferrets within the SPG group are expected to remain negative (titers ≤100) for the duration of the study. Ferrets who were immunized with M2SR-SARS-COV-2 at a dose of $1\times10^8$ $TCID_{50}$ are expected to have high geometric mean titers (GMT). Ferrets who were immunized with M2SR-SARS-COV-2 at a dose of $1\times10^9$ $TCID_{50}$ are expected to have higher GMT VN titers. All ferrets immunized with 3 doses of H3N2 M2SR-SARS-COV-2 at $1\times10^9$ $TCID_{50}$ are expected to exhibit the highest $PRNT_{50}$ titers.

Clinical Pathology: For all surviving ferrets, blood samples for the analysis of clinical chemistry, hematology and coagulation parameters will be collected from the jugular vein or vena cava pre-study and on days 3, 14, 16, 30, and 49. Animals will be fasted for 4-6 hours prior to blood collection. Ethylenediaminetetraacetic acid (EDTA) will be used as the anticoagulant for hematology samples, while sodium citrate will be used for coagulation samples. Samples for clinical chemistry will be collected without an anticoagulant. Urine samples will be collected directly from the bladder of each ferret at necropsy.

No treatment-related or toxicologically significant findings are expected to be noted for any of the clinical chemistry or hematology parameters evaluated during the study.

Gross Necropsy and Histopathology: Gross necropsy and histopathology will be carried out on study days 3, 30, and 49 for 5 males and 5 females per group. Intranasal immunization of M2SR-SARS-COV-2 to ferrets at a dose of $1\times10^8$ $TCID_{50}$ is expected to result in no gross findings. At a dose of $1\times10^9$ $TCID_{50}$, gross findings are expected to be noted in the lung (pigmentation, dark or mottled), and microscopic findings are expected to be noted in the lung (mixed cell infiltrates) on Day 3 and 30. After a 3-week recovery, on study day 49, no test article-related gross lesions are expected to be observed.

This example is expected to show that intranasal immunization of the M2SR-SARS-COV-2 vaccine virus does not spread in the vaccinated host and is not associated with any vaccine-related adverse events (e.g., elevated body temperature, loss of weight, or clinical signs). These results are expected to indicate that the M2SR-SARS-COV-2 virus elicits protective immune responses against homologous test virus after a single dose that can be further elevated with repeat dosing and is useful as an intranasal coronavirus vaccine.

Example 9

This example demonstrates the successful design and generation of several M2SR virus strains that express a variety of antigens derived from SARS-CoV-2 spike protein.

Influenza A NS segment 8 that encodes two non-structural proteins NS1 and NEP (nuclear export protein) can be modified to use influenza A as a vaccine vector to express antigens. NEP is required, while the NS1 ORF can be dispensable for viral replication. NS1 truncations can be isolated by repeated passage in Vero cell culture and even complete NS1 deletion strains can be constructed. NS1 does play very important roles in promoting influenza infection including alterations to splicing and blocking host cell innate response. NS1 mutations reduce viral titer making manufacture difficult, and more importantly they impair viral replication in primary cells and in vivo. A second major obstacle to vectorizing the NS segment is that the essential NEP protein is expressed from a spliced form of segment 8 mRNA. Splicing joins a short exon 1 sequence to an exon 2 in an alternate translational reading frame that overlaps with NS1 ORF coded for by unspliced mRNA.

To encode an antigen two important changes are made to the NS segment. First, splice donor (SEQ ID NO: 109) and acceptor sites are abolished. Then the sequences encoding NEP exon 1 and exon 2 are joined to construct the NEP ORF without intron. The result is an ORF encoding a single polypeptide wherein NS1 C-terminus is fused to NEP ORF separated by NS1 P2A peptide derived from porcine teschovirus-1 2A and a GSG flexible linker (SEQ ID NOs: 80, 85, 87-91, 97-104). During translation, the P2A site allows expression of NEP protein as a separate polypeptide by an unknown mechanism, thought to involve ribosome slippage. Genetic information encoding a desired vaccine antigen is inserted between the influenza ORFs, expressed either by fusion to NS1 or by addition of a second P2A or T2A peptide to cleave both sides of the antigen (SEQ ID NO: 86, 99). This arrangement results in an enlarged segment 8 carrying long repeats of the nucleotide sequences from within the NS1 ORF.

Unfortunately, such duplications are genetically unstable. Atypical hybridization between two portions of the segment during genome replication may induce influenza RNA polymerase errors typically leading to deletions and insertions and defective genomic RNA synthesis. The instability may be exacerbated in this case because the gene duplication includes NEP exon 1 sequences only 26 bp from the segment 8 terminus that are likely to important for genome packaging. Assembly of influenza genomic segments into the virion is mediated via the double stranded "pan handle" RNA structure formed by hybridization of inverted repeat sequences in the 5' and 3' UTR. Coding sequences near segment ends are also involved in packaging and silent mutations that are near segment termini have been shown to block viral replication. The duplicated region internal to the segment could compete for essential hybridization with the terminal UTR packaging sequences impairing virus assembly. The result is poor virus growth, low viral titer, and loss of transgene expression.

To improve genetic stability by reducing homology between tandem duplications in the engineered segment, key mutations were introduced to sequences encoding both the NS1 and NEP ORFs (SEQ ID NOs: 110, 111). Silent mutations were made to 3rd positions of codons encoding NS1 to cut potential for unintended expression by eliminating start codons and adding stop codons to any potential alternate translation reading frames. This reduces the chance for production of unintended neoantigens from both vector and insert sequences or both.

The exon 1 sequence duplication coding for the 10 N-terminal amino acids of NEP was significantly altered in two ways to reduce sequence identity between copies (FIG. 21, SEQ ID NOs: 80, 97, 110). The NEP is expressed by this construct via P2A cleavage site. Although the mechanism is not understood cleavage always leaves a single prolyl residue as a protein scar appended to the N terminus of the cleaved downstream peptide. The 3rd amino acid of NEP is already proline, suggesting these first 2 residues are not structurally relevant. Thus, the constructed NS segment was designed to express a 6 bp deletion N terminal mutant of NEP that begins at proline with no scar (SEQ ID NO: 117). The deleterious homology was further ameliorated by changing codon third positions yet maintaining high % A-T. Additionally, both the GSG and the P2A site sequences were codon optimized to reflect the A-T rich codon bias of influenza.

The splice negative NS segment containing the duplication (SEQ ID NO: 85, 98) was inserted into RNA Pol I plasmid vector for expression as negative sense vRNA. Standard plasmid-based influenza virus reverse genetics procedure was used to rescue M2 deficient single replication (M2SR) virus containing the engineered and control A PR/8/1934 segments 8. Recovered virus strains were amplified in M2VeroA cells and viral titer was determined. The strains were used to inoculate triplicate cultures at MOI=0.001 for comparison of growth kinetics. The four days following inoculation viral cultures were sampled and aliquots were stored frozen for later titration analysis. Following determination of virus titer by $TCID_{50}$, daily mean titers were computed. A plot (FIG. 12) of the curves for the two strains show that virus growth is not impaired by the synthetic segment expressing NS1 and NEP as a single self-cleaving peptide.

Several M2SR virus strains were generated that are designed to express a variety of antigens derived from SARS-CoV-2 spike protein were grown in M2VeroA cells as given in Table 5.

TABLE 5

M2SR SARS CoV-2 Vaccine Candidate Strains and Maximum Viral Titer

| Description | Vector | MAX Titer | SARS-CoV-2 S1 Position Start | End | Length |
|---|---|---|---|---|---|
| WT | PR8 M2SR, PR8 NS (unmodified) (SEQ ID NO: 107, 60) | 7.91 | N/A | N/A | N/A |
| A PR8 NS P2A no insert | PR8 NS1 P2A NEP (SEQ ID NOs: 85, 98) | 8.14 | N/A | N/A | N/A |
| A PR8 NS CoV-2 RBD fusion | PR8 NS1 Fusion P2A NEP (SEQ ID NOs: 80, 97) | 7.81[a] | 331 | 530 | 200 |
| CoV-2 RBD | PR8 NS1 T2A CoV2 P2A NEP (SEQ ID NO: 99) | 7.74 | 330 | 530 | 201 |
| NS1-CoV2 NTD fusion | PR8 NS1 Fusion P2A NEP (SEQ ID NOs: 87, 100) | <0.67[b] | 26 | 295 | 270 |
| NS1-CoV-2 NoP HELIX fusion | PR8 NS1 Fusion P2A NEP (SEQ ID NOs: 88, 101) | 6.67 | 942 | 1031 | 90 |
| NS1 CoV-2 2P HELIX fusion | PR8 NS1 Fusion P2A NEP (SEQ ID NOs: 89, 102) | 7.67 | 942 | 1031 | 90 |
| NS1 CoV-2 Connector fusion | PR8 NS1 Fusion P2A NEP (SEQ ID NOs: 90, 103) | 7.67 | 1073 | 1139 | 67 |
| NS1 CoV-2 HR2 fusion | PR8 NS1 Fusion P2A NEP (SEQ ID NOs: 91, 104) | 7.69 | 1140 | 1213 | 74 |
| CoV-2 MHC RBD 5.1 M2 fusion | PR8 M2SR M2 Fusion (SEQ ID NOs: 10, 55) | 7.19 | 365 | 382 | 18 |
| CoV-2 MHC RBD 2.X M2 fusion | PR8 M2SR M2 Fusion (SEQ ID NOs: 8, 105) | 7.50 | 440 | 466 | 27 |
| CoV-2 MHC TM1.1 M2 fusion | PR8 M2SR M2 Fusion (SEQ ID NOs: 6, 106) | 8.08 | 1198 | 1228 | 31 |
| CoV-2 RBD M2 fusion | PR8 M2SR Replacement M2 Exon 2 (SEQ ID NOs: 79, 92) | <0.67[b] | | | |
| CoV-2 RBD M1 fusion | PR8 M2SR splice negative with M1 fusion to S1 RBD with P2A site (SEQ ID NOs: 81, 93) | <0.67[b] | | | |
| CoV-2 RBD M2 fusion | PR8 M2SR splice negative with M1 fusion to S1 RBD with pentamer site (SEQ ID NOs: 82, 94) | <0.67[b] | | | |

[a]= $TCID_{50}$ performed in Vero cells
[b]= Assay limit of Detection

Example 10

This example demonstrates that the functionality of the NS vector segment to express an antigen that is the spike helix of the SARS-CoV-2 S1 protein.

The spike helix of the SARS-CoV-2 S1 protein is known to undergo a large conformational change that drives fusion between viral and cell membranes. Study of other viral spike protein helices including those of RSV and PIV has identified a set of 2 tandem proline mutations that improve performance by stabilizing the spike proteins as recombinant antigens. These two proline residues (2P) are in a turn between two shorter helices that exist in the spike protein pre-fusion conformation. This change locks the protein in pre-fusion conformation which results in dual benefits of far better recombinant protein expression and in neutralizing immunologic response to vaccination. The growth curve in FIG. 13 shows that segment 8 with NS1 fusion to unmodified SARS-CoV-2 helix antigen impairs the virus growth (SEQ ID NOs: 88, 101) as compared to wild-type. Replacement of the turn residues with 2P to lock the spike helix into prefusion form improves growth (SEQ ID NOs: 88, 102), perhaps by improving NS1 functionality.

Example 11

This example demonstrates successful expression of SARS-CoV-2 receptor binding domain (RBD) from the influenza A M2SR segment.

Various SARS-CoV-2 RBD antigens were expressed from engineered influenza A M2SR influenza A M2-deficient vector segments 7 (SEQ ID NOs: 122-124) that were constructed synthetically (FIG. 14). The designed gene segments were then inserted into an RNA Pol I vector for expression as negative sense vRNA. The segment 7 is designed to express 2 polypeptide open reading frames (ORFs) from a spliced viral mRNA: first the complete influenza A/PR/8/34 M1 protein, and second a fusion protein of M2 to antigens of SARS-COV-2 Wuhan-Hu-1 spike S1 protein. The viral expression of M2 in a second reading frame of the influenza A segment 7 occurs by splicing. To maintain essential M1 protein function from the synthetic SARS-CoV-2 containing influenza A segment 7 a portion of the M2 ORF is fused to the S1 RBD (SEQ ID NOs: 6, 8, 10, 79).

The vectors encoding SARS-CoV-2 M2SR segments were used in standard plasmid-based influenza virus reverse genetics procedure to rescue the M2-deficient single-replication (M2SR) viruses containing SARS-CoV-2 RBD M2SR segment 7. Both viruses were obtained successfully using the HA and NA segments from WHO-recommended vaccine strain of A/Singapore/2016 (H3N2). Virus were recovered using M2Vero cells that are engineered to constitutively express the M2 protein missing from M2SR virus grown in AOF media. This virus rescue and culture system is appropriate for preparation of virus seed for cGMP production of M2SR vaccine candidate intended for testing in human clinical trial.

Example 12

This example demonstrates that M2SR influenza virus is capable of driving expression of antigen anchored to the extracellular membrane of infected cells (see FIGS. 15-20 and 24-27).

Packaged virus produced in supportive M2 expressing substrate cells were anticipated to substantially lack protein encoded by the gene of interest, multimerization domain, or transmembrane domain, unless the antigen was directly fused with an influenza subunit that is incorporated, such as hemagglutinin, HA. The gene of interest (GOI) can be antigenically relevant elements of viral (including influenza), bacterial, fungal, or protozoal origin.

Proper expression of the antigen on the cell surface can be confirmed by immune fluorescence staining analyzed by flow cytometry of infected cells with monoclonal antibodies specific for an intended vaccine antigen encoded by virus. Different segments can be used to express the same antigen. An example antigen is SARS-CoV-2 Spike protein human ACE2 receptor binding domain (RBD). The RBD antigen can be expressed at cell surface using TM domains from another membrane protein. Fusion of RBD to the TM from respiratory syncytial virus (RSV) F protein was encoded by the NS1 segment from a single open reading frame (ORF) that contains P2A and T2A translational slippage sites that produce three peptides: NS1, NEP and the RBD-RSV TM fusion with T4 trimer domain. An alternate approach is fusion directly to the HA protein itself. HA is a membrane protein so fused antigen will be displayed as a trimer on the surface of infected cells and incorporated into the virion.

M2VeroA cells were inoculated at multiplicity of infection (MOI) between 1 to 10 by M2SR viruses expressing RBD at the membrane from either the NS1 segment or the HA segment. Infected cells were immune stained for surface expression of SARS-CoV-2 S1 RBD at 18-hours post-inoculation in FACS buffer (1×DPBS, 1% FBS) at 4° C. Live intact cells were stained using as primary a neutralizing monoclonal antibody CR3022 isolated from convalescent SARS-CoV-1 patient (ter Meulen et al., *PLoS Med.* 3(7): e237 (2006)) followed by detection with Alexa Fluor 488-labeled anti-human IgG secondary antibody as seen in FIGS. 24-25. Surface expression above background was detected from cells infected with virus expressing SARS-CoV-2 RBD antigen from either the NS or the HA segments.

Another respiratory virus that can be targeted is respiratory syncytial virus (RSV). The two major surface proteins of RSV, Fusion (F) and surface glycoprotein (G), are both important binding sites for monoclonal antibodies that can neutralize RSV. Human 293T cells were chemically transfected by influenza A replicon of 4 DNA plasmids to constitutively over express PA, PB1, PB2 and NP viral subunits required to express proteins encoded by an influenza RNA segment; and by a single plasmid expressing influenza HA genomic segment from RNA polymerase I promoter. The RSV G protein antigen was directly fused to the HA glycoprotein leading to expression of RSV G antigen on cell membrane. Live, intact cells were immune stained 48 hours post-transfection for surface expression of RSV G surface glycoprotein antigen at 48-hours post-transfection. Staining was in FACS buffer using primary mouse monoclonal antibody 131-2G (Chemicon) followed by detection with Alexa Fluor 488-labeled anti-mouse IgG secondary antibody. Surface expression above background was detected from cells infected with virus expressing RSV G protein antigen.

Multiple antigens from a single pathogen may be displayed on the membrane. Cells inoculated at MOI=1 with M2SR virus encoding SARS-CoV-2 S2 antigen express second alternate COVID vaccine target other than RBD on the surface as shown in FIG. 27. Intact live M2VeroA cells infected by virus at MOI=1 were immune stained for surface expression of SARS-CoV-2 spike S2 subunit antigen at 18-hours post-inoculation. Staining was in FACS buffer using primary rabbit monoclonal antibody 3C4 (Genscript) raised against SARS-CoV-2 S2 immuogen followed by detection with Alexa Fluor 488-labeled anti-rabbit IgG secondary antibody. Surface expression above background was detected from cells infected with virus expressing SARS-CoV-2 S2 connector and TM antigen.

Packaging signals are maintained upstream of the GOI for constructs for both HA and NS segments, and in the case of HA, the packaging signal can be duplicated to maintain proper HA processing. The duplicated packaging signal shall have silent mutations to eliminate its secondary interaction with the 5' packaging signal and help prevent undesired recombination events. Other embodiments may employ direct fusion of the antigen (e.g., sequences from Respiratory Syncytial Virus (RSV) Fusion (F) or Glycoprotein (G) or SARS-CoV2 spike sequences) to HA itself, in which case the packing sequence is not duplicated (FIGS. 24-27, SEQ ID NOs: 116-118). In many cases, the use of a multimerization domain (MD) would be preferred to enhance immunogenicity. Such a MD can be selected from a variety of motifs such as C-terminal domain of T4 fibritin (SEQ ID NO: 115, Foldon) or GCN4-p1 leucine zipper domain. The transmembrane domain (TM) can be that of the SARS-CoV2 spike predicted transmembrane helix amino acid 1214 through 1246 (Genebank Accession: YP_009724390.1, SEQ ID NOs: 36-41, 77, 119), the use of at least amino acids 1201 to 1246 would a priori include the top ranked MHC I compatible epitope in Table 1 (SEQ ID NO: 21). Other TM can include that of RSV fusion protein (SEQ ID NO: 115)

Table 6 shows mini spike proteins that are portions of SARS-CoV-2 S1 protein or fusions of portions of S1 designed to be membrane anchored using the Spike TM. Use of the S1 signal sequence (SEQ ID NOs: 39-41, 42, 115, 119) will direct the peptide to the cellular secretory apparatus for display on the cell surface membrane and for post-translational modifications such as N-linked glycosylation.

TABLE 6

Mini Spike Proteins Including Portions of SARS-COV-2 S1 Protein

SEQ ID NO: 36
167 AA Protein - Mini Spike No Head
Spike S2 protein 1069 to 1235
PAQEKNFTTAPAICHDGKAHFPREGVFVSNGTHWFVTQRNFYEPQIITTDNTFVSGNCDVVIGIVNNTVY
DPLQPELDSFKEELDKYFKNHTSPDVDLGDISGINASVVNIQKEIDRLNEVAKNLNESLIDLQELGKYEQ
YIKWPWYIWLGFIAGLIAIVMVTIMLC SEQ ID NO: 37
Protein - Mini Spike No 2P Helix Spike S2 protein 942 to 1235
ASALGKLQDVVNQNAQALNTLVKQLSSNFGAISSVLNDILSRLDKVEAEVQIDRLITGRLQSLQTYVTQQ
LIRAAEIRASANLAATKMSECVLGQSKRVDFCGKGYHLMSFPQSAPHGVVFLHVTYVPAQEKNFTTAPAI
CHDGKAHFPREGVFVSNGTHWFVTQRNFYEPQIITTDNTFVSGNCDVVIGIVNNTVYDPLQPELDSFKEE
LDKYFKNHTSPDVDLGDISGINASVVNIQKEIDRLNEVAKNLNESLIDLQELGKYEQYIKWPWYIWLGFI
AGLIAIVMVTIMLC SEQ ID NO: 38
Protein - Mini Spike 2P Helix
Spike S2 protein 942 to 1235
ASALGKLQDVVNQNAQALNTLVKQLSSNFGAISSVLNDILSRLDPPEAEVQIDRLITGRLQSLQTYVTQQ
LIRAAEIRASANLAATKMSECVLGQSKRVDFCGKGYHLMSFPQSAPHGVVFLHVTYVPAQEKNFTTAPAI
CHDGKAHFPREGVFVSNGTHWFVTQRNFYEPQIITTDNTFVSGNCDVVTGIVNNTVYDPLQPELDSFKEE
LDKYFKNHTSPDVDLGDISGINASVVNIQKEIDRLNEVAKNLNESLIDLQELGKYEQYIKWPWYIWLGFI
AGLIAIVMVTIMLC
Bold = 2 P Mutation SEQ ID NO: 39
Protein - Mini Spike 2P Helix with Signal Peptide
Spike protein 1 to 26, 942 to 1235
MFVFLVLLPLVSSQCVNLTTRTQLPPASALGKLQDVVNQNAQALNTLVKQLSSNFGAISSVLNDILSRLD
PPEAEVQIDRLITGRLQSLQTYVTQQLIRAAEIRASANLAATKMSECVLGQSKRVDFCGKGYHLMSFPQS
APHGVVFLHVTYVPAQEKNFTTAPAICHDGKAHFPREGVFVSNGTHWFVTQRNFYEPQIITTDNTFVSGN
CDVVIGIVNNTVYDPLQPELDSFKEELDKYFKNHTSPDVDLGDISGINASVVNIQKEIDRLNEVAKNLNE
SLIDLQELGKYEQYIKWPWYIWLGFIAGLIAIVMVTIMLC
Bold = 2 P Mutation
Underline = S1 signal peptide SEQ ID NO: 40
Protein - Mini Spike NTD with Signal Peptide Spike protein 1 to
294, 1069 to 1235
MFVFLVLLPLVSSQCVNLTTRTQLPP*AYTNSFTRGVYYPDKVFRSSVLHSTQDLFLPFFSNVTWFHAIHV*
*SGTNGTKRFDNPVLPFNDGVYFASTEKSNIIRGWIFGTTLDSKTQSLLIVNNATNVVIKVCEFQFCNDPF*
*LGVYYHKNNKSWMESEFRVYSSANNCTFEYVSQPFLMDLEGKQGNFKNLREFVFKNIDGYFKIYSKHTPI*
*NLVRDLPQGFSALEPLVDLPIGINITRFQTLLALHRSYLTPGDSSSGWTAGAAAYYVGYLQPRTFLLKYN*
*ENGTITDAVDCALD*PALQPELDSFKEELDKYFKNHTSPDVDLGDISGINASVVNIQKEIDRLNEVAKNLN
ESLIDLQELGKYEQYIKWPWYIWLGFIAGLIAIVMVTIMLC
Underline = S1 signal peptide
Underline Italics = S1 NTD SEQ ID NO: 41
Protein - Mini Spike RBD with Signal Peptide Spike protein 1 to
26, 331 to 530, 1069 to 1235
MFVFLVLLPLVSSQCVNLTTRTQLPPNITNLCPFGEVFNATRFASVYAWNRKRISNCVADYSVLYNSASF
STFKCYGVSPTKLNDLCFTNVYADSFVIRGDEVRQIAPGQTGKIADYNYKLPDDFTGCVIAWNSNNLDSK
VGGNYNYLYRLFRKSNLKPFERDISTEIYQAGSTPCNGVEGFNCYFPLQSYGFQPTNGVGYQPYRVVVLS
FELLHAPATVCGPKKSTYVPAQEKNFTTAPAICHDGKAHFPREGVFVSNGTHWFVTQRNFYEPQUITTDN
TFVSGNCDVVIGIVNNTVYDPLQPELDSFKEELDKYFKNHTSPDVDLGDISGINASVVNIQKEIDRLNEV
AKNLNESLIDLQELGKYEQYIKWPWYIWLGFIAGLIAIVMVTIMLC
Underline = S1 signal peptide
BOLD = S1 RBD SEQ ID NO: 115
Protein - Mini Spike RBD with Mini-Signal Peptide, Trimerization
Domain, and RSV TM Spike S1 protein 2 to 14, 331 to 530,
T4 fibritin 457 to 454 (Foldon), RSV F 521 to 552
FVFLVLLPLVSSQPNITNLCPFGEVFNATRFASVYAWNRKRISNCVADYSVLYNSASFSTFKCYGVSPTK
LNDLCFTNVYADSFVIRGDEVRQIAPGQTGKIADYNYKLPDDFTGCVIAWNSNNLDSKVGGNYNYLYRLF
RKSNLKPFERDISTEIYQAGSTPCNGVEGFNCYFPLQSYGFQPTNGVGYQPYRVVVLSFELLHAPATVCG
PKK*SGYIPEAPRDGQAYVRKDGEWVLLSTFLGSTTNIMITTIIIVIIVILLSLIAVGLLLYCKAR*
Underline = S1 signal peptide
BOLD = S1 RBD
Italics = T4 Foldon
Underline Italics = RSV TM SEQ ID NO. 119
Protein: - Mini Spike with SARS-COV-2 S protein signal
peptide 2 to 26 and S2 helical connector domain to TM
1069 to 1235 with GSG linkers, N-terminal T2A, C and
P2A site.

TABLE 6-continued

| Mini Spike Proteins Including Portions of SARS-COV-2 S1 Protein |
|---|
| **GSG***EGRGSLLTCGDVEENPGP***FVFLVLLPLVSSQCVNLTTRTQLPP**AQEKNFTTAPAICHDGKAHFPREG VFVSNGTHWFVTQRNFYEPQIITTDNTFVSGNCDVVIGIVNNTVYDPLQPELDSFKEELDKYFKNHTSPD VDLGDISGINASVVNIQKEIDRLNEVAKNLNESLIDLQELGKYEQYIKWPWYIWLGFIAGLIAIVMVTIM LC**GSG**ATNFSLLKQAGDVEENPGP |
| BOLD: GSG linker |
| Italics: T2A site |
| Underline: P2A site |
| BOLD Underline = S1 signal peptide |

Example 13

This example demonstrates that the functionality of the NS vector segment of M2SR containing silent mutations (FIGS. 21-22) to express an antigen (SEQ ID NO: 113) that is also a marker gene (SEQ ID NO: 114), the EGFP fluorescent protein. M2SR virus containing NS segment designed to express EGFP was used to infect M2VeroA cells at MOI=10. Fluorescence microscopy over a three-day period post-inoculation showed that robust EGFP expression could be detected within 24 hours, spreading until nearly 100% of cells were seen to express the antigen at 48 hours. By 72 hours, cells detached from the substrate and exhibited strong cytopathic effect (CPE), as expected due to influenza infection (FIG. 23). Strong CPE that was observed at Day 3 shows that the virus replication was not substantially inhibited by the inserted EGFP gene.

Example 14

This example demonstrates that M2SR and BM2SR viruses encoding SARS-CoV-2 sequences from Example 4 retain the ability to elicit antibody responses against the influenza HA (hemagglutinin) surface protein.

Serum was collected from mice before prime immunization and about 3 weeks after the primary dose. Serum samples were pooled for each group and anti-HA IgG antibody titers were determined by enzyme-linked immunosorbent assay (ELISA).

The ELISA was performed using recombinant HA protein as the capture antigen. Recombinant H3 HA(ΔTM)(A/Singapore/INFIMH-16-0019/2006)(H3N2) [Immune-Tech, New York, NY] was used for serum ELISA analysis of mice administered M2SR vector virus or M2SR virus that encode SARS-CoV-2 sequences. Recombinant InfB HA1 (B/Phuket/3073/2013) [Immune-Tech, New York, NY] was used for serum ELISA analysis of mice administered BM2SR vector virus or BM2SR virus that encode SARS-CoV-2 sequences.

The ELISA plates were coated overnight at 4° C. with 100 µL of the capture antigen at a concentration of 2 µg/mL in phosphate-buffered saline (PBS). After blocking the plate with PBS containing 0.1% polysorbate 20 (PBS-T) and 1% gelatin from cold water fish skin, the plates were incubated in duplicate with mouse serum diluted in PBS-T with 1% gelatin from cold water fish skin. After a two-hour incubation at room temperature, the plates were washed with PBS-T six times and then incubated with anti-mouse IgG secondary antibody conjugated with horseradish peroxidase (KPL; 1:2,000 dilution in PBS-T with 1% gelatin from cold water fish skin). After a one-hour incubation with the secondary antibody, the plates were washed six times with PBS-T and then developed with 1-STEP™ Ultra TMB-ELISA Substrate Solution (Thermo Fisher Scientific, Waltham, MA). After a ten-minute incubation, the reaction was stopped with the addition of 4N sulfuric acid. The absorbance was measured at a wavelength of 450 nm ($OD_{450}$). Endpoint titers were the reciprocal of the dilution that was above the cut-off value determined by subtracting the mean value of the blanks plus 0.3 $OD_{450}$.

No difference in serum anti-HA IgG levels were observed between the M2SR and BM2SR viruses encoding SARS-CoV-2 sequences and their corresponding vector virus as shown in Table 7.

TABLE 7

| Anti-HA Titer Levels | |
|---|---|
| Prime antigen | Anti- HA Titer |
| AM2SR-CovidS-1 | >12,500 |
| M2SR-Sing V5 | >12,500 |
| PBS/SPGNa | <100 |
| BM2SR-CovidS-1 | >12,500 |
| BM2SR-CA12 | >12,500 |
| PBS/SPGNa | <100 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Sequencing conventions are based on DNA referring to the four nucleotides: adenine (A), guanine (G), cytosine (C), and thymine (T). When referring to RNA or influenza virus, T means uracil (U).

The invention claimed is:

1. A recombinant virus comprising an influenza viral backbone, wherein the influenza viral backbone comprises PB1, PB2, PA, NP, M, NS, HA, and NA gene segments, wherein at least one of the PB1, PB2, PA, NP, M, NS, HA, and NA gene segments comprises at least one nucleotide sequence that encodes one or more antigens, and wherein (a) the PB1 gene segment encodes a PB1 protein having an amino acid sequence comprising selected amino acids, wherein the selected amino acids comprise a leucine at position 40 and a tryptophan at position 180, and at least one of an asparagine at position 464, an isoleucine at position 563, or a serine at position 607, and wherein the PB1 gene segment optionally comprises a cytosine to uracil promoter mutation at nucleotide position 4;

(b) the PB2 gene segment encodes a PB2 protein having an amino acid sequence comprising selected amino acids, wherein the selected amino acids comprise a valine at position 504, and optionally an isoleucine at position 467 and a valine at position 529, and wherein the PB2 gene segment optionally comprises a cytosine to uracil promoter mutation at nucleotide position 4;

(c) the PA gene segment encodes a PA protein having an amino acid sequence comprising selected amino acids, wherein the selected amino acids comprise a lysine at position 401, and wherein the PA gene segment optionally comprises a cytosine to uracil promoter mutation at nucleotide position 4;

(d) the NP gene segment encodes an NP protein having an amino acid sequence comprising selected amino acids, wherein the selected amino acids comprise a leucine at position 116, and at least one of a lysine at position 294 or an arginine at position 311; and (e) the NS gene segment encodes an NS1 protein having amino acid sequence comprising selected amino acids, wherein the selected amino acids comprise a proline at position 30, a lysine at position 55, and a lysine at position 118.

2. The recombinant virus of claim 1, wherein the antigen is an immunogenic fragment of SARS-CoV-2 spike glycoprotein.

3. The recombinant virus of claim 1, wherein the M gene segment comprises at least one nucleotide sequence that encodes an antigen, wherein the antigen is an immunogenic fragment of SARS-CoV-2 spike glycoprotein.

4. The recombinant virus of claim 1, wherein the M gene segment encodes a mutated M2 protein.

5. The recombinant virus of claim 4, wherein the M gene segment encodes a protein comprising at least one linker protein and FLAG epitope tag.

6. The recombinant virus of claim 1, wherein the M segment encodes a protein comprising any one of SEQ ID NOs: 1-14 and 92-96.

7. The recombinant virus of claim 1, wherein the NS gene segment comprises at least one nucleotide sequence that encodes one or more antigens.

8. The recombinant virus of claim 1 wherein the antigen is an immunogenic fragment of SARS-CoV-2 spike glycoprotein.

9. The recombinant virus of claim 1, wherein the NS gene segment encodes (1) a NS1 protein, (2) at least one flexible linker protein, (3) an immunogenic fragment of SARS-CoV-2 spike glycoprotein, (4) at least one cleavable cleavage sequence, and (5) a NEP protein.

10. The recombinant virus of claim 9, wherein the at least one cleavable cleavage sequence is a T2A peptide sequence or a P2A peptide sequence.

11. The recombinant virus of claim 1, wherein the NS gene segment encodes a protein comprising any one of SEQ ID NOs: 97-104.

12. The recombinant virus of claim 1, wherein each of the M and NS gene segments comprises at least one nucleotide sequence that encodes one or more antigens, and wherein the antigens are immunogenic fragments of SARS-CoV-2 spike glycoprotein.

13. The recombinant virus of claim 1, wherein each of the NA and NS gene segments comprises at least one nucleotide sequence that encodes one or more antigens, and wherein the antigens are immunogenic fragments of SARS-CoV-2 glycoprotein.

14. The recombinant virus of claim 1, wherein each of the M and NA gene segments comprises at least one nucleotide sequence that encodes one or more antigens, and wherein the antigens are immunogenic fragments of SARS-CoV-2 glycoprotein.

15. The recombinant virus of claim 1, wherein each of the M and HA gene segments comprises at least one nucleotide sequence that encodes one or more antigens, and wherein the antigens are immunogenic fragments of SARS-CoV-2 glycoprotein.

16. The recombinant virus of claim 1, wherein each of the NS and NA gene segments comprises at least one nucleotide sequence that encodes one or more antigens, and wherein the antigens are immunogenic fragments of SARS-CoV-2 glycoprotein.

17. The recombinant virus of claim 1, wherein each of the NS and HA gene segments comprises at least one nucleotide sequence that encodes one or more antigens, and wherein the antigens are immunogenic fragments of SARS-CoV-2 spike glycoprotein.

18. The recombinant virus of claim 1, wherein the virus is capable of replication in human cells.

19. The recombinant virus of claim 1, wherein the virus has enhanced growth as compared to a recombinant virus that is the same except without the selected amino acids in Vero cells under the same conditions.

20. The recombinant virus of claim 1, wherein the gene segment that comprises at least one nucleotide sequence that encodes one or more antigens further comprises a downstream duplication and wherein the downstream duplication comprises at least one silent nucleotide mutation.

21. A pharmaceutical formulation comprising the recombinant virus of claim 1.

22. The pharmaceutical formulation of claim 21, wherein the vaccine is formulated as a monovalent vaccine, a bivalent vaccine, a trivalent vaccine, or a quadrivalent vaccine.

23. A method of eliciting an immune response in a mammal, the method comprising administering the recombinant virus of claim 1 to the mammal, thereby eliciting an immune response to the antigen in the mammal.

24. The method of claim 23, wherein the mammal is a human.

* * * * *

SEQUENCE LISTING

<160> NUMBER OF SEQ ID NOS: 119

<210> SEQ ID NO 1
<211> LENGTH: 97
<212> TYPE: PRT
<213> ORGANISM: Artificial Sequence
<220> FEATURE:
<223> OTHER INFORMATION: Synthetic Sequence

<400> SEQUENCE: 1

Met Ser Leu Leu Thr Glu Val Glu Thr Pro Ile Arg Asn Glu Trp Gly
1               5                   10                  15

Cys Arg Cys Asn Gly Ser Ser Asp Pro Leu Thr Ile Ala Ala Asn Ile
            20                  25                  30

Ile Gly Ile Leu His Leu Thr Leu Trp Ile Leu Asp Arg Leu Phe Phe
        35                  40                  45

Lys Cys Ile Tyr Arg Arg Phe Lys Tyr Gly Leu Lys Gly Gly Pro Ser
    50                  55                  60

Thr Glu Gly Val Pro Lys Ser Met Arg Glu Glu Tyr Arg Lys Glu Gln
65                  70                  75                  80

Gln Ser Ala Val Asp Ala Asp Asp Gly His Phe Val Ser Ile Glu Leu
                85                  90                  95

Glu

<210> SEQ ID NO 2
<211> LENGTH: 109
<212> TYPE: PRT
<213> ORGANISM: Artificial Sequence
<220> FEATURE:
<223> OTHER INFORMATION: Synthetic Sequence

<400> SEQUENCE: 2

Met Leu Glu Pro Leu Gln Ile Leu Ser Ile Cys Ser Phe Ile Leu Ser
1               5                   10                  15

Ala Leu His Phe Met Ala Trp Thr Ile Gly His Leu Asn Gln Ile Arg
            20                  25                  30

Arg Gly Val Asn Leu Lys Ile Gln Ile Arg Asn Pro Asn Lys Glu Ala
        35                  40                  45

Ile Asn Arg Glu Val Ser Ile Leu Arg His Asn Tyr Gln Lys Glu Ile
    50                  55                  60

Gln Ala Lys Glu Thr Met Lys Lys Ile Leu Ser Asp Asn Met Glu Val
65                  70                  75                  80

Leu Gly Asp His Ile Val Val Glu Gly Leu Ser Thr Asp Glu Ile Ile
                85                  90                  95

Lys Met Gly Glu Thr Val Leu Glu Val Glu Glu Leu Gln
            100                 105

<210> SEQ ID NO 3

-continued

<211> LENGTH: 25
<212> TYPE: PRT
<213> ORGANISM: Artificial Sequence
<220> FEATURE:
<223> OTHER INFORMATION: Synthetic Sequence

<400> SEQUENCE: 3

```
Met Ser Leu Leu Thr Glu Val Glu Thr Pro Ile Arg Asn Glu Trp Gly
1               5                   10                  15

Cys Arg Cys Asn Gly Ser Ser Asp Pro
            20                  25
```

<210> SEQ ID NO 4
<211> LENGTH: 37
<212> TYPE: PRT
<213> ORGANISM: Artificial Sequence
<220> FEATURE:
<223> OTHER INFORMATION: Synthetic Sequence

<400> SEQUENCE: 4

```
Met Ser Leu Leu Thr Glu Val Glu Thr Pro Ile Arg Asn Glu Trp Gly
1               5                   10                  15

Cys Arg Cys Asn Gly Ser Ser Asp Pro Ala Gly Ala Gly Asp Tyr Lys
            20                  25                  30

Asp Asp Asp Asp Lys
        35
```

<210> SEQ ID NO 5
<211> LENGTH: 56
<212> TYPE: PRT
<213> ORGANISM: Artificial Sequence
<220> FEATURE:
<223> OTHER INFORMATION: Synthetic Sequence

<400> SEQUENCE: 5

```
Met Ser Leu Leu Thr Glu Val Glu Thr Pro Ile Arg Asn Glu Trp Gly
1               5                   10                  15

Cys Arg Cys Asn Gly Ser Ser Asp Pro Ile Asp Leu Gln Glu Leu Gly
            20                  25                  30

Lys Tyr Glu Gln Tyr Ile Lys Trp Pro Trp Tyr Ile Trp Leu Gly Phe
        35                  40                  45

Ile Ala Gly Leu Ile Ala Ile Val
    50                  55
```

<210> SEQ ID NO 6
<211> LENGTH: 68
<212> TYPE: PRT
<213> ORGANISM: Artificial Sequence
<220> FEATURE:
<223> OTHER INFORMATION: Synthetic Sequence

<400> SEQUENCE: 6

```
Met Ser Leu Leu Thr Glu Val Glu Thr Pro Ile Arg Asn Glu Trp Gly
1               5                   10                  15

Cys Arg Cys Asn Gly Ser Ser Asp Pro Ile Asp Leu Gln Glu Leu Gly
            20                  25                  30

Lys Tyr Glu Gln Tyr Ile Lys Trp Pro Trp Tyr Ile Trp Leu Gly Phe
        35                  40                  45

Ile Ala Gly Leu Ile Ala Ile Val Ala Gly Ala Gly Asp Tyr Lys Asp
    50                  55                  60

Asp Asp Asp Lys
65
```

<210> SEQ ID NO 7
<211> LENGTH: 52
<212> TYPE: PRT
<213> ORGANISM: Artificial Sequence
<220> FEATURE:
<223> OTHER INFORMATION: Synthetic Sequence

<400> SEQUENCE: 7

```
Met Ser Leu Leu Thr Glu Val Glu Thr Pro Ile Arg Asn Glu Trp Gly
1               5                   10                  15

Cys Arg Cys Asn Gly Ser Ser Asp Pro Asn Leu Asp Ser Lys Val Gly
            20                  25                  30

Gly Asn Tyr Asn Tyr Leu Tyr Arg Leu Phe Arg Lys Ser Asn Leu Lys
        35                  40                  45

Pro Phe Glu Arg
    50
```

<210> SEQ ID NO 8
<211> LENGTH: 64
<212> TYPE: PRT
<213> ORGANISM: Artificial Sequence
<220> FEATURE:
<223> OTHER INFORMATION: Synthetic Sequence

<400> SEQUENCE: 8

```
Met Ser Leu Leu Thr Glu Val Glu Thr Pro Ile Arg Asn Glu Trp Gly
1               5                   10                  15

Cys Arg Cys Asn Gly Ser Ser Asp Pro Asn Leu Asp Ser Lys Val Gly
            20                  25                  30

Gly Asn Tyr Asn Tyr Leu Tyr Arg Leu Phe Arg Lys Ser Asn Leu Lys
        35                  40                  45

Pro Phe Glu Arg Ala Gly Ala Gly Asp Tyr Lys Asp Asp Asp Asp Lys
    50                  55                  60
```

<210> SEQ ID NO 9
<211> LENGTH: 43
<212> TYPE: PRT
<213> ORGANISM: Artificial Sequence
<220> FEATURE:
<223> OTHER INFORMATION: Synthetic Sequence

<400> SEQUENCE: 9

```
Met Ser Leu Leu Thr Glu Val Glu Thr Pro Ile Arg Asn Glu Trp Gly
1               5                   10                  15

Cys Arg Cys Asn Gly Ser Ser Asp Pro Tyr Ser Val Leu Tyr Asn Ser
            20                  25                  30

Ala Ser Phe Ser Thr Phe Lys Cys Tyr Gly Val
        35                  40
```

<210> SEQ ID NO 10
<211> LENGTH: 55
<212> TYPE: PRT
<213> ORGANISM: Artificial Sequence
<220> FEATURE:
<223> OTHER INFORMATION: Synthetic Sequence

<400> SEQUENCE: 10

```
Met Ser Leu Leu Thr Glu Val Glu Thr Pro Ile Arg Asn Glu Trp Gly
1               5                   10                  15

Cys Arg Cys Asn Gly Ser Ser Asp Pro Tyr Ser Val Leu Tyr Asn Ser
            20                  25                  30
```

```
Ala Ser Phe Ser Thr Phe Lys Cys Tyr Gly Val Ala Gly Ala Gly Asp
        35                  40                  45

Tyr Lys Asp Asp Asp Asp Lys
    50                  55
```

<210> SEQ ID NO 11
<211> LENGTH: 205
<212> TYPE: PRT
<213> ORGANISM: Artificial Sequence
<220> FEATURE:
<223> OTHER INFORMATION: Synthetic Sequence

<400> SEQUENCE: 11

```
Met Ser Leu Leu Thr Glu Val Glu Thr Pro Ile Arg Asn Glu Trp Gly
1               5                   10                  15

Cys Arg Cys Asn Gly Ser Ser Asp Pro Leu Pro Pro Leu Leu Thr Asp
            20                  25                  30

Glu Met Ile Ala Gln Tyr Thr Ser Ala Leu Leu Met Asn Asp Asn Leu
        35                  40                  45

Asp Ser Lys Val Gly Gly Asn Tyr Asn Tyr Leu Tyr Arg Leu Phe Arg
    50                  55                  60

Lys Ser Asn Leu Lys Pro Phe Glu Arg Trp Asn Trp Ser Pro Arg Arg
65                  70                  75                  80

Ala Arg Ser Val Ala Ser Gln Ser Ile Ile Ala Tyr Ser Asn Trp Ala
                85                  90                  95

Ala Leu Gln Ile Pro Phe Ala Met Gln Met Ala Tyr Arg Phe Asn Gly
            100                 105                 110

Ile Gly Val Ser Trp Tyr Ser Val Leu Tyr Asn Ser Ala Ser Phe Ser
        115                 120                 125

Thr Phe Lys Cys Tyr Gly Val Ser Trp Gly Glu Val Phe Asn Ala Thr
    130                 135                 140

Arg Phe Ala Ser Val Tyr Ala Trp Asn Arg Lys Arg Ile Gly Trp Met
145                 150                 155                 160

Ser Leu Gly Ala Glu Asn Ser Val Ala Tyr Ser Asn Asn Ser Ile Ala
                165                 170                 175

Ile Tyr Phe Trp Gln Glu Leu Gly Lys Tyr Glu Gln Tyr Ile Lys Trp
            180                 185                 190

Pro Trp Tyr Ile Trp Leu Gly Phe Ile Ala Gly Leu Ile
        195                 200                 205
```

<210> SEQ ID NO 12
<211> LENGTH: 217
<212> TYPE: PRT
<213> ORGANISM: Artificial Sequence
<220> FEATURE:
<223> OTHER INFORMATION: Synthetic Sequence

<400> SEQUENCE: 12

```
Met Ser Leu Leu Thr Glu Val Glu Thr Pro Ile Arg Asn Glu Trp Gly
1               5                   10                  15

Cys Arg Cys Asn Gly Ser Ser Asp Pro Leu Pro Pro Leu Leu Thr Asp
            20                  25                  30

Glu Met Ile Ala Gln Tyr Thr Ser Ala Leu Leu Met Asn Asp Asn Leu
        35                  40                  45

Asp Ser Lys Val Gly Gly Asn Tyr Asn Tyr Leu Tyr Arg Leu Phe Arg
    50                  55                  60

Lys Ser Asn Leu Lys Pro Phe Glu Arg Trp Asn Trp Ser Pro Arg Arg
```

-continued

```
65                  70                  75                  80

Ala Arg Ser Val Ala Ser Gln Ser Ile Ile Ala Tyr Ser Asn Trp Ala
                85                  90                  95

Ala Leu Gln Ile Pro Phe Ala Met Gln Met Ala Tyr Arg Phe Asn Gly
            100                 105                 110

Ile Gly Val Ser Trp Tyr Ser Val Leu Tyr Asn Ser Ala Ser Phe Ser
        115                 120                 125

Thr Phe Lys Cys Tyr Gly Val Ser Trp Gly Glu Val Phe Asn Ala Thr
    130                 135                 140

Arg Phe Ala Ser Val Tyr Ala Trp Asn Arg Lys Arg Ile Gly Trp Met
145                 150                 155                 160

Ser Leu Gly Ala Glu Asn Ser Val Ala Tyr Ser Asn Asn Ser Ile Ala
                165                 170                 175

Ile Tyr Phe Trp Gln Glu Leu Gly Lys Tyr Glu Gln Tyr Ile Lys Trp
            180                 185                 190

Pro Trp Tyr Ile Trp Leu Gly Phe Ile Ala Gly Leu Ile Ala Gly Ala
        195                 200                 205

Gly Asp Tyr Lys Asp Asp Asp Asp Lys
    210                 215


<210> SEQ ID NO 13
<211> LENGTH: 205
<212> TYPE: PRT
<213> ORGANISM: Artificial Sequence
<220> FEATURE:
<223> OTHER INFORMATION: Synthetic Sequence

<400> SEQUENCE: 13

Met Ser Leu Leu Thr Glu Val Glu Thr Pro Ile Arg Asn Glu Trp Gly
1               5                   10                  15

Cys Arg Cys Asn Gly Ser Ser Asp Pro Leu Pro Pro Leu Leu Thr Asp
            20                  25                  30

Glu Met Ile Ala Gln Tyr Thr Ser Ala Leu Leu Met Asn Asp Asn Leu
        35                  40                  45

Asp Ser Lys Val Gly Gly Asn Tyr Asn Tyr Leu Tyr Arg Leu Phe Arg
    50                  55                  60

Lys Ser Asn Leu Lys Pro Phe Glu Arg Trp Asn Trp Ser Pro Arg Arg
65                  70                  75                  80

Ala Arg Ser Val Ala Ser Gln Ser Ile Ile Ala Tyr Ser Asn Trp Ala
                85                  90                  95

Ala Leu Gln Ile Pro Phe Ala Met Gln Met Ala Tyr Arg Phe Asn Gly
            100                 105                 110

Ile Gly Val Ser Trp Tyr Ser Val Leu Tyr Asn Ser Ala Ser Phe Ser
        115                 120                 125

Thr Phe Lys Cys Tyr Gly Val Ser Trp Gly Glu Val Phe Asn Ala Thr
    130                 135                 140

Arg Phe Ala Ser Val Tyr Ala Trp Asn Arg Lys Arg Ile Gly Trp Met
145                 150                 155                 160

Ser Leu Gly Ala Glu Asn Ser Val Ala Tyr Ser Asn Asn Ser Ile Ala
                165                 170                 175

Ile Tyr Phe Trp Gln Glu Leu Gly Lys Tyr Glu Gln Tyr Ile Lys Trp
            180                 185                 190

Pro Trp Tyr Ile Trp Leu Gly Phe Ile Ala Gly Leu Ile
        195                 200                 205
```

<210> SEQ ID NO 14
<211> LENGTH: 217
<212> TYPE: PRT
<213> ORGANISM: Artificial Sequence
<220> FEATURE:
<223> OTHER INFORMATION: Synthetic Sequence

<400> SEQUENCE: 14

```
Met Ser Leu Leu Thr Glu Val Glu Thr Pro Ile Arg Asn Glu Trp Gly
1               5                   10                  15

Cys Arg Cys Asn Gly Ser Ser Asp Pro Leu Pro Pro Leu Leu Thr Asp
            20                  25                  30

Glu Met Ile Ala Gln Tyr Thr Ser Ala Leu Leu Met Asn Asp Asn Leu
        35                  40                  45

Asp Ser Lys Val Gly Gly Asn Tyr Asn Tyr Leu Tyr Arg Leu Phe Arg
    50                  55                  60

Lys Ser Asn Leu Lys Pro Phe Glu Arg Trp Asn Trp Ser Pro Arg Arg
65                  70                  75                  80

Ala Arg Ser Val Ala Ser Gln Ser Ile Ile Ala Tyr Ser Asn Trp Ala
                85                  90                  95

Ala Leu Gln Ile Pro Phe Ala Met Gln Met Ala Tyr Arg Phe Asn Gly
            100                 105                 110

Ile Gly Val Ser Trp Tyr Ser Val Leu Tyr Asn Ser Ala Ser Phe Ser
        115                 120                 125

Thr Phe Lys Cys Tyr Gly Val Ser Trp Gly Glu Val Phe Asn Ala Thr
    130                 135                 140

Arg Phe Ala Ser Val Tyr Ala Trp Asn Arg Lys Arg Ile Gly Trp Met
145                 150                 155                 160

Ser Leu Gly Ala Glu Asn Ser Val Ala Tyr Ser Asn Asn Ser Ile Ala
                165                 170                 175

Ile Tyr Phe Trp Gln Glu Leu Gly Lys Tyr Glu Gln Tyr Ile Lys Trp
            180                 185                 190

Pro Trp Tyr Ile Trp Leu Gly Phe Ile Ala Gly Leu Ile Ala Gly Ala
        195                 200                 205

Gly Asp Tyr Lys Asp Asp Asp Asp Lys
    210                 215
```

<210> SEQ ID NO 15
<211> LENGTH: 294
<212> TYPE: DNA
<213> ORGANISM: Artificial Sequence
<220> FEATURE:
<223> OTHER INFORMATION: Synthetic Sequence

<400> SEQUENCE: 15

```
atgagtcttc taaccgaggt cgaaacgcct atcagaaacg aatgggggtg cagatgcaac     60

ggttcaagtg atcctctcac tattgccgca aatatcattg ggatcttgca cttgacattg    120

tggattcttg atcgtctttt tttcaaatgc atttaccgtc gctttaaata cggactgaaa    180

ggagggcctt ctacggaagg agtgccaaag tctatgaggg aagaatatcg aaaggaacag    240

cagagtgctg tggatgctga cgatggtcat tttgtcagca tagagctgga gtaa          294
```

<210> SEQ ID NO 16
<211> LENGTH: 330
<212> TYPE: DNA
<213> ORGANISM: Artificial Sequence
<220> FEATURE:
<223> OTHER INFORMATION: Synthetic Sequence

<400> SEQUENCE: 16
atgctcgaac cacttcagat tctttcaatt tgttctttca ttttatcagc tctccatttc 60
atggcttgga caatagggca tttgaatcaa ataagaagag gggtaaacct gaaaatacaa 120
ataaggaatc caaataagga ggcaataaac agagaggtgt caattctgag acacaattac 180
caaaaggaaa tccaagccaa agaaacaatg aagaaaatac tctctgacaa catggaagta 240
ttgggtgacc acatagtagt tgaagggctt tcaactgatg agataataaa aatgggtgaa 300
acagttttgg aggtggaaga attgcaataa 330

<210> SEQ ID NO 17
<211> LENGTH: 294
<212> TYPE: DNA
<213> ORGANISM: Artificial Sequence
<220> FEATURE:
<223> OTHER INFORMATION: Synthetic Sequence

<400> SEQUENCE: 17
atgtccctgc tgaccgaagt ggaaactcct attagaaacg agtggggctg tagatgtaac 60
ggctcaagcg accctctgac cattgctgcc aacatcattg gcatcctgca cctgaccctg 120
tggattctgg accgactgtt ctttaagtgc atctaccgga gattcaagta tggactgaaa 180
ggaggaccaa gcacagaggg agtgcctaaa tccatgaggg aggaataccg caaagagcag 240
cagagcgccg tggacgcaga tgatggacat ttcgtgagca ttgaactgga atga 294

<210> SEQ ID NO 18
<211> LENGTH: 330
<212> TYPE: DNA
<213> ORGANISM: Artificial Sequence
<220> FEATURE:
<223> OTHER INFORMATION: Synthetic Sequence

<400> SEQUENCE: 18
atgctggaac cactgcagat cctgagtatt tgctctttta tcctgagcgc actgcacttt 60
atggcctgga ctatcgggca cctgaaccag atcagaaggg gcgtgaacct gaagatccag 120
atcagaaacc caaacaagga ggccatcaac cgcgaagtga gcatcctgag acacaattac 180
cagaaggaga tccaggctaa agaaaccatg aagaaaatcc tgtctgacaa tatggaggtg 240
ctgggcgatc acatcgtggt ggaaggactg agcaccgacg aaatcatcaa aatgggcgag 300
actgtcctgg aagtggaaga actgcagtaa 330

<210> SEQ ID NO 19
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (5)..(5)
<223> OTHER INFORMATION: Xaa can be any naturally occurring amino acid

<400> SEQUENCE: 19

Gly Asp Val Glu Xaa Asn Pro Gly Pro
1 5

<210> SEQ ID NO 20
<211> LENGTH: 5
<212> TYPE: DNA
<213> ORGANISM: Artificial Sequence
<220> FEATURE:

-continued

<223> OTHER INFORMATION: Synthetic Sequence

<400> SEQUENCE: 20 ttatg 5

<210> SEQ ID NO 21
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 21

Gln Glu Leu Gly Lys Tyr Glu Gln Tyr Ile Lys Trp Pro Trp Tyr Ile
1 5 10 15

Trp Leu Gly Phe Ile Ala Gly Leu Ile
20 25

<210> SEQ ID NO 22
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 22

Asn Leu Asp Ser Lys Val Gly Gly Asn Tyr Asn Tyr Leu Tyr Arg Leu
1 5 10 15

Phe Arg Lys

<210> SEQ ID NO 23
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 23

Tyr Arg Leu Phe Arg Lys Ser Asn Leu Lys Pro Phe Glu Arg
1 5 10

<210> SEQ ID NO 24
<211> LENGTH: 27
<212> TYPE: PRT
<213> ORGANISM: Artificial Sequence
<220> FEATURE:
<223> OTHER INFORMATION: Synthetic Sequence

<400> SEQUENCE: 24

Asn Leu Asp Ser Lys Val Gly Gly Asn Tyr Asn Tyr Leu Tyr Arg Leu
1 5 10 15

Phe Arg Lys Ser Asn Leu Lys Pro Phe Glu Arg
20 25

<210> SEQ ID NO 25
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 25

Ala Ala Leu Gln Ile Pro Phe Ala Met Gln Met Ala Tyr Arg Phe Asn
1 5 10 15

```
Gly Ile Gly Val
            20


<210> SEQ ID NO 26
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 26

Glu Val Phe Asn Ala Thr Arg Phe Ala Ser Val Tyr Ala Trp Asn Arg
1               5                   10                  15

Lys Arg Ile


<210> SEQ ID NO 27
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 27

Gly Glu Val Phe Asn Ala Thr Arg Phe
1               5


<210> SEQ ID NO 28
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 28

Gly Glu Val Phe Asn Ala Thr Arg Phe Ala Ser Val Tyr Ala Trp Asn
1               5                   10                  15

Arg Lys Arg Ile
            20


<210> SEQ ID NO 29
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 29

Tyr Ser Val Leu Tyr Asn Ser Ala Ser Phe Ser Thr Phe Lys Cys Tyr
1               5                   10                  15

Gly Val


<210> SEQ ID NO 30
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 30

Ser Pro Arg Arg Ala Arg Ser Val Ala Ser Gln Ser Ile Ile Ala Tyr
1               5                   10                  15


<210> SEQ ID NO 31
<211> LENGTH: 18
<212> TYPE: PRT
```

```
<213> ORGANISM: Artificial Sequence
<220> FEATURE:
<223> OTHER INFORMATION: Synthetic Sequence

<400> SEQUENCE: 31

Met Ser Leu Gly Ala Glu Asn Ser Val Ala Tyr Ser Asn Asn Ser Ile
1               5                   10                  15

Ala Ile


<210> SEQ ID NO 32
<211> LENGTH: 35
<212> TYPE: PRT
<213> ORGANISM: Artificial Sequence
<220> FEATURE:
<223> OTHER INFORMATION: Synthetic Sequence

<400> SEQUENCE: 32

Ser Pro Arg Arg Ala Arg Ser Val Ala Ser Gln Ser Ile Ile Ala Tyr
1               5                   10                  15

Thr Met Ser Leu Gly Ala Glu Asn Ser Val Ala Tyr Ser Asn Asn Ser
            20                  25                  30

Ile Ala Ile
        35


<210> SEQ ID NO 33
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 33

Leu Pro Pro Leu Leu Thr Asp Glu Met Ile Ala Gln Tyr Thr Ser Ala
1               5                   10                  15

Leu


<210> SEQ ID NO 34
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 34

Met Ile Ala Gln Tyr Thr Ser Ala Leu Leu
1               5                   10


<210> SEQ ID NO 35
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 35

Leu Pro Pro Leu Leu Thr Asp Glu Met Ile Ala Gln Tyr Thr Ser Ala
1               5                   10                  15

Leu Leu


<210> SEQ ID NO 36
<211> LENGTH: 177
<212> TYPE: PRT
<213> ORGANISM: Artificial Sequence
<220> FEATURE:
```

<223> OTHER INFORMATION: Synthetic Sequence

<400> SEQUENCE: 36

Pro Ala Gln Glu Lys Asn Phe Thr Thr Ala Pro Ala Ile Cys His Asp
1               5                   10                  15

Gly Lys Ala His Phe Pro Arg Glu Gly Val Phe Val Ser Asn Gly Thr
            20                  25                  30

His Trp Phe Val Thr Gln Arg Asn Phe Tyr Glu Pro Gln Ile Ile Thr
        35                  40                  45

Thr Asp Asn Thr Phe Val Ser Gly Asn Cys Asp Val Val Ile Gly Ile
    50                  55                  60

Val Asn Asn Thr Val Tyr Asp Pro Leu Gln Pro Glu Leu Asp Ser Phe
65                  70                  75                  80

Lys Glu Glu Leu Asp Lys Tyr Phe Lys Asn His Thr Ser Pro Asp Val
                85                  90                  95

Asp Leu Gly Asp Ile Ser Gly Ile Asn Ala Ser Val Val Asn Ile Gln
            100                 105                 110

Lys Glu Ile Asp Arg Leu Asn Glu Val Ala Lys Asn Leu Asn Glu Ser
        115                 120                 125

Leu Ile Asp Leu Gln Glu Leu Gly Lys Tyr Glu Gln Tyr Ile Lys Trp
    130                 135                 140

Pro Trp Tyr Ile Trp Leu Gly Phe Ile Ala Gly Leu Ile Ala Ile Val
145                 150                 155                 160

Met Val Thr Ile Met Leu Cys Cys Met Thr Ser Cys Cys Ser Cys Leu
                165                 170                 175

Lys

<210> SEQ ID NO 37
<211> LENGTH: 304
<212> TYPE: PRT
<213> ORGANISM: Artificial Sequence
<220> FEATURE:
<223> OTHER INFORMATION: Synthetic Sequence

<400> SEQUENCE: 37

Ala Ser Ala Leu Gly Lys Leu Gln Asp Val Val Asn Gln Asn Ala Gln
1               5                   10                  15

Ala Leu Asn Thr Leu Val Lys Gln Leu Ser Ser Asn Phe Gly Ala Ile
            20                  25                  30

Ser Ser Val Leu Asn Asp Ile Leu Ser Arg Leu Asp Lys Val Glu Ala
        35                  40                  45

Glu Val Gln Ile Asp Arg Leu Ile Thr Gly Arg Leu Gln Ser Leu Gln
    50                  55                  60

Thr Tyr Val Thr Gln Gln Leu Ile Arg Ala Ala Glu Ile Arg Ala Ser
65                  70                  75                  80

Ala Asn Leu Ala Ala Thr Lys Met Ser Glu Cys Val Leu Gly Gln Ser
                85                  90                  95

Lys Arg Val Asp Phe Cys Gly Lys Gly Tyr His Leu Met Ser Phe Pro
            100                 105                 110

Gln Ser Ala Pro His Gly Val Val Phe Leu His Val Thr Tyr Val Pro
        115                 120                 125

Ala Gln Glu Lys Asn Phe Thr Thr Ala Pro Ala Ile Cys His Asp Gly
    130                 135                 140

Lys Ala His Phe Pro Arg Glu Gly Val Phe Val Ser Asn Gly Thr His
145                 150                 155                 160

-continued

```
Trp Phe Val Thr Gln Arg Asn Phe Tyr Glu Pro Gln Ile Ile Thr Thr
                165                 170                 175

Asp Asn Thr Phe Val Ser Gly Asn Cys Asp Val Val Ile Gly Ile Val
            180                 185                 190

Asn Asn Thr Val Tyr Asp Pro Leu Gln Pro Glu Leu Asp Ser Phe Lys
        195                 200                 205

Glu Glu Leu Asp Lys Tyr Phe Lys Asn His Thr Ser Pro Asp Val Asp
    210                 215                 220

Leu Gly Asp Ile Ser Gly Ile Asn Ala Ser Val Val Asn Ile Gln Lys
225                 230                 235                 240

Glu Ile Asp Arg Leu Asn Glu Val Ala Lys Asn Leu Asn Glu Ser Leu
                245                 250                 255

Ile Asp Leu Gln Glu Leu Gly Lys Tyr Glu Gln Tyr Ile Lys Trp Pro
            260                 265                 270

Trp Tyr Ile Trp Leu Gly Phe Ile Ala Gly Leu Ile Ala Ile Val Met
        275                 280                 285

Val Thr Ile Met Leu Cys Cys Met Thr Ser Cys Cys Ser Cys Leu Lys
    290                 295                 300


<210> SEQ ID NO 38
<211> LENGTH: 304
<212> TYPE: PRT
<213> ORGANISM: Artificial Sequence
<220> FEATURE:
<223> OTHER INFORMATION: Synthetic Sequence

<400> SEQUENCE: 38

Ala Ser Ala Leu Gly Lys Leu Gln Asp Val Val Asn Gln Asn Ala Gln
1               5                   10                  15

Ala Leu Asn Thr Leu Val Lys Gln Leu Ser Ser Asn Phe Gly Ala Ile
            20                  25                  30

Ser Ser Val Leu Asn Asp Ile Leu Ser Arg Leu Asp Pro Pro Glu Ala
        35                  40                  45

Glu Val Gln Ile Asp Arg Leu Ile Thr Gly Arg Leu Gln Ser Leu Gln
    50                  55                  60

Thr Tyr Val Thr Gln Gln Leu Ile Arg Ala Ala Glu Ile Arg Ala Ser
65                  70                  75                  80

Ala Asn Leu Ala Ala Thr Lys Met Ser Glu Cys Val Leu Gly Gln Ser
                85                  90                  95

Lys Arg Val Asp Phe Cys Gly Lys Gly Tyr His Leu Met Ser Phe Pro
            100                 105                 110

Gln Ser Ala Pro His Gly Val Val Phe Leu His Val Thr Tyr Val Pro
        115                 120                 125

Ala Gln Glu Lys Asn Phe Thr Thr Ala Pro Ala Ile Cys His Asp Gly
    130                 135                 140

Lys Ala His Phe Pro Arg Glu Gly Val Phe Val Ser Asn Gly Thr His
145                 150                 155                 160

Trp Phe Val Thr Gln Arg Asn Phe Tyr Glu Pro Gln Ile Ile Thr Thr
                165                 170                 175

Asp Asn Thr Phe Val Ser Gly Asn Cys Asp Val Val Ile Gly Ile Val
            180                 185                 190

Asn Asn Thr Val Tyr Asp Pro Leu Gln Pro Glu Leu Asp Ser Phe Lys
        195                 200                 205

Glu Glu Leu Asp Lys Tyr Phe Lys Asn His Thr Ser Pro Asp Val Asp
    210                 215                 220
```

-continued

```
Leu Gly Asp Ile Ser Gly Ile Asn Ala Ser Val Val Asn Ile Gln Lys
225                 230                 235                 240

Glu Ile Asp Arg Leu Asn Glu Val Ala Lys Asn Leu Asn Glu Ser Leu
                245                 250                 255

Ile Asp Leu Gln Glu Leu Gly Lys Tyr Glu Gln Tyr Ile Lys Trp Pro
            260                 265                 270

Trp Tyr Ile Trp Leu Gly Phe Ile Ala Gly Leu Ile Ala Ile Val Met
        275                 280                 285

Val Thr Ile Met Leu Cys Cys Met Thr Ser Cys Cys Ser Cys Leu Lys
    290                 295                 300


<210> SEQ ID NO 39
<211> LENGTH: 330
<212> TYPE: PRT
<213> ORGANISM: Artificial Sequence
<220> FEATURE:
<223> OTHER INFORMATION: Synthetic Sequence

<400> SEQUENCE: 39

Met Phe Val Phe Leu Val Leu Leu Pro Leu Val Ser Ser Gln Cys Val
1               5                   10                  15

Asn Leu Thr Thr Arg Thr Gln Leu Pro Pro Ala Ser Ala Leu Gly Lys
            20                  25                  30

Leu Gln Asp Val Val Asn Gln Asn Ala Gln Ala Leu Asn Thr Leu Val
        35                  40                  45

Lys Gln Leu Ser Ser Asn Phe Gly Ala Ile Ser Ser Val Leu Asn Asp
    50                  55                  60

Ile Leu Ser Arg Leu Asp Pro Pro Glu Ala Glu Val Gln Ile Asp Arg
65                  70                  75                  80

Leu Ile Thr Gly Arg Leu Gln Ser Leu Gln Thr Tyr Val Thr Gln Gln
                85                  90                  95

Leu Ile Arg Ala Ala Glu Ile Arg Ala Ser Ala Asn Leu Ala Ala Thr
            100                 105                 110

Lys Met Ser Glu Cys Val Leu Gly Gln Ser Lys Arg Val Asp Phe Cys
        115                 120                 125

Gly Lys Gly Tyr His Leu Met Ser Phe Pro Gln Ser Ala Pro His Gly
    130                 135                 140

Val Val Phe Leu His Val Thr Tyr Val Pro Ala Gln Glu Lys Asn Phe
145                 150                 155                 160

Thr Thr Ala Pro Ala Ile Cys His Asp Gly Lys Ala His Phe Pro Arg
                165                 170                 175

Glu Gly Val Phe Val Ser Asn Gly Thr His Trp Phe Val Thr Gln Arg
            180                 185                 190

Asn Phe Tyr Glu Pro Gln Ile Ile Thr Thr Asp Asn Thr Phe Val Ser
        195                 200                 205

Gly Asn Cys Asp Val Val Ile Gly Ile Val Asn Asn Thr Val Tyr Asp
    210                 215                 220

Pro Leu Gln Pro Glu Leu Asp Ser Phe Lys Glu Glu Leu Asp Lys Tyr
225                 230                 235                 240

Phe Lys Asn His Thr Ser Pro Asp Val Asp Leu Gly Asp Ile Ser Gly
                245                 250                 255

Ile Asn Ala Ser Val Val Asn Ile Gln Lys Glu Ile Asp Arg Leu Asn
            260                 265                 270

Glu Val Ala Lys Asn Leu Asn Glu Ser Leu Ile Asp Leu Gln Glu Leu
        275                 280                 285
```

-continued

```
Gly Lys Tyr Glu Gln Tyr Ile Lys Trp Pro Trp Tyr Ile Trp Leu Gly
    290                 295                 300

Phe Ile Ala Gly Leu Ile Ala Ile Val Met Val Thr Ile Met Leu Cys
305                 310                 315                 320

Cys Met Thr Ser Cys Cys Ser Cys Leu Lys
                325                 330


<210> SEQ ID NO 40
<211> LENGTH: 471
<212> TYPE: PRT
<213> ORGANISM: Artificial Sequence
<220> FEATURE:
<223> OTHER INFORMATION: Synthetic Sequence

<400> SEQUENCE: 40

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Ala Gln Glu Lys Asn Phe Thr Thr Ala
    290                 295                 300

Pro Ala Ile Cys His Asp Gly Lys Ala His Phe Pro Arg Glu Gly Val
305                 310                 315                 320
```

-continued

```
Phe Val Ser Asn Gly Thr His Trp Phe Val Thr Gln Arg Asn Phe Tyr
                325                 330                 335

Glu Pro Gln Ile Ile Thr Thr Asp Asn Thr Phe Val Ser Gly Asn Cys
            340                 345                 350

Asp Val Val Ile Gly Ile Val Asn Asn Thr Val Tyr Asp Pro Leu Gln
        355                 360                 365

Pro Glu Leu Asp Ser Phe Lys Glu Glu Leu Asp Lys Tyr Phe Lys Asn
    370                 375                 380

His Thr Ser Pro Asp Val Asp Leu Gly Asp Ile Ser Gly Ile Asn Ala
385                 390                 395                 400

Ser Val Val Asn Ile Gln Lys Glu Ile Asp Arg Leu Asn Glu Val Ala
                405                 410                 415

Lys Asn Leu Asn Glu Ser Leu Ile Asp Leu Gln Glu Leu Gly Lys Tyr
            420                 425                 430

Glu Gln Tyr Ile Lys Trp Pro Trp Tyr Ile Trp Leu Gly Phe Ile Ala
        435                 440                 445

Gly Leu Ile Ala Ile Val Met Val Thr Ile Met Leu Cys Cys Met Thr
    450                 455                 460

Ser Cys Cys Ser Cys Leu Lys
465                 470


<210> SEQ ID NO 41
<211> LENGTH: 406
<212> TYPE: PRT
<213> ORGANISM: Artificial Sequence
<220> FEATURE:
<223> OTHER INFORMATION: Synthetic Sequence

<400> SEQUENCE: 41

Met Phe Val Phe Leu Val Leu Leu Pro Leu Val Ser Ser Gln Cys Val
1               5                   10                  15

Asn Leu Thr Thr Arg Thr Gln Leu Pro Pro Asn Ile Thr Asn Leu Cys
            20                  25                  30

Pro Phe Gly Glu Val Phe Asn Ala Thr Arg Phe Ala Ser Val Tyr Ala
        35                  40                  45

Trp Asn Arg Lys Arg Ile Ser Asn Cys Val Ala Asp Tyr Ser Val Leu
    50                  55                  60

Tyr Asn Ser Ala Ser Phe Ser Thr Phe Lys Cys Tyr Gly Val Ser Pro
65                  70                  75                  80

Thr Lys Leu Asn Asp Leu Cys Phe Thr Asn Val Tyr Ala Asp Ser Phe
                85                  90                  95

Val Ile Arg Gly Asp Glu Val Arg Gln Ile Ala Pro Gly Gln Thr Gly
            100                 105                 110

Lys Ile Ala Asp Tyr Asn Tyr Lys Leu Pro Asp Asp Phe Thr Gly Cys
        115                 120                 125

Val Ile Ala Trp Asn Ser Asn Asn Leu Asp Ser Lys Val Gly Gly Asn
    130                 135                 140

Tyr Asn Tyr Leu Tyr Arg Leu Phe Arg Lys Ser Asn Leu Lys Pro Phe
145                 150                 155                 160

Glu Arg Asp Ile Ser Thr Glu Ile Tyr Gln Ala Gly Ser Thr Pro Cys
                165                 170                 175

Asn Gly Val Glu Gly Phe Asn Cys Tyr Phe Pro Leu Gln Ser Tyr Gly
            180                 185                 190

Phe Gln Pro Thr Asn Gly Val Gly Tyr Gln Pro Tyr Arg Val Val Val
        195                 200                 205
```

-continued

```
Leu Ser Phe Glu Leu Leu His Ala Pro Ala Thr Val Cys Gly Pro Lys
    210                 215                 220

Lys Ser Thr Tyr Val Pro Ala Gln Glu Lys Asn Phe Thr Thr Ala Pro
225                 230                 235                 240

Ala Ile Cys His Asp Gly Lys Ala His Phe Pro Arg Glu Gly Val Phe
                245                 250                 255

Val Ser Asn Gly Thr His Trp Phe Val Thr Gln Arg Asn Phe Tyr Glu
            260                 265                 270

Pro Gln Ile Ile Thr Thr Asp Asn Thr Phe Val Ser Gly Asn Cys Asp
        275                 280                 285

Val Val Ile Gly Ile Val Asn Asn Thr Val Tyr Asp Pro Leu Gln Pro
    290                 295                 300

Glu Leu Asp Ser Phe Lys Glu Glu Leu Asp Lys Tyr Phe Lys Asn His
305                 310                 315                 320

Thr Ser Pro Asp Val Asp Leu Gly Asp Ile Ser Gly Ile Asn Ala Ser
                325                 330                 335

Val Val Asn Ile Gln Lys Glu Ile Asp Arg Leu Asn Glu Val Ala Lys
            340                 345                 350

Asn Leu Asn Glu Ser Leu Ile Asp Leu Gln Glu Leu Gly Lys Tyr Glu
        355                 360                 365

Gln Tyr Ile Lys Trp Pro Trp Tyr Ile Trp Leu Gly Phe Ile Ala Gly
    370                 375                 380

Leu Ile Ala Ile Val Met Val Thr Ile Met Leu Cys Cys Met Thr Ser
385                 390                 395                 400

Cys Cys Ser Cys Leu Lys
                405


<210> SEQ ID NO 42
<211> LENGTH: 26
<212> TYPE: PRT
<213> ORGANISM: Artificial Sequence
<220> FEATURE:
<223> OTHER INFORMATION: Synthetic Sequence

<400> SEQUENCE: 42

Met Phe Val Phe Leu Val Leu Leu Pro Leu Val Ser Ser Gln Cys Val
1               5                   10                  15

Asn Leu Thr Thr Arg Thr Gln Leu Pro Pro
            20                  25


<210> SEQ ID NO 43
<211> LENGTH: 1565
<212> TYPE: DNA
<213> ORGANISM: Artificial Sequence
<220> FEATURE:
<223> OTHER INFORMATION: Synthetic Sequence

<400> SEQUENCE: 43

agcaaaagca gggtagataa tcactcactg agtgacatca aaatcatggc gtctcaaggc      60

accaaacgat cttacgaaca gatggagact gatggagaac gccagaatgc cactgaaatc     120

agagcatccg tcggaaaaat gattggtgga attggacgat tctacatcca aatgtgcacc     180

gaactcaaac tcagtgatta tgagggacgg ttgatccaaa acagcttaac aatagagaga     240

atggtgctct ctgcttttga cgaaaggaga aataaatacc ttgaagaaca tcccagtgcg     300

gggaaagatc ctaagaaaac tggaggacct atatacagga gagtaaacgg aaagtggatg     360

agagaactca tcctttatga caaagaagaa ttaaggcgaa tctggcgcca agctaataat     420
```

-continued

```
ggtgacgatg caacggctgg tctgactcac atgatgatct ggcattccaa tttgaatgat    480

gcaacttatc agaggacaag agctcttgtt cgcaccggaa tggatcccag gatgtgctct    540

ctgatgcaag gttcaactct ccctaggagg tctggagccg caggtgctgc agtcaaagga    600

gttggaacaa tggtgatgga attggtcaga atgatcaaac gtgggatcaa tgatcggaac    660

ttctggaggg gtgagaatgg acgaaaaaca agaattgctt atgaaagaat gtgcaacatt    720

ctcaaaggga aatttcaaac tgctgcacaa aaagcaatga tggatcaagt gagagagagc    780

cggaacccag ggaatgctga gttcgaagat ctcacttttc tagcacggtc tgcactcata    840

ttgagagggt cggttgctca caagtcctgc ctgcctgcct gtgtgtatgg acctgccgta    900

gccagtgggt acgactttga aaggaaggga tactctctag tcggaataga ccctttcaga    960

ctgcttcaaa acagccaagt gtacagccta atcagaccaa atgagaatcc agcacacaag   1020

agtcaactgg tgtggatggc atgccattct gccgcatttg aagatctaag agtattaagc   1080

ttcatcaaag ggacgaaggt gctcccaaga gggaagcttt ccactagagg agttcaaatt   1140

gcttccaatg aaaatatgga gactatggaa tcaagtacac ttgaactgag aagcaggtac   1200

tgggccataa ggaccagaag tggaggaaac accaatcaac agagggcatc tgcgggccaa   1260

atcagcatac aacctacgtt ctcagtacag agaaatctcc cttttgacag aacaaccatt   1320

atggcagcat tcaatgggaa tacagagggg agaacatctg acatgaggac cgaaatcata   1380

aggatgatgg aaagtgcaag accagaagat gtgtctttcc aggggcgggg agtcttcgag   1440

ctctcggacg aaaaggcagc gagcccgatc gtgccttcct ttgacatgag taatgaagga   1500

tcttatttct tcggagacaa tgcagaggag tacgacaatt aaagaaaaat acccttgttt   1560

ctact                                                               1565
```

<210> SEQ ID NO 44
<211> LENGTH: 2341
<212> TYPE: DNA
<213> ORGANISM: Artificial Sequence
<220> FEATURE:
<223> OTHER INFORMATION: Synthetic Sequence

<400> SEQUENCE: 44

```
agcaaaagca ggcaaaccat ttgaatggat gtcaatccga ccttactttt cttaaaagtg     60

ccagcacaaa atgctataag cacaactttc ccttatactg gagatcctcc ttacagccat    120

gggacaggaa caggatacac cttggatact gtcaacagga cacatcagta ctcagaaaag    180

ggaagatgga caacaaacac cgaaactgga gcaccgcaac tcaacccgat tgatgggcca    240

ctgccagaag acaatgaacc aagtggttat gcccaaacag attgtgtatt ggaggcgatg    300

gctttccttg aggaatccca tcctggtatt tttgaaaact cgtgtattga aacgatggag    360

gttgttcagc aaacacgagt agacaagctg acacaaggcc gacagaccta tgactggact    420

ctaaatagaa accaacctgc tgcaacagca ttggccaaca caatagaagt gttcagatca    480

aatggcctca cggccaatga gtctggaagg ctcatagact tccttaagga tgtaatggag    540

tcaatgaaca aagaagaaat gtggatcaca actcattttc agagaaagag acgggtgaga    600

gacaatatga ctaagaaaat gataacacag agaacaatgg gtaaaaagaa gcagagattg    660

aacaaaagga gttatctaat tagagcattg accctgaaca caatgaccaa agatgctgag    720

agagggaagc taaaacggag agcaattgca accccaggga tgcaaataag gggggtttgta    780

tactttgttg agacactggc aaggagtata tgtgagaaac ttgaacaatc agggttgcca    840

gttggaggca atgagaagaa agcaaagttg gcaaatgttg taaggaagat gatgaccaat    900
```

-continued

```
tctcaggaca ccgaactttc tttcaccatc actggagata acaccaaatg gaacgaaaat    960

cagaatcctc ggatgttttt ggccatgatc acatatatga ccagaaatca gcccgaatgg   1020

ttcagaaatg ttctaagtat tgctccaata atgttctcaa acaaaatggc gagactggga   1080

aaagggtata tgtttgagag caagagtatg aaacttagaa ctcaaatacc tgcagaaatg   1140

ctagcaagca tcgatttgaa atatttcaat gattcaacaa gaaagaagat tgaaaaaatc   1200

cgaccgctct taatagaggg gactgcatca ttgagccctg gaatgatgat gggcatgttc   1260

aatatgttaa gcactgtatt aggcgtctcc atcctgaatc ttggacaaaa gagatacacc   1320

aagactactt actggtggga tggtcttcaa tcctctgacg attttgctct gattgtgaat   1380

gcacccaatc atgaagggat tcaagccgga gtcaacaggt tttatcgaac ctgtaagcta   1440

cttggaatca atatgagcaa gaaaaagtct tacataaaca gaacaggtac atttgaattc   1500

acaagttttt tctatcgtta tgggtttgtt gccaatttca gcatggagct tcccagtttt   1560

ggggtgtctg ggatcaacga gtcagcggac atgagtattg gagttactgt catcaaaaac   1620

aatatgataa acaatgatct tggtccagca acagctcaaa tggcccttca gttgttcatc   1680

aaagattaca ggtacacgta ccgatgccat ataggtgaca cacaaataca aacccgaaga   1740

tcatttgaaa taaagaaact gtgggagcaa acccgttcca aagctggact gctagtctcc   1800

gacggaggcc caaatttata caacattaga aatctccaca ttcctgaagt ctgcctaaaa   1860

tgggaattga tggatgagga ttaccagggg cgtttatgca acccactgaa cccatttgtc   1920

agccataaag aaattgaatc aatgaacaat gcagtgatga tgccagcaca tggtccagcc   1980

aaaaacatgg agtatgatgc tgttgcaaca acacactcct ggatccccaa aagaaatcga   2040

tccatcttga atacaagtca aagaggagta cttgaggatg aacaaatgta ccaaaggtgc   2100

tgcaatttat ttgaaaaatt cttccccagc agttcataca gaagaccagt cgggatatcc   2160

agtatggtgg aggctatggt ttccagagcc cgaattgatg cacggattga tttcgaatct   2220

ggaaggataa agaaagaaga gttcactgag atcatgaaga tctgttccac cattgaagag   2280

ctcagacggc aaaaatagtg aatttagctt gtccttcatg aaaaaatgcc ttgtttctac   2340

t                                                                   2341
```

<210> SEQ ID NO 45
<211> LENGTH: 1565
<212> TYPE: DNA
<213> ORGANISM: Artificial Sequence
<220> FEATURE:
<223> OTHER INFORMATION: Synthetic Sequence

<400> SEQUENCE: 45

```
agcaaaagca gggtagataa tcactcactg agtgacatca aaatcatggc gtctcaaggc     60

accaaacgat cttacgaaca gatggagact gatggagaac gccagaatgc cactgaaatc    120

agagcatccg tcggaaaaat gattggtgga attggacgat tctacatcca aatgtgcacc    180

gaactcaaac tcagtgatta tgagggacgg ttgatccaaa acagcttaac aatagagaga    240

atggtgctct ctgcttttga cgaaaggaga aataaatacc ttgaagaaca tcccagtgcg    300

gggaaagatc ctaagaaaac tggaggacct atatacagga gagtaaacgg aaagtggatg    360

agagaactca tcctttatga caaagaagaa ttaaggcgaa tctggcgcca agctaataat    420

ggtgacgatg caacggctgg tctgactcac atgatgatct ggcattccaa tttgaatgat    480

gcaacttatc agaggacaag agctcttgtt cgcaccggaa tggatcccag gatgtgctct    540
```

```
ctgatgcaag gttcaactct ccctaggagg tctggagccg caggtgctgc agtcaaagga    600

gttggaacaa tggtgatgga attggtcaga atgatcaaac gtgggatcaa tgatcggaac    660

ttctggaggg gtgagaatgg acgaaaaaca agaattgctt atgaaagaat gtgcaacatt    720

ctcaaaggga aatttcaaac tgctgcacaa aaagcaatga tggatcaagt gagagagagc    780

cggaacccag ggaatgctga gttcgaagat ctcacttttc tagcacggtc tgcactcata    840

ttgagagggt cggttgctca caagtcctgc ctgcctgcct gtgtgtatgg acctgccgta    900

gccagtgggt acgactttga aagggaggga tactctctag tcggaataga ccctttcaga    960

ctgcttcaaa acagccgagt gtacagccta atcagaccaa atgagaatcc agcacacaag   1020

agtcaactgg tgtggatggc atgccattct gccgcatttg aagatctaag agtattaagc   1080

ttcatcaaag ggacgaaggt gctcccaaga gggaagcttt ccactagagg agttcaaatt   1140

gcttccaatg aaaatatgga gactatggaa tcaagtacac ttgaactgag aagcaggtac   1200

tgggccataa ggaccagaag tggaggaaac accaatcaac agagggcatc tgcgggccaa   1260

atcagcatac aacctacgtt ctcagtacag agaaatctcc cttttgacag aacaaccatt   1320

atggcagcat tcaatgggaa tacagagggg agaacatctg acatgaggac cgaaatcata   1380

aggatgatgg aaagtgcaag accagaagat gtgtctttcc aggggcgggg agtcttcgag   1440

ctctcggacg aaaaggcagc gagcccgatc gtgccttcct ttgacatgag taatgaagga   1500

tcttatttct tcggagacaa tgcagaggag tacgacaatt aaagaaaaat acccttgttt   1560

ctact                                                               1565
```

<210> SEQ ID NO 46
<211> LENGTH: 2341
<212> TYPE: DNA
<213> ORGANISM: Artificial Sequence
<220> FEATURE:
<223> OTHER INFORMATION: Synthetic Sequence

<400> SEQUENCE: 46

```
agcaaaagca ggcaaaccat ttgaatggat gtcaatccga ccttactttt cttaaaagtg     60

ccagcacaaa atgctataag cacaactttc ccttatactg gagatcctcc ttacagccat    120

gggacaggaa caggatacac cttggatact gtcaacagga cacatcagta ctcagaaaag    180

ggaagatgga caacaaacac cgaaactgga gcaccgcaac tcaacccgat tgatgggcca    240

ctgccagaag acaatgaacc aagtggttat gcccaaacag attgtgtatt ggaggcgatg    300

gctttccttg aggaatccca tcctggtatt tttgaaaact cgtgtattga aacgatggag    360

gttgttcagc aaacacgagt agacaagctg acacaaggcc gacagaccta tgactggact    420

ctaaatagaa accaacctgc tgcaacagca ttggccaaca caatagaagt gttcagatca    480

aatggcctca cggccaatga gtctggaagg ctcatagact tccttaagga tgtaatggag    540

tcaatgaaca aagaagaaat gtggatcaca actcattttc agagaaagag acgggtgaga    600

gacaatatga ctaagaaaat gataacacag agaacaatgg gtaaaaagaa gcagagattg    660

aacaaaagga gttatctaat tagagcattg accctgaaca caatgaccaa agatgctgag    720

agagggaagc taaaacggag agcaattgca accccaggga tgcaaataag ggggtttgta    780

tactttgttg agacactggc aaggagtata tgtgagaaac ttgaacaatc agggttgcca    840

gttggaggca atgagaagaa agcaaagttg gcaaatgttg taaggaagat gatgaccaat    900

tctcaggaca ccgaactttc tttcaccatc actggagata acaccaaatg gaacgaaaat    960

cagaatcctc ggatgttttt ggccatgatc acatatatga ccagaaatca gcccgaatgg   1020
```

-continued

```
ttcagaaatg ttctaagtat tgctccaata atgttctcaa acaaaatggc gagactggga   1080

aaagggtata tgtttgagag caagagtatg aaacttagaa ctcaaatacc tgcagaaatg   1140

ctagcaagca tcgatttgaa atatttcaat gattcaacaa gaaagaagat tgaaaaaatc   1200

cgaccgctct taatagaggg gactgcatca ttgagccctg gaatgatgat gggcatgttc   1260

aatatgttaa gcactgtatt aggcgtctcc atcctgaatc ttggacaaaa gagatacacc   1320

aagactactt actggtggga tggtcttcaa tcctctgacg attttgctct gattgtgaat   1380

gcacccaatc atgaagggat tcaagccgga gtcgacaggt tttatcgaac ctgtaagcta   1440

cttggaatca atatgagcaa gaaaaagtct tacataaaca gaacaggtac atttgaattc   1500

acaagttttt tctatcgtta tgggtttgtt gccaatttca gcatggagct tcccagtttt   1560

ggggtgtctg ggatcaacga gtcagcggac atgagtattg gagttactgt catcaaaaac   1620

aatatgataa acaatgatct tggtccagca acagctcaaa tggcccttca gttgttcatc   1680

aaagattaca ggtacacgta ccgatgccat ataggtgaca cacaaataca aacccgaaga   1740

tcatttgaaa taaagaaact gtgggagcaa acccgttcca aagctggact gctagtctcc   1800

gacggaggcc caaatttata caacattaga aatctccaca tttctgaagt ctgcctaaaa   1860

tgggaattga tggatgagga ttaccagggg cgtttatgca acccactgaa cccatttgtc   1920

agccataaag aaattgaatc aatgaacaat gcagtgatga tgccagcaca tggtccagcc   1980

aaaaacatgg agtatgatgc tgttgcaaca acacactcct ggatccccaa aagaaatcga   2040

tccatcttga atacaagtca aagaggagta cttgaggatg aacaaatgta ccaaaggtgc   2100

tgcaatttat ttgaaaaatt cttccccagc agttcataca gaagaccagt cgggatatcc   2160

agtatggtgg aggctatggt ttccagagcc cgaattgatg cacggattga tttcgaatct   2220

ggaaggataa agaaagaaga gttcactgag atcatgaaga tctgttccac cattgaagag   2280

ctcagacggc aaaaatagtg aatttagctt gtccttcatg aaaaaatgcc ttgtttctac   2340

t                                                                   2341


<210> SEQ ID NO 47
<211> LENGTH: 2341
<212> TYPE: DNA
<213> ORGANISM: Artificial Sequence
<220> FEATURE:
<223> OTHER INFORMATION: Synthetic Sequence

<400> SEQUENCE: 47

agcaaaagca ggtcaattat attcaatatg gaaagaataa aagaactacg aaatctaatg     60

tcgcagtctc gcacccgcga gatactcaca aaaaccaccg tggaccatat ggccataatc    120

aagaagtaca catcaggaag acaggagaag aacccagcac ttaggatgaa atggatgatg    180

gcaatgaaat atccaattac agcagacaag aggataacgg aaatgattcc tgagagaaat    240

gagcaaggac aaactttatg gagtaaaatg aatgatgccg gatcagaccg agtgatggta    300

tcacctctgg ctgtgacatg gtggaatagg aatggaccaa taacaaatac agttcattat    360

ccaaaaatct acaaaactta ttttgaaaga gtcgaaaggc taaagcatgg aacctttggc    420

cctgtccatt ttagaaacca agtcaaaata cgtcggagag ttgacataaa tcctggtcat    480

gcagatctca gtgccaagga ggcacaggat gtaatcatgg aagttgtttt ccctaacgaa    540

gtgggagcca ggatactaac atcggaatcg caactaacga taaccaaaga gaagaaagaa    600

gaactccagg attgcaaaat ttctcctttg atggttgcat acatgttgga gagagaactg    660
```

```
gtccgcaaaa cgagattcct cccagtggct ggtggaacaa gcagtgtgta cattgaagtg    720
ttgcatttga ctcaaggaac atgctgggaa cagatgtata ctccaggagg ggaagtgagg    780
aatgatgatg ttgatcaaag cttgattatt gctgctagga acatagtgag aagagctgca    840
gtatcagcag atccactagc atctttattg gagatgtgcc acagcacaca gattggtgga    900
attaggatgg tagacatcct taggcagaac ccaacagaag agcaagccgt ggatatatgc    960
aaggctgcaa tgggactgag aattagctca tccttcagtt ttggtggatt cacatttaag   1020
agaacaagcg gatcatcagt caagagagag gaagaggtgc ttacgggcaa tcttcaaaca   1080
ttgaagataa gagtgcatga gggatatgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
aaagcagtca gaggtgatct gaatttcgtc aatagggcga atcaacgatt gaatcctatg   1320
catcaacttt taagacattt tcagaaggat gcgaaagtgc tttttcaaaa ttggggagtt   1380
gaacctatcg acaatgtgat gggaatgatt gggatattgc ccgacataac tccaagcatc   1440
gagatgtcaa tgagaggagt gagaatcagc aaaatgggtg tagatgagta ctccagcacg   1500
gagagggtag tggtgagcat tgaccgtttt ttgagagtcc gggaccaacg aggaaatgta   1560
ctactgtctc ccgaggaggt cagtgaaaca cagggaacag agaaactgac agtaacttac   1620
tcatcgtcaa tgatgtggga gattaatggt cctgaatcag tgttggtcaa tacctatcaa   1680
tggatcatca gaaactggga aactgttaaa attcagtggt cccagaaccc tacaatgcta   1740
tacaataaaa tggaatttga accatttcag tctttagtac ctaaggccat tagaggccaa   1800
tacagtgggt ttgtaagaac tctgttccaa caaatgaggg atgtgcttgg gacatttgat   1860
accgcacaga taataaaact tcttcccttc gcagccgctc caccaaagca aagtagaatg   1920
cagttctcct catttactgt gaatgtgagg ggatcaggaa tgagaatact tgtaaggggc   1980
aattctcctg tattcaacta taacaaggcc acgaagagac tcacagttct cggaaaggat   2040
gctggcactt taactgaaga cccagatgaa ggcacagctg gagtggagtc cgctgttctg   2100
aggggattcc tcattctggg caaagaagac aagagatatg ggccagcact aagcatcaat   2160
gaactgagca accttgcgaa aggagagaag gctaatgtgc taattgggca aggagacgtg   2220
gtgttggtaa tgaaacggaa acgggactct agcatactta ctgacagcca gacagcgacc   2280
aaaagaattc ggatggccat caattagtgt cgaatagttt aaaaacgacc ttgtttctac   2340
t                                                                   2341
```

<210> SEQ ID NO 48
<211> LENGTH: 498
<212> TYPE: PRT
<213> ORGANISM: Artificial Sequence
<220> FEATURE:
<223> OTHER INFORMATION: Synthetic Sequence

<400> SEQUENCE: 48

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60
```

-continued

Arg Met Val Leu Ser Ala Phe Asp Glu Arg Arg Asn Lys Tyr Leu Glu
65 70 75 80

Glu His Pro Ser Ala Gly Lys Asp Pro Lys Lys Thr Gly Gly Pro Ile
85 90 95

Tyr Arg Arg Val Asn Gly Lys Trp Met Arg Glu Leu Ile Leu Tyr Asp
100 105 110

Lys Glu Glu Leu Arg Arg Ile Trp Arg Gln Ala Asn Asn Gly Asp Asp
115 120 125

Ala Thr Ala Gly Leu Thr His Met Met Ile Trp His Ser Asn Leu Asn
130 135 140

Asp Ala Thr Tyr Gln Arg Thr Arg Ala Leu Val Arg Thr Gly Met Asp
145 150 155 160

Pro Arg Met Cys Ser Leu Met Gln Gly Ser Thr Leu Pro Arg Arg Ser
165 170 175

Gly Ala Ala Gly Ala Ala Val Lys Gly Val Gly Thr Met Val Met Glu
180 185 190

Leu Val Arg Met Ile Lys Arg Gly Ile Asn Asp Arg Asn Phe Trp Arg
195 200 205

Gly Glu Asn Gly Arg Lys Thr Arg Ile Ala Tyr Glu Arg Met Cys Asn
210 215 220

Ile Leu Lys Gly Lys Phe Gln Thr Ala Ala Gln Lys Ala Met Met Asp
225 230 235 240

Gln Val Arg Glu Ser Arg Asn Pro Gly Asn Ala Glu Phe Glu Asp Leu
245 250 255

Thr Phe Leu Ala Arg Ser Ala Leu Ile Leu Arg Gly Ser Val Ala His
260 265 270

Lys Ser Cys Leu Pro Ala Cys Val Tyr Gly Pro Ala Val Ala Ser Gly
275 280 285

Tyr Asp Phe Glu Arg Lys Gly Tyr Ser Leu Val Gly Ile Asp Pro Phe
290 295 300

Arg Leu Leu Gln Asn Ser Gln Val Tyr Ser Leu Ile Arg Pro Asn Glu
305 310 315 320

Asn Pro Ala His Lys Ser Gln Leu Val Trp Met Ala Cys His Ser Ala
325 330 335

Ala Phe Glu Asp Leu Arg Val Leu Ser Phe Ile Lys Gly Thr Lys Val
340 345 350

Leu Pro Arg Gly Lys Leu Ser Thr Arg Gly Val Gln Ile Ala Ser Asn
355 360 365

Glu Asn Met Glu Thr Met Glu Ser Ser Thr Leu Glu Leu Arg Ser Arg
370 375 380

Tyr Trp Ala Ile Arg Thr Arg Ser Gly Gly Asn Thr Asn Gln Gln Arg
385 390 395 400

Ala Ser Ala Gly Gln Ile Ser Ile Gln Pro Thr Phe Ser Val Gln Arg
405 410 415

Asn Leu Pro Phe Asp Arg Thr Thr Ile Met Ala Ala Phe Asn Gly Asn
420 425 430

Thr Glu Gly Arg Thr Ser Asp Met Arg Thr Glu Ile Ile Arg Met Met
435 440 445

Glu Ser Ala Arg Pro Glu Asp Val Ser Phe Gln Gly Arg Gly Val Phe
450 455 460

Glu Leu Ser Asp Glu Lys Ala Ala Ser Pro Ile Val Pro Ser Phe Asp
465 470 475 480

-continued

Met Ser Asn Glu Gly Ser Tyr Phe Phe Gly Asp Asn Ala Glu Glu Tyr
485 490 495

Asp Asn

<210> SEQ ID NO 49
<211> LENGTH: 757
<212> TYPE: PRT
<213> ORGANISM: Artificial Sequence
<220> FEATURE:
<223> OTHER INFORMATION: Synthetic Sequence

<400> SEQUENCE: 49

Met Asp Val Asn Pro Thr Leu Leu Phe Leu Lys Val Pro Ala Gln Asn
1 5 10 15

Ala Ile Ser Thr Thr Phe Pro Tyr Thr Gly Asp Pro Pro Tyr Ser His
20 25 30

Gly Thr Gly Thr Gly Tyr Thr Leu Asp Thr Val Asn Arg Thr His Gln
35 40 45

Tyr Ser Glu Lys Gly Arg Trp Thr Thr Asn Thr Glu Thr Gly Ala Pro
50 55 60

Gln Leu Asn Pro Ile Asp Gly Pro Leu Pro Glu Asp Asn Glu Pro Ser
65 70 75 80

Gly Tyr Ala Gln Thr Asp Cys Val Leu Glu Ala Met Ala Phe Leu Glu
85 90 95

Glu Ser His Pro Gly Ile Phe Glu Asn Ser Cys Ile Glu Thr Met Glu
100 105 110

Val Val Gln Gln Thr Arg Val Asp Lys Leu Thr Gln Gly Arg Gln Thr
115 120 125

Tyr Asp Trp Thr Leu Asn Arg Asn Gln Pro Ala Ala Thr Ala Leu Ala
130 135 140

Asn Thr Ile Glu Val Phe Arg Ser Asn Gly Leu Thr Ala Asn Glu Ser
145 150 155 160

Gly Arg Leu Ile Asp Phe Leu Lys Asp Val Met Glu Ser Met Asn Lys
165 170 175

Glu Glu Met Trp Ile Thr Thr His Phe Gln Arg Lys Arg Arg Val Arg
180 185 190

Asp Asn Met Thr Lys Lys Met Ile Thr Gln Arg Thr Met Gly Lys Lys
195 200 205

Lys Gln Arg Leu Asn Lys Arg Ser Tyr Leu Ile Arg Ala Leu Thr Leu
210 215 220

Asn Thr Met Thr Lys Asp Ala Glu Arg Gly Lys Leu Lys Arg Arg Ala
225 230 235 240

Ile Ala Thr Pro Gly Met Gln Ile Arg Gly Phe Val Tyr Phe Val Glu
245 250 255

Thr Leu Ala Arg Ser Ile Cys Glu Lys Leu Glu Gln Ser Gly Leu Pro
260 265 270

Val Gly Gly Asn Glu Lys Lys Ala Lys Leu Ala Asn Val Val Arg Lys
275 280 285

Met Met Thr Asn Ser Gln Asp Thr Glu Leu Ser Phe Thr Ile Thr Gly
290 295 300

Asp Asn Thr Lys Trp Asn Glu Asn Gln Asn Pro Arg Met Phe Leu Ala
305 310 315 320

Met Ile Thr Tyr Met Thr Arg Asn Gln Pro Glu Trp Phe Arg Asn Val
325 330 335

Leu Ser Ile Ala Pro Ile Met Phe Ser Asn Lys Met Ala Arg Leu Gly

-continued

```
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
    370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asn
    450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Ile Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Met
625                 630                 635                 640

Asn Asn Ala Val Met Met Pro Ala His Gly Pro Ala Lys Asn Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Val Leu Glu Asp Glu Gln Met
        675                 680                 685

Tyr Gln Arg Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Thr Glu Ile Met Lys Ile Cys Ser Thr Ile Glu Glu
            740                 745                 750

Leu Arg Arg Gln Lys
        755
```

<210> SEQ ID NO 50
<211> LENGTH: 498
<212> TYPE: PRT
<213> ORGANISM: Artificial Sequence
<220> FEATURE:
<223> OTHER INFORMATION: Synthetic Sequence

<400> SEQUENCE: 50

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Leu Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Arg Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Leu Pro Arg Gly Lys Leu Ser Thr Arg Gly Val Gln Ile Ala Ser Asn
        355                 360                 365
```

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Asn Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 51
<211> LENGTH: 757
<212> TYPE: PRT
<213> ORGANISM: Artificial Sequence
<220> FEATURE:
<223> OTHER INFORMATION: Synthetic Sequence

<400> SEQUENCE: 51

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Leu Asp Thr Val Asn Arg Thr His Gln
        35                  40                  45

Tyr Ser Glu Lys Gly Arg Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asn Lys
                165                 170                 175

Glu Glu Met Trp Ile Thr Thr His Phe Gln Arg Lys Arg Arg Val Arg
            180                 185                 190

Asp Asn Met Thr Lys Lys Met Ile Thr Gln Arg Thr Met Gly Lys Lys
        195                 200                 205

Lys Gln Arg Leu Asn Lys Arg Ser Tyr Leu Ile Arg Ala Leu Thr Leu
    210                 215                 220

-continued

Asn Thr Met Thr Lys Asp Ala Glu Arg Gly Lys Leu Lys Arg Arg Ala
225 230 235 240

Ile Ala Thr Pro Gly Met Gln Ile Arg Gly Phe Val Tyr Phe Val Glu
245 250 255

Thr Leu Ala Arg Ser Ile Cys Glu Lys Leu Glu Gln Ser Gly Leu Pro
260 265 270

Val Gly Gly Asn Glu Lys Lys Ala Lys Leu Ala Asn Val Val Arg Lys
275 280 285

Met Met Thr Asn Ser Gln Asp Thr Glu Leu Ser Phe Thr Ile Thr Gly
290 295 300

Asp Asn Thr Lys Trp Asn Glu Asn Gln Asn Pro Arg Met Phe Leu Ala
305 310 315 320

Met Ile Thr Tyr Met Thr Arg Asn Gln Pro Glu Trp Phe Arg Asn Val
325 330 335

Leu Ser Ile Ala Pro Ile Met Phe Ser Asn Lys Met Ala Arg Leu Gly
340 345 350

Lys Gly Tyr Met Phe Glu Ser Lys Ser Met Lys Leu Arg Thr Gln Ile
355 360 365

Pro Ala Glu Met Leu Ala Ser Ile Asp Leu Lys Tyr Phe Asn Asp Ser
370 375 380

Thr Arg Lys Lys Ile Glu Lys Ile Arg Pro Leu Leu Ile Glu Gly Thr
385 390 395 400

Ala Ser Leu Ser Pro Gly Met Met Met Gly Met Phe Asn Met Leu Ser
405 410 415

Thr Val Leu Gly Val Ser Ile Leu Asn Leu Gly Gln Lys Arg Tyr Thr
420 425 430

Lys Thr Thr Tyr Trp Trp Asp Gly Leu Gln Ser Ser Asp Asp Phe Ala
435 440 445

Leu Ile Val Asn Ala Pro Asn His Glu Gly Ile Gln Ala Gly Val Asp
450 455 460

Arg Phe Tyr Arg Thr Cys Lys Leu Leu Gly Ile Asn Met Ser Lys Lys
465 470 475 480

Lys Ser Tyr Ile Asn Arg Thr Gly Thr Phe Glu Phe Thr Ser Phe Phe
485 490 495

Tyr Arg Tyr Gly Phe Val Ala Asn Phe Ser Met Glu Leu Pro Ser Phe
500 505 510

Gly Val Ser Gly Ile Asn Glu Ser Ala Asp Met Ser Ile Gly Val Thr
515 520 525

Val Ile Lys Asn Asn Met Ile Asn Asn Asp Leu Gly Pro Ala Thr Ala
530 535 540

Gln Met Ala Leu Gln Leu Phe Ile Lys Asp Tyr Arg Tyr Thr Tyr Arg
545 550 555 560

Cys His Ile Gly Asp Thr Gln Ile Gln Thr Arg Arg Ser Phe Glu Ile
565 570 575

Lys Lys Leu Trp Glu Gln Thr Arg Ser Lys Ala Gly Leu Leu Val Ser
580 585 590

Asp Gly Gly Pro Asn Leu Tyr Asn Ile Arg Asn Leu His Ile Ser Glu
595 600 605

Val Cys Leu Lys Trp Glu Leu Met Asp Glu Asp Tyr Gln Gly Arg Leu
610 615 620

Cys Asn Pro Leu Asn Pro Phe Val Ser His Lys Glu Ile Glu Ser Met
625 630 635 640

Asn Asn Ala Val Met Met Pro Ala His Gly Pro Ala Lys Asn Met Glu

```
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Val Leu Glu Asp Glu Gln Met
        675                 680                 685

Tyr Gln Arg Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Thr Glu Ile Met Lys Ile Cys Ser Thr Ile Glu Glu
            740                 745                 750

Leu Arg Arg Gln Lys
        755


<210> SEQ ID NO 52
<211> LENGTH: 759
<212> TYPE: PRT
<213> ORGANISM: Artificial Sequence
<220> FEATURE:
<223> OTHER INFORMATION: Synthetic Sequence

<400> SEQUENCE: 52

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Thr
    50                  55                  60

Glu Met Ile Pro Glu Arg Asn Glu Gln Gly Gln Thr Leu Trp Ser Lys
65                  70                  75                  80

Met Asn Asp Ala Gly Ser Asp Arg Val Met Val Ser Pro Leu Ala Val
                85                  90                  95

Thr Trp Trp Asn Arg Asn Gly Pro Ile Thr Asn Thr Val His Tyr Pro
            100                 105                 110

Lys Ile Tyr Lys Thr Tyr Phe Glu Arg Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
```

-continued

```
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Val Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Val Glu Pro Ile Asp Asn Val Met Gly Met Ile Gly Ile Leu
    450                 455                 460

Pro Asp Ile Thr Pro Ser Ile Glu Met Ser Met Arg Gly Val Arg Ile
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Val Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Lys Gln Ser Arg Met Gln Phe Ser Ser Phe Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670
```

```
Gly Thr Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Lys Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755
```

```
<210> SEQ ID NO 53
<211> LENGTH: 976
<212> TYPE: DNA
<213> ORGANISM: Artificial Sequence
<220> FEATURE:
<223> OTHER INFORMATION: Synthetic Sequence

<400> SEQUENCE: 53

agcaaaagca ggtagatatt gaaagatgag tcttctaacc gaggtcgaaa cgtacgtact     60

ctctatcatc ccgtcaggcc ccctcaaagc cgagatcgca cagagacttg aagatgtctt    120

tgcagggaag aacaccgatc ttgaggttct catggaatgg ctaaagacaa gaccaatcct    180

gtcacctctg actaagggga ttttaggatt tgtgttcacg ctcaccgtgc ccagtgagcg    240

aggactgcag cgtagacgct ttgtccaaaa tgcccttaat gggaacgggg atccaaataa    300

catggacaaa gcagttaaac tgtataggaa gctcaagagg gagataacat tccatggggc    360

caaagaaatc tcactcagtt attctgctgg tgcacttgcc agttgtatgg gcctcatata    420

caacaggatg gggctgtga ccactgaagt ggcatttggc ctggtatgtg caacctgtga    480

acagattgct gactcccagc atcggtctca taggcaaatg gtgacaacaa ccaatccact    540

aatcagacat gagaacagaa tggttttagc cagcactaca gctaaggcta tggagcaaat    600

ggctggatcg agtgagcaag cagcagaggc catggaggtt gctagtcagg ctagacaaat    660

ggtgcaagcg atgagaacca ttgggactca tcctagctcc agtgctggtc tgaaaaatga    720

tcttcttgaa aatttgcagg cctatcagaa acgaatgggg gtgcagatgc aacggttcaa    780

gtgattaata ggatcgtctt tttttcaaat gcatttaccg tcgctttaaa tacggactga    840

aaggagggcc ttctacggaa ggagtgccaa agtctatgag ggaagaatat cgaaaggaac    900

agcagagtgc tgtggatgct gacgatggtc attttgtcag catagagctg gagtaaaaaa    960

ctaccttgtt tctact                                                    976
```

```
<210> SEQ ID NO 54
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 54

Met Ser Leu Leu Thr Glu Val Glu Thr Pro Ile Arg Asn Glu Trp Gly
1               5                   10                  15

Cys Arg Cys Asn Gly Ser Ser Asp
            20
```

<210> SEQ ID NO 55
<211> LENGTH: 1069
<212> TYPE: DNA
<213> ORGANISM: Artificial Sequence
<220> FEATURE:
<223> OTHER INFORMATION: Synthetic Sequence

<400> SEQUENCE: 55

```
agcaaaagca ggtagatatt gaaagatgag tcttctaacc gaggtcgaaa cgtacgtact     60
ctctatcatc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggaacgggg atccaaataa    300
catggacaaa gcagctaaac tgtataggaa gctcaagagg gagataacat tccatggggc    360
caaagaaatc tcactcagtt attctgctgg tgcacttgcc agttgtatgg gcctcatata    420
caacaggatg gggctgtga ccactgaagt ggcatttggc ctggtatgtg caacctgtga    480
acagattgct gactcccagc atcggtctca taggcaaatg gtgacaacaa ccaatccact    540
aatcagacat gagaacagaa tggttttagc cagcactaca gctaaggcta tggagcaaat    600
ggctggatcg agtgagcaag cagcagaggc catggaggtt gctagtcagg ctagacaaat    660
ggtgcaagcg atgagaacca ttgggactca tcctagctcc agtgctggtc tgaaaaatga    720
tcttcttgaa aatttgcagg cctatcagaa acgaatgggg gtgcagatgc aacggttcaa    780
gtgatcctta ttctgtccta tataattccg catcattttc cacttttaag tgttatggag    840
tggcaggtgc aggtgattac aaggatgacg acgataagta ataggatcgt ctttttttca    900
aatgcattta ccgtcgcttt aaatacggac tgaaaggagg gccttctacg gaaggagtgc    960
caaagtctat gagggaagaa tatcgaaagg aacagcagag tgctgtggat gctgacgatg   1020
gtcattttgt cagcatagag ctggagtaaa aaactacctt gtttctact               1069
```

<210> SEQ ID NO 56
<211> LENGTH: 2341
<212> TYPE: DNA
<213> ORGANISM: Artificial Sequence
<220> FEATURE:
<223> OTHER INFORMATION: Synthetic Sequence

<400> SEQUENCE: 56

```
agcaaaagca ggtcaattat attcaatatg gaaagaataa aagaactacg aaatctaatg     60
tcgcagtctc gcacccgcga gatactcaca aaaaccaccg tggaccatat ggccataatc    120
aagaagtaca catcaggaag acaggagaag aacccagcac ttaggatgaa atggatgatg    180
gcaatgaaat atccaattac agcagacaag aggataacgg aaatgattcc tgagagaaat    240
gagcaaggac aaactttatg gagtaaaatg aatgatgccg gatcagaccg agtgatggta    300
tcacctctgg ctgtgacatg gtggaatagg aatggaccaa taacaaatac agttcattat    360
ccaaaaatct acaaaactta ttttgaaaga gtcgaaaggc taaagcatgg aacctttggc    420
cctgtccatt ttagaaacca agtcaaaata cgtcggagag ttgacataaa tcctggtcat    480
gcagatctca gtgccaagga ggcacaggat gtaatcatgg aagttgtttt ccctaacgaa    540
gtgggagcca ggatactaac atcggaatcg caactaacga taaccaaaga gaagaaagaa    600
gaactccagg attgcaaaat ttctcctttg atggttgcat acatgttgga gagagaactg    660
gtccgcaaaa cgagattcct cccagtggct ggtggaacaa gcagtgtgta cattgaagtg    720
```

```
ttgcatttga ctcaaggaac atgctgggaa cagatgtata ctccaggagg ggaagtgagg    780
aatgatgatg ttgatcaaag cttgattatt gctgctagga acatagtgag aagagctgca    840
gtatcagcag atccactagc atctttattg gagatgtgcc acagcacaca gattggtgga    900
attaggatgg tagacatcct taggcagaac ccaacagaag agcaagccgt ggatatatgc    960
aaggctgcaa tgggactgag aattagctca tccttcagtt ttggtggatt cacatttaag   1020
agaacaagcg gatcatcagt caagagagag gaagaggtgc ttacgggcaa tcttcaaaca   1080
ttgaagataa gagtgcatga gggatatgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
aaagcagtca gaggtgatct gaatttcgtc aatagggcga atcaacgatt gaatcctatg   1320
catcaacttt taagacattt tcagaaggat gcgaaagtgc tttttcaaaa ttggggagtt   1380
gaacctatcg acaatgtgat gggaatgatt gggatattgc ccgacatgac tccaagcatc   1440
gagatgtcaa tgagaggagt gagaatcagc aaaatgggtg tagatgagta ctccagcacg   1500
gagagggtag tggtgagcat tgaccgtttt ttgagagtcc gggaccaacg aggaaatgta   1560
ctactgtctc ccgaggaggt cagtgaaaca cagggaacag agaaactgac aataacttac   1620
tcatcgtcaa tgatgtggga gattaatggt cctgaatcag tgttggtcaa tacctatcaa   1680
tggatcatca gaaactggga aactgttaaa attcagtggt cccagaaccc tacaatgcta   1740
tacaataaaa tggaatttga accatttcag tctttagtac ctaaggccat tagaggccaa   1800
tacagtgggt ttgtaagaac tctgttccaa caaatgaggg atgtgcttgg gacatttgat   1860
accgcacaga taataaaact tcttcccttc gcagccgctc caccaaagca aagtagaatg   1920
cagttctcct catttactgt gaatgtgagg ggatcaggaa tgagaatact tgtaaggggc   1980
aattctcctg tattcaacta taacaaggcc acgaagagac tcacagttct cggaaaggat   2040
gctggcactt taactgaaga cccagatgaa ggcacagctg gagtggagtc cgctgttctg   2100
aggggattcc tcattctggg caaagaagac aagagatatg ggccagcact aagcatcaat   2160
gaactgagca accttgcgaa aggagagaag gctaatgtgc taattgggca aggagacgtg   2220
gtgttggtaa tgaaacggaa acgggactct agcatactta ctgacagcca gacagcgacc   2280
aaaagaattc ggatggccat caattagtgt cgaatagttt aaaaacgacc ttgtttctac   2340
t                                                                   2341
```

<210> SEQ ID NO 57
<211> LENGTH: 759
<212> TYPE: PRT
<213> ORGANISM: Artificial Sequence
<220> FEATURE:
<223> OTHER INFORMATION: Synthetic Sequence

<400> SEQUENCE: 57

```
Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Thr
    50                  55                  60
```

-continued

```
Glu Met Ile Pro Glu Arg Asn Glu Gln Gly Gln Thr Leu Trp Ser Lys
65                  70                  75                  80

Met Asn Asp Ala Gly Ser Asp Arg Val Met Val Ser Pro Leu Ala Val
                85                  90                  95

Thr Trp Trp Asn Arg Asn Gly Pro Ile Thr Asn Thr Val His Tyr Pro
            100                 105                 110

Lys Ile Tyr Lys Thr Tyr Phe Glu Arg Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Val Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Val Glu Pro Ile Asp Asn Val Met Gly Met Ile Gly Ile Leu
    450                 455                 460

Pro Asp Met Thr Pro Ser Ile Glu Met Ser Met Arg Gly Val Arg Ile
465                 470                 475                 480

Ser Lys Met Gly Val Asp Glu Tyr Ser Ser Thr Glu Arg Val Val Val
```

-continued

```
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
    610                 615                 620

Pro Pro Lys Gln Ser Arg Met Gln Phe Ser Ser Phe Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Thr Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Lys Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755


<210> SEQ ID NO 58
<211> LENGTH: 2233
<212> TYPE: DNA
<213> ORGANISM: Artificial Sequence
<220> FEATURE:
<223> OTHER INFORMATION: Synthetic Sequence

<400> SEQUENCE: 58

agcaaaagca ggtactgatc caaaatggaa gattttgtgc gacaatgctt caatccgatg     60

attgtcgagc ttgcggaaaa aacaatgaaa gagtatgggg aggacctgaa aatcgaaaca    120

aacaaatttg cagcaatatg cactcacttg gaagtatgct tcatgtattc agattttcac    180

ttcatcaatg agcaaggcga gtcaataatc gtagaacttg gtgatccaaa tgcacttttg    240

aagcacagat ttgaaataat cgagggaaga gatcgcacaa tggcctggac agtagtaaac    300

agtatttgca acactacagg ggctgagaaa ccaaagtttc taccagattt gtatgattac    360

aaggagaata gattcatcga aattggagta acaaggagag aagttcacat atactatctg    420

gaaaaggcca ataaaattaa atctgagaaa acacacatcc acattttctc gttcactggg    480
```

-continued

```
gaagaaatgg ccacaaaggc agactacact ctcgatgaag aaagcagggc taggatcaaa    540

accagactat tcaccataag acaagaaatg gccagcagag gcctctggga ttcctttcgt    600

cagtccgaga gaggagaaga gacaattgaa gaaaggtttg aaatcacagg aacaatgcgc    660

aagcttgccg accaaagtct cccgccgaac ttctccagcc ttgaaaattt tagagcctat    720

gtggatggat tcgaaccgaa cggctacatt gagggcaagc tgtctcaaat gtccaaagaa    780

gtaaatgcta gaattgaacc tttttgaaa acaacaccac gaccacttag acttccgaat     840

gggcctccct gttctcagcg gtccaaattc ctgctgatgg atgccttaaa attaagcatt    900

gaggacccaa gtcatgaagg agagggaata ccgctatatg atgcaatcaa atgcatgaga    960

acattctttg gatggaagga acccaatgtt gttaaaccac acgaaaaggg aataaatcca   1020

aattatcttc tgtcatggaa gcaagtactg gcagaactgc aggacattga gaatgaggag   1080

aaaattccaa agactaaaaa tatgaagaaa acaagtcagc taaagtgggc acttggtgag   1140

aacatggcac cagaaaaggt agactttgac gactgtaaag atgtaggtga tttgaagcaa   1200

tatgatagtg atgaaccaga attgaagtcg cttgcaagtt ggattcagaa tgagtttaac   1260

aaggcatgcg aactgacaga ttcaagctgg atagagctcg atgagattgg agaagatgtg   1320

gctccaattg aacacattgc aagcatgaga aggaattatt tcacatcaga ggtgtctcac   1380

tgcagagcca cagaatacat aatgaaggga gtgtacatca atactgcctt gcttaatgca   1440

tcttgtgcag caatggatga tttccaatta attccaatga taagcaagtg tagaactaag   1500

gagggaaggc gaaagaccaa cttgtatggt ttcatcataa aaggaagatc ccacttaagg   1560

aatgacaccg acgtggtaaa ctttgtgagc atggagtttt ctctcactga cccaagactt   1620

gaaccacata aatgggagaa gtactgtgtt cttgagatag gagatatgct tataagaagt   1680

gccataggcc aggtttcaag gcccatgttc ttgtatgtga gaacaaatgg aacctcaaaa   1740

attaaaatga aatggggaat ggagatgagg cgttgcctcc tccagtcact tcaacaaatt   1800

gagagtatga ttgaagctga gtcctctgtc aaagagaaag acatgaccaa agagttcttt   1860

gagaacaaat cagaaacatg gcccattgga gagtccccca aaggagtgga ggaaagttcc   1920

attgggaagg tctgcaggac tttattagca aagtcggtat tcaacagctt gtatgcatct   1980

ccacaactag aaggattttc agctgaatca agaaaactgc ttcttatcgt tcaggctctt   2040

agggacaacc tggaacctgg gacctttgat cttgggggc tatatgaagc aattgaggag    2100

tgcctgatta atgatccctg ggttttgctt aatgcttctt ggttcaactc cttccttaca   2160

catgcattga gttagttgtg gcagtgctac tatttgctat ccatactgtc caaaaaagta   2220

ccttgtttct act                                                      2233
```

<210> SEQ ID NO 59
<211> LENGTH: 716
<212> TYPE: PRT
<213> ORGANISM: Artificial Sequence
<220> FEATURE:
<223> OTHER INFORMATION: Synthetic Sequence

<400> SEQUENCE: 59

```
Met Glu Asp Phe Val Arg Gln Cys Phe Asn Pro Met Ile Val Glu Leu
1               5                   10                  15

Ala Glu Lys Thr Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45
```

-continued

```
Ser Asp Phe His Phe Ile Asn Glu Gln Gly Glu Ser Ile Ile Val Glu
    50                  55                  60

Leu Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asn
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Leu
385                 390                 395                 400

Lys Ser Leu Ala Ser Trp Ile Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ser
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
```

```
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Ile Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Ser Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Ser
705                 710                 715


<210> SEQ ID NO 60
<211> LENGTH: 890
<212> TYPE: DNA
<213> ORGANISM: Artificial Sequence
<220> FEATURE:
<223> OTHER INFORMATION: Synthetic Sequence

<400> SEQUENCE: 60

agcaaaagca gggtgacaaa aacataatgg atccaaacac tgtgtcaagc tttcaggtag     60

attgctttct ttggcatgtc cgcaaacgag ttgcagacca agaactaggc gatcccccat    120

tccttgatcg gcttcgccga gatcagaaat ccctaagagg aaggggcagt actctcggtc    180

tggacatcaa gacagccaca cgtgctggaa agcagatagt ggagcggatt ctgaaagaag    240

aatccgatga ggcacttaaa atgaccatgg cctctgtacc tgcgtcgcgt tacctaactg    300

acatgactct tgaggaaatg tcaagggact ggtccatgct catacccaag cagaaagtgg    360

caggccctct ttgtatcaaa atggaccagg cgatcatgga taagaacatc atactgaaag    420

cgaacttcag tgtgattttt gaccggctgg agactctaat attgctaagg gctttcaccg    480

aagagggagc aattgttggc gaaatttcac cattgccttc tcttccagga catactgctg    540

aggatgtcaa aaatgcagtt ggagtcctca tcggaggact tgaatggaat gataacacag    600

ttcgagtctc tgaaactcta cagagattcg cttggagaag cagtaatgag aatgggagac    660
```

-continued

```
ctccactcac tccaaaacag aaacgagaaa tggcgggaac aattaggtca gaagtttgaa    720

gaaataagat ggttgattga agaagtgaga cacaaactga agataacaga gaatagtttt    780

gagcaaataa catttatgca agccttacat ctattgcttg aagtggagca agagataaga    840

actttctcgt ttcagcttat ttagtactaa aaaacaccct tgtttctact              890
```

<210> SEQ ID NO 61
<211> LENGTH: 230
<212> TYPE: PRT
<213> ORGANISM: Artificial Sequence
<220> FEATURE:
<223> OTHER INFORMATION: Synthetic Sequence

<400> SEQUENCE: 61

```
Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Pro Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Lys Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Asp Trp Ser Met Leu Ile Pro Lys Gln Lys Val Ala
            100                 105                 110

Gly Pro Leu Cys Ile Lys Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Asp Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Glu Met Ala Gly
    210                 215                 220

Thr Ile Arg Ser Glu Val
225                 230
```

<210> SEQ ID NO 62
<211> LENGTH: 121
<212> TYPE: PRT
<213> ORGANISM: Artificial Sequence
<220> FEATURE:
<223> OTHER INFORMATION: Synthetic Sequence

<400> SEQUENCE: 62

```
Met Asp Pro Asn Thr Val Ser Ser Phe Gln Asp Ile Leu Leu Arg Met
1               5                   10                  15

Ser Lys Met Gln Leu Glu Ser Ser Ser Glu Asp Leu Asn Gly Met Ile
            20                  25                  30
```

-continued

Thr Gln Phe Glu Ser Leu Lys Leu Tyr Arg Asp Ser Leu Gly Glu Ala
35 40 45

Val Met Arg Met Gly Asp Leu His Ser Leu Gln Asn Arg Asn Glu Lys
50 55 60

Trp Arg Glu Gln Leu Gly Gln Lys Phe Glu Glu Ile Arg Trp Leu Ile
65 70 75 80

Glu Glu Val Arg His Lys Leu Lys Ile Thr Glu Asn Ser Phe Glu Gln
85 90 95

Ile Thr Phe Met Gln Ala Leu His Leu Leu Leu Glu Val Glu Gln Glu
100 105 110

Ile Arg Thr Phe Ser Phe Gln Leu Ile
115 120

<210> SEQ ID NO 63
<211> LENGTH: 2369
<212> TYPE: DNA
<213> ORGANISM: Artificial Sequence
<220> FEATURE:
<223> OTHER INFORMATION: Synthetic Sequence

<400> SEQUENCE: 63
agcagaagcg gagcctttaa gatgaatata aatccttatt ttctcttcat agatgtaccc 60
atacaggcag caatttcaac aacattccca tacaccggtg ttccccctta ttcccatgga 120
acgggaacag gctacacaat agacaccgtg atcagaacac atgagtactc aaacaaggga 180
aaacagtaca tttctgatgt tacaggatgt acaatggtag atccaacaaa tgggccatta 240
cccgaagaca atgagccgag tgcctatgca caattagatt gcgttctgga ggctttggat 300
agaatggatg aagaacatcc aggtctgttt caagcagcct cacagaatgc catggaggca 360
ctaatggtca caactgtaga caaattaacc caggggagac agacttttga ttggacagta 420
tgcagaaacc aacctgctgc aacggcactg aacacaacaa taacctcttt taggttgaat 480
gatttgaatg gagccgacaa gggtggatta gtaccctttt gccaagatat cattgattca 540
ttggacagac ctgaaatgac tttcttctca gtaaagaata taaagaaaaa attgcctgct 600
aaaaacagaa agggtttcct cataaagaga ataccaatga aggtaaaaga cagaataacc 660
agagtggaat acatcaaaag agcattatca ttaaacacaa tgacaaaaga tgctgaaaga 720
ggcaaactaa aaagaagagc gattgccacc gctggaatac aaatcagagg gtttgtatta 780
gtagttgaaa acttggctaa aaatatctgt gaaaatctag aacaaagtgg tttgccagta 840
ggtggaaacg agaagaaggc caaactgtca aatgcagtgg ccaaaatgct cagtaactgc 900
ccaccaggag ggatcagcat gacagtaaca ggagacaata ccaaatggaa tgaatgctta 960
aatccaagaa tctttttggc tatgactgaa agaataacca gagacagccc aatttggttc 1020
cgggattttt gtagtatagc accggtcttg ttctccaata aaatagccag attgggaaaa 1080
gggtttatga taacaagcaa aacaaaaaga ctgaaggctc aaataccttg tcctgatctg 1140
tttagtatac cattagaaag atataatgaa gaaacaaggg caaaattgaa aaagctgaaa 1200
ccattcttca atgaagaagg aacggcatct ttgtcgcctg ggatgatgat gggaatgttt 1260
aatatgctat ctaccgtgtt gggagtagcc gcactaggta tcaaaaacat tggaaacaaa 1320
gaatacttat gggatggact gcaatcttct gatgattttg ctctgtttgt taatgcaaaa 1380
gatgaagaga catgtatgga aggaataaac gacttttacc gaacatgtaa actattggga 1440
ataaacatga gcaaaaagaa aagttactgt aatgaaactg gaatgtttga atttacaagc 1500
atgttctaca gagatggatt tgtatctaat tttgcaatgg aacttccttc atttggagtt 1560
gctggagtaa atgaatcagc agatatggca ataggaatga caataataaa gaacaatatg 1620
atcaacaatg ggatgggtcc agcaacagca caaacagcca tacaattatt catagctgat 1680
tatagataca cctacaaatg ccacagggga gattccaaag tggaaggaaa gagaatgaaa 1740
attataaagg agctatggga aaacactaaa ggaagagatg gtctgttagt agcagatggt 1800
gggcctaaca tttacaattt gagaaacttg catatcccag aaatagtatt aaagtacaac 1860
ctaatggacc ctgaatacaa agggcggtta cttcatcctc aaaatccctt tgtaggacat 1920
ttgtctattg agggcatcaa agaggcagat ataaccccag cacatggtcc agtaaagaaa 1980
atggactatg atgcggtgtc tggaactcat agttggagaa ccaaaaggaa cagatctata 2040
ctaaacactg atcagaggaa catgattctt gaggaacaat gctacgctaa gtgttgcaac 2100
ctttttgagg cctgttttaa cagtgcatca tacaggaaac cagtaggtca gcacagcatg 2160
cttgaggcta tggcccacag attaagaatg gatgcacgac tagattatga atcaggaaga 2220
atgtcaaagg atgattttga gaaagcaatg gctcaccttg gtgagattgg gtacatataa 2280
gcttcgaaga tgtctatggg gttattggtc atcattgaat acatgcggta cacaaatgat 2340
taaaatgaaa aaaggctcgt gtttctact 2369

<210> SEQ ID NO 64
<211> LENGTH: 2396
<212> TYPE: DNA
<213> ORGANISM: Artificial Sequence
<220> FEATURE:
<223> OTHER INFORMATION: Synthetic Sequence

<400> SEQUENCE: 64
agcagaagcg gagcgttttc aagatgacat tggctaaaat tgaattgtta aaacaactgt 60
taagggacaa cgaagccaaa acagtattga aacaaacaac ggtagaccaa tataacataa 120
taagaaaatt caatacatca agaattgaaa agaacccttc attaaggatg aagtgggcca 180
tgtgttctaa ttttcccttg gctctgacca agggtgatat ggcaaataga atccccttgg 240
aatacaaggg aatacaactt aaaacaaatg ctgaagacat aggaaccaaa ggccaaatgt 300
gctcaatagc agcagttacc tggtggaata catatggacc aataggagac actgaaggtt 360
tcgaaaaggt ctacgaaagc ttctttctca gaaagatgag acttgacaat gccacttggg 420
gccgaataac ttttggccca gttgaaagag taagaaaaag ggtactgcta aaccctctca 480
ccaaggaaat gcctccagat gaagcgagca atgtgataat ggaaatattg ttccctaagg 540
aagcaggaat accaagagaa tctacttgga tacataggga actgataaaa gaaaaaagag 600
aaaaattgaa aggaacgatg ataactccca ttgtactggc atacatgctt gagagagaat 660
tggttgcccg aagaaggttc ctgccagtgg caggagcaac atcagctgag ttcatagaaa 720
tgctacactg cttacaaggt gaaaattgga gacaaatata tcacccagga gggaataaac 780
taactgaatc taggtctcaa tcaatgattg tagcttgtag aaaaataatc agaagatcaa 840
tagtcgcatc aaacccacta gagctagctg tagaaattgc aaacaagact gtgatagata 900
ctgaaccttt aaaatcatgt ctggcagcca tagacggagg tgatgtagcc tgtgacataa 960
tgagagctgc attaggacta aagatcagac aaagacaaag atttggacgg cttgaactaa 1020
agagaatatc aggaagagga ttcaaaaatg atgaagaaat attgatcggg aacggaacaa 1080
tacagaagat tggaatatgg gacggagaag aggagttcca tgtaagatgt ggtgaatgca 1140
ggggaatatt aaaaaagagc aaaatgagaa tggaaaaact actaataaat tcagccaaaa 1200

-continued aggaggacat gaaagattta ataatcttgt gcatggtatt ttctcaagac actaggatgt 1260
tccaaggagt gagaggagaa ataaattttc ttaatcgagc aggccaactt ttatctccaa 1320
tgtaccaact ccaaagatat tttttgaata ggagcaacga tctttttgat caatgggggt 1380
atgaggaatc acccaaagca agtgaactac atgggataaa tgaattaatg aatgcatctg 1440
attatacgtt gaaaggggtt gtagtaacaa aaaatgtgat tgatgacttt agttctactg 1500
aaacagaaaa agtatctata acaaaaaatc ttagtttaat aaaaagaact ggggaagtca 1560
taatgggggc taatgacgta agtgaattag aatcacaagc tcagctaatg ataacatatg 1620
atacacctaa gatgtgggag atgggaacaa ccaaagaact ggtgcaaaac acctaccaat 1680
gggtgctaaa aaatttggta acactgaagg ctcagtttct tctaggaaaa gaagacatgt 1740
tccaatggga tgcatttgaa gcatttgaaa gcataatccc ccagaagatg gctggccagt 1800
acagtggatt tgcaagggca gtgctcaaac aaatgagaga ccaagaggtt atgaaaactg 1860
accagttcat aaagttgttg cctttctgtt tctcaccacc aaaattaagg agcaatgggg 1920
agccttatca attcttgagg cttatattga agggaggagg agaaaatttc atcgaagtaa 1980
ggaaagggtc ccctctattc tcctacaatc cacaaacaga agtcctaact atatgcggca 2040
gaatgatgtc attaaaaggg aaaattgaag atgaagaaag gaatagatca atggggaatg 2100
cagtattggc aggctttctc gttagtggca agtatgaccc agatcttgga gatttcaaaa 2160
ctattgaaga acttgaaaag ctaaaaccgg gggagaaagc aaacatctta ctttatcaag 2220
gaaagcccgt taaagtagtt aaaaggaaaa gatatagtgc tttatccaat gacatttcac 2280
aaggaattaa gagacaaaga atgacagttg agtccatggg gtgggccttg agctaatata 2340
aatttatcca ttaattcaat aaacacaatt gagtgaaaaa tgctcgtgtt tctact 2396

<210> SEQ ID NO 65
<211> LENGTH: 2308
<212> TYPE: DNA
<213> ORGANISM: Artificial Sequence
<220> FEATURE:
<223> OTHER INFORMATION: Synthetic Sequence

<400> SEQUENCE: 65
agcagaagcg gtgcgtttga tttgccataa tggatacttt tattacaaga aacttccaga 60
ctacaataat acaaaaggcc aaaaacacaa tggcagaatt tagtgaagat cctgaattac 120
aaccagcaat gctattcaac atctgcgtcc atctggaggt ctgctatgta ataagtgata 180
tgaattttct tgatgaagaa ggaaaagcat atacagcatt agaaggacaa ggaaaagaac 240
aaaacttgag accacaatat gaagtgattg agggaatgcc aagaaacata gcatggatgg 300
ttcaaagatc cttagcccaa gagcatggga tagagactcc aaggtatctg gctgatttgt 360
tcgattataa aactaagagg tttatagaag ttggaataac aaagggattg gctgatgatt 420
acttctggaa aaagaaagaa aagctgggga atagcatgga actgatgata ttcagctaca 480
atcaagacta ttcgttaagt aatgaatcct cattggatga ggaaggaaaa gggagagtgc 540
taagcagact cacagaactt caggctgagt taagtctgaa aaatctatgg caagttctca 600
taggagaaga agatattgaa aaaggaattg acttcaaact tggacaaaca atatctaaac 660
taagggatat atctgttcca gctggtttct ccaattttga aggaatgagg agctacatag 720
acaatataga tcctaaagga gcaatagaga gaaatctagc aaggatgtct cccttagtat 780
cagttacacc taaaaagttg aaatgggagg acctaagacc aatagggcct cacatttaca 840
accatgagct accagaagtt ccatataatg cctttcttct aatgtctgat gaattggggc 900

-continued tggctaatat gactgaaggg aagtccaaga aaccgaagac cttagccaaa gagtgcctag 960
aaaagtactc aacactacgg gatcaaactg acccaatatt aataatgaaa agcgaaaaag 1020
ctaatgaaca cttcctatgg aaactgtgga gggactgtgt aaatacaata agtaatgagg 1080
aaacaagtaa cgaattacag aaaaccaatt atgccaagtg ggccacagga gatggattaa 1140
catatcagaa aataatgaaa gaagtagcaa tagatgacga aacaatgtac caagaagagc 1200
ccaaaatacc taacaaatgt agagtggctg cttgggttca aacagagatg aatctattga 1260
gcactctgac aagtaaaagg gccctggatc tgccagaaat agggccagac gtagcacccg 1320
tggagcatgt agggagtgaa agaaggaaat actttgttaa tgaaatcaac tactgtaagg 1380
cctctaccgt tatgatgaag tatgtgcttt ttcacacttc attattaaat gaaagcaatg 1440
ccagtatggg aaaatataaa gtaataccaa taaccaacag agtagtaaat gaaaagggag 1500
aaagttttga catgctttat ggtctagcgg ttaaagggca atctcatctg aggggagata 1560
ctgatgttgt aacagttgtg actttcgaat ttagtagtac agatcccaga gtggactcag 1620
gaaagtggcc aaaatatact gtatttagaa ttggctcctt atttgtgagt gggagggaaa 1680
aatctgtata cctatattgc cgagtgaatg gtacaaataa gatccaaatg aaatggggaa 1740
tggaagctag aagatgtctg cttcaatcaa tgcaacaaat ggaagcaatt gttgaacaag 1800
aatcatcgat acaaggatat gacatgacca aagcttgttt caagggagac agagtgaata 1860
gtccaaaaac tttcagtatt gggactcaag aaggaaaact agtgaaagga tcctttggga 1920
aagcactaag agtaatattc accaaatgtt tgatgcacta tgtatttgga aatgcccaat 1980
tggaggggtt tagtgccgaa tctaggagac ttctactgtt aattcaggca ttaaaagaca 2040
gaaagggccc ttgggtattc gacttagagg gaatgtattc tggaatagaa gaatgtatta 2100
gtaacaaccc ttgggtaata cagagtgcat actggtttaa tgaatggttg ggctttgaaa 2160
aagaggggag taaagtatta gaatcagtag atgaaataat ggatgaatga aagaagggca 2220
tagtgctcaa tttggtacta ttttgttcat tatgtatcta aacatccaat ataaagaatt 2280
gagaattaaa aatgcacgtg tttctact 2308

<210> SEQ ID NO 66
<211> LENGTH: 1843
<212> TYPE: DNA
<213> ORGANISM: Artificial Sequence
<220> FEATURE:
<223> OTHER INFORMATION: Synthetic Sequence

<400> SEQUENCE: 66
agcagaagca cagcattttc ttgtgaactt caagtaccaa caaaaaactg aaaatcaaaa 60
tgtccaacat ggacattgac ggcatcaaca ctggaataat tgacaaaaca ccagaagaaa 120
taacttccgg aaccagtggg gcaaccagac caatcatcag accagcaacc cttgcctcac 180
caagcaacaa acgaaccaga aacccatccc cggaaagggc aaccacaagc agtgaagctg 240
atgtcggaag gaaaacccaa aagaaacaaa ctccgacaga gataaagaag agcgtctaca 300
atatggtagt gaaactgggt gaattctaca accagatgat ggtcaaagct ggactcaacg 360
atgacatgga gagaaaccta atccaaaatg cacatgctgt ggaaagaatt ctattggctg 420
ctactgatga caagaaaact gaattccaaa agaaaaagaa tgccagagac gtcaaagaag 480
ggaaagaaga aatagaccat aacaaaacag gaggcacctt ttacaagatg gtaagagata 540
ataaaaccat ctacttcagc cctataagaa ttaccttttt aaaagaagag gtgaaaacaa 600
tgtacaaaac caccatgggg agtgacggtt tcagtggact aaatcacatc atgattgggc 660
attcacagac gaacgatgtc tgtttccaaa gatcaaaggc actaaaaaga gttggacttg 720
acccttcatt aatcagtact tttgcaggaa gcacactccc cagaagatca ggtacaactg 780
gtgttgcgac caaaggaggt ggaactttag tggcagaagc cattcgattt ataggaagag 840
caatggcaga cagagggcta ttgagagaca tcagagccaa gacggcctat gaaaagattc 900
ttctgaatct gaaaaacaag tgctctgcgc cccaacaaaa ggctctggtt gatcaagtga 960
tcggaagtag aaatccaggg attgcagaca tagaagatct caccctgctt gctcgaagta 1020
tggtcgttgt taggccctct gtagcaagca aagtggtgct tcccataagc atctatgcta 1080
aaatacctca actggggttc aacgttgaag aatactctat ggttgggtat gaagccatgg 1140
ctctttataa tatggcaaca cctgtttcca tattaagaat gggagacgat gcaaaagata 1200
aatcacaatt attcttcatg tcttgctttg gagctgccta tgaagaccta agagttctgt 1260
ctgcactaac aggcacggaa ttcaagccta ggtcagcatt aaagtgcaaa ggtttccacg 1320
ttccagcaaa ggagcaagtg gaaggaatgg gggcagctct gatgtccatc aagctccagt 1380
tttgggctcc aatgaccaga tctgggggga atgaagtagg tggagacgga gggtctggtc 1440
aaataagttg cagccccgtg tttgcagtag aaagacctat tgctctaagc aagcaagctg 1500
taagaagaat gctgtcaatg aatattgagg gacgtgatgc agatgtcaaa ggaaatctac 1560
tcaagatgat gaatgattca atggctaaga aaaccaatgg aaatgctttc attgggaaga 1620
aaatgttcca aatatcagac aaaaacaaaa ccaatcccgt tgagattcca attaagcaga 1680
ccatccccag tttcttcttt gggagggaca cagcagagga ttatgatgac ctcgattatt 1740
aaagcaacaa aatagacact atggctgtga ttgtttcagt acgtttggaa tgtgggtgtt 1800
tactcttatt gaaataaatg taaaaaatgc tgttgtttct act 1843

<210> SEQ ID NO 67
<211> LENGTH: 1098
<212> TYPE: DNA
<213> ORGANISM: Artificial Sequence
<220> FEATURE:
<223> OTHER INFORMATION: Synthetic Sequence

<400> SEQUENCE: 67
agcagaagca gaggatttgt ttagtcactg gcaaacggga aaaaatggcg gacaacatga 60
ccacaacaca aattgaggtg ggtccgggag caaccaatgc cactataaac tttgaagcag 120
gaattttgga gtgctatgaa aggctttcat ggcaaagagc ccttgactac cctggtcaag 180
accgcctaaa cagactaaag agaaaattag aatcaagaat aaagactcac aacaaaagtg 240
agcctgaaag taaaaggatg tctcttgaag agagaaaagc aattggggta aaaatgatga 300
aagtgctcct atttatgaac ccatctgctg gaattgaagg gtttgagcca tactgtatga 360
aaaattcctc caatagcaac tgcccaaact gcaattgggc cgattaccct ccaacatcag 420
gaaagtgcct tgatgacata gaagaagaac cggagaatgt tgatgaccca actgaaatag 480
tattaaggga catgaacaac aaagatgcaa ggcaaaagat aaaagaggaa gtaaacactc 540
agaaagaagg gaagttccgt ttgacaatac aaagggatat acgtaatgtg ttgtccttga 600
gagtgttggt aaacggaaca ttcctcaagc accctaatgg atacaagtcc ttatcaactc 660
tgcatagatt gaatgcatat gaccagagtg gaaggcttgt tgctaaactt gttgctactg 720
atgatcttac agtggaggat gaagaagatg gccatcggat cctcaactca ctcttcgagc 780
gttttaatga aggacattca aagccaattc gagcagctga aactgcggtg ggagtcttat 840
cccaatttgg tcaagagcac cgattatcac cagaggaggg agacaattag actggttacg 900
gaagaacttt atcttttaag taaaagaatt gatgataaca tattgttcca caaaacagta 960
atagctaaca gctccataat agctgacatg attgtatcat tatcattatt ggaaacattg 1020
tatgagatga aggatgtggt tgaagtgtac agcaggcagt gcttgtgaat ttaaaataaa 1080
aatcctcttg ttactact 1098

<210> SEQ ID NO 68
<211> LENGTH: 752
<212> TYPE: PRT
<213> ORGANISM: Artificial Sequence
<220> FEATURE:
<223> OTHER INFORMATION: Synthetic Sequence

<400> SEQUENCE: 68

Met Asn Ile Asn Pro Tyr Phe Leu Phe Ile Asp Val Pro Ile Gln Ala
1 5 10 15

Ala Ile Ser Thr Thr Phe Pro Tyr Thr Gly Val Pro Pro Tyr Ser His
20 25 30

Gly Thr Gly Thr Gly Tyr Thr Ile Asp Thr Val Ile Arg Thr His Glu
35 40 45

Tyr Ser Asn Lys Gly Lys Gln Tyr Ile Ser Asp Val Thr Gly Cys Thr
50 55 60

Met Val Asp Pro Thr Asn Gly Pro Leu Pro Glu Asp Asn Glu Pro Ser
65 70 75 80

Ala Tyr Ala Gln Leu Asp Cys Val Leu Glu Ala Leu Asp Arg Met Asp
85 90 95

Glu Glu His Pro Gly Leu Phe Gln Ala Ala Ser Gln Asn Ala Met Glu
100 105 110

Ala Leu Met Val Thr Thr Val Asp Lys Leu Thr Gln Gly Arg Gln Thr
115 120 125

Phe Asp Trp Thr Val Cys Arg Asn Gln Pro Ala Ala Thr Ala Leu Asn
130 135 140

Thr Thr Ile Thr Ser Phe Arg Leu Asn Asp Leu Asn Gly Ala Asp Lys
145 150 155 160

Gly Gly Leu Val Pro Phe Cys Gln Asp Ile Ile Asp Ser Leu Asp Arg
165 170 175

Pro Glu Met Thr Phe Phe Ser Val Lys Asn Ile Lys Lys Lys Leu Pro
180 185 190

Ala Lys Asn Arg Lys Gly Phe Leu Ile Lys Arg Ile Pro Met Lys Val
195 200 205

Lys Asp Arg Ile Thr Arg Val Glu Tyr Ile Lys Arg Ala Leu Ser Leu
210 215 220

Asn Thr Met Thr Lys Asp Ala Glu Arg Gly Lys Leu Lys Arg Arg Ala
225 230 235 240

Ile Ala Thr Ala Gly Ile Gln Ile Arg Gly Phe Val Leu Val Val Glu
245 250 255

Asn Leu Ala Lys Asn Ile Cys Glu Asn Leu Glu Gln Ser Gly Leu Pro
260 265 270

Val Gly Gly Asn Glu Lys Lys Ala Lys Leu Ser Asn Ala Val Ala Lys
275 280 285

Met Leu Ser Asn Cys Pro Pro Gly Gly Ile Ser Met Thr Val Thr Gly
290 295 300

Asp Asn Thr Lys Trp Asn Glu Cys Leu Asn Pro Arg Ile Phe Leu Ala

-continued

```
305                 310                 315                 320

Met Thr Glu Arg Ile Thr Arg Asp Ser Pro Ile Trp Phe Arg Asp Phe
                325                 330                 335

Cys Ser Ile Ala Pro Val Leu Phe Ser Asn Lys Ile Ala Arg Leu Gly
            340                 345                 350

Lys Gly Phe Met Ile Thr Ser Lys Thr Lys Arg Leu Lys Ala Gln Ile
        355                 360                 365

Pro Cys Pro Asp Leu Phe Ser Ile Pro Leu Glu Arg Tyr Asn Glu Glu
    370                 375                 380

Thr Arg Ala Lys Leu Lys Lys Leu Lys Pro Phe Phe Asn Glu Glu Gly
385                 390                 395                 400

Thr Ala Ser Leu Ser Pro Gly Met Met Met Gly Met Phe Asn Met Leu
                405                 410                 415

Ser Thr Val Leu Gly Val Ala Ala Leu Gly Ile Lys Asn Ile Gly Asn
            420                 425                 430

Lys Glu Tyr Leu Trp Asp Gly Leu Gln Ser Ser Asp Asp Phe Ala Leu
        435                 440                 445

Phe Val Asn Ala Lys Asp Glu Glu Thr Cys Met Glu Gly Ile Asn Asp
    450                 455                 460

Phe Tyr Arg Thr Cys Lys Leu Leu Gly Ile Asn Met Ser Lys Lys Lys
465                 470                 475                 480

Ser Tyr Cys Asn Glu Thr Gly Met Phe Glu Phe Thr Ser Met Phe Tyr
                485                 490                 495

Arg Asp Gly Phe Val Ser Asn Phe Ala Met Glu Leu Pro Ser Phe Gly
            500                 505                 510

Val Ala Gly Val Asn Glu Ser Ala Asp Met Ala Ile Gly Met Thr Ile
        515                 520                 525

Ile Lys Asn Asn Met Ile Asn Asn Gly Met Gly Pro Ala Thr Ala Gln
    530                 535                 540

Thr Ala Ile Gln Leu Phe Ile Ala Asp Tyr Arg Tyr Thr Tyr Lys Cys
545                 550                 555                 560

His Arg Gly Asp Ser Lys Val Glu Gly Lys Arg Met Lys Ile Ile Lys
                565                 570                 575

Glu Leu Trp Glu Asn Thr Lys Gly Arg Asp Gly Leu Leu Val Ala Asp
            580                 585                 590

Gly Gly Pro Asn Ile Tyr Asn Leu Arg Asn Leu His Ile Pro Glu Ile
        595                 600                 605

Val Leu Lys Tyr Asn Leu Met Asp Pro Glu Tyr Lys Gly Arg Leu Leu
    610                 615                 620

His Pro Gln Asn Pro Phe Val Gly His Leu Ser Ile Glu Gly Ile Lys
625                 630                 635                 640

Glu Ala Asp Ile Thr Pro Ala His Gly Pro Val Lys Lys Met Asp Tyr
                645                 650                 655

Asp Ala Val Ser Gly Thr His Ser Trp Arg Thr Lys Arg Asn Arg Ser
            660                 665                 670

Ile Leu Asn Thr Asp Gln Arg Asn Met Ile Leu Glu Glu Gln Cys Tyr
        675                 680                 685

Ala Lys Cys Cys Asn Leu Phe Glu Ala Cys Phe Asn Ser Ala Ser Tyr
    690                 695                 700

Arg Lys Pro Val Gly Gln His Ser Met Leu Glu Ala Met Ala His Arg
705                 710                 715                 720

Leu Arg Met Asp Ala Arg Leu Asp Tyr Glu Ser Gly Arg Met Ser Lys
                725                 730                 735
```

Asp Asp Phe Glu Lys Ala Met Ala His Leu Gly Glu Ile Gly Tyr Ile
740 745 750

<210> SEQ ID NO 69
<211> LENGTH: 770
<212> TYPE: PRT
<213> ORGANISM: Artificial Sequence
<220> FEATURE:
<223> OTHER INFORMATION: Synthetic Sequence

<400> SEQUENCE: 69

Met Thr Leu Ala Lys Ile Glu Leu Leu Lys Gln Leu Leu Arg Asp Asn
1 5 10 15

Glu Ala Lys Thr Val Leu Lys Gln Thr Thr Val Asp Gln Tyr Asn Ile
20 25 30

Ile Arg Lys Phe Asn Thr Ser Arg Ile Glu Lys Asn Pro Ser Leu Arg
35 40 45

Met Lys Trp Ala Met Cys Ser Asn Phe Pro Leu Ala Leu Thr Lys Gly
50 55 60

Asp Met Ala Asn Arg Ile Pro Leu Glu Tyr Lys Gly Ile Gln Leu Lys
65 70 75 80

Thr Asn Ala Glu Asp Ile Gly Thr Lys Gly Gln Met Cys Ser Ile Ala
85 90 95

Ala Val Thr Trp Trp Asn Thr Tyr Gly Pro Ile Gly Asp Thr Glu Gly
100 105 110

Phe Glu Lys Val Tyr Glu Ser Phe Phe Leu Arg Lys Met Arg Leu Asp
115 120 125

Asn Ala Thr Trp Gly Arg Ile Thr Phe Gly Pro Val Glu Arg Val Arg
130 135 140

Lys Arg Val Leu Leu Asn Pro Leu Thr Lys Glu Met Pro Pro Asp Glu
145 150 155 160

Ala Ser Asn Val Ile Met Glu Ile Leu Phe Pro Lys Glu Ala Gly Ile
165 170 175

Pro Arg Glu Ser Thr Trp Ile His Arg Glu Leu Ile Lys Glu Lys Arg
180 185 190

Glu Lys Leu Lys Gly Thr Met Ile Thr Pro Ile Val Leu Ala Tyr Met
195 200 205

Leu Glu Arg Glu Leu Val Ala Arg Arg Arg Phe Leu Pro Val Ala Gly
210 215 220

Ala Thr Ser Ala Glu Phe Ile Glu Met Leu His Cys Leu Gln Gly Glu
225 230 235 240

Asn Trp Arg Gln Ile Tyr His Pro Gly Gly Asn Lys Leu Thr Glu Ser
245 250 255

Arg Ser Gln Ser Met Ile Val Ala Cys Arg Lys Ile Ile Arg Arg Ser
260 265 270

Ile Val Ala Ser Asn Pro Leu Glu Leu Ala Val Glu Ile Ala Asn Lys
275 280 285

Thr Val Ile Asp Thr Glu Pro Leu Lys Ser Cys Leu Ala Ala Ile Asp
290 295 300

Gly Gly Asp Val Ala Cys Asp Ile Met Arg Ala Ala Leu Gly Leu Lys
305 310 315 320

Ile Arg Gln Arg Gln Arg Phe Gly Arg Leu Glu Leu Lys Arg Ile Ser
325 330 335

Gly Arg Gly Phe Lys Asn Asp Glu Glu Ile Leu Ile Gly Asn Gly Thr
340 345 350

-continued

```
Ile Gln Lys Ile Gly Ile Trp Asp Gly Glu Glu Glu Phe His Val Arg
        355                 360                 365

Cys Gly Glu Cys Arg Gly Ile Leu Lys Lys Ser Lys Met Arg Met Glu
    370                 375                 380

Lys Leu Leu Ile Asn Ser Ala Lys Lys Glu Asp Met Lys Asp Leu Ile
385                 390                 395                 400

Ile Leu Cys Met Val Phe Ser Gln Asp Thr Arg Met Phe Gln Gly Val
                405                 410                 415

Arg Gly Glu Ile Asn Phe Leu Asn Arg Ala Gly Gln Leu Leu Ser Pro
            420                 425                 430

Met Tyr Gln Leu Gln Arg Tyr Phe Leu Asn Arg Ser Asn Asp Leu Phe
        435                 440                 445

Asp Gln Trp Gly Tyr Glu Glu Ser Pro Lys Ala Ser Glu Leu His Gly
    450                 455                 460

Ile Asn Glu Leu Met Asn Ala Ser Asp Tyr Thr Leu Lys Gly Val Val
465                 470                 475                 480

Val Thr Lys Asn Val Ile Asp Asp Phe Ser Ser Thr Glu Thr Glu Lys
                485                 490                 495

Val Ser Ile Thr Lys Asn Leu Ser Leu Ile Lys Arg Thr Gly Glu Val
            500                 505                 510

Ile Met Gly Ala Asn Asp Val Ser Glu Leu Glu Ser Gln Ala Gln Leu
        515                 520                 525

Met Ile Thr Tyr Asp Thr Pro Lys Met Trp Glu Met Gly Thr Thr Lys
    530                 535                 540

Glu Leu Val Gln Asn Thr Tyr Gln Trp Val Leu Lys Asn Leu Val Thr
545                 550                 555                 560

Leu Lys Ala Gln Phe Leu Leu Gly Lys Glu Asp Met Phe Gln Trp Asp
                565                 570                 575

Ala Phe Glu Ala Phe Glu Ser Ile Ile Pro Gln Lys Met Ala Gly Gln
            580                 585                 590

Tyr Ser Gly Phe Ala Arg Ala Val Leu Lys Gln Met Arg Asp Gln Glu
        595                 600                 605

Val Met Lys Thr Asp Gln Phe Ile Lys Leu Leu Pro Phe Cys Phe Ser
    610                 615                 620

Pro Pro Lys Leu Arg Ser Asn Gly Glu Pro Tyr Gln Phe Leu Arg Leu
625                 630                 635                 640

Ile Leu Lys Gly Gly Gly Glu Asn Phe Ile Glu Val Arg Lys Gly Ser
                645                 650                 655

Pro Leu Phe Ser Tyr Asn Pro Gln Thr Glu Val Leu Thr Ile Cys Gly
            660                 665                 670

Arg Met Met Ser Leu Lys Gly Lys Ile Glu Asp Glu Glu Arg Asn Arg
        675                 680                 685

Ser Met Gly Asn Ala Val Leu Ala Gly Phe Leu Val Ser Gly Lys Tyr
    690                 695                 700

Asp Pro Asp Leu Gly Asp Phe Lys Thr Ile Glu Glu Leu Glu Lys Leu
705                 710                 715                 720

Lys Pro Gly Glu Lys Ala Asn Ile Leu Leu Tyr Gln Gly Lys Pro Val
                725                 730                 735

Lys Val Val Lys Arg Lys Arg Tyr Ser Ala Leu Ser Asn Asp Ile Ser
            740                 745                 750

Gln Gly Ile Lys Arg Gln Arg Met Thr Val Glu Ser Met Gly Trp Ala
        755                 760                 765
```

Leu Ser
770

<210> SEQ ID NO 70
<211> LENGTH: 726
<212> TYPE: PRT
<213> ORGANISM: Artificial Sequence
<220> FEATURE:
<223> OTHER INFORMATION: Synthetic Sequence

<400> SEQUENCE: 70

Met Asp Thr Phe Ile Thr Arg Asn Phe Gln Thr Thr Ile Ile Gln Lys
1 5 10 15

Ala Lys Asn Thr Met Ala Glu Phe Ser Glu Asp Pro Glu Leu Gln Pro
20 25 30

Ala Met Leu Phe Asn Ile Cys Val His Leu Glu Val Cys Tyr Val Ile
35 40 45

Ser Asp Met Asn Phe Leu Asp Glu Glu Gly Lys Ala Tyr Thr Ala Leu
50 55 60

Glu Gly Gln Gly Lys Glu Gln Asn Leu Arg Pro Gln Tyr Glu Val Ile
65 70 75 80

Glu Gly Met Pro Arg Asn Ile Ala Trp Met Val Gln Arg Ser Leu Ala
85 90 95

Gln Glu His Gly Ile Glu Thr Pro Arg Tyr Leu Ala Asp Leu Phe Asp
100 105 110

Tyr Lys Thr Lys Arg Phe Ile Glu Val Gly Ile Thr Lys Gly Leu Ala
115 120 125

Asp Asp Tyr Phe Trp Lys Lys Lys Glu Lys Leu Gly Asn Ser Met Glu
130 135 140

Leu Met Ile Phe Ser Tyr Asn Gln Asp Tyr Ser Leu Ser Asn Glu Ser
145 150 155 160

Ser Leu Asp Glu Glu Gly Lys Gly Arg Val Leu Ser Arg Leu Thr Glu
165 170 175

Leu Gln Ala Glu Leu Ser Leu Lys Asn Leu Trp Gln Val Leu Ile Gly
180 185 190

Glu Glu Asp Ile Glu Lys Gly Ile Asp Phe Lys Leu Gly Gln Thr Ile
195 200 205

Ser Lys Leu Arg Asp Ile Ser Val Pro Ala Gly Phe Ser Asn Phe Glu
210 215 220

Gly Met Arg Ser Tyr Ile Asp Asn Ile Asp Pro Lys Gly Ala Ile Glu
225 230 235 240

Arg Asn Leu Ala Arg Met Ser Pro Leu Val Ser Val Thr Pro Lys Lys
245 250 255

Leu Lys Trp Glu Asp Leu Arg Pro Ile Gly Pro His Ile Tyr Asn His
260 265 270

Glu Leu Pro Glu Val Pro Tyr Asn Ala Phe Leu Leu Met Ser Asp Glu
275 280 285

Leu Gly Leu Ala Asn Met Thr Glu Gly Lys Ser Lys Lys Pro Lys Thr
290 295 300

Leu Ala Lys Glu Cys Leu Glu Lys Tyr Ser Thr Leu Arg Asp Gln Thr
305 310 315 320

Asp Pro Ile Leu Ile Met Lys Ser Glu Lys Ala Asn Glu His Phe Leu
325 330 335

Trp Lys Leu Trp Arg Asp Cys Val Asn Thr Ile Ser Asn Glu Glu Thr
340 345 350

-continued

```
Ser Asn Glu Leu Gln Lys Thr Asn Tyr Ala Lys Trp Ala Thr Gly Asp
        355                 360                 365

Gly Leu Thr Tyr Gln Lys Ile Met Lys Glu Val Ala Ile Asp Asp Glu
    370                 375                 380

Thr Met Tyr Gln Glu Glu Pro Lys Ile Pro Asn Lys Cys Arg Val Ala
385                 390                 395                 400

Ala Trp Val Gln Thr Glu Met Asn Leu Leu Ser Thr Leu Thr Ser Lys
                405                 410                 415

Arg Ala Leu Asp Leu Pro Glu Ile Gly Pro Asp Val Ala Pro Val Glu
            420                 425                 430

His Val Gly Ser Glu Arg Arg Lys Tyr Phe Val Asn Glu Ile Asn Tyr
        435                 440                 445

Cys Lys Ala Ser Thr Val Met Met Lys Tyr Val Leu Phe His Thr Ser
    450                 455                 460

Leu Leu Asn Glu Ser Asn Ala Ser Met Gly Lys Tyr Lys Val Ile Pro
465                 470                 475                 480

Ile Thr Asn Arg Val Val Asn Glu Lys Gly Glu Ser Phe Asp Met Leu
                485                 490                 495

Tyr Gly Leu Ala Val Lys Gly Gln Ser His Leu Arg Gly Asp Thr Asp
            500                 505                 510

Val Val Thr Val Val Thr Phe Glu Phe Ser Ser Thr Asp Pro Arg Val
        515                 520                 525

Asp Ser Gly Lys Trp Pro Lys Tyr Thr Val Phe Arg Ile Gly Ser Leu
    530                 535                 540

Phe Val Ser Gly Arg Glu Lys Ser Val Tyr Leu Tyr Cys Arg Val Asn
545                 550                 555                 560

Gly Thr Asn Lys Ile Gln Met Lys Trp Gly Met Glu Ala Arg Arg Cys
                565                 570                 575

Leu Leu Gln Ser Met Gln Gln Met Glu Ala Ile Val Glu Gln Glu Ser
            580                 585                 590

Ser Ile Gln Gly Tyr Asp Met Thr Lys Ala Cys Phe Lys Gly Asp Arg
        595                 600                 605

Val Asn Ser Pro Lys Thr Phe Ser Ile Gly Thr Gln Glu Gly Lys Leu
    610                 615                 620

Val Lys Gly Ser Phe Gly Lys Ala Leu Arg Val Ile Phe Thr Lys Cys
625                 630                 635                 640

Leu Met His Tyr Val Phe Gly Asn Ala Gln Leu Glu Gly Phe Ser Ala
                645                 650                 655

Glu Ser Arg Arg Leu Leu Leu Leu Ile Gln Ala Leu Lys Asp Arg Lys
            660                 665                 670

Gly Pro Trp Val Phe Asp Leu Glu Gly Met Tyr Ser Gly Ile Glu Glu
        675                 680                 685

Cys Ile Ser Asn Asn Pro Trp Val Ile Gln Ser Ala Tyr Trp Phe Asn
    690                 695                 700

Glu Trp Leu Gly Phe Glu Lys Glu Gly Ser Lys Val Leu Glu Ser Val
705                 710                 715                 720

Asp Glu Ile Met Asp Glu
                725
```

<210> SEQ ID NO 71
<211> LENGTH: 560
<212> TYPE: PRT
<213> ORGANISM: Artificial Sequence
<220> FEATURE:
<223> OTHER INFORMATION: Synthetic Sequence

<400> SEQUENCE: 71

Met Ser Asn Met Asp Ile Asp Gly Ile Asn Thr Gly Ile Ile Asp Lys
1 5 10 15

Thr Pro Glu Glu Ile Thr Ser Gly Thr Ser Gly Ala Thr Arg Pro Ile
20 25 30

Ile Arg Pro Ala Thr Leu Ala Ser Pro Ser Asn Lys Arg Thr Arg Asn
35 40 45

Pro Ser Pro Glu Arg Ala Thr Thr Ser Ser Glu Ala Asp Val Gly Arg
50 55 60

Lys Thr Gln Lys Lys Gln Thr Pro Thr Glu Ile Lys Lys Ser Val Tyr
65 70 75 80

Asn Met Val Val Lys Leu Gly Glu Phe Tyr Asn Gln Met Met Val Lys
85 90 95

Ala Gly Leu Asn Asp Asp Met Glu Arg Asn Leu Ile Gln Asn Ala His
100 105 110

Ala Val Glu Arg Ile Leu Leu Ala Ala Thr Asp Asp Lys Lys Thr Glu
115 120 125

Phe Gln Lys Lys Lys Asn Ala Arg Asp Val Lys Glu Gly Lys Glu Glu
130 135 140

Ile Asp His Asn Lys Thr Gly Gly Thr Phe Tyr Lys Met Val Arg Asp
145 150 155 160

Asn Lys Thr Ile Tyr Phe Ser Pro Ile Arg Ile Thr Phe Leu Lys Glu
165 170 175

Glu Val Lys Thr Met Tyr Lys Thr Thr Met Gly Ser Asp Gly Phe Ser
180 185 190

Gly Leu Asn His Ile Met Ile Gly His Ser Gln Thr Asn Asp Val Cys
195 200 205

Phe Gln Arg Ser Lys Ala Leu Lys Arg Val Gly Leu Asp Pro Ser Leu
210 215 220

Ile Ser Thr Phe Ala Gly Ser Thr Leu Pro Arg Arg Ser Gly Thr Thr
225 230 235 240

Gly Val Ala Thr Lys Gly Gly Gly Thr Leu Val Ala Glu Ala Ile Arg
245 250 255

Phe Ile Gly Arg Ala Met Ala Asp Arg Gly Leu Leu Arg Asp Ile Arg
260 265 270

Ala Lys Thr Ala Tyr Glu Lys Ile Leu Leu Asn Leu Lys Asn Lys Cys
275 280 285

Ser Ala Pro Gln Gln Lys Ala Leu Val Asp Gln Val Ile Gly Ser Arg
290 295 300

Asn Pro Gly Ile Ala Asp Ile Glu Asp Leu Thr Leu Leu Ala Arg Ser
305 310 315 320

Met Val Val Val Arg Pro Ser Val Ala Ser Lys Val Val Leu Pro Ile
325 330 335

Ser Ile Tyr Ala Lys Ile Pro Gln Leu Gly Phe Asn Val Glu Glu Tyr
340 345 350

Ser Met Val Gly Tyr Glu Ala Met Ala Leu Tyr Asn Met Ala Thr Pro
355 360 365

Val Ser Ile Leu Arg Met Gly Asp Asp Ala Lys Asp Lys Ser Gln Leu
370 375 380

Phe Phe Met Ser Cys Phe Gly Ala Ala Tyr Glu Asp Leu Arg Val Leu
385 390 395 400

Ser Ala Leu Thr Gly Thr Glu Phe Lys Pro Arg Ser Ala Leu Lys Cys

-continued

```
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
        435                 440                 445

Gly Gly Asn Glu Val Gly Gly Asp Gly Gly Ser Gly Gln Ile Ser Cys
    450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495

Lys Gly Asn Leu Leu Lys Met Met Asn Asp Ser Met Ala Lys Lys Thr
            500                 505                 510

Asn Gly Asn Ala Phe Ile Gly Lys Lys Met Phe Gln Ile Ser Asp Lys
        515                 520                 525

Asn Lys Thr Asn Pro Val Glu Ile Pro Ile Lys Gln Thr Ile Pro Ser
    530                 535                 540

Phe Phe Phe Gly Arg Asp Thr Ala Glu Asp Tyr Asp Asp Leu Asp Tyr
545                 550                 555                 560


<210> SEQ ID NO 72
<211> LENGTH: 281
<212> TYPE: PRT
<213> ORGANISM: Artificial Sequence
<220> FEATURE:
<223> OTHER INFORMATION: Synthetic Sequence

<400> SEQUENCE: 72

Met Ala Asp Asn Met Thr Thr Thr Gln Ile Glu Val Gly Pro Gly Ala
1               5                   10                  15

Thr Asn Ala Thr Ile Asn Phe Glu Ala Gly Ile Leu Glu Cys Tyr Glu
            20                  25                  30

Arg Leu Ser Trp Gln Arg Ala Leu Asp Tyr Pro Gly Gln Asp Arg Leu
        35                  40                  45

Asn Arg Leu Lys Arg Lys Leu Glu Ser Arg Ile Lys Thr His Asn Lys
    50                  55                  60

Ser Glu Pro Glu Ser Lys Arg Met Ser Leu Glu Glu Arg Lys Ala Ile
65                  70                  75                  80

Gly Val Lys Met Met Lys Val Leu Leu Phe Met Asn Pro Ser Ala Gly
                85                  90                  95

Ile Glu Gly Phe Glu Pro Tyr Cys Met Lys Asn Ser Ser Asn Ser Asn
            100                 105                 110

Cys Pro Asn Cys Asn Trp Ala Asp Tyr Pro Pro Thr Ser Gly Lys Cys
        115                 120                 125

Leu Asp Asp Ile Glu Glu Glu Pro Glu Asn Val Asp Asp Pro Thr Glu
    130                 135                 140

Ile Val Leu Arg Asp Met Asn Asn Lys Asp Ala Arg Gln Lys Ile Lys
145                 150                 155                 160

Glu Glu Val Asn Thr Gln Lys Glu Gly Lys Phe Arg Leu Thr Ile Gln
                165                 170                 175

Arg Asp Ile Arg Asn Val Leu Ser Leu Arg Val Leu Val Asn Gly Thr
            180                 185                 190

Phe Leu Lys His Pro Asn Gly Tyr Lys Ser Leu Ser Thr Leu His Arg
        195                 200                 205

Leu Asn Ala Tyr Asp Gln Ser Gly Arg Leu Val Ala Lys Leu Val Ala
```

210 215 220

Thr Asp Asp Leu Thr Val Glu Asp Glu Glu Asp Gly His Arg Ile Leu
225 230 235 240

Asn Ser Leu Phe Glu Arg Phe Asn Glu Gly His Ser Lys Pro Ile Arg
245 250 255

Ala Ala Glu Thr Ala Val Gly Val Leu Ser Gln Phe Gly Gln Glu His
260 265 270

Arg Leu Ser Pro Glu Glu Gly Asp Asn
275 280

<210> SEQ ID NO 73
<211> LENGTH: 1111
<212> TYPE: DNA
<213> ORGANISM: Artificial Sequence
<220> FEATURE:
<223> OTHER INFORMATION: Synthetic Sequence

<400> SEQUENCE: 73
agcagaagca cgcactttct taaaatgtcg ctgtttggag acacaattgc ctacctgctt 60
tcattgacag aagatggaga aggcaaagca gaactagcag aaaaattaca ctgttggttc 120
ggtgggaaag aatttgacct agactctgcc ttggaatgga taaaaaacaa aagatgctta 180
actgacatac agaaagcact aattggcgcc tctatctgct tttaaaacc caaagaccag 240 gaaagaaaaa gaagattcat cacagagccc ctatcaggaa tggggacaac agcaacaaaa 300
aagaagggcc tgattctagc tgagagaaaa atgagaagat gtgtgagctt ccatgaagca 360
tttgaaatag cagaaggcca tgaaagctca gcgttactat attgtctcat ggtcatgtac 420
ctgaatcctg gaaattattc aatgcaagta aaactaggaa cgctctgtgc tttgtgcgaa 480
aaacaagcat cacattcaca cagggctcat agcagagcag cgagatcttc agtgcctgga 540
gtgagacggg aaatgcagat ggtctcagct atgaacacag caaaaacaat gaatggaatg 600
ggaaaaggag aagacgttca aaaactggca gaagaactgc aaagcaacat tggagtattg 660
agatctcttg ggcaagtca aaagaatggg gaaggaattg caaaggatgt aatggaagtg 720
ctaaagcaga gctctatggg aaattcagct cttgtgaaga aatacctata atgctcgaac 780
catttcagat tctttcaatt tgttagatag ctaaaagggg ccaaataaag agacaataaa 840
cagagaggta tcaattttga gacacagtta ccaaaaagaa atccaggcca aagaagcaat 900
gaaggaagta ctctctgaca acatggaggt attgagtgac cacatagtaa ttgaggggct 960
ttctgctgaa gagataataa aaatgggtga aacagttttg gaggtagaag aattgcatta 1020
aattcaattt ttactgtact tcttactatg catttaagca aattgtaatc aatgtcagca 1080
aataaactgg aaaaagtgcg ttgtttctac t 1111

<210> SEQ ID NO 74
<211> LENGTH: 109
<212> TYPE: PRT
<213> ORGANISM: Artificial Sequence
<220> FEATURE:
<223> OTHER INFORMATION: Synthetic Sequence

<400> SEQUENCE: 74

Met Leu Glu Pro Leu Gln Ile Leu Ser Ile Cys Ser Phe Ile Leu Ser
1 5 10 15

Ala Leu His Phe Met Ala Trp Thr Ile Gly His Leu Asn Gln Ile Arg
20 25 30

Arg Gly Val Asn Leu Lys Ile Gln Ile Arg Asn Pro Asn Lys Glu Ala

```
        35                  40                  45

Ile Asn Arg Glu Val Ser Ile Leu Arg His Asn Tyr Gln Lys Glu Ile
    50                  55                  60

Gln Ala Lys Glu Thr Met Lys Lys Ile Leu Ser Asp Asn Met Glu Val
65                  70                  75                  80

Leu Gly Asp His Ile Val Val Glu Gly Leu Ser Thr Asp Glu Ile Ile
                85                  90                  95

Lys Met Gly Glu Thr Val Leu Glu Val Glu Glu Leu Gln
            100                 105


<210> SEQ ID NO 75
<211> LENGTH: 3
<212> TYPE: PRT
<213> ORGANISM: Artificial Sequence
<220> FEATURE:
<223> OTHER INFORMATION: Synthetic Sequence

<400> SEQUENCE: 75

Gly Ser Gly
1


<210> SEQ ID NO 76
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 76

Gly Gly Gly Gly Ser Gly Gly Gly Gly Ser Gly Gly Gly Gly Ser
1               5                   10                  15


<210> SEQ ID NO 77
<211> LENGTH: 1273
<212> TYPE: PRT
<213> ORGANISM: Artificial Sequence
<220> FEATURE:
<223> OTHER INFORMATION: Synthetic Sequence

<400> SEQUENCE: 77

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160
```

-continued

```
Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575
```

-continued

```
Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
```

-continued

```
        995                 1000                1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270
```

<210> SEQ ID NO 78
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 78

```
Met Leu Glu Pro Phe Gln Ile Leu Ser Ile Cys
1               5                   10
```

<210> SEQ ID NO 79
<211> LENGTH: 1423
<212> TYPE: DNA
<213> ORGANISM: Artificial Sequence
<220> FEATURE:
<223> OTHER INFORMATION: Synthetic Sequence

<400> SEQUENCE: 79

-continued

```
agcaaaagca ggtagatatt gaaagatgag tcttctaacc gaggtcgaaa cgtacgtact     60
ctctatcatc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggaacgggg atccaaataa    300
catggacaaa gcagttaaac tgtataggaa gctcaagagg gagataacat tccatggggc    360
caaagaaatc tcactcagtt attctgctgg tgcacttgcc agttgtatgg gcctcatata    420
caacaggatg gggctgtga ccactgaagt ggcatttggc ctggtatgtg caacctgtga    480
acagattgct gactcccagc atcggtctca taggcaaatg gtgacaacaa ccaatccact    540
aatcagacat gagaacagaa tggttttagc cagcactaca gctaaggcta tggagcaaat    600
ggctggatcg agtgagcaag cagcagaggc catggaggtt gctagtcagg ctagacaaat    660
ggtgcaagcg atgagaacca ttggaactca tcctagctcc agtgctggtc tgaaaaatga    720
tcttcttgaa aatttgcagg cctatcagaa acgaatgggg gtgcagatgc aacggttcaa    780
gtgatcctaa tattacaaac ttgtgccctt ttggtgaagt ttttaacgcc accagatttg    840
catctgttta tgcttggaac aggaagagaa tcagcaactg tgttgctgat tattctgtcc    900
tatataattc cgcatcattt tccactttta agtgttatgg agtgtctcct actaaattaa    960
atgatctctg ctttactaat gtctatgcag attcatttgt aattagaggt gatgaagtca   1020
gacaaatcgc tccagggcaa actggaaaga ttgctgatta taattataaa ttaccagatg   1080
attttacagg ctgcgttata gcttggaatt ctaacaatct tgattctaag gttggtggta   1140
attataatta cctgtataga ttgtttagga agtctaatct caaacctttt gagagagata   1200
tttcaactga aatctatcag gccggtagca caccttgtaa tggtgttgaa ggttttaatt   1260
gttactttcc tttacaatca tatggtttcc aacccactaa tggtgttggt taccaaccat   1320
acagagtagt agtactttct tttgaacttc tacatgcacc agcaactgtt tgtggaccta   1380
aaaagtctat agagctggag taaaaaacta ccttgtttct act                      1423
```

<210> SEQ ID NO 80
<211> LENGTH: 1774
<212> TYPE: DNA
<213> ORGANISM: Artificial Sequence
<220> FEATURE:
<223> OTHER INFORMATION: Synthetic Sequence

<400> SEQUENCE: 80

```
agcaaaagca gggtgacaaa aacataatgg atccaaacac tgtgtcaagc tttcaagtag     60
attgctttct ttggcatgtc cgcaaacgag ttgcagacca agaactaggc gatcccccat    120
tccttgatcg gcttcgccga gatcagaaat ccctaagagg aaggggcagt actctcggtc    180
tggacatcaa gacagccaca cgtgctggaa agcagatagt ggagcggatt ctgaaagaag    240
aatccgatga ggcacttaaa atgaccatgg cctctgtacc tgcgtcgcgt tacctaactg    300
acatgactct tgaggaaatg tcaagggact ggtccatgct catacccaag cagaaagtgg    360
caggccctct ttgtatcaaa atggaccagg cgatcatgga taagaacatc atactgaaag    420
cgaacttcag tgtgattttt gaccggctgg agactctaat attgctaagg gctttcaccg    480
aagagggagc aattgttggc gaaatttcac cattgccttc tctcccggga catactgctg    540
aggttgtcaa aaatgcagtt ggagtcctaa tcggaggact tgaatggaac gataacacag    600
ttcgagtctc tgaaactcta cagagattcg cttggagaag cagtaatgag aacgggagac    660
```

-continued

```
ctccactgac tccaaaacag aaacgagaaa tggcgggaac aattaggtca gaagttggta    720

gtggaaatat tacaaacttg tgcccttttg gtgaagtttt taacgccacc agatttgcat    780

ctgtttatgc ttggaacagg aagagaatca gcaactgtgt tgctgattat tctgtcctat    840

ataattccgc atcattttcc acttttaagt gttatggagt gtctcctact aaattaaatg    900

atctctgctt tactaatgtc tatgcagatt catttgtaat tagaggtgat gaagtcagac    960

aaatcgctcc agggcaaact ggaaagattg ctgattataa ttataaatta ccagatgatt   1020

ttacaggctg cgttatagct tggaattcta acaatcttga ttctaaggtt ggtggtaatt   1080

ataattacct gtatagattg tttaggaagt ctaatctcaa accttttgag agagatattt   1140

caactgaaat ctatcaggcc ggtagcacac cttgtaatgg tgttgaaggt tttaattgtt   1200

actttccttt acaatcatat ggtttccaac ccactaatgg tgttggttac caaccataca   1260

gagtagtagt actttctttt gaacttctac atgcaccagc aactgtttgt ggacctaaaa   1320

agtctggatc aggtgcaact aactttagtc ttcttaaaca agctggtgat gttgaagaaa   1380

atcctggacc taatacagtg tctagcttcc aggacatact gctgaggatg tcaaaaatgc   1440

agttggagtc ctcatcggag gacttgaatg gaatgataac acagttcgag tctctgaaac   1500

tctacagaga ttcgcttgga gaagcagtaa tgagaatggg agacctccac tcactccaaa   1560

acagaaacga gaaatggcgg gaacaattag gtcagaagtt tgaagaaata agatggttga   1620

ttgaagaagt gagacacaaa ctgaagataa cagagaatag ttttgagcaa ataacattta   1680

tgcaagcctt acatctattg cttgaagtgg agcaagagat aagaactttc tcgtttcagc   1740

ttatttagta ctaaaaaaca cccttgtttc tact                                1774
```

<210> SEQ ID NO 81
<211> LENGTH: 1482
<212> TYPE: DNA
<213> ORGANISM: Artificial Sequence
<220> FEATURE:
<223> OTHER INFORMATION: Synthetic Sequence

<400> SEQUENCE: 81

```
agcaaaagca ggtagatatt gaaagatgag tcttctaacc gaggtcgaaa cttacgtact     60

ctctatcatc ccgtcaggcc ccctcaaagc cgagatcgca cagagacttg aagatgtctt    120

tgcagggaag aacaccgatc ttgaggttct catggaatgg ctaaagacaa gaccaatcct    180

gtcacctctg actaagggga ttttaggatt tgtgttcacg ctcaccgtgc ccagtgagcg    240

aggactgcag cgtagacgct ttgtccaaaa tgcccttaat gggaacgggg atccaaataa    300

catggacaaa gcagttaaac tgtataggaa gctcaagagg gagataacat tccatggggc    360

caaagaaatc tcactcagtt attctgctgg tgcacttgcc agttgtatgg gcctcatata    420

caacaggatg gggctgtga ccactgaagt ggcatttggc ctggtatgtg caacctgtga    480

acagattgct gactcccagc atcggtctca taggcaaatg gtgacaacaa ccaatccact    540

aatcagacat gagaacagaa tggttttagc cagcactaca gctaaggcta tggagcaaat    600

ggctggatcg agtgagcaag cagcagaggc catggaggtt gctagtcagg ctagacaaat    660

ggtgcaagcg atgagaacca ttggaactca tcctagctcc agtgctggtc tgaaaaatga    720

tcttcttgaa aatttgcaag cctatcagaa acgaatgggg gtgcagatgc aacggttcaa    780

gggatcaggt gcaactaact ttagtcttct taaacaagct ggtgatgttg aagaaaatcc    840

tggacctaat attacaaact tgtgcccttt tggtgaagtt tttaacgcca ccagatttgc    900
```

-continued

```
atctgtttat gcttggaaca ggaagagaat cagcaactgt gttgctgatt attctgtcct    960

atataattcc gcatcatttt ccacttttaa gtgttatgga gtgtctccta ctaaattaaa   1020

tgatctctgc tttactaatg tctatgcaga ttcatttgta attagaggtg atgaagtcag   1080

acaaatcgct ccagggcaaa ctggaaagat tgctgattat aattataaat taccagatga   1140

ttttacaggc tgcgttatag cttggaattc taacaatctt gattctaagg ttggtggtaa   1200

ttataattac ctgtatagat tgtttaggaa gtctaatctc aaaccttttg agagagatat   1260

ttcaactgaa atctatcagg ccggtagcac accttgtaat ggtgttgaag gttttaattg   1320

ttactttcct ttacaatcat atggtttcca acccactaat ggtgttggtt accaaccata   1380

cagagtagta gtactttctt ttgaacttct acatgcacca gcaactgttt gtggacctaa   1440

aaagtctata gagctggagt aaaaaactac cttgtttcta ct                      1482
```

<210> SEQ ID NO 82
<211> LENGTH: 1424
<212> TYPE: DNA
<213> ORGANISM: Artificial Sequence
<220> FEATURE:
<223> OTHER INFORMATION: Synthetic Sequence

<400> SEQUENCE: 82

```
agcaaaagca ggtagatatt gaaagatgag tcttctaacc gaggtcgaaa cttacgtact     60

ctctatcatc ccgtcaggcc ccctcaaagc cgagatcgca cagagacttg aagatgtctt    120

tgcagggaag aacaccgatc ttgaggttct catggaatgg ctaaagacaa gaccaatcct    180

gtcacctctg actaagggga ttttaggatt tgtgttcacg ctcaccgtgc ccagtgagcg    240

aggactgcag cgtagacgct ttgtccaaaa tgcccttaat gggaacgggg atccaaataa    300

catggacaaa gcagttaaac tgtataggaa gctcaagagg gagataacat tccatggggc    360

caaagaaatc tcactcagtt attctgctgg tgcacttgcc agttgtatgg gcctcatata    420

caacaggatg gggctgtga ccactgaagt ggcatttggc ctggtatgtg caacctgtga     480

acagattgct gactcccagc atcggtctca taggcaaatg gtgacaacaa ccaatccact    540

aatcagacat gagaacagaa tggttttagc cagcactaca gctaaggcta tggagcaaat    600

ggctggatcg agtgagcaag cagcagaggc catggaggtt gctagtcagg ctagacaaat    660

ggtgcaagcg atgagaacca ttggaactca tcctagctcc agtgctggtc tgaaaaatga    720

tcttcttgaa aatttgcaag cctatcagaa acgaatgggg gtgcagatgc aacggttcaa    780

gtaatgccta atattacaaa cttgtgccct tttggtgaag tttttaacgc caccagattt    840

gcatctgttt atgcttggaa caggaagaga atcagcaact gtgttgctga ttattctgtc    900

ctatataatt ccgcatcatt ttccactttt aagtgttatg gagtgtctcc tactaaatta    960

aatgatctct gctttactaa tgtctatgca gattcatttg taattagagg tgatgaagtc   1020

agacaaatcg ctccagggca aactggaaag attgctgatt ataattataa attaccagat   1080

gattttacag gctgcgttat agcttggaat tctaacaatc ttgattctaa ggttggtggt   1140

aattataatt acctgtatag attgtttagg aagtctaatc tcaaaccttt tgagagagat   1200

atttcaactg aaatctatca ggccggtagc acaccttgta atggtgttga aggttttaat   1260

tgttactttc ctttacaatc atatggtttc caacccacta atggtgttgg ttaccaacca   1320

tacagagtag tagtactttc ttttgaactt ctacatgcac cagcaactgt ttgtggacct   1380

aaaaagtcta tagagctgga gtaaaaaact accttgtttc tact                    1424
```

<210> SEQ ID NO 83
<211> LENGTH: 1472
<212> TYPE: DNA
<213> ORGANISM: Artificial Sequence
<220> FEATURE:
<223> OTHER INFORMATION: Synthetic Sequence

<400> SEQUENCE: 83

```
agcagaagca cgcactttct taaaatgtcg ctgtttggag acacaattgc ctacctgctt     60
tcattgacag aagatggaga aggcaaagca gaactagcag aaaaattaca ctgttggttc    120
ggtgggaaag aatttgacct agactctgcc ttggaatgga taaaaaacaa aagatgctta    180
actgacatac agaaagcact aattggcgcc tctatctgct ttttaaaacc caaagaccag    240
gaaagaaaaa gaagattcat cacagagccc ctatcaggaa tggggacaac agcaacaaaa    300
aagaagggcc tgattctagc tgagagaaaa atgagaagat gtgtgagctt ccatgaagca    360
tttgaaatag cagaaggcca tgaaagctca gcgttactat attgtctcat ggtcatgtac    420
ctgaatcctg gaaattattc aatgcaagta aaactaggaa cgctctgtgc tttgtgcgaa    480
aaacaagcat cacattcaca cagggctcat agcagagcag cgagatcttc agtgcctgga    540
gtgagacggg aaatgcagat ggtctcagct atgaacacag caaaaacaat gaatggaatg    600
ggaaaaggag aagacgttca aaaactggca gaagaactgc aaagcaacat tggagtattg    660
agatctcttg ggcaagtcaa aaagaatggg gaaggaattg caaaggatgt aatggaagtg    720
ctaaagcaga gctctatggg aaattcagct cttgtgaaga aatacctata atgctcgaat    780
caattgttag atttcctaat attacaaact tgtgcccttt tggtgaagtt tttaacgcca    840
ccagatttgc atctgtttat gcttggaaca ggaagagaat cagcaactgt gttgctgatt    900
attctgtcct atataattcc gcatcatttt ccacttttaa gtgttatgga gtgtctccta    960
ctaaattaaa tgatctctgc tttactaatg tctatgcaga ttcatttgta attagaggtg   1020
atgaagtcag acaaatcgct ccagggcaaa ctggaaagat tgctgattat aattataaat   1080
taccagatga ttttacaggc tgcgttatag cttggaattc taacaatctt gattctaagg   1140
ttggtggtaa ttataattac ctgtatagat tgtttaggaa gtctaatctc aaaccttttg   1200
agagagatat ttcaactgaa atctatcagg ccggtagcac accttgtaat ggtgttgaag   1260
gttttaattg ttactttcct ttacaatcat atggtttcca acccactaat ggtgttggtt   1320
accaaccata cagagtagta gtactttctt ttgaacttct acatgcacca gcaacagttt   1380
aaattcaatt tttactgtac ttcttactat gcatttaagc aaattgtaat caatgtcagc   1440
aaataaactg gaaaaagtgc gttgtttcta ct                                 1472
```

<210> SEQ ID NO 84
<211> LENGTH: 1508
<212> TYPE: DNA
<213> ORGANISM: Artificial Sequence
<220> FEATURE:
<223> OTHER INFORMATION: Synthetic Sequence

<400> SEQUENCE: 84

```
agcagaagca cgcactttct taaaatgtcg ctgtttggag acacaattgc ctacctgctt     60
tcattgacag aagatggaga aggcaaagca gaactagcag aaaaattaca ctgttggttc    120
ggtgggaaag aatttgacct agactctgcc ttggaatgga taaaaaacaa aagatgctta    180
actgacatac agaaagcact aattggcgcc tctatctgct ttttaaaacc caaagaccag    240
gaaagaaaaa gaagattcat cacagagccc ctatcaggaa tggggacaac agcaacaaaa    300
```

-continued

```
aagaagggcc tgattctagc tgagagaaaa atgagaagat gtgtgagctt ccatgaagca    360
tttgaaatag cagaaggcca tgaaagctca gcgttactat attgtctcat ggtcatgtac    420
ctgaatcctg gaaattattc aatgcaagta aaactaggaa cgctctgtgc tttgtgcgaa    480
aaacaagcat cacattcaca cagggctcat agcagagcag cgagatcttc agtgcctgga    540
gtgagacggg aaatgcagat ggtctcagct atgaacacag caaaaacaat gaatggaatg    600
ggaaaaggag aagacgttca aaaactggca gaagaactgc aaagcaacat tggagtattg    660
agatctcttg ggcaagtca aaagaatggg gaaggaattg caaaggatgt aatggaagtg     720
ctaaagcaga gctctatggg aaattcagct cttgtgaaga aatacctata atgctcgaac    780
catttcagat tctttcaatt gttagatttc ctaatattac aaacttgtgc ccttttggtg    840
aagtttttaa cgccaccaga tttgcatctg tttatgcttg gaacaggaag agaatcagca    900
actgtgttgc tgattattct gtcctatata attccgcatc attttccact tttaagtgtt    960
atggagtgtc tcctactaaa ttaaatgatc tctgctttac taatgtctat gcagattcat   1020
ttgtaattag aggtgatgaa gtcagacaaa tcgctccagg gcaaactgga aagattgctg   1080
attataatta taaattacca gatgatttta caggctgcgt tatagcttgg aattctaaca   1140
atcttgattc taaggttggt ggtaattata attacctgta tagattgttt aggaagtcta   1200
atctcaaacc ttttgagaga gatatttcaa ctgaaatcta tcaggccggt agcacacctt   1260
gtaatggtgt tgaaggtttt aattgttact ttcctttaca atcatatggt ttccaaccca   1320
ctaatggtgt tggttaccaa ccatacagag tagtagtact ttcttttgaa cttctacatg   1380
caccagcaac agttttggag gtagaagaat tgcattaaat tcaattttta ctgtacttct   1440
tactatgcat ttaagcaaat tgtaatcaat gtcagcaaat aaactggaaa aagtgcgttg   1500
tttctact                                                            1508
```

<210> SEQ ID NO 85
<211> LENGTH: 1165
<212> TYPE: DNA
<213> ORGANISM: Artificial Sequence
<220> FEATURE:
<223> OTHER INFORMATION: Synthetic Sequence

<400> SEQUENCE: 85

```
agcaaaagca gggtgacaaa aacataatgg atccaaacac tgtgtcaagc tttcaagtag     60
attgctttct ttggcatgtc cgcaaacgag ttgcagacca agaactaggc gatcccccat    120
tccttgatcg gcttcgccga gatcagaaat ccctaagagg aaggggcagt actctcggtc    180
tggacatcaa gacagccaca cgtgctggaa agcagatagt ggagcggatt ctgaaagaag    240
aatccgatga ggcacttaaa atgaccatgg cctctgtacc tgcgtcgcgt tacctaactg    300
acatgactct tgaggaaatg tcaagggact ggtccatgct catacccaag cagaaagtgg    360
caggccctct ttgtatcaaa atggaccagg cgatcatgga taagaacatc atactgaaag    420
cgaacttcag tgtgattttt gaccggctgg agactctaat attgctaagg gctttcaccg    480
aagagggagc aattgttggc gaaatttcac cattgccttc tctcccggga catactgctg    540
aggttgtcaa gaatgctgtt ggagtgctaa tcggaggact tgaatggaac gacaacactg    600
tgcgagtcag cgaaactttg cagagatttg cttggagaag ctctaatgag aacgggagac    660
ctccactgac tccaaagcag aaacgagaca tggctggaac aattagaagc gaagttggat    720
caggtgcaac taactttagt cttcttaaac aagctggtga tgttgaagaa aatcctggac    780
ctaatacagt gtctagcttc caggacatac tgctgaggat gtcaaaaatg cagttggagt    840
```

```
cctcatcgga ggacttgaat ggaatgataa cacagttcga gtctctgaaa ctctacagag    900

attcgcttgg agaagcagta atgagaatgg gagacctcca ctcactccaa aacagaaacg    960

agaaatggcg ggaacaatta ggtcagaagt ttgaagaaat aagatggttg attgaagaag   1020

tgagacacaa actgaagata acagagaata gttttgagca aataacattt atgcaagcct   1080

tacatctatt gcttgaagtg gagcaagaga taagaacttt ctcgtttcag cttatttagt   1140

actaaaaaac acccttgttt ctact                                         1165
```

<210> SEQ ID NO 86
<211> LENGTH: 1828
<212> TYPE: DNA
<213> ORGANISM: Artificial Sequence
<220> FEATURE:
<223> OTHER INFORMATION: Synthetic Sequence

<400> SEQUENCE: 86

```
agcaaaagca gggtgacaaa aacataatgg atccaaacac tgtgtcaagc tttcaagtag     60

attgctttct ttggcatgtc cgcaaacgag ttgcagacca agaactaggc gatcccccat    120

tccttgatcg gcttcgccga gatcagaaat ccctaagagg aaggggcagt actctcggtc    180

tggacatcaa gacagccaca cgtgctggaa agcagatagt ggagcggatt ctgaaagaag    240

aatccgatga ggcacttaaa atgaccatgg cctctgtacc tgcgtcgcgt tacctaactg    300

acatgactct tgaggaaatg tcaagggact ggtccatgct catacccaag cagaaagtgg    360

caggccctct ttgtatcaaa atggaccagg cgatcatgga taagaacatc atactgaaag    420

cgaacttcag tgtgattttt gaccggctgg agactctaat attgctaagg gctttcaccg    480

aagagggagc aattgttggc gaaatttcac cattgccttc tctcccggga catactgctg    540

aggttgtcaa aaatgcagtt ggagtcctaa tcggaggact tgaatggaac gataacacag    600

ttcgagtctc tgaaactcta cagagattcg cttggagaag cagtaatgag aacgggagac    660

ctccactgac tccaaaacag aaacgagaaa tggcgggaac aattaggtca gaagttggta    720

gtggagaagg tagaggaagt cttctaacat gtggtgatgt agaagagaat ccaggtccta    780

atattacaaa cttgtgccct tttggtgaag tttttaacgc caccagattt gcatctgttt    840

atgcttggaa caggaagaga atcagcaact gtgttgctga ttattctgtc ctatataatt    900

ccgcatcatt ttccactttt aagtgttatg gagtgtctcc tactaaatta aatgatctct    960

gctttactaa tgtctatgca gattcatttg taattagagg tgatgaagtc agacaaatcg   1020

ctccagggca aactggaaag attgctgatt ataattataa attaccagat gattttacag   1080

gctgcgttat agcttggaat tctaacaatc ttgattctaa ggttggtggt aattataatt   1140

acctgtatag attgtttagg aagtctaatc tcaaaccttt tgagagagat atttcaactg   1200

aaatctatca ggccggtagc acaccttgta atggtgttga aggttttaat tgttactttc   1260

ctttacaatc atatggtttc caacccacta atggtgttgg ttaccaacca tacagagtag   1320

tagtactttc ttttgaactt ctacatgcac cagcaactgt ttgtggacct aaaaagtctg   1380

gatcaggtgc aactaacttt agtcttctta aacaagctgg tgatgttgaa gaaaatcctg   1440

gacctaatac agtgtctagc ttccaggaca tactgctgag gatgtcaaaa atgcagttgg   1500

agtcctcatc ggaggacttg aatggaatga taacacagtt cgagtctctg aaactctaca   1560

gagattcgct tggagaagca gtaatgagaa tgggagacct ccactcactc caaaacagaa   1620

acgagaaatg gcgggaacaa ttaggtcaga agtttgaaga aataagatgg ttgattgaag   1680
```

-continued

```
aagtgagaca caaactgaag ataacagaga atagttttga gcaaataaca tttatgcaag   1740

ccttacatct attgcttgaa gtggagcaag agataagaac tttctcgttt cagcttattt   1800

agtactaaaa aacacccttg tttctact                                      1828
```

<210> SEQ ID NO 87
<211> LENGTH: 1984
<212> TYPE: DNA
<213> ORGANISM: Artificial Sequence
<220> FEATURE:
<223> OTHER INFORMATION: Synthetic Sequence

<400> SEQUENCE: 87

```
agcaaaagca gggtgacaaa aacataatgg atccaaacac tgtgtcaagc tttcaagtag     60

attgctttct ttggcatgtc cgcaaacgag ttgcagacca agaactaggc gatcccccat    120

tccttgatcg gcttcgccga gatcagaaat ccctaagagg aaggggcagt actctcggtc    180

tggacatcaa gacagccaca cgtgctggaa agcagatagt ggagcggatt ctgaaagaag    240

aatccgatga ggcacttaaa atgaccatgg cctctgtacc tgcgtcgcgt tacctaactg    300

acatgactct tgaggaaatg tcaagggact ggtccatgct catacccaag cagaaagtgg    360

caggccctct ttgtatcaaa atggaccagg cgatcatgga taagaacatc atactgaaag    420

cgaacttcag tgtgattttt gaccggctgg agactctaat attgctaagg gctttcaccg    480

aagagggagc aattgttggc gaaatttcac cattgccttc tctcccggga catactgctg    540

aggttgtcaa aaatgcagtt ggagtcctaa tcggaggact tgaatggaac gataacacag    600

ttcgagtctc tgaaactcta cagagattcg cttggagaag cagtaatgag aacgggagac    660

ctccactgac tccaaaacag aaacgagaaa tggcgggaac aattaggtca gaagttggta    720

gtggacctgc atacactaat tctttcacac gtggtgttta ttaccctgac aaagttttca    780

gatcctcagt tttacattca actcaggact tgttcttacc tttcttttcc aatgttactt    840

ggttccatgc tatacatgtc tctgggacca atggtactaa gaggtttgat aaccctgtcc    900

taccatttaa tgatggtgtt tattttgctt ccactgagaa gtctaacata ataagaggct    960

ggatttttgg tactacttta gattcgaaga cccagtccct acttattgtt aataacgcta   1020

ctaatgttgt tattaaagtc tgtgaatttc aattttgtaa tgatccattt ttgggtgttt   1080

attaccacaa aaacaacaaa agttggatgg aaagtgagtt cagagtttat tctagtgcga   1140

ataattgcac ttttgaatat gtctctcagc cttttcttat ggaccttgaa ggaaaacagg   1200

gtaatttcaa aaatcttagg gaatttgtgt ttaagaatat tgatggttat tttaaaatat   1260

attctaagca cacgcctatt aatttagtgc gtgatctccc tcagggtttt tcggctttag   1320

aaccattggt agatttgcca ataggtatta acatcactag gtttcaaact ttacttgctt   1380

tacatagaag ttatttgact cctggtgatt cttcttcagg ttggacagct ggtgctgcag   1440

cttattatgt gggttatctt caacctagga cttttctatt aaaatataat gaaaatggaa   1500

ccattacaga tgctgtagac tgtgcacttg acccaggatc aggtgcaact aactttagtc   1560

ttcttaaaca agctggtgat gttgaagaaa atcctggacc taatacagtg tctagcttcc   1620

aggacatact gctgaggatg tcaaaaatgc agttggagtc ctcatcggag gacttgaatg   1680

gaatgataac acagttcgag tctctgaaac tctacagaga ttcgcttgga gaagcagtaa   1740

tgagaatggg agacctccac tcactccaaa acagaaacga gaaatggcgg gaacaattag   1800

gtcagaagtt tgaagaaata agatggttga ttgaagaagt gagacacaaa ctgaagataa   1860

cagagaatag ttttgagcaa ataacattta tgcaagcctt acatctattg cttgaagtgg   1920
```

agcaagagat aagaactttc tcgtttcagc ttatttagta ctaaaaaaca cccttgtttc 1980
tact 1984

<210> SEQ ID NO 88
<211> LENGTH: 1444
<212> TYPE: DNA
<213> ORGANISM: Artificial Sequence
<220> FEATURE:
<223> OTHER INFORMATION: Synthetic Sequence

<400> SEQUENCE: 88
agcaaaagca gggtgacaaa aacataatgg atccaaacac tgtgtcaagc tttcaagtag 60
attgctttct ttggcatgtc cgcaaacgag ttgcagacca agaactaggc gatcccccat 120
tccttgatcg gcttcgccga gatcagaaat ccctaagagg aaggggcagt actctcggtc 180
tggacatcaa gacagccaca cgtgctggaa agcagatagt ggagcggatt ctgaaagaag 240
aatccgatga ggcacttaaa atgaccatgg cctctgtacc tgcgtcgcgt tacctaactg 300
acatgactct tgaggaaatg tcaagggact ggtccatgct catacccaag cagaaagtgg 360
caggccctct ttgtatcaaa atggaccagg cgatcatgga taagaacatc atactgaaag 420
cgaacttcag tgtgattttt gaccggctgg agactctaat attgctaagg gctttcaccg 480
aagagggagc aattgttggc gaaatttcac cattgccttc tctcccggga catactgctg 540
aggttgtcaa aaatgcagtt ggagtcctaa tcggaggact tgaatggaac gataacacag 600
ttcgagtctc tgaaactcta cagagattcg cttggagaag cagtaatgag aacgggagac 660
ctccactgac tccaaaacag aaacgagaaa tggcgggaac aattaggtca gaagttggta 720
gtggagcaag tgcacttgga aaacttcaag atgtggtcaa ccaaaatgca caagctttaa 780
acacgcttgt taaacaactt agctccaatt ttggtgcaat ttcaagtgtt ttaaatgata 840
tcctttcacg tcttgacaaa gttgaggctg aagtgcaaat tgataggttg atcacaggca 900
gacttcaaag tttgcagaca tatgtgactc aacaattaat tagagctgca gaaatcagag 960
cttctgctaa tcttgctgct actaaaatgt cagagggatc aggtgcaact aactttagtc 1020
ttcttaaaca agctggtgat gttgaagaaa atcctggacc taatacagtg tctagcttcc 1080
aggacatact gctgaggatg tcaaaaatgc agttggagtc ctcatcggag gacttgaatg 1140
gaatgataac acagttcgag tctctgaaac tctacagaga ttcgcttgga gaagcagtaa 1200
tgagaatggg agacctccac tcactccaaa acagaaacga gaaatggcgg gaacaattag 1260
gtcagaagtt tgaagaaata agatggttga ttgaagaagt gagacacaaa ctgaagataa 1320
cagagaatag ttttgagcaa ataacattta tgcaagcctt acatctattg cttgaagtgg 1380
agcaagagat aagaactttc tcgtttcagc ttatttagta ctaaaaaaca cccttgtttc 1440
tact 1444

<210> SEQ ID NO 89
<211> LENGTH: 1444
<212> TYPE: DNA
<213> ORGANISM: Artificial Sequence
<220> FEATURE:
<223> OTHER INFORMATION: Synthetic Sequence

<400> SEQUENCE: 89
agcaaaagca gggtgacaaa aacataatgg atccaaacac tgtgtcaagc tttcaagtag 60
attgctttct ttggcatgtc cgcaaacgag ttgcagacca agaactaggc gatcccccat 120

-continued

```
tccttgatcg gcttcgccga gatcagaaat ccctaagagg aaggggcagt actctcggtc    180

tggacatcaa gacagccaca cgtgctggaa agcagatagt ggagcggatt ctgaaagaag    240

aatccgatga ggcacttaaa atgaccatgg cctctgtacc tgcgtcgcgt tacctaactg    300

acatgactct tgaggaaatg tcaagggact ggtccatgct catacccaag cagaaagtgg    360

caggccctct ttgtatcaaa atggaccagg cgatcatgga taagaacatc atactgaaag    420

cgaacttcag tgtgattttt gaccggctgg agactctaat attgctaagg gctttcaccg    480

aagagggagc aattgttggc gaaatttcac cattgccttc tctcccggga catactgctg    540

aggttgtcaa aaatgcagtt ggagtcctaa tcggaggact tgaatggaac gataacacag    600

ttcgagtctc tgaaactcta cagagattcg cttggagaag cagtaatgag aacgggagac    660

ctccactgac tccaaaacag aaacgagaaa tggcgggaac aattaggtca gaagttggta    720

gtggagcaag tgcacttgga aaacttcaag atgtggtcaa ccaaaatgca caagctttaa    780

acacgcttgt taaacaactt agctccaatt ttggtgcaat ttcaagtgtt ttaaatgata    840

tcctttcacg tcttgaccca cctgaggctg aagtgcaaat tgataggttg atcacaggca    900

gacttcaaag tttgcagaca tatgtgactc aacaattaat tagagctgca gaaatcagag    960

cttctgctaa tcttgctgct actaaaatgt cagagggatc aggtgcaact aactttagtc   1020

ttcttaaaca agctggtgat gttgaagaaa atcctggacc taatacagtg tctagcttcc   1080

aggacatact gctgaggatg tcaaaaatgc agttggagtc ctcatcggag gacttgaatg   1140

gaatgataac acagttcgag tctctgaaac tctacagaga ttcgcttgga gaagcagtaa   1200

tgagaatggg agacctccac tcactccaaa acagaaacga gaaatggcgg gaacaattag   1260

gtcagaagtt tgaagaaata agatggttga ttgaagaagt gagacacaaa ctgaagataa   1320

cagagaatag ttttgagcaa ataacattta tgcaagcctt acatctattg cttgaagtgg   1380

agcaagagat aagaactttc tcgtttcagc ttatttagta ctaaaaaaca cccttgtttc   1440

tact                                                                1444
```

<210> SEQ ID NO 90
<211> LENGTH: 1375
<212> TYPE: DNA
<213> ORGANISM: Artificial Sequence
<220> FEATURE:
<223> OTHER INFORMATION: Synthetic Sequence

<400> SEQUENCE: 90

```
agcaaaagca gggtgacaaa aacataatgg atccaaacac tgtgtcaagc tttcaagtag     60

attgctttct ttggcatgtc cgcaaacgag ttgcagacca agaactaggc gatcccccat    120

tccttgatcg gcttcgccga gatcagaaat ccctaagagg aaggggcagt actctcggtc    180

tggacatcaa gacagccaca cgtgctggaa agcagatagt ggagcggatt ctgaaagaag    240

aatccgatga ggcacttaaa atgaccatgg cctctgtacc tgcgtcgcgt tacctaactg    300

acatgactct tgaggaaatg tcaagggact ggtccatgct catacccaag cagaaagtgg    360

caggccctct ttgtatcaaa atggaccagg cgatcatgga taagaacatc atactgaaag    420

cgaacttcag tgtgattttt gaccggctgg agactctaat attgctaagg gctttcaccg    480

aagagggagc aattgttggc gaaatttcac cattgccttc tctcccggga catactgctg    540

aggttgtcaa aaatgcagtt ggagtcctaa tcggaggact tgaatggaac gataacacag    600

ttcgagtctc tgaaactcta cagagattcg cttggagaag cagtaatgag aacgggagac    660

ctccactgac tccaaaacag aaacgagaaa tggcgggaac aattaggtca gaagttggta    720
```

-continued gtggaaagaa cttcacaact gctcctgcca tttgtcatga tggaaaagca cactttcctc 780
gtgaaggtgt ctttgtttca aatggcacac actggtttgt aacacaaagg aatttttatg 840
aaccacaaat cattactaca gacaacacat ttgtgtctgg taactgtgat gttgtaatag 900
gaattgtcaa caacacagtt tatgatggat caggtgcaac taactttagt cttcttaaac 960
aagctggtga tgttgaagaa aatcctggac ctaatacagt gtctagcttc caggacatac 1020
tgctgaggat gtcaaaaatg cagttggagt cctcatcgga ggacttgaat ggaatgataa 1080
cacagttcga gtctctgaaa ctctacagag attcgcttgg agaagcagta atgagaatgg 1140
gagacctcca ctcactccaa aacagaaacg agaaatggcg ggaacaatta ggtcagaagt 1200
ttgaagaaat aagatggttg attgaagaag tgagacacaa actgaagata acagagaata 1260
gttttgagca aataacattt atgcaagcct tacatctatt gcttgaagtg gagcaagaga 1320
taagaacttt ctcgtttcag cttatttagt actaaaaaac acccttgttt ctact 1375

<210> SEQ ID NO 91
<211> LENGTH: 1396
<212> TYPE: DNA
<213> ORGANISM: Artificial Sequence
<220> FEATURE:
<223> OTHER INFORMATION: Synthetic Sequence

<400> SEQUENCE: 91
agcaaaagca gggtgacaaa aacataatgg atccaaacac tgtgtcaagc tttcaagtag 60
attgctttct ttggcatgtc cgcaaacgag ttgcagacca agaactaggc gatcccccat 120
tccttgatcg gcttcgccga gatcagaaat ccctaagagg aaggggcagt actctcggtc 180
tggacatcaa gacagccaca cgtgctggaa agcagatagt ggagcggatt ctgaaagaag 240
aatccgatga ggcacttaaa atgaccatgg cctctgtacc tgcgtcgcgt tacctaactg 300
acatgactct tgaggaaatg tcaagggact ggtccatgct catacccaag cagaaagtgg 360
caggccctct ttgtatcaaa atggaccagg cgatcatgga taagaacatc atactgaaag 420
cgaacttcag tgtgattttt gaccggctgg agactctaat attgctaagg gctttcaccg 480
aagagggagc aattgttggc gaaatttcac cattgccttc tctcccggga catactgctg 540
aggttgtcaa aaatgcagtt ggagtcctaa tcggaggact tgaatggaac gataacacag 600
ttcgagtctc tgaaactcta cagagattcg cttggagaag cagtaatgag aacgggagac 660
ctccactgac tccaaaacag aaacgagaaa tggcgggaac aattaggtca gaagttggta 720
gtggaccttt gcaacctgaa ttagactcat tcaaggagga gttagataaa tattttaaga 780
atcatacatc accagatgtt gatttaggtg acatctctgg cattaatgct tcagttgtaa 840
acattcaaaa agaaattgac cgcctcaatg aggttgccaa gaatttaaat gaatctctca 900
tcgatctcca agaacttgga aagtatgagc agtatataaa atggccagga tcaggtgcaa 960
ctaactttag tcttcttaaa caagctggtg atgttgaaga aaatcctgga cctaatacag 1020
tgtctagctt ccaggacata ctgctgagga tgtcaaaaat gcagttggag tcctcatcgg 1080
aggacttgaa tggaatgata acacagttcg agtctctgaa actctacaga gattcgcttg 1140
gagaagcagt aatgagaatg ggagacctcc actcactcca aaacagaaac gagaaatggc 1200
gggaacaatt aggtcagaag tttgaagaaa taagatggtt gattgaagaa gtgagacaca 1260
aactgaagat aacagagaat agttttgagc aaataacatt tatgcaagcc ttacatctat 1320
tgcttgaagt ggagcaagag ataagaactt tctcgtttca gcttatttag tactaaaaaa 1380 caccccttgtt tctact 1396

<210> SEQ ID NO 92
<211> LENGTH: 229
<212> TYPE: PRT
<213> ORGANISM: Artificial Sequence
<220> FEATURE:
<223> OTHER INFORMATION: Synthetic Sequence

<400> SEQUENCE: 92

```
Met Ser Leu Leu Thr Glu Val Glu Thr Pro Ile Arg Asn Glu Trp Gly
1               5                   10                  15

Cys Arg Cys Asn Gly Ser Ser Asp Pro Asn Ile Thr Asn Leu Cys Pro
            20                  25                  30

Phe Gly Glu Val Phe Asn Ala Thr Arg Phe Ala Ser Val Tyr Ala Trp
        35                  40                  45

Asn Arg Lys Arg Ile Ser Asn Cys Val Ala Asp Tyr Ser Val Leu Tyr
    50                  55                  60

Asn Ser Ala Ser Phe Ser Thr Phe Lys Cys Tyr Gly Val Ser Pro Thr
65                  70                  75                  80

Lys Leu Asn Asp Leu Cys Phe Thr Asn Val Tyr Ala Asp Ser Phe Val
                85                  90                  95

Ile Arg Gly Asp Glu Val Arg Gln Ile Ala Pro Gly Gln Thr Gly Lys
            100                 105                 110

Ile Ala Asp Tyr Asn Tyr Lys Leu Pro Asp Asp Phe Thr Gly Cys Val
        115                 120                 125

Ile Ala Trp Asn Ser Asn Asn Leu Asp Ser Lys Val Gly Gly Asn Tyr
    130                 135                 140

Asn Tyr Leu Tyr Arg Leu Phe Arg Lys Ser Asn Leu Lys Pro Phe Glu
145                 150                 155                 160

Arg Asp Ile Ser Thr Glu Ile Tyr Gln Ala Gly Ser Thr Pro Cys Asn
                165                 170                 175

Gly Val Glu Gly Phe Asn Cys Tyr Phe Pro Leu Gln Ser Tyr Gly Phe
            180                 185                 190

Gln Pro Thr Asn Gly Val Gly Tyr Gln Pro Tyr Arg Val Val Val Leu
        195                 200                 205

Ser Phe Glu Leu Leu His Ala Pro Ala Thr Val Cys Gly Pro Lys Lys
    210                 215                 220

Ser Ile Glu Leu Glu
225
```

<210> SEQ ID NO 93
<211> LENGTH: 478
<212> TYPE: PRT
<213> ORGANISM: Artificial Sequence
<220> FEATURE:
<223> OTHER INFORMATION: Synthetic Sequence

<400> SEQUENCE: 93

```
Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60
```

-continued

```
Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys Gly Ser Gly Ala
                245                 250                 255

Thr Asn Phe Ser Leu Leu Lys Gln Ala Gly Asp Val Glu Glu Asn Pro
            260                 265                 270

Gly Pro Asn Ile Thr Asn Leu Cys Pro Phe Gly Glu Val Phe Asn Ala
        275                 280                 285

Thr Arg Phe Ala Ser Val Tyr Ala Trp Asn Arg Lys Arg Ile Ser Asn
    290                 295                 300

Cys Val Ala Asp Tyr Ser Val Leu Tyr Asn Ser Ala Ser Phe Ser Thr
305                 310                 315                 320

Phe Lys Cys Tyr Gly Val Ser Pro Thr Lys Leu Asn Asp Leu Cys Phe
                325                 330                 335

Thr Asn Val Tyr Ala Asp Ser Phe Val Ile Arg Gly Asp Glu Val Arg
            340                 345                 350

Gln Ile Ala Pro Gly Gln Thr Gly Lys Ile Ala Asp Tyr Asn Tyr Lys
        355                 360                 365

Leu Pro Asp Asp Phe Thr Gly Cys Val Ile Ala Trp Asn Ser Asn Asn
    370                 375                 380

Leu Asp Ser Lys Val Gly Gly Asn Tyr Asn Tyr Leu Tyr Arg Leu Phe
385                 390                 395                 400

Arg Lys Ser Asn Leu Lys Pro Phe Glu Arg Asp Ile Ser Thr Glu Ile
                405                 410                 415

Tyr Gln Ala Gly Ser Thr Pro Cys Asn Gly Val Glu Gly Phe Asn Cys
            420                 425                 430

Tyr Phe Pro Leu Gln Ser Tyr Gly Phe Gln Pro Thr Asn Gly Val Gly
        435                 440                 445

Tyr Gln Pro Tyr Arg Val Val Val Leu Ser Phe Glu Leu Leu His Ala
    450                 455                 460

Pro Ala Thr Val Cys Gly Pro Lys Lys Ser Ile Glu Leu Glu
465                 470                 475
```

<210> SEQ ID NO 94
<211> LENGTH: 206
<212> TYPE: PRT
<213> ORGANISM: Artificial Sequence
<220> FEATURE:
<223> OTHER INFORMATION: Synthetic Sequence

<400> SEQUENCE: 94

```
Met Pro Asn Ile Thr Asn Leu Cys Pro Phe Gly Glu Val Phe Asn Ala
1               5                   10                  15

Thr Arg Phe Ala Ser Val Tyr Ala Trp Asn Arg Lys Arg Ile Ser Asn
            20                  25                  30

Cys Val Ala Asp Tyr Ser Val Leu Tyr Asn Ser Ala Ser Phe Ser Thr
        35                  40                  45

Phe Lys Cys Tyr Gly Val Ser Pro Thr Lys Leu Asn Asp Leu Cys Phe
    50                  55                  60

Thr Asn Val Tyr Ala Asp Ser Phe Val Ile Arg Gly Asp Glu Val Arg
65                  70                  75                  80

Gln Ile Ala Pro Gly Gln Thr Gly Lys Ile Ala Asp Tyr Asn Tyr Lys
                85                  90                  95

Leu Pro Asp Asp Phe Thr Gly Cys Val Ile Ala Trp Asn Ser Asn Asn
            100                 105                 110

Leu Asp Ser Lys Val Gly Gly Asn Tyr Asn Tyr Leu Tyr Arg Leu Phe
        115                 120                 125

Arg Lys Ser Asn Leu Lys Pro Phe Glu Arg Asp Ile Ser Thr Glu Ile
    130                 135                 140

Tyr Gln Ala Gly Ser Thr Pro Cys Asn Gly Val Glu Gly Phe Asn Cys
145                 150                 155                 160

Tyr Phe Pro Leu Gln Ser Tyr Gly Phe Gln Pro Thr Asn Gly Val Gly
                165                 170                 175

Tyr Gln Pro Tyr Arg Val Val Val Leu Ser Phe Glu Leu Leu His Ala
            180                 185                 190

Pro Ala Thr Val Cys Gly Pro Lys Lys Ser Ile Glu Leu Glu
        195                 200                 205
```

<210> SEQ ID NO 95
<211> LENGTH: 203
<212> TYPE: PRT
<213> ORGANISM: Artificial Sequence
<220> FEATURE:
<223> OTHER INFORMATION: Synthetic Sequence

<400> SEQUENCE: 95

```
Met Leu Glu Ser Ile Val Arg Phe Pro Asn Ile Thr Asn Leu Cys Pro
1               5                   10                  15

Phe Gly Glu Val Phe Asn Ala Thr Arg Phe Ala Ser Val Tyr Ala Trp
            20                  25                  30

Asn Arg Lys Arg Ile Ser Asn Cys Val Ala Asp Tyr Ser Val Leu Tyr
        35                  40                  45

Asn Ser Ala Ser Phe Ser Thr Phe Lys Cys Tyr Gly Val Ser Pro Thr
    50                  55                  60

Lys Leu Asn Asp Leu Cys Phe Thr Asn Val Tyr Ala Asp Ser Phe Val
65                  70                  75                  80

Ile Arg Gly Asp Glu Val Arg Gln Ile Ala Pro Gly Gln Thr Gly Lys
                85                  90                  95

Ile Ala Asp Tyr Asn Tyr Lys Leu Pro Asp Asp Phe Thr Gly Cys Val
            100                 105                 110
```

```
Ile Ala Trp Asn Ser Asn Asn Leu Asp Ser Lys Val Gly Gly Asn Tyr
        115                 120                 125

Asn Tyr Leu Tyr Arg Leu Phe Arg Lys Ser Asn Leu Lys Pro Phe Glu
    130                 135                 140

Arg Asp Ile Ser Thr Glu Ile Tyr Gln Ala Gly Ser Thr Pro Cys Asn
145                 150                 155                 160

Gly Val Glu Gly Phe Asn Cys Tyr Phe Pro Leu Gln Ser Tyr Gly Phe
                165                 170                 175

Gln Pro Thr Asn Gly Val Gly Tyr Gln Pro Tyr Arg Val Val Val Leu
            180                 185                 190

Ser Phe Glu Leu Leu His Ala Pro Ala Thr Val
        195                 200


<210> SEQ ID NO 96
<211> LENGTH: 215
<212> TYPE: PRT
<213> ORGANISM: Artificial Sequence
<220> FEATURE:
<223> OTHER INFORMATION: Synthetic Sequence

<400> SEQUENCE: 96

Met Leu Glu Pro Phe Gln Ile Leu Ser Ile Val Arg Phe Pro Asn Ile
1               5                   10                  15

Thr Asn Leu Cys Pro Phe Gly Glu Val Phe Asn Ala Thr Arg Phe Ala
            20                  25                  30

Ser Val Tyr Ala Trp Asn Arg Lys Arg Ile Ser Asn Cys Val Ala Asp
        35                  40                  45

Tyr Ser Val Leu Tyr Asn Ser Ala Ser Phe Ser Thr Phe Lys Cys Tyr
    50                  55                  60

Gly Val Ser Pro Thr Lys Leu Asn Asp Leu Cys Phe Thr Asn Val Tyr
65                  70                  75                  80

Ala Asp Ser Phe Val Ile Arg Gly Asp Glu Val Arg Gln Ile Ala Pro
                85                  90                  95

Gly Gln Thr Gly Lys Ile Ala Asp Tyr Asn Tyr Lys Leu Pro Asp Asp
            100                 105                 110

Phe Thr Gly Cys Val Ile Ala Trp Asn Ser Asn Asn Leu Asp Ser Lys
        115                 120                 125

Val Gly Gly Asn Tyr Asn Tyr Leu Tyr Arg Leu Phe Arg Lys Ser Asn
    130                 135                 140

Leu Lys Pro Phe Glu Arg Asp Ile Ser Thr Glu Ile Tyr Gln Ala Gly
145                 150                 155                 160

Ser Thr Pro Cys Asn Gly Val Glu Gly Phe Asn Cys Tyr Phe Pro Leu
                165                 170                 175

Gln Ser Tyr Gly Phe Gln Pro Thr Asn Gly Val Gly Tyr Gln Pro Tyr
            180                 185                 190

Arg Val Val Val Leu Ser Phe Glu Leu Leu His Ala Pro Ala Thr Val
        195                 200                 205

Leu Glu Val Glu Glu Leu His
    210                 215


<210> SEQ ID NO 97
<211> LENGTH: 573
<212> TYPE: PRT
<213> ORGANISM: Artificial Sequence
<220> FEATURE:
<223> OTHER INFORMATION: Synthetic Sequence

<400> SEQUENCE: 97
```

-continued

```
Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Pro Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Lys Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Asp Trp Ser Met Leu Ile Pro Lys Gln Lys Val Ala
            100                 105                 110

Gly Pro Leu Cys Ile Lys Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Val Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Glu Met Ala Gly
    210                 215                 220

Thr Ile Arg Ser Glu Val Gly Ser Gly Asn Ile Thr Asn Leu Cys Pro
225                 230                 235                 240

Phe Gly Glu Val Phe Asn Ala Thr Arg Phe Ala Ser Val Tyr Ala Trp
                245                 250                 255

Asn Arg Lys Arg Ile Ser Asn Cys Val Ala Asp Tyr Ser Val Leu Tyr
            260                 265                 270

Asn Ser Ala Ser Phe Ser Thr Phe Lys Cys Tyr Gly Val Ser Pro Thr
        275                 280                 285

Lys Leu Asn Asp Leu Cys Phe Thr Asn Val Tyr Ala Asp Ser Phe Val
    290                 295                 300

Ile Arg Gly Asp Glu Val Arg Gln Ile Ala Pro Gly Gln Thr Gly Lys
305                 310                 315                 320

Ile Ala Asp Tyr Asn Tyr Lys Leu Pro Asp Asp Phe Thr Gly Cys Val
                325                 330                 335

Ile Ala Trp Asn Ser Asn Asn Leu Asp Ser Lys Val Gly Gly Asn Tyr
            340                 345                 350

Asn Tyr Leu Tyr Arg Leu Phe Arg Lys Ser Asn Leu Lys Pro Phe Glu
        355                 360                 365

Arg Asp Ile Ser Thr Glu Ile Tyr Gln Ala Gly Ser Thr Pro Cys Asn
    370                 375                 380

Gly Val Glu Gly Phe Asn Cys Tyr Phe Pro Leu Gln Ser Tyr Gly Phe
385                 390                 395                 400

Gln Pro Thr Asn Gly Val Gly Tyr Gln Pro Tyr Arg Val Val Val Leu
                405                 410                 415
```

-continued

```
Ser Phe Glu Leu Leu His Ala Pro Ala Thr Val Cys Gly Pro Lys Lys
            420                 425                 430

Ser Gly Ser Gly Ala Thr Asn Phe Ser Leu Leu Lys Gln Ala Gly Asp
        435                 440                 445

Val Glu Glu Asn Pro Gly Pro Asn Thr Val Ser Ser Phe Gln Asp Ile
    450                 455                 460

Leu Leu Arg Met Ser Lys Met Gln Leu Glu Ser Ser Ser Glu Asp Leu
465                 470                 475                 480

Asn Gly Met Ile Thr Gln Phe Glu Ser Leu Lys Leu Tyr Arg Asp Ser
                485                 490                 495

Leu Gly Glu Ala Val Met Arg Met Gly Asp Leu His Ser Leu Gln Asn
            500                 505                 510

Arg Asn Glu Lys Trp Arg Glu Gln Leu Gly Gln Lys Phe Glu Glu Ile
        515                 520                 525

Arg Trp Leu Ile Glu Glu Val Arg His Lys Leu Lys Ile Thr Glu Asn
    530                 535                 540

Ser Phe Glu Gln Ile Thr Phe Met Gln Ala Leu His Leu Leu Leu Glu
545                 550                 555                 560

Val Glu Gln Glu Ile Arg Thr Phe Ser Phe Gln Leu Ile
                565                 570


<210> SEQ ID NO 98
<211> LENGTH: 370
<212> TYPE: PRT
<213> ORGANISM: Artificial Sequence
<220> FEATURE:
<223> OTHER INFORMATION: Synthetic Sequence

<400> SEQUENCE: 98

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Pro Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Lys Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Asp Trp Ser Met Leu Ile Pro Lys Gln Lys Val Ala
            100                 105                 110

Gly Pro Leu Cys Ile Lys Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Val Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205
```

```
Asn Gly Arg Pro Pro Leu Thr Pro Lys Gln Lys Arg Asp Met Ala Gly
    210                 215                 220

Thr Ile Arg Ser Glu Val Gly Ser Gly Ala Thr Asn Phe Ser Leu Leu
225                 230                 235                 240

Lys Gln Ala Gly Asp Val Glu Glu Asn Pro Gly Pro Asn Thr Val Ser
                245                 250                 255

Ser Phe Gln Asp Ile Leu Leu Arg Met Ser Lys Met Gln Leu Glu Ser
            260                 265                 270

Ser Ser Glu Asp Leu Asn Gly Met Ile Thr Gln Phe Glu Ser Leu Lys
        275                 280                 285

Leu Tyr Arg Asp Ser Leu Gly Glu Ala Val Met Arg Met Gly Asp Leu
    290                 295                 300

His Ser Leu Gln Asn Arg Asn Glu Lys Trp Arg Glu Gln Leu Gly Gln
305                 310                 315                 320

Lys Phe Glu Glu Ile Arg Trp Leu Ile Glu Glu Val Arg His Lys Leu
                325                 330                 335

Lys Ile Thr Glu Asn Ser Phe Glu Gln Ile Thr Phe Met Gln Ala Leu
            340                 345                 350

His Leu Leu Leu Glu Val Glu Gln Glu Ile Arg Thr Phe Ser Phe Gln
        355                 360                 365

Leu Ile
    370


<210> SEQ ID NO 99
<211> LENGTH: 591
<212> TYPE: PRT
<213> ORGANISM: Artificial Sequence
<220> FEATURE:
<223> OTHER INFORMATION: Synthetic Sequence

<400> SEQUENCE: 99

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Pro Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Lys Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Asp Trp Ser Met Leu Ile Pro Lys Gln Lys Val Ala
            100                 105                 110

Gly Pro Leu Cys Ile Lys Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Val Val Lys Asn
                165                 170                 175

Ala Val Gly Val Leu Ile Gly Gly Leu Glu Trp Asn Asp Asn Thr Val
            180                 185                 190
```

-continued

```
Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Glu Met Ala Gly
    210                 215                 220

Thr Ile Arg Ser Glu Val Gly Ser Gly Glu Gly Arg Gly Ser Leu Leu
225                 230                 235                 240

Thr Cys Gly Asp Val Glu Glu Asn Pro Gly Pro Asn Ile Thr Asn Leu
                245                 250                 255

Cys Pro Phe Gly Glu Val Phe Asn Ala Thr Arg Phe Ala Ser Val Tyr
            260                 265                 270

Ala Trp Asn Arg Lys Arg Ile Ser Asn Cys Val Ala Asp Tyr Ser Val
        275                 280                 285

Leu Tyr Asn Ser Ala Ser Phe Ser Thr Phe Lys Cys Tyr Gly Val Ser
    290                 295                 300

Pro Thr Lys Leu Asn Asp Leu Cys Phe Thr Asn Val Tyr Ala Asp Ser
305                 310                 315                 320

Phe Val Ile Arg Gly Asp Glu Val Arg Gln Ile Ala Pro Gly Gln Thr
                325                 330                 335

Gly Lys Ile Ala Asp Tyr Asn Tyr Lys Leu Pro Asp Asp Phe Thr Gly
            340                 345                 350

Cys Val Ile Ala Trp Asn Ser Asn Asn Leu Asp Ser Lys Val Gly Gly
        355                 360                 365

Asn Tyr Asn Tyr Leu Tyr Arg Leu Phe Arg Lys Ser Asn Leu Lys Pro
    370                 375                 380

Phe Glu Arg Asp Ile Ser Thr Glu Ile Tyr Gln Ala Gly Ser Thr Pro
385                 390                 395                 400

Cys Asn Gly Val Glu Gly Phe Asn Cys Tyr Phe Pro Leu Gln Ser Tyr
                405                 410                 415

Gly Phe Gln Pro Thr Asn Gly Val Gly Tyr Gln Pro Tyr Arg Val Val
            420                 425                 430

Val Leu Ser Phe Glu Leu Leu His Ala Pro Ala Thr Val Cys Gly Pro
        435                 440                 445

Lys Lys Ser Gly Ser Gly Ala Thr Asn Phe Ser Leu Leu Lys Gln Ala
    450                 455                 460

Gly Asp Val Glu Glu Asn Pro Gly Pro Asn Thr Val Ser Ser Phe Gln
465                 470                 475                 480

Asp Ile Leu Leu Arg Met Ser Lys Met Gln Leu Glu Ser Ser Ser Glu
                485                 490                 495

Asp Leu Asn Gly Met Ile Thr Gln Phe Glu Ser Leu Lys Leu Tyr Arg
            500                 505                 510

Asp Ser Leu Gly Glu Ala Val Met Arg Met Gly Asp Leu His Ser Leu
        515                 520                 525

Gln Asn Arg Asn Glu Lys Trp Arg Glu Gln Leu Gly Gln Lys Phe Glu
    530                 535                 540

Glu Ile Arg Trp Leu Ile Glu Glu Val Arg His Lys Leu Lys Ile Thr
545                 550                 555                 560

Glu Asn Ser Phe Glu Gln Ile Thr Phe Met Gln Ala Leu His Leu Leu
                565                 570                 575

Leu Glu Val Glu Gln Glu Ile Arg Thr Phe Ser Phe Gln Leu Ile
            580                 585                 590
```

<210> SEQ ID NO 100
<211> LENGTH: 643
<212> TYPE: PRT

-continued

```
<213> ORGANISM: Artificial Sequence
<220> FEATURE:
<223> OTHER INFORMATION: Synthetic Sequence

<400> SEQUENCE: 100

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Pro Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Lys Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Asp Trp Ser Met Leu Ile Pro Lys Gln Lys Val Ala
            100                 105                 110

Gly Pro Leu Cys Ile Lys Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Val Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Glu Met Ala Gly
    210                 215                 220

Thr Ile Arg Ser Glu Val Gly Ser Gly Pro Ala Tyr Thr Asn Ser Phe
225                 230                 235                 240

Thr Arg Gly Val Tyr Tyr Pro Asp Lys Val Phe Arg Ser Ser Val Leu
                245                 250                 255

His Ser Thr Gln Asp Leu Phe Leu Pro Phe Phe Ser Asn Val Thr Trp
            260                 265                 270

Phe His Ala Ile His Val Ser Gly Thr Asn Gly Thr Lys Arg Phe Asp
        275                 280                 285

Asn Pro Val Leu Pro Phe Asn Asp Gly Val Tyr Phe Ala Ser Thr Glu
    290                 295                 300

Lys Ser Asn Ile Ile Arg Gly Trp Ile Phe Gly Thr Thr Leu Asp Ser
305                 310                 315                 320

Lys Thr Gln Ser Leu Leu Ile Val Asn Asn Ala Thr Asn Val Val Ile
                325                 330                 335

Lys Val Cys Glu Phe Gln Phe Cys Asn Asp Pro Phe Leu Gly Val Tyr
            340                 345                 350

Tyr His Lys Asn Asn Lys Ser Trp Met Glu Ser Glu Phe Arg Val Tyr
        355                 360                 365

Ser Ser Ala Asn Asn Cys Thr Phe Glu Tyr Val Ser Gln Pro Phe Leu
    370                 375                 380

Met Asp Leu Glu Gly Lys Gln Gly Asn Phe Lys Asn Leu Arg Glu Phe
```

385 390 395 400

Val Phe Lys Asn Ile Asp Gly Tyr Phe Lys Ile Tyr Ser Lys His Thr
405 410 415

Pro Ile Asn Leu Val Arg Asp Leu Pro Gln Gly Phe Ser Ala Leu Glu
420 425 430

Pro Leu Val Asp Leu Pro Ile Gly Ile Asn Ile Thr Arg Phe Gln Thr
435 440 445

Leu Leu Ala Leu His Arg Ser Tyr Leu Thr Pro Gly Asp Ser Ser Ser
450 455 460

Gly Trp Thr Ala Gly Ala Ala Ala Tyr Tyr Val Gly Tyr Leu Gln Pro
465 470 475 480

Arg Thr Phe Leu Leu Lys Tyr Asn Glu Asn Gly Thr Ile Thr Asp Ala
485 490 495

Val Asp Cys Ala Leu Asp Pro Gly Ser Gly Ala Thr Asn Phe Ser Leu
500 505 510

Leu Lys Gln Ala Gly Asp Val Glu Glu Asn Pro Gly Pro Asn Thr Val
515 520 525

Ser Ser Phe Gln Asp Ile Leu Leu Arg Met Ser Lys Met Gln Leu Glu
530 535 540

Ser Ser Ser Glu Asp Leu Asn Gly Met Ile Thr Gln Phe Glu Ser Leu
545 550 555 560

Lys Leu Tyr Arg Asp Ser Leu Gly Glu Ala Val Met Arg Met Gly Asp
565 570 575

Leu His Ser Leu Gln Asn Arg Asn Glu Lys Trp Arg Glu Gln Leu Gly
580 585 590

Gln Lys Phe Glu Glu Ile Arg Trp Leu Ile Glu Glu Val Arg His Lys
595 600 605

Leu Lys Ile Thr Glu Asn Ser Phe Glu Gln Ile Thr Phe Met Gln Ala
610 615 620

Leu His Leu Leu Leu Glu Val Glu Gln Glu Ile Arg Thr Phe Ser Phe
625 630 635 640

Gln Leu Ile

<210> SEQ ID NO 101
<211> LENGTH: 463
<212> TYPE: PRT
<213> ORGANISM: Artificial Sequence
<220> FEATURE:
<223> OTHER INFORMATION: Synthetic Sequence

<400> SEQUENCE: 101

Met Asp Pro Asn Thr Val Ser Ser Phe Gln Val Asp Cys Phe Leu Trp
1 5 10 15

His Val Arg Lys Arg Val Ala Asp Gln Glu Leu Gly Asp Pro Pro Phe
20 25 30

Leu Asp Arg Leu Arg Arg Asp Gln Lys Ser Leu Arg Gly Arg Gly Ser
35 40 45

Thr Leu Gly Leu Asp Ile Lys Thr Ala Thr Arg Ala Gly Lys Gln Ile
50 55 60

Val Glu Arg Ile Leu Lys Glu Glu Ser Asp Glu Ala Leu Lys Met Thr
65 70 75 80

Met Ala Ser Val Pro Ala Ser Arg Tyr Leu Thr Asp Met Thr Leu Glu
85 90 95

Glu Met Ser Arg Asp Trp Ser Met Leu Ile Pro Lys Gln Lys Val Ala
100 105 110

-continued

```
Gly Pro Leu Cys Ile Lys Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Val Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Glu Met Ala Gly
    210                 215                 220

Thr Ile Arg Ser Glu Val Gly Ser Gly Ala Ser Ala Leu Gly Lys Leu
225                 230                 235                 240

Gln Asp Val Val Asn Gln Asn Ala Gln Ala Leu Asn Thr Leu Val Lys
                245                 250                 255

Gln Leu Ser Ser Asn Phe Gly Ala Ile Ser Ser Val Leu Asn Asp Ile
            260                 265                 270

Leu Ser Arg Leu Asp Lys Val Glu Ala Glu Val Gln Ile Asp Arg Leu
        275                 280                 285

Ile Thr Gly Arg Leu Gln Ser Leu Gln Thr Tyr Val Thr Gln Gln Leu
    290                 295                 300

Ile Arg Ala Ala Glu Ile Arg Ala Ser Ala Asn Leu Ala Ala Thr Lys
305                 310                 315                 320

Met Ser Glu Gly Ser Gly Ala Thr Asn Phe Ser Leu Leu Lys Gln Ala
                325                 330                 335

Gly Asp Val Glu Glu Asn Pro Gly Pro Asn Thr Val Ser Ser Phe Gln
            340                 345                 350

Asp Ile Leu Leu Arg Met Ser Lys Met Gln Leu Glu Ser Ser Ser Glu
        355                 360                 365

Asp Leu Asn Gly Met Ile Thr Gln Phe Glu Ser Leu Lys Leu Tyr Arg
    370                 375                 380

Asp Ser Leu Gly Glu Ala Val Met Arg Met Gly Asp Leu His Ser Leu
385                 390                 395                 400

Gln Asn Arg Asn Glu Lys Trp Arg Glu Gln Leu Gly Gln Lys Phe Glu
                405                 410                 415

Glu Ile Arg Trp Leu Ile Glu Glu Val Arg His Lys Leu Lys Ile Thr
            420                 425                 430

Glu Asn Ser Phe Glu Gln Ile Thr Phe Met Gln Ala Leu His Leu Leu
        435                 440                 445

Leu Glu Val Glu Gln Glu Ile Arg Thr Phe Ser Phe Gln Leu Ile
    450                 455                 460
```

<210> SEQ ID NO 102
<211> LENGTH: 463
<212> TYPE: PRT
<213> ORGANISM: Artificial Sequence
<220> FEATURE:
<223> OTHER INFORMATION: Synthetic Sequence

<400> SEQUENCE: 102

```
Met Asp Pro Asn Thr Val Ser Ser Phe Gln Val Asp Cys Phe Leu Trp
1               5                   10                  15
```

```
His Val Arg Lys Arg Val Ala Asp Gln Glu Leu Gly Asp Pro Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Lys Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Asp Trp Ser Met Leu Ile Pro Lys Gln Lys Val Ala
            100                 105                 110

Gly Pro Leu Cys Ile Lys Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Val Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Glu Met Ala Gly
    210                 215                 220

Thr Ile Arg Ser Glu Val Gly Ser Gly Ala Ser Ala Leu Gly Lys Leu
225                 230                 235                 240

Gln Asp Val Val Asn Gln Asn Ala Gln Ala Leu Asn Thr Leu Val Lys
                245                 250                 255

Gln Leu Ser Ser Asn Phe Gly Ala Ile Ser Ser Val Leu Asn Asp Ile
            260                 265                 270

Leu Ser Arg Leu Asp Pro Pro Glu Ala Glu Val Gln Ile Asp Arg Leu
        275                 280                 285

Ile Thr Gly Arg Leu Gln Ser Leu Gln Thr Tyr Val Thr Gln Gln Leu
    290                 295                 300

Ile Arg Ala Ala Glu Ile Arg Ala Ser Ala Asn Leu Ala Ala Thr Lys
305                 310                 315                 320

Met Ser Glu Gly Ser Gly Ala Thr Asn Phe Ser Leu Leu Lys Gln Ala
                325                 330                 335

Gly Asp Val Glu Glu Asn Pro Gly Pro Asn Thr Val Ser Ser Phe Gln
            340                 345                 350

Asp Ile Leu Leu Arg Met Ser Lys Met Gln Leu Glu Ser Ser Ser Glu
        355                 360                 365

Asp Leu Asn Gly Met Ile Thr Gln Phe Glu Ser Leu Lys Leu Tyr Arg
    370                 375                 380

Asp Ser Leu Gly Glu Ala Val Met Arg Met Gly Asp Leu His Ser Leu
385                 390                 395                 400

Gln Asn Arg Asn Glu Lys Trp Arg Glu Gln Leu Gly Gln Lys Phe Glu
                405                 410                 415

Glu Ile Arg Trp Leu Ile Glu Glu Val Arg His Lys Leu Lys Ile Thr
            420                 425                 430
```

Glu Asn Ser Phe Glu Gln Ile Thr Phe Met Gln Ala Leu His Leu Leu
435 440 445

Leu Glu Val Glu Gln Glu Ile Arg Thr Phe Ser Phe Gln Leu Ile
450 455 460

<210> SEQ ID NO 103
<211> LENGTH: 440
<212> TYPE: PRT
<213> ORGANISM: Artificial Sequence
<220> FEATURE:
<223> OTHER INFORMATION: Synthetic Sequence

<400> SEQUENCE: 103

Met Asp Pro Asn Thr Val Ser Ser Phe Gln Val Asp Cys Phe Leu Trp
1 5 10 15

His Val Arg Lys Arg Val Ala Asp Gln Glu Leu Gly Asp Pro Pro Phe
20 25 30

Leu Asp Arg Leu Arg Arg Asp Gln Lys Ser Leu Arg Gly Arg Gly Ser
35 40 45

Thr Leu Gly Leu Asp Ile Lys Thr Ala Thr Arg Ala Gly Lys Gln Ile
50 55 60

Val Glu Arg Ile Leu Lys Glu Glu Ser Asp Glu Ala Leu Lys Met Thr
65 70 75 80

Met Ala Ser Val Pro Ala Ser Arg Tyr Leu Thr Asp Met Thr Leu Glu
85 90 95

Glu Met Ser Arg Asp Trp Ser Met Leu Ile Pro Lys Gln Lys Val Ala
100 105 110

Gly Pro Leu Cys Ile Lys Met Asp Gln Ala Ile Met Asp Lys Asn Ile
115 120 125

Ile Leu Lys Ala Asn Phe Ser Val Ile Phe Asp Arg Leu Glu Thr Leu
130 135 140

Ile Leu Leu Arg Ala Phe Thr Glu Glu Gly Ala Ile Val Gly Glu Ile
145 150 155 160

Ser Pro Leu Pro Ser Leu Pro Gly His Thr Ala Glu Val Val Lys Asn
165 170 175

Ala Val Gly Val Leu Ile Gly Gly Leu Glu Trp Asn Asp Asn Thr Val
180 185 190

Arg Val Ser Glu Thr Leu Gln Arg Phe Ala Trp Arg Ser Ser Asn Glu
195 200 205

Asn Gly Arg Pro Pro Leu Thr Pro Lys Gln Lys Arg Glu Met Ala Gly
210 215 220

Thr Ile Arg Ser Glu Val Gly Ser Gly Lys Asn Phe Thr Thr Ala Pro
225 230 235 240

Ala Ile Cys His Asp Gly Lys Ala His Phe Pro Arg Glu Gly Val Phe
245 250 255

Val Ser Asn Gly Thr His Trp Phe Val Thr Gln Arg Asn Phe Tyr Glu
260 265 270

Pro Gln Ile Ile Thr Thr Asp Asn Thr Phe Val Ser Gly Asn Cys Asp
275 280 285

Val Val Ile Gly Ile Val Asn Asn Thr Val Tyr Asp Gly Ser Gly Ala
290 295 300

Thr Asn Phe Ser Leu Leu Lys Gln Ala Gly Asp Val Glu Glu Asn Pro
305 310 315 320

Gly Pro Asn Thr Val Ser Ser Phe Gln Asp Ile Leu Leu Arg Met Ser
325 330 335

```
Lys Met Gln Leu Glu Ser Ser Ser Glu Asp Leu Asn Gly Met Ile Thr
            340                 345                 350

Gln Phe Glu Ser Leu Lys Leu Tyr Arg Asp Ser Leu Gly Glu Ala Val
        355                 360                 365

Met Arg Met Gly Asp Leu His Ser Leu Gln Asn Arg Asn Glu Lys Trp
    370                 375                 380

Arg Glu Gln Leu Gly Gln Lys Phe Glu Glu Ile Arg Trp Leu Ile Glu
385                 390                 395                 400

Glu Val Arg His Lys Leu Lys Ile Thr Glu Asn Ser Phe Glu Gln Ile
                405                 410                 415

Thr Phe Met Gln Ala Leu His Leu Leu Leu Glu Val Glu Gln Glu Ile
            420                 425                 430

Arg Thr Phe Ser Phe Gln Leu Ile
        435                 440


<210> SEQ ID NO 104
<211> LENGTH: 447
<212> TYPE: PRT
<213> ORGANISM: Artificial Sequence
<220> FEATURE:
<223> OTHER INFORMATION: Synthetic Sequence

<400> SEQUENCE: 104

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Pro Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Lys Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Asp Trp Ser Met Leu Ile Pro Lys Gln Lys Val Ala
            100                 105                 110

Gly Pro Leu Cys Ile Lys Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Val Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Glu Met Ala Gly
    210                 215                 220

Thr Ile Arg Ser Glu Val Gly Ser Gly Pro Leu Gln Pro Glu Leu Asp
225                 230                 235                 240

Ser Phe Lys Glu Glu Leu Asp Lys Tyr Phe Lys Asn His Thr Ser Pro
                245                 250                 255
```

-continued

Asp Val Asp Leu Gly Asp Ile Ser Gly Ile Asn Ala Ser Val Val Asn
            260                 265                 270

Ile Gln Lys Glu Ile Asp Arg Leu Asn Glu Val Ala Lys Asn Leu Asn
        275                 280                 285

Glu Ser Leu Ile Asp Leu Gln Glu Leu Gly Lys Tyr Glu Gln Tyr Ile
    290                 295                 300

Lys Trp Pro Gly Ser Gly Ala Thr Asn Phe Ser Leu Leu Lys Gln Ala
305                 310                 315                 320

Gly Asp Val Glu Glu Asn Pro Gly Pro Asn Thr Val Ser Ser Phe Gln
                325                 330                 335

Asp Ile Leu Leu Arg Met Ser Lys Met Gln Leu Glu Ser Ser Ser Glu
            340                 345                 350

Asp Leu Asn Gly Met Ile Thr Gln Phe Glu Ser Leu Lys Leu Tyr Arg
        355                 360                 365

Asp Ser Leu Gly Glu Ala Val Met Arg Met Gly Asp Leu His Ser Leu
    370                 375                 380

Gln Asn Arg Asn Glu Lys Trp Arg Glu Gln Leu Gly Gln Lys Phe Glu
385                 390                 395                 400

Glu Ile Arg Trp Leu Ile Glu Glu Val Arg His Lys Leu Lys Ile Thr
                405                 410                 415

Glu Asn Ser Phe Glu Gln Ile Thr Phe Met Gln Ala Leu His Leu Leu
            420                 425                 430

Leu Glu Val Glu Gln Glu Ile Arg Thr Phe Ser Phe Gln Leu Ile
        435                 440                 445

<210> SEQ ID NO 105
<211> LENGTH: 1096
<212> TYPE: DNA
<213> ORGANISM: Artificial Sequence
<220> FEATURE:
<223> OTHER INFORMATION: Synthetic Sequence

<400> SEQUENCE: 105
agcaaaagca ggtagatatt gaaagatgag tcttctaacc gaggtcgaaa cgtacgtact 60
ctctatcatc ccgtcaggcc ccctcaaagc cgagatcgca cagagacttg aagatgtctt 120
tgcagggaag aacaccgatc ttgaggttct catggaatgg ctaaagacaa gaccaatcct 180
gtcacctctg actaagggga ttttaggatt tgtgttcacg ctcaccgtgc ccagtgagcg 240
aggactgcag cgtagacgct ttgtccaaaa tgcccttaat gggaacgggg atccaaataa 300
catggacaaa gcagctaaac tgtataggaa gctcaagagg gagataacat tccatggggc 360
caaagaaatc tcactcagtt attctgctgg tgcacttgcc agttgtatgg gcctcatata 420
caacaggatg gggctgtga ccactgaagt ggcatttggc ctggtatgtg caacctgtga 480
acagattgct gactcccagc atcggtctca taggcaaatg gtgacaacaa ccaatccact 540
aatcagacat gagaacagaa tggttttagc cagcactaca gctaaggcta tggagcaaat 600
ggctggatcg agtgagcaag cagcagaggc catggaggtt gctagtcagg ctagacaaat 660
ggtgcaagcg atgagaacca ttgggactca tcctagctcc agtgctggtc tgaaaaatga 720
tcttcttgaa aatttgcagg cctatcagaa acgaatgggg gtgcagatgc aacggttcaa 780
gtgatcctaa tcttgattct aaggttggtg gtaattataa ttacctgtat agattgttta 840
ggaagtctaa tctcaaacct tttgagagag caggtgcagg tgattacaag gatgacgacg 900
ataagtaata ggatcgtctt tttttcaaat gcatttaccg tcgctttaaa tacggactga 960
aaggagggcc ttctacggaa ggagtgccaa agtctatgag ggaagaatat cgaaaggaac 1020

-continued agcagagtgc tgtggatgct gacgatggtc attttgtcag catagagctg gagtaaaaaa 1080
ctaccttgtt tctact 1096

<210> SEQ ID NO 106
<211> LENGTH: 1108
<212> TYPE: DNA
<213> ORGANISM: Artificial Sequence
<220> FEATURE:
<223> OTHER INFORMATION: Synthetic Sequence

<400> SEQUENCE: 106
agcaaaagca ggtagatatt gaaagatgag tcttctaacc gaggtcgaaa cgtacgtact 60
ctctatcatc ccgtcaggcc ccctcaaagc cgagatcgca cagagacttg aagatgtctt 120
tgcagggaag aacaccgatc ttgaggttct catggaatgg ctaaagacaa gaccaatcct 180
gtcacctctg actaagggga ttttaggatt tgtgttcacg ctcaccgtgc ccagtgagcg 240
aggactgcag cgtagacgct ttgtccaaaa tgcccttaat gggaacgggg atccaaataa 300
catggacaaa gcagctaaac tgtataggaa gctcaagagg gagataacat tccatggggc 360
caaagaaatc tcactcagtt attctgctgg tgcacttgcc agttgtatgg gcctcatata 420
caacaggatg gggctgtga ccactgaagt ggcatttggc ctggtatgtg caacctgtga 480
acagattgct gactcccagc atcggtctca taggcaaatg gtgacaacaa ccaatccact 540
aatcagacat gagaacagaa tggttttagc cagcactaca gctaaggcta tggagcaaat 600
ggctggatcg agtgagcaag cagcagaggc catggaggtt gctagtcagg ctagacaaat 660
ggtgcaagcg atgagaacca ttgggactca tcctagctcc agtgctggtc tgaaaaatga 720
tcttcttgaa aatttgcagg cctatcagaa acgaatgggg gtgcagatgc aacggttcaa 780
gtgatcctat cgatctccaa gaacttggaa agtatgagca gtatataaaa tggccatggt 840
acatttggct aggttttata gctggcttga ttgccatagt agcaggtgca ggtgattaca 900
aggatgacga cgataagtaa taggatcgtc ttttttcaa atgcatttac cgtcgcttta 960
aatacggact gaaaggaggg ccttctacgg aaggagtgcc aaagtctatg agggaagaat 1020
atcgaaagga acagcagagt gctgtggatg ctgacgatgg tcattttgtc agcatagagc 1080
tggagtaaaa aactaccttg tttctact 1108

<210> SEQ ID NO 107
<211> LENGTH: 976
<212> TYPE: DNA
<213> ORGANISM: Artificial Sequence
<220> FEATURE:
<223> OTHER INFORMATION: Synthetic Sequence

<400> SEQUENCE: 107
agcaaaagca ggtagatatt gaaagatgag tcttctaacc gaggtcgaaa cgtacgtact 60
ctctatcatc ccgtcaggcc ccctcaaagc cgagatcgca cagagacttg aagatgtctt 120
tgcagggaag aacaccgatc ttgaggttct catggaatgg ctaaagacaa gaccaatcct 180
gtcacctctg actaagggga ttttaggatt tgtgttcacg ctcaccgtgc ccagtgagcg 240
aggactgcag cgtagacgct ttgtccaaaa tgcccttaat gggaacgggg atccaaataa 300
catggacaaa gcagttaaac tgtataggaa gctcaagagg gagataacat tccatggggc 360
caaagaaatc tcactcagtt attctgctgg tgcacttgcc agttgtatgg gcctcatata 420
caacaggatg gggctgtga ccactgaagt ggcatttggc ctggtatgtg caacctgtga 480

-continued acagattgct gactcccagc atcggtctca taggcaaatg gtgacaacaa ccaatccact 540
aatcagacat gagaacagaa tggttttagc cagcactaca gctaaggcta tggagcaaat 600
ggctggatcg agtgagcaag cagcagaggc catggaggtt gctagtcagg ctagacaaat 660
ggtgcaagcg atgagaacca ttgggactca tcctagctcc agtgctggtc tgaaaaatga 720
tcttcttgaa aatttgcagg cctatcagaa acgaatgggg gtgcagatgc aacggttcaa 780
gtgattaata ggatcgtctt tttttcaaat gcatttaccg tcgctttaaa tacggactga 840
aaggagggcc ttctacggaa ggagtgccaa agtctatgag ggaagaatat cgaaaggaac 900
agcagagtgc tgtggatgct gacgatggtc attttgtcag catagagctg gagtaaaaaa 960
ctaccttgtt tctact 976

<210> SEQ ID NO 108
<211> LENGTH: 119
<212> TYPE: PRT
<213> ORGANISM: Artificial Sequence
<220> FEATURE:
<223> OTHER INFORMATION: Synthetic Sequence

<400> SEQUENCE: 108

Pro Asn Thr Val Ser Ser Phe Gln Asp Ile Leu Leu Arg Met Ser Lys
1 5 10 15

Met Gln Leu Glu Ser Ser Ser Glu Asp Leu Asn Gly Met Ile Thr Gln
20 25 30

Phe Glu Ser Leu Lys Leu Tyr Arg Asp Ser Leu Gly Glu Ala Val Met
35 40 45

Arg Met Gly Asp Leu His Ser Leu Gln Asn Arg Asn Glu Lys Trp Arg
50 55 60

Glu Gln Leu Gly Gln Lys Phe Glu Glu Ile Arg Trp Leu Ile Glu Glu
65 70 75 80

Val Arg His Lys Leu Lys Ile Thr Glu Asn Ser Phe Glu Gln Ile Thr
85 90 95

Phe Met Gln Ala Leu His Leu Leu Leu Glu Val Glu Gln Glu Ile Arg
100 105 110

Thr Phe Ser Phe Gln Leu Ile
115

<210> SEQ ID NO 109
<211> LENGTH: 30
<212> TYPE: DNA
<213> ORGANISM: Artificial Sequence
<220> FEATURE:
<223> OTHER INFORMATION: Synthetic Sequence

<400> SEQUENCE: 109
atggatccaa acactgtgtc aagctttcaa 30

<210> SEQ ID NO 110
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 110
cctaatacag tgtctagctt ccag 24

<210> SEQ ID NO 111
<211> LENGTH: 188

<212> TYPE: DNA
<213> ORGANISM: Artificial Sequence
<220> FEATURE:
<223> OTHER INFORMATION: Synthetic Sequence

<400> SEQUENCE: 111
gacatactgc tgaggttgtc aagaatgctg ttggagtgct aatcggagga cttgaatgga 60
acgacaacac tgtgcgagtc agcgaaactt tgcagagatt tgcttggaga agctctaatg 120
agaacgggag acctccactg actccaaagc agaaacgaga catggctgga acaattagaa 180
gcgaagtt 188

<210> SEQ ID NO 112
<211> LENGTH: 188
<212> TYPE: DNA
<213> ORGANISM: Artificial Sequence
<220> FEATURE:
<223> OTHER INFORMATION: Synthetic Sequence

<400> SEQUENCE: 112
gacatactgc tgaggatgtc aaaaatgcag ttggagtcct catcggagga cttgaatgga 60
atgataacac agttcgagtc tctgaaactc tacagagatt cgcttggaga agcagtaatg 120
agaatgggag acctccactc actccaaaac agaaacgaga aatggcggga acaattaggt 180
cagaagtt 188

<210> SEQ ID NO 113
<211> LENGTH: 282
<212> TYPE: PRT
<213> ORGANISM: Artificial Sequence
<220> FEATURE:
<223> OTHER INFORMATION: Synthetic Sequence

<400> SEQUENCE: 113

Gly Ser Gly Glu Gly Arg Gly Ser Leu Leu Thr Cys Gly Asp Val Glu
1 5 10 15

Glu Asn Pro Gly Pro Val Ser Lys Gly Glu Glu Leu Phe Thr Gly Val
20 25 30

Val Pro Ile Leu Val Glu Leu Asp Gly Asp Val Asn Gly His Lys Phe
35 40 45

Ser Val Ser Gly Glu Gly Glu Gly Asp Ala Thr Tyr Gly Lys Leu Thr
50 55 60

Leu Lys Phe Ile Cys Thr Thr Gly Lys Leu Pro Val Pro Trp Pro Thr
65 70 75 80

Leu Val Thr Thr Leu Thr Tyr Gly Val Gln Cys Phe Ser Arg Tyr Pro
85 90 95

Asp His Met Lys Gln His Asp Phe Phe Lys Ser Ala Met Pro Glu Gly
100 105 110

Tyr Val Gln Glu Arg Thr Ile Phe Phe Lys Asp Asp Gly Asn Tyr Lys
115 120 125

Thr Arg Ala Glu Val Lys Phe Glu Gly Asp Thr Leu Val Asn Arg Ile
130 135 140

Glu Leu Lys Gly Ile Asp Phe Lys Glu Asp Gly Asn Ile Leu Gly His
145 150 155 160

Lys Leu Glu Tyr Asn Tyr Asn Ser His Asn Val Tyr Ile Met Ala Asp
165 170 175

Lys Gln Lys Asn Gly Ile Lys Val Asn Phe Lys Ile Arg His Asn Ile
180 185 190

-continued

```
Glu Asp Gly Ser Val Gln Leu Ala Asp His Tyr Gln Gln Asn Thr Pro
        195                 200                 205

Ile Gly Asp Gly Pro Val Leu Leu Pro Asp Asn His Tyr Leu Ser Thr
    210                 215                 220

Gln Ser Ala Leu Ser Lys Asp Pro Asn Glu Lys Arg Asp His Met Val
225                 230                 235                 240

Leu Leu Glu Phe Val Thr Ala Ala Gly Ile Thr Leu Gly Met Asp Glu
                245                 250                 255

Leu Tyr Lys Ser Gly Ser Gly Ala Thr Asn Phe Ser Leu Leu Lys Gln
            260                 265                 270

Ala Gly Asp Val Glu Glu Asn Pro Gly Pro
        275                 280


<210> SEQ ID NO 114
<211> LENGTH: 846
<212> TYPE: DNA
<213> ORGANISM: Artificial Sequence
<220> FEATURE:
<223> OTHER INFORMATION: Synthetic Sequence

<400> SEQUENCE: 114

ggtagtggag aaggtagagg aagtcttcta acatgtggtg atgtagaaga gaatccaggt      60

cctgtatcta aaggtgaaga attattcact ggtgttgtcc caattttggt tgaattagat     120

ggtgatgtta atggtcataa atttctgtc tccggtgaag gtgaaggtga tgctacttac     180

ggtaaattga ccttaaaatt tatttgtact actggtaaat tgccagttcc atggccaacc     240

ttagtcacta ctttaactta tggtgttcaa tgtttttcaa gatacccaga tcatatgaaa     300

caacatgact ttttcaagtc tgccatgcca gaaggttatg ttcaagaaag aactattttt     360

ttcaaagatg acggtaacta caagaccaga gctgaagtca agtttgaagg tgatacctta     420

gttaatagaa tcgaattaaa aggtattgat tttaaagaag atggtaacat tttaggtcac     480

aaacttgaat acaactataa ctctcacaat gtttacatca tggctgacaa acaaaagaat     540

ggtatcaaag ttaacttcaa aattagacac aacattgaag atggtagcgt tcaattagct     600

gaccattatc aacaaaatac tccaattggt gatggtccag tcttgttacc agacaaccat     660

tacttatcca cacaatctgc cttatccaaa gatccaaacg aaaagagaga tcacatggtc     720

ttgttagaat ttgttactgc tgctggtatt acccttggta tggatgaatt gtacaaatca     780

ggatcaggtg caactaactt tagtcttctt aaacaagctg gtgatgttga agaaaatcct     840

ggacct                                                                846


<210> SEQ ID NO 115
<211> LENGTH: 275
<212> TYPE: PRT
<213> ORGANISM: Artificial Sequence
<220> FEATURE:
<223> OTHER INFORMATION: Synthetic Sequence

<400> SEQUENCE: 115

Phe Val Phe Leu Val Leu Leu Pro Leu Val Ser Ser Gln Pro Asn Ile
1               5                   10                  15

Thr Asn Leu Cys Pro Phe Gly Glu Val Phe Asn Ala Thr Arg Phe Ala
            20                  25                  30

Ser Val Tyr Ala Trp Asn Arg Lys Arg Ile Ser Asn Cys Val Ala Asp
        35                  40                  45

Tyr Ser Val Leu Tyr Asn Ser Ala Ser Phe Ser Thr Phe Lys Cys Tyr
    50                  55                  60
```

```
Gly Val Ser Pro Thr Lys Leu Asn Asp Leu Cys Phe Thr Asn Val Tyr
65                  70                  75                  80

Ala Asp Ser Phe Val Ile Arg Gly Asp Glu Val Arg Gln Ile Ala Pro
                85                  90                  95

Gly Gln Thr Gly Lys Ile Ala Asp Tyr Asn Tyr Lys Leu Pro Asp Asp
            100                 105                 110

Phe Thr Gly Cys Val Ile Ala Trp Asn Ser Asn Asn Leu Asp Ser Lys
        115                 120                 125

Val Gly Gly Asn Tyr Asn Tyr Leu Tyr Arg Leu Phe Arg Lys Ser Asn
    130                 135                 140

Leu Lys Pro Phe Glu Arg Asp Ile Ser Thr Glu Ile Tyr Gln Ala Gly
145                 150                 155                 160

Ser Thr Pro Cys Asn Gly Val Glu Gly Phe Asn Cys Tyr Phe Pro Leu
                165                 170                 175

Gln Ser Tyr Gly Phe Gln Pro Thr Asn Gly Val Gly Tyr Gln Pro Tyr
            180                 185                 190

Arg Val Val Val Leu Ser Phe Glu Leu Leu His Ala Pro Ala Thr Val
        195                 200                 205

Cys Gly Pro Lys Lys Ser Gly Tyr Ile Pro Glu Ala Pro Arg Asp Gly
    210                 215                 220

Gln Ala Tyr Val Arg Lys Asp Gly Glu Trp Val Leu Leu Ser Thr Phe
225                 230                 235                 240

Leu Gly Ser Thr Thr Asn Ile Met Ile Thr Thr Ile Ile Ile Val Ile
                245                 250                 255

Ile Val Ile Leu Leu Ser Leu Ile Ala Val Gly Leu Leu Leu Tyr Cys
            260                 265                 270

Lys Ala Arg
        275


<210> SEQ ID NO 116
<211> LENGTH: 773
<212> TYPE: PRT
<213> ORGANISM: Artificial Sequence
<220> FEATURE:
<223> OTHER INFORMATION: Synthetic Sequence

<400> SEQUENCE: 116

Met Lys Thr Ile Ile Ala Leu Ser Tyr Ile Leu Ser Leu Val Phe Ala
1               5                   10                  15

Gln Lys Pro Asn Ile Thr Asn Leu Cys Pro Phe Gly Glu Val Phe Asn
            20                  25                  30

Ala Thr Arg Phe Ala Ser Val Tyr Ala Trp Asn Arg Lys Arg Ile Ser
        35                  40                  45

Asn Cys Val Ala Asp Tyr Ser Val Leu Tyr Asn Ser Ala Ser Phe Ser
    50                  55                  60

Thr Phe Lys Cys Tyr Gly Val Ser Pro Thr Lys Leu Asn Asp Leu Cys
65                  70                  75                  80

Phe Thr Asn Val Tyr Ala Asp Ser Phe Val Ile Arg Gly Asp Glu Val
                85                  90                  95

Arg Gln Ile Ala Pro Gly Gln Thr Gly Lys Ile Ala Asp Tyr Asn Tyr
            100                 105                 110

Lys Leu Pro Asp Asp Phe Thr Gly Cys Val Ile Ala Trp Asn Ser Asn
        115                 120                 125

Asn Leu Asp Ser Lys Val Gly Gly Asn Tyr Asn Tyr Leu Tyr Arg Leu
    130                 135                 140
```

```
Phe Arg Lys Ser Asn Leu Lys Pro Phe Glu Arg Asp Ile Ser Thr Glu
145                 150                 155                 160

Ile Tyr Gln Ala Gly Ser Thr Pro Cys Asn Gly Val Glu Gly Phe Asn
                165                 170                 175

Cys Tyr Phe Pro Leu Gln Ser Tyr Gly Phe Gln Pro Thr Asn Gly Val
            180                 185                 190

Gly Tyr Gln Pro Tyr Arg Val Val Val Leu Ser Phe Glu Leu Leu His
        195                 200                 205

Ala Pro Ala Thr Val Cys Gly Pro Lys Lys Gly Gly Gly Gly Ser Gln
    210                 215                 220

Lys Ile Pro Gly Asn Asp Asn Ser Thr Ala Thr Leu Cys Leu Gly His
225                 230                 235                 240

His Ala Val Pro Asn Gly Thr Ile Val Lys Thr Ile Thr Asn Asp Arg
                245                 250                 255

Ile Glu Val Thr Asn Ala Thr Glu Leu Val Gln Asn Ser Ser Ile Gly
            260                 265                 270

Glu Ile Cys Asp Ser Pro His Gln Ile Leu Asp Gly Glu Asn Cys Thr
        275                 280                 285

Leu Ile Asp Ala Leu Leu Gly Asp Pro Gln Cys Asp Gly Phe Gln Asn
    290                 295                 300

Lys Lys Trp Asp Leu Phe Val Glu Arg Ser Lys Ala Tyr Ser Asn Cys
305                 310                 315                 320

Tyr Pro Tyr Asp Val Pro Asp Tyr Ala Ser Leu Arg Ser Leu Val Ala
                325                 330                 335

Ser Ser Gly Thr Leu Glu Phe Lys Asn Glu Ser Phe Asn Trp Thr Gly
            340                 345                 350

Val Thr Gln Asn Gly Thr Ser Ser Ala Cys Ile Arg Gly Ser Ser Ser
        355                 360                 365

Ser Phe Phe Ser Arg Leu Asn Trp Leu Thr His Leu Asn Tyr Lys Tyr
    370                 375                 380

Pro Ala Leu Asn Val Thr Met Pro Asn Lys Glu Gln Phe Asp Lys Leu
385                 390                 395                 400

Tyr Ile Trp Gly Val His His Pro Gly Thr Asp Lys Asp Gln Ile Phe
                405                 410                 415

Pro Tyr Ala Gln Ser Ser Gly Arg Ile Thr Val Ser Thr Lys Arg Ser
            420                 425                 430

Gln Gln Ala Val Ile Pro Asn Ile Gly Ser Arg Pro Arg Ile Arg Gly
        435                 440                 445

Ile Pro Ser Arg Ile Ser Ile Tyr Trp Thr Ile Val Lys Pro Gly Asp
    450                 455                 460

Ile Leu Leu Ile Asn Ser Thr Gly Asn Leu Ile Ala Pro Arg Gly Tyr
465                 470                 475                 480

Phe Lys Ile Arg Ser Gly Lys Ser Ser Ile Met Arg Ser Asp Ala Pro
                485                 490                 495

Ile Gly Lys Cys Lys Ser Glu Cys Ile Thr Pro Asn Gly Ser Ile Pro
            500                 505                 510

Asn Asp Lys Pro Phe Gln Asn Val Asn Arg Ile Thr Tyr Gly Ala Cys
        515                 520                 525

Pro Arg Tyr Val Lys His Ser Thr Leu Lys Leu Ala Thr Gly Met Arg
    530                 535                 540

Asn Val Pro Glu Lys Gln Thr Arg Gly Ile Phe Gly Ala Ile Ala Gly
545                 550                 555                 560
```

Phe Ile Glu Asn Gly Trp Glu Gly Met Val Asp Gly Trp Tyr Gly Phe
565 570 575

Arg His Gln Asn Ser Glu Gly Arg Gly Gln Ala Ala Asp Leu Lys Ser
580 585 590

Thr Gln Ala Ala Ile Asp Gln Ile Asn Gly Lys Leu Asn Arg Leu Ile
595 600 605

Gly Lys Thr Asn Glu Lys Phe His Gln Ile Glu Lys Glu Phe Ser Glu
610 615 620

Val Glu Gly Arg Val Gln Asp Leu Glu Lys Tyr Val Glu Asp Thr Lys
625 630 635 640

Ile Asp Leu Trp Ser Tyr Asn Ala Glu Leu Leu Val Ala Leu Glu Asn
645 650 655

Gln His Thr Ile Asp Leu Thr Asp Ser Glu Met Asn Lys Leu Phe Glu
660 665 670

Lys Thr Lys Lys Gln Leu Arg Glu Asn Ala Glu Asp Met Gly Asn Gly
675 680 685

Cys Phe Lys Ile Tyr His Lys Cys Asp Asn Ala Cys Ile Glu Ser Ile
690 695 700

Arg Asn Glu Thr Tyr Asp His Asn Val Tyr Arg Asp Glu Ala Leu Asn
705 710 715 720

Asn Arg Phe Gln Ile Lys Gly Val Glu Leu Lys Ser Gly Tyr Lys Asp
725 730 735

Trp Ile Leu Trp Ile Ser Phe Ala Ile Ser Cys Phe Leu Leu Cys Val
740 745 750

Ala Leu Leu Gly Phe Ile Met Trp Ala Cys Gln Lys Gly Asn Ile Arg
755 760 765

Cys Asn Ile Cys Ile
770

<210> SEQ ID NO 117
<211> LENGTH: 625
<212> TYPE: PRT
<213> ORGANISM: Artificial Sequence
<220> FEATURE:
<223> OTHER INFORMATION: Synthetic Sequence

<400> SEQUENCE: 117

Met Lys Thr Ile Ile Ala Leu Ser Tyr Ile Leu Cys Leu Val Phe Ala
1 5 10 15

Gln Lys Ile Pro Val Ser Thr Tyr Met Leu Thr Asn Ser Glu Leu Leu
20 25 30

Ser Leu Ile Asn Asp Met Pro Ile Thr Asn Asp Gln Lys Lys Leu Met
35 40 45

Ser Asn Asn Val Gln Ile Val Arg Gln Gln Ser Tyr Ser Ile Met Ser
50 55 60

Ile Ile Lys Glu Ala Ala Ala Pro Gly Ala Ala Gln Lys Ile Pro Gly
65 70 75 80

Asn Asp Asn Ser Thr Ala Thr Leu Cys Leu Gly His His Ala Val Pro
85 90 95

Asn Gly Thr Ile Val Lys Thr Ile Thr Asn Asp Arg Ile Glu Val Thr
100 105 110

Asn Ala Thr Glu Leu Val Gln Asn Ser Ser Ile Gly Glu Ile Cys Asp
115 120 125

Ser Pro His Gln Ile Leu Asp Gly Glu Asn Cys Thr Leu Ile Asp Ala
130 135 140

-continued

```
Leu Leu Gly Asp Pro Gln Cys Asp Gly Phe Gln Asn Lys Lys Trp Asp
145                 150                 155                 160

Leu Phe Val Glu Arg Ser Lys Ala Tyr Ser Asn Cys Tyr Pro Tyr Asp
                165                 170                 175

Val Pro Asp Tyr Ala Ser Leu Arg Ser Leu Val Ala Ser Ser Gly Thr
            180                 185                 190

Leu Glu Phe Lys Asn Glu Ser Phe Asn Trp Thr Gly Val Thr Gln Asn
        195                 200                 205

Gly Thr Ser Ser Ala Cys Ile Arg Gly Ser Ser Ser Ser Phe Phe Ser
    210                 215                 220

Arg Leu Asn Trp Leu Thr His Leu Asn Tyr Lys Tyr Pro Ala Leu Asn
225                 230                 235                 240

Val Thr Met Pro Asn Lys Glu Gln Phe Asp Lys Leu Tyr Ile Trp Gly
                245                 250                 255

Val His His Pro Gly Thr Asp Lys Asp Gln Ile Phe Pro Tyr Ala Gln
            260                 265                 270

Ser Ser Gly Arg Ile Thr Val Ser Thr Lys Arg Ser Gln Gln Ala Val
        275                 280                 285

Ile Pro Asn Ile Gly Ser Arg Pro Arg Ile Arg Gly Ile Pro Ser Arg
    290                 295                 300

Ile Ser Ile Tyr Trp Thr Ile Val Lys Pro Gly Asp Ile Leu Leu Ile
305                 310                 315                 320

Asn Ser Thr Gly Asn Leu Ile Ala Pro Arg Gly Tyr Phe Lys Ile Arg
                325                 330                 335

Ser Gly Lys Ser Ser Ile Met Arg Ser Asp Ala Pro Ile Gly Lys Cys
            340                 345                 350

Lys Ser Glu Cys Ile Thr Pro Asn Gly Ser Ile Pro Asn Asp Lys Pro
        355                 360                 365

Phe Gln Asn Val Asn Arg Ile Thr Tyr Gly Ala Cys Pro Arg Tyr Val
    370                 375                 380

Lys His Ser Thr Leu Lys Leu Ala Thr Gly Met Arg Asn Val Pro Glu
385                 390                 395                 400

Lys Gln Thr Arg Gly Ile Phe Gly Ala Ile Ala Gly Phe Ile Glu Asn
                405                 410                 415

Gly Trp Glu Gly Met Val Asp Gly Trp Tyr Gly Phe Arg His Gln Asn
            420                 425                 430

Ser Glu Gly Arg Gly Gln Ala Ala Asp Leu Lys Ser Thr Gln Ala Ala
        435                 440                 445

Ile Asp Gln Ile Asn Gly Lys Leu Asn Arg Leu Ile Gly Lys Thr Asn
    450                 455                 460

Glu Lys Phe His Gln Ile Glu Lys Glu Phe Ser Glu Val Glu Gly Arg
465                 470                 475                 480

Val Gln Asp Leu Glu Lys Tyr Val Glu Asp Thr Lys Ile Asp Leu Trp
                485                 490                 495

Ser Tyr Asn Ala Glu Leu Leu Val Ala Leu Glu Asn Gln His Thr Ile
            500                 505                 510

Asp Leu Thr Asp Ser Glu Met Asn Lys Leu Phe Glu Lys Thr Lys Lys
        515                 520                 525

Gln Leu Arg Glu Asn Ala Glu Asp Met Gly Asn Gly Cys Phe Lys Ile
    530                 535                 540

Tyr His Lys Cys Asp Asn Ala Cys Ile Glu Ser Ile Arg Asn Glu Thr
545                 550                 555                 560

Tyr Asp His Asn Val Tyr Arg Asp Glu Ala Leu Asn Asn Arg Phe Gln
```

```
                565                 570                 575

Ile Lys Gly Val Glu Leu Lys Ser Gly Tyr Lys Asp Trp Ile Leu Trp
            580                 585                 590

Ile Ser Phe Ala Ile Ser Cys Phe Leu Leu Cys Val Ala Leu Leu Gly
        595                 600                 605

Phe Ile Met Trp Ala Cys Gln Lys Gly Asn Ile Arg Cys Asn Ile Cys
    610                 615                 620

Ile
625


<210> SEQ ID NO 118
<211> LENGTH: 673
<212> TYPE: PRT
<213> ORGANISM: Artificial Sequence
<220> FEATURE:
<223> OTHER INFORMATION: Synthetic Sequence

<400> SEQUENCE: 118

Met Lys Thr Ile Ile Ala Leu Ser Tyr Ile Leu Cys Leu Val Phe Ala
1               5                   10                  15

Gln Lys Thr Lys Asn Thr Thr Thr Thr Gln Thr Gln Pro Ser Lys Pro
            20                  25                  30

Thr Thr Lys Gln Arg Gln Asn Lys Pro Pro Ser Lys Pro Asn Asn Asp
        35                  40                  45

Phe His Phe Glu Val Phe Asn Phe Val Pro Cys Ser Ile Cys Ser Asn
    50                  55                  60

Asn Pro Thr Cys Trp Ala Ile Cys Lys Arg Ile Pro Asn Lys Lys Pro
65                  70                  75                  80

Gly Lys Lys Thr Thr Thr Lys Pro Thr Lys Lys Pro Thr Leu Lys Thr
                85                  90                  95

Thr Lys Lys Asp Pro Lys Pro Gln Thr Thr Lys Ser Lys Glu Val Pro
            100                 105                 110

Thr Thr Lys Pro Ala Ala Ala Pro Gly Ala Ala Gln Lys Ile Pro Gly
        115                 120                 125

Asn Asp Asn Ser Thr Ala Thr Leu Cys Leu Gly His His Ala Val Pro
    130                 135                 140

Asn Gly Thr Ile Val Lys Thr Ile Thr Asn Asp Arg Ile Glu Val Thr
145                 150                 155                 160

Asn Ala Thr Glu Leu Val Gln Asn Ser Ser Ile Gly Glu Ile Cys Asp
                165                 170                 175

Ser Pro His Gln Ile Leu Asp Gly Glu Asn Cys Thr Leu Ile Asp Ala
            180                 185                 190

Leu Leu Gly Asp Pro Gln Cys Asp Gly Phe Gln Asn Lys Lys Trp Asp
        195                 200                 205

Leu Phe Val Glu Arg Ser Lys Ala Tyr Ser Asn Cys Tyr Pro Tyr Asp
    210                 215                 220

Val Pro Asp Tyr Ala Ser Leu Arg Ser Leu Val Ala Ser Ser Gly Thr
225                 230                 235                 240

Leu Glu Phe Lys Asn Glu Ser Phe Asn Trp Thr Gly Val Thr Gln Asn
                245                 250                 255

Gly Thr Ser Ser Ala Cys Ile Arg Gly Ser Ser Ser Ser Phe Phe Ser
            260                 265                 270

Arg Leu Asn Trp Leu Thr His Leu Asn Tyr Lys Tyr Pro Ala Leu Asn
        275                 280                 285

Val Thr Met Pro Asn Lys Glu Gln Phe Asp Lys Leu Tyr Ile Trp Gly
```

-continued

```
    290                 295                 300

Val His His Pro Gly Thr Asp Lys Asp Gln Ile Phe Pro Tyr Ala Gln
305                 310                 315                 320

Ser Ser Gly Arg Ile Thr Val Ser Thr Lys Arg Ser Gln Gln Ala Val
                325                 330                 335

Ile Pro Asn Ile Gly Ser Arg Pro Arg Ile Arg Gly Ile Pro Ser Arg
            340                 345                 350

Ile Ser Ile Tyr Trp Thr Ile Val Lys Pro Gly Asp Ile Leu Leu Ile
        355                 360                 365

Asn Ser Thr Gly Asn Leu Ile Ala Pro Arg Gly Tyr Phe Lys Ile Arg
    370                 375                 380

Ser Gly Lys Ser Ser Ile Met Arg Ser Asp Ala Pro Ile Gly Lys Cys
385                 390                 395                 400

Lys Ser Glu Cys Ile Thr Pro Asn Gly Ser Ile Pro Asn Asp Lys Pro
                405                 410                 415

Phe Gln Asn Val Asn Arg Ile Thr Tyr Gly Ala Cys Pro Arg Tyr Val
            420                 425                 430

Lys His Ser Thr Leu Lys Leu Ala Thr Gly Met Arg Asn Val Pro Glu
        435                 440                 445

Lys Gln Thr Arg Gly Ile Phe Gly Ala Ile Ala Gly Phe Ile Glu Asn
    450                 455                 460

Gly Trp Glu Gly Met Val Asp Gly Trp Tyr Gly Phe Arg His Gln Asn
465                 470                 475                 480

Ser Glu Gly Arg Gly Gln Ala Ala Asp Leu Lys Ser Thr Gln Ala Ala
                485                 490                 495

Ile Asp Gln Ile Asn Gly Lys Leu Asn Arg Leu Ile Gly Lys Thr Asn
            500                 505                 510

Glu Lys Phe His Gln Ile Glu Lys Glu Phe Ser Glu Val Glu Gly Arg
        515                 520                 525

Val Gln Asp Leu Glu Lys Tyr Val Glu Asp Thr Lys Ile Asp Leu Trp
    530                 535                 540

Ser Tyr Asn Ala Glu Leu Leu Val Ala Leu Glu Asn Gln His Thr Ile
545                 550                 555                 560

Asp Leu Thr Asp Ser Glu Met Asn Lys Leu Phe Glu Lys Thr Lys Lys
                565                 570                 575

Gln Leu Arg Glu Asn Ala Glu Asp Met Gly Asn Gly Cys Phe Lys Ile
            580                 585                 590

Tyr His Lys Cys Asp Asn Ala Cys Ile Glu Ser Ile Arg Asn Glu Thr
        595                 600                 605

Tyr Asp His Asn Val Tyr Arg Asp Glu Ala Leu Asn Asn Arg Phe Gln
    610                 615                 620

Ile Lys Gly Val Glu Leu Lys Ser Gly Tyr Lys Asp Trp Ile Leu Trp
625                 630                 635                 640

Ile Ser Phe Ala Ile Ser Cys Phe Leu Leu Cys Val Ala Leu Leu Gly
                645                 650                 655

Phe Ile Met Trp Ala Cys Gln Lys Gly Asn Ile Arg Cys Asn Ile Cys
            660                 665                 670

Ile
```

<210> SEQ ID NO 119
<211> LENGTH: 234
<212> TYPE: PRT
<213> ORGANISM: Artificial Sequence
<220> FEATURE:

-continued

```
<223> OTHER INFORMATION: Synthetic Sequence

<400> SEQUENCE: 119

Gly Ser Gly Glu Gly Arg Gly Ser Leu Leu Thr Cys Gly Asp Val Glu
1               5                   10                  15

Glu Asn Pro Gly Pro Phe Val Phe Leu Val Leu Leu Pro Leu Val Ser
            20                  25                  30

Ser Gln Cys Val Asn Leu Thr Thr Arg Thr Gln Leu Pro Pro Ala Gln
        35                  40                  45

Glu Lys Asn Phe Thr Thr Ala Pro Ala Ile Cys His Asp Gly Lys Ala
    50                  55                  60

His Phe Pro Arg Glu Gly Val Phe Val Ser Asn Gly Thr His Trp Phe
65                  70                  75                  80

Val Thr Gln Arg Asn Phe Tyr Glu Pro Gln Ile Ile Thr Thr Asp Asn
                85                  90                  95

Thr Phe Val Ser Gly Asn Cys Asp Val Val Ile Gly Ile Val Asn Asn
            100                 105                 110

Thr Val Tyr Asp Pro Leu Gln Pro Glu Leu Asp Ser Phe Lys Glu Glu
        115                 120                 125

Leu Asp Lys Tyr Phe Lys Asn His Thr Ser Pro Asp Val Asp Leu Gly
    130                 135                 140

Asp Ile Ser Gly Ile Asn Ala Ser Val Val Asn Ile Gln Lys Glu Ile
145                 150                 155                 160

Asp Arg Leu Asn Glu Val Ala Lys Asn Leu Asn Glu Ser Leu Ile Asp
                165                 170                 175

Leu Gln Glu Leu Gly Lys Tyr Glu Gln Tyr Ile Lys Trp Pro Trp Tyr
            180                 185                 190

Ile Trp Leu Gly Phe Ile Ala Gly Leu Ile Ala Ile Val Met Val Thr
        195                 200                 205

Ile Met Leu Cys Gly Ser Gly Ala Thr Asn Phe Ser Leu Leu Lys Gln
    210                 215                 220

Ala Gly Asp Val Glu Glu Asn Pro Gly Pro
225                 230
```